(12) United States Patent
Kobayashi et al.

(10) Patent No.: US 9,365,879 B2
(45) Date of Patent: Jun. 14, 2016

(54) UK-2 BIOSYNTHETIC GENE AND METHOD FOR IMPROVING UK-2 PRODUCTIVITY USING THE SAME

(71) Applicant: MEIJI SEIKA PHARMA CO., LTD., Chuo-ku, Tokyo (JP)

(72) Inventors: Koei Kobayashi, Odawara (JP); Naomi Sumida, Odawara (JP); Koji Yanai, Odawara (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 149 days.

(21) Appl. No.: 13/936,771

(22) Filed: Jul. 8, 2013

(65) Prior Publication Data

US 2014/0011203 A1 Jan. 9, 2014

(30) Foreign Application Priority Data

Jul. 9, 2012 (JP) ................................. 2012-153986

(51) Int. Cl.
| | |
|---|---|
| *C12Q 1/68* | (2006.01) |
| *C12P 17/16* | (2006.01) |
| *C12N 15/113* | (2010.01) |
| *C12N 15/52* | (2006.01) |
| *C12N 15/63* | (2006.01) |
| *C07K 14/36* | (2006.01) |
| *C12N 15/76* | (2006.01) |

(52) U.S. Cl.
CPC ............. *C12P 17/165* (2013.01); *C07K 14/36* (2013.01); *C12N 15/113* (2013.01); *C12N 15/52* (2013.01); *C12N 15/63* (2013.01); *C12N 15/76* (2013.01); *C12Q 1/689* (2013.01)

(58) Field of Classification Search
CPC .... C12P 17/165; C07K 14/36; C12N 15/113; C12N 15/52; C12N 15/63; C12N 15/76; C12Q 1/689
See application file for complete search history.

(56) References Cited

FOREIGN PATENT DOCUMENTS

| JP | 7-233165 A | 9/1995 |
|---|---|---|
| WO | 99/11127 A1 | 3/1999 |
| WO | 01/18179 A1 | 3/2001 |
| WO | 03035617 | 5/2003 |

OTHER PUBLICATIONS

Usuki et al., "Semi-synthesis and biological evaluation of analogues of UK-2A, a novel antifungal antibiotic from *Streptomyces* sp. 517-02", Bioorganic and Medicinal Chemistry Letters, 15(8):2011-2014 (2005).
Usuki et al., "UK-2A, B, C and D, Novel Antifungal Antibiotics from *Streptomyces* sp. 517-02", The Journal of Antibiotics, 54(7):600-602 (2001).
Yan et al., "*Streptomyces blastmyceticus* DNA, antimycin biosynthetic gene cluster, strain: NBRC 12747", Database Accession No. AB727666 dated Jun. 10, 2012.
International Search Report for PCT/JP2013/069081 dated Nov. 4, 2013, with Written Opinion.
Office Action for EP Application No. 13 740 383.8 dated Jul. 31, 2015.
Wises Namwat, et al, "Identification by Heterologous Expression and Gene Disruption of VisA as L-Lysine 2-Aminotransferase Essential for Virginiamycin S Biosynthesis in Streptomyces virginiae", Journal of Bacteriology, Sep. 2002, pp. 4811 to 4818, vol. 184, No. 17.
Masashi Ueki, et al., "UK-2A, B, C and D, Novel Antifungal Antibiotics from *Streptomyces* sp. 517-02 I. Fermentation, Isolation, and Biological Properties", Journal of Antibiotics, Jul. 1996, pp. 639 to 643, vol. 49, No. 7.

*Primary Examiner* — Reza Ghafoorian
(74) *Attorney, Agent, or Firm* — Sughrue Mion, PLLC

(57) ABSTRACT

The genomic DNA of *Streptoverticillium* sp. 3-7, which produces UK-2, was analyzed to identify a region expected to be a UK-2 biosynthetic gene cluster. Moreover, by colony hybridization, DNAs in the region were successfully isolated. Further, the DNAs were used to prepare a strain in which the genes present in the region were disrupted. The strain was found not to produce UK-2. It was verified that the genomic region was the UK-2 biosynthetic gene cluster. Furthermore, *Streptoverticillium* sp. 3-7 was transformed by introduction of a vector in which the isolated UK-2 biosynthetic gene cluster was inserted. It was also found out that the UK-2 productivity by the transformant was improved about 10 to 60 times or more in comparison with that of the parental strain. Moreover, it was revealed that 2 copies of the UK-2 biosynthetic gene cluster were present per cell in these transformants, respectively.

7 Claims, No Drawings

```
                         SEQUENCE LISTING

<160> NUMBER OF SEQ ID NOS: 48

<210> SEQ ID NO 1
<211> LENGTH: 31318
<212> TYPE: DNA
<213> ORGANISM: Streptoverticillium

<400> SEQUENCE: 1
atgagttcct tggcgacccc cacccccact ctcgagggcc tcctcacgac accggcggcg      60
cagcacgccg aagcacaccc cccgctccac cggccgggct cggccacggc ctgcctcgac     120
cggggcctgg tcctccggca ggcggacgag gagttcttcc gccggttcgg cggctcggcc     180
ccgcgcctcg tcggccggtc cttcaccgag ctggtgcacc ccggctgccg ggagcccctg     240
ctgcggcagt tcgccgggct caccgagggc cggcgcgacc ggttcggcac cgaggtcatc     300
gcggtgggcc cggacggcac cccgttccgg accgacctga cggcgctggc ggtacgcggc     360
```

```
ggaaccccg  acatctcggc  cgtctggctg  acgctggcgg  cggccggcga  gaccgcgcag    420
cccgccgccg  cgacgccccg  caagaagatc  ctcagcgaga  tcgacgcccg  catcctcgaa    480
ggcatcgcgg  ccggtgtctc  caccgtcccc  ctggccgcac  gcctgtatct  gagccggcag    540
ggggtcgagt  accacgtgaa  gagcctgttc  cggcagctcc  gcgtgcccaa  ccgggccgcg    600
ctcgtctccc  gcgcctactc  catgggcctg  ctcaaggtgg  ggacctggcc  gcccaaggtg    660
gcgccggact  tcgtcaagtg  agcccggacc  gcggggtgat  gacgtgtcgc  ggcgcggggt    720
ccgcgtgcag  ccgggcgacc  agcggcgcgc  gggcggccag  cacccggcgc  tggttgacgt    780
agcccttgtc  ggtgatctcg  cccgcgtcca  ggtcggcgg   gtccgcgagc  accagcagcc    840
gctggacccg  ggacgcggac  ccggcgcccc  ggttgagtcg  ctccagtgcc  gcgccgaggt    900
gggcggccag  cgcgtcggag  tacagcaccc  cgccgtccgc  ggccggccgc  cggccgagca    960
gccgctcggc  ctcggccggg  tcgagccacg  ccagcgcgca  gaccgcgtcc  cggtgctccc   1020
cggtgatcac  cgcgtcggag  aggaccggcc  cggccgaaag  cagcgcgccg  cgcacggctt   1080
cgacgtgcac  gaacgtaccg  gtggacagct  tgaagtcctc  ggtcagccgg  ccccggaaca   1140
ccagccccgc  gcccgcgtcg  ccggggtcgg  cgaacgcgac  ggcgtctccc  ggccggtagt   1200
agccctcctc  gtcgaaggcg  cgcgcgtcga  ggtccgggcg  gccgaggtag  ccgggcgtca   1260
cgtgcgggcc  gcgcacccgg  acctcgtagc  cgtcaccctc  cgccggtacg  agcttcagct   1320 ccaccccgg   cagcggcacg  ccgatgcacc  gcgggtcggt  gaacgggaag  tgcgcgctgg   1380
tggacgccgg  cgaggtctcg  gtggcgcccc  acgagcccgt  caccggcacg  tcccgcccgg   1440
tcacttcgcg  gcccagcgcc  cggagccgtt  cgcgcagggc  cggggccagc  gccgccgccg   1500
cgttgaagac  gagccgcagc  cgggcgaaga  accgctccgc  cagctcccgg  tcgcgctcca   1560
gggcggggac  gagccgcgcg  tacccggccg  ggacgttgaa  cgccagggtc  ggggagacct   1620
cgcgcaggtt  ggccagggtg  cgcccgaaca  gctccggggt  cgggcggccg  tcgtcgaggt   1680
acagagtgcc  gccgttggcc  agcaccaggt  tcacgttgtg  gttgccgccg  aaggtgtggc   1740
tccacggcag  ccagtccagc  agcaccggcc  gctccccggc  caggaacggc  cacacctgcc   1800
gcatcatccg  ctggttggca  cagagcatgc  cgtgcgtggt  gacgacgccc  ttcggcgctc   1860
ccgtcgagcc  cgacgtgaag  aggaccttcg  cgaccgtcgc  gctcgtgacg  cccgcacggg   1920
ccgcctcgaa  cgcgcggccc  ggcaccgtac  gcagcagggc  gtccagcgag  tgctccgccg   1980
gcccgccccg  cgccgccacg  acgatggctc  caccgcccgc  cgcggccagc  gcgggaccga   2040
acggcccggc  gtcctcggcg  tacaccgcgc  ccggccgcag  cagttccgcg  atcgcccgga   2100
tccgcgcgtg  gtcccggctc  agcagggagt  aggcgacgct  gaccggcgcc  accgggatcc   2160
cggcgctcag  cgcgccgagc  gtcatcagca  ggtgccggt   ggagttgccg  gacaggacca   2220
tcagcggccg  ccgcgccgac  agcccgcggt  cgagcagcgc  ctgcccgacc  gcctccgccg   2280
ccgccagcac  ctcgccgtac  gtgccggtgcc  ccaccggcc  gtcggccccg  cgctcggcga   2340
ccagcgggcg  gtcgggcccg  gcctgggccc  aggtgcggag  atggtcggtc  acggaggcgg   2400
gatacacccc  cagcggctgc  gccgacgaga  ggagcacggt  cccgtccggc  cggtcccgcc   2460
ggacggtccg  ggcgggcgcg  aacagcggtg  acgaggtctc  ccggcggtg   gtcccaccgg   2520 cggcggagtg  cggggcggtg  cgcgtggtcg  ggtgcggcat  cggggttccc  tcccggtctc   2580
gcggggctgt  cagacgtgcc  gctcgaccgc  gcggcggagc  tcgcccgcgc  gcagcagggc   2640
ggcgacggtc  tcgatgtcgg  cgtccagcgg  ccggtcggcg  gagaggaacg  gcgagtaccc   2700
gcggacgagc  gtgtgcgcgg  cccgggtcgc  gctccccagc  cgcccgaccc  cggtgaggtc   2760
```

```
cgcggcctgg cacagggcga gcaggtggat ggcggtgacc tggctcgtca gccggaccac   2820
cgtgtgcgcg tgccgcgcgg cgatggtgcc catgctcacc ttgtcctggt tgtgcgcctc   2880
ggtcgaacgg gagaacgagc tcacgggcat cgtcaggtgc agcgcctcgg cggtcagcgc   2940
ggacgcggcg atctgcgcgc ccttgaaccc gtggtgcagc cctgcctccg ggtcgtcggg   3000
accgaccggg acgaccaggt tcggggtgag gccgatgctg aacttgtcgt ccaccaggat   3060
cgccagctgg cggtcgagca ggtcggcgac cccggccacg cgggcggaga ccgcctgcgc   3120
cgcctgggcg acgtgcccgc cgtagaagtt gccgctgtag tggacggtgt cggtggccgc   3180
ctcgaagagc gggttgtcgt tcgaggagtt gatctcggtg gtcagccagt cctcggccca   3240
gccgagcgtg tcccgcagca cgccgacgac gtgcggcgcg caccggatcg agtacgggtc   3300
ctggatgcgg cgctccagct cgacgtaccg gcgctcctcg ctcgaaccgg gcccacgag    3360 atcggtgtcg gcgaccacgg cgggggagtc gcccagcatc cggtggacgt tcgcggcgct   3420
cgcgagctgg ccggggtgcg gcttgtgctc gtgcgggaac gcggtgaact ggtcgcggct   3480
gctgcgccgg acctccgtcg acagcacggt gcacagctcg gccgcccacg ccagctcggc   3540
cgcctcggcg accgccaggg cggcgtaggc ggccatgaag gacgtcccgt tgacgagcgc   3600
cagcccctcc ttggcccgga gcgtgacggg cgcgaggccg caggcccgga tggcctcgcc   3660
cgcgtcgagc gcccggccct ggctgcgcag ggtgccctcg ccggtgagcg cggcggcgag   3720
gtagccgagc ggcgcgaggt cgccgctggc gccgaccgaa ccgcgctccg gtatctgcgg   3780
cagcaggtcc ttctccagca gtgacaggat cagctccacc ggcgccgtgc ggatgccgga   3840
gttgccccgc gcggcactgt tggcgcggat cagcatggtg gcgcggacga cctcgtcggg   3900
tgccatgtcc ccggtgccga cccgcaggaa gcggagcagg ttccgttgca gcgccccggc   3960
cttgtcggcg ctgacctggc ggccgctgct gtcgccgaag ccggtcgtca ccccgtagat   4020
cgggatgccg gaggcgacga tccgctccgt ggcctcccgc gacgcgtca tgcgctcggc    4080 cgcggccgcc gcgagggcga ttctctgctt gcccggctgg gtcgcgaccc gccgcacggc   4140
ccgcagcgag aggctgtggc cgtccagctc gatggtggtg tcgtcggtgg gcgaggccat   4200
gtcggtcccc ttcggtcggt gggcgatggg cggtgggcga tcgaccgcgt gcgccgctcc   4260
ttgccgggcg gcccgcggac gccggtccgc ggtcgcggag ccgtgggtgt gcgcgccggc   4320
ggtacgggag aggggcccgt cgccgccggc gggatgggtg ggcgtggggg cgttgctcag   4380
ccgggcgttc cgccgatgcc ccactggtcg cgggggatgc cctggagcgt cacccacgtc   4440
acgtcgcggc actcggggcc gagggcgcgg accgccgcct cggtgagctc cccgatcagg   4500
gcgcggcggg tctcgggcgt gaggcggtct tcgtagaggc tgacctggat caggggcacg   4560
agggttcctt ctctcgtcgg gcgggtgctt cccggccact cagcgcggcg ccaggttgg   4620 cgccgagggt ctcgacctgg cgatcggtca tggcggggtg gcagggcagg ttgaggtgct   4680
cgccgaacca caggcgttcg gcgaccgggc actcgccctc gccgtgcccg cgcagccgcc   4740
actcgggcag caggtgcacc gggtggtagc gcaactgggc gggggtaccg gagcgttgca   4800
gggcgtccag cacgcggtcg cggcgtccgt cgccggggac gagcgcggtg tagaggtggt   4860
acgggtgcac cgcgtcgggc gcggcggtca gcggccggac gtcgaagcgg cggcacaccg   4920
cgtcgagttc cgcggcgatc gcccgccggc gggcgacgaa ctccggcagc cgttccagct   4980
gcaccaggcc caccgcgcag gcggcctcgg agagcgcggc gttggtcccg ctgccccgca   5040
gccccgtgca gtcctcccgg taggcgtagt cggcgtacgc catccacggc agcgccgcgg   5100
```

```
ggggccggcg gtgcgcggac gaggtgaagg tgccgtccac cgcgttcgac cggatccggt   5160
cgatcctgcg ggccagttcg ggcgacgggg tgcacaccat gccgccctcg ccagggtgg    5220 tgatgttctt ggacgcctgg aagctgaagc aggacaggtc gccgagcgcg ccggggcggc   5280
ggccccggta ctcggcgccg atcgcgtgcg cgcagtcctc caccacgagg cgccgtgcg    5340 cgtgcgcgat ggcggtgatc cggtccatgt cggcggggtt gccgccgtag tggacgagga   5400
tgacggcctt cgtgcgctcg ttgacgagag tctccagcgc gtccgggtcc atgttgaggc   5460
tgcccggctc cacgtcgcag aatcgcaccg ttgcctcggt cgcgagcagc ggctgcgcgg   5520
tggcgtggta cgtctgcggc gtcacgacga cctcgtcccc ggcccgcagg tcagcagcc    5580 ggatcgcgat ctccagcgcg accgtcccgc tggtgaccgt cagggcgtgc gcggcgccga   5640
cgtgccgggc gaaggcccgc tcgaactcct cgcgcaccgg gcccatcgac aggggcgcgt   5700
ccgcgcgcag cacctcggcc acggcccgca cctccgcctc gccgagcagg ctgccccggt   5760
gcgggtggac gtcgccggcg cggtccgccg tcgcccggct cacgagcggg caccggccgg   5820
ctcggggtcg gacccggcgg cgtccgggcc cggcggcgcg tcgaggccga ggtcggccac   5880
gaggcgcttc ttgtcgacct tgccgaggcc gctcttgggg aacgcctcga cgcacacgac   5940
ccggtcgggg aacttgtagg acgccagccc gcggtcgcgc aggtagcggc gcagctcgcc   6000
cagggtcggg ggcgtgccga ccgggatgat cacggcgcag gtgcgctcgc cgaggacggc   6060
gtcggccatc ggcaccacgg cggcctggtc gatccgctcg tggccggtga ggtggccctc   6120
cagctcgggg gcggacacct tgtcgccgcc gcggacgatg acgtccttcg cgcggcccat   6180
caccacgacg ccgccgtcgt cggtgatccg caccaggtcg ccggtgcggt agaagccgtc   6240
cggggtgaac gccccggcgt tgtgctcctc ggcccggtag tagccgcgca gggtgtacgg   6300 gccccggggta gcagctcgc ccgtcccgcc ggccgccacc tcgtcgcccg ccgcgtccac   6360
cacccgcagt tcgtcgtggg gggagatggg ccggccctgg gtggtgagga cggtctcggg   6420
cgcgtcctcg cggcgcgtga ggcacagcag gccctcggac atcccgaaca cctgctggag   6480
acgggccgtc agcgccggtc cgacctcctc ggcgagcgac cggtgcacca ccgcgctgcc   6540
gacctgcacc agctccagcg tcgccagctc ctcccgcgc ccgtcggcgg cggcgatcca    6600
ggagtgcgcg atcgtcggca cgaccgacgt cgtggtgacc ccgtgccggg cgatgagcgg   6660
gaagcacacc tggggtcgg gcacggtgct cagcacgacg gcgcccccgt tggcgaacac    6720
cccgaccaca cccgggcagc cccacgtgaa gttgaaggcg atcggcaggg tggcgaggta   6780
gcgggtgtcc tcggagtact cgcagatccc ggcggcggta cgggcctggt acaggtagtc   6840
gtcgtgcgtc cgcgggatga gcttcggcag cgccgtggtg ccgccggaca gcaggaagaa   6900
ggccacgtcc gacgcgtcgg gaccggtcgc gccggccggg tccaggggcg tctccgcctc   6960
gggaagcggc gcgaactccc cggggtcgcc gaccacgaac acgtgccgga gcgacgcgtg   7020
ccgctcgcgc agggaccggg ccagcccgcg gtggtcgaac cccaggaacc ggtcgagggt   7080
cacgtaggcg ctcgccccgg tcaggccgca gatgtggtcc agctccgcca tgcggtggtt   7140
gggcagcgtg aagaccggca gcacaccgat gcggaagaag gcgaacgaca ccgccacgtg   7200
ctcggcgacg ttgggcagtt ggagcacggc ccggtcgccc gcccgcaggc ggcggccga    7260 gaacccggcg gccaggcggt cggcccaccg gtcgagggcg gcgtaggtga aggaccgctc   7320
cccgtcgatc agagccacgt tgtccggggt gcgcgcggcc tgggaacgca gcagctcgcc   7380
caggggctca ccgcccaggt gccgtcggc ccggtagcgc tccgcggtct cggccggcca    7440
ggggacgaaa ccatcgagtc catcgagtcc atcgagaaga ggcatggcag gggctcacct   7500
```

```
tcgttctgtg acggctggca tcggagaacg gtctatcaac ggagctctga ggaattcctt    7560
agtcctgccg cggctagcct cacgtcccgg tcgggccggt cgggccggac gcaccggaca    7620
gaggggagca cccgtcatga ccgtcgacga ggcttcggcg cacgagggcc gcctgccggc    7680
cttcgaggtg ttcgaccagg gcttcaagac cgatccgtac ccgtggtacc gcaagctgcg    7740
cgaggcggcg ccgatccacc gggtacggat gaccctgggc gcggacgtgt ggctggtgac    7800
cggctacgag ctggcgaaga ccgtgctcgc ggacggccgg ttctccaaga tgaccgtcaa    7860
cgccgagcgc gcgtggcgct ccctggagct catcccggac gaccccgacg ccctggtcaa    7920
ccggatgctg ctgatgagcg atccgcccga ccacgagcgc ctccgccgcc tggtgtcccg    7980
ggcgttcacg gcgcgctcga tggaggcgat gcggccccgc atcgccgagg tcgccgacga    8040
actcgtcgca cggttcgccg gccggggccg cgtcgacctc atccgcgagt tcgcgttccc    8100
gctgcccgcc atgatcatct gcgatctgct cggcgtcccc gccgaacacc gcacccggtt    8160
cgaggagtac ctgcggctgc tctgcctggc cgaacccgag gacgtccacc ggatgcccgc    8220
cgtcttcgcc gaactcacgg cggaactcgc cgagttggtc gagcgcaagc gggccgagcc    8280
cgacgggcac ctgctctccg cgctggtcgg gatccgggac ggcagcgacc ggctcaccga    8340
cgacgaactg gtctccatgg ccttccagct catgtacggc gcccaggaca ccaccgtcaa    8400
cctcatcgga aacggcatgc tcgccctgct ggacaacccc gccgccatgg ccgaactgcg    8460
ggagaacccg gagctcatcc cgggcgccgt cgaggagatc ctccgcttcg accgccggt    8520 ggagaccgcc accccgcggt acgccctgga accgctcgac gtcggcggga tgcgcgtgga    8580
gaagggcggg gtcgtgctcg tctccctcgc gagcgcctcc cgcgaccccg gcagttcga    8640 ggaccccgac gtcttcgaca tccaccgcga ggtgcgcgga cagctcgcgt tcgggcacgg    8700
gctgcactac tgcctcgggg ccgtgatggc ccgcgtgaag gcgaggtcg ccctgcgggc    8760 cctgctgtgc ggcctggacg acctgcgccc ggacgaggac gccgaaccgc tcgcgcgcca    8820
cgccgggttc atcatgcgcg gctgaaggc gctccccgtc cgcttcaccc cgcgcgccgc    8880
gtgaaccgga cgcgcccgcc ccgcaccgcc tcgggaccct gggtgccgca ccggcccggc    8940
accgccccgg gaccggtgac gctgttctgc ttccccacg ggggaggcgg cagccgcgcc    9000
tacgccgaac tgctggaacc gctgccccc tgggtggccg ccgtgaccgc gcggctgccc    9060
ggccgcgaga gcgcgcggcg gcagcccgtc ctcaccgacg tcggcgccat ggccgacctg    9120
ctcctccccg gcgtcctcga agcggccgac cgcccgttcg tcttctacgg ccactcgctc    9180
ggcgcgcgcg tcgcctacga gacggcccac cgcctcgcgg acaccggccg gccgctgccc    9240
gccgcgctct ggtctccgg ggcgcccgcc ccggccctcg cgtccacac cccgtgccac    9300 gaccagcccc gcgcggaatt cctccgcacc ctgcgggcga tgggcggcgt cgccccggag    9360
gtgctcgccg acgaggagct gtgcgactac gtcctgccgg tcatccgcgc cgacatgcgg    9420
gccgccgaga cataccggcc accgcgccgg acccgctgc gcacaccgat cagggcgctc    9480
gccggacggg acgaccccg ggtgccggtg agcacgtgc ggcggtggtc ggacgaggcc    9540 ggtgggggagt ccgctgcac ggtcttcgag ggaggccact tcttcttccg tgaccacccg    9600
tcggaggtcg ccgcggtgtt ggacggcctg ctgcgggaag tcgccggggg ataggggccc    9660
ggcccgggcg tcagggccgc agcagtccgc ccacccacca gtcgtgcggt acgccgtcgt    9720
tggcgatgcc gcgcttgcgc agtgtcccct cgacggtgaa gccgagtctc tcggcgacgt    9780
cacgcgagcc ggcgttcccg accatggccc accactcgat gcggtgcacg tcgagcgtgg    9840
```

-continued

```
cccatcccca gtcgcacagg gctcgggcgg cctccaccga atacccgtga ccgcgctgct    9900
ccttgaccgc ccagtagccg agctcccaga cgccgcggct gacgcgggtc aggcagtacg    9960
agccggccag ggcgccggtg tcctcgcgga acgcgccgaa ggtgtagtcc tcgtccgcgg   10020
cccactgggc gggcagcttc tcgccgacga gcttctccgc gtccgcacgc aggtacggca   10080
ccggcaccgg ggtgtagagc tggatgtcct cgtcctggca ggcctcgtac accgcatcca   10140
cgtcggcagg cgtgaaggcc cgcagcacca ggcggtcggt ccgaagggtc accgggtcca   10200
tcgcggcagt atgaccgccg acgacaagcg gcggccagtg gatttccgac cggccgccgc   10260
tccgggccgg gcactgccct cccgtctgga gcccttcccg cctagagtcc gagcggacg    10320
cccccccgacg cctcgatgcg ctgcccggtg acccagcggc cgcccggtcc cgccaggtag   10380
gcgacgacgt cggcgacctc gccgggcgta ccgacccggt ggagtgcggt ggtggcggcc   10440
atggcctcgc gctgggcggg caccttcatg tccggttga tgtcggtgtc ggtgtacccc   10500
ggggcgaccg cgttgacggt gatgccgcgc ggccccagct ccagggcgag gtcgacggtg   10560
aaggtctcca gcgccgcctt ggtcatggtg tacgcggcga tcaccggcat cgccacccgg   10620
gtcgcggcgg tggtgacgtt gacgatccgg cccccgtcgc gcagccgcgg cagcgcgccc   10680
tgcaccagga agaacggggc cttggcgttg accgcgaaca gccggtccca gtcggcctct   10740
tcgaggtccc gtacgccacg cgggacggtg atcccggcgt tgttcacgag gatgtccacc   10800
ggcgcgggac ccgagccgcc gcggacgcg gcgacgccct cgtcgtaacc gcgccacagc   10860
tcgtcgaggg cgccgagctc gccgaactcc gcgcggacgg ggaaggccga cccgccggct   10920
tcgcggatct cccgcaccgt cgaccgcgcg gcttcgtcgt cccgtccgta gtggacggcg   10980
accagcgcgc cctccgcggc gaggcggacg cgacggcac ggccgatgcc gcggccggcc   11040
ccggtcacca gggcgatgcg gtcggtcgga tctgacatgg gttcctccgg gaggggtgg    11100
tggtcggatc aggcaagggg tcagacggac agcgcggcac cgcccccggc gtccgcgacc   11160
cgctccagcg tcgccagcgt ccgcgcccgc accgctcga tctgggcggg cggggagcag   11220
acggggggtgt acgggatctc cagcgagaac cgccgtcca cggtgctgac acaggcgaag   11280
agcggaccct gcccgaaccc ggggccgtag tcctcgcgtc cggccgtcag ccgggtgtcg   11340
cgcagccgca gcccgggcgg ggacaccggg ccggcgatcc ggcccatgtt cgacacgatc   11400
acggtggtgg ccagcagctc cgggtggtcg acgaggcggg cgagcagagc ggtctccacg   11460
gcccagccgt cgccggccag ggcgccgcgc agcccctcgg tgacccggcg cgccagcgga   11520
cccacgtgct ccgggccctc gccggccgcg acgtccacca cgtccgggaa ccccgagacc   11580
agcggcagca tcacgccggc cgccgccggg ggctcgaccc gggagcgcag gtccacgggc   11640
gagaagcagc cgagggcggc ggtaccggaa ccgccgagct cctcccgtat cgccaggagc   11700
agcgccgcgg cggtcacgcc gtgcaccgag gtgcccaacc tccgtgcgcc cgccgcgagt   11760
tcgccggtcc tgtcgcggga cagggcgacg cggacgttgt gcaccggctg ccgcccggcc   11820
ggcggcgcac cgtccccgcc cgcctccacg tacggcaact cgccggcgg acggtcgcgc   11880
gcctgttcca ggcgctcggc gagcagcgcc gcgacggcgt cccccggacac ggccggcagc   11940
cgctccgaca ccggggccgg ccacgcggtc ccgccgggg gggccggttc gccggccagc   12000
accgcggcgt agtgccgcca gagttccgtg tggagggtga gggcgctggt gccgtcggtc   12060
accacgtggt ccacgacgag ccccacgacc gtgtccgagc cccgcgcggc cgtcgacagc   12120
cgcgcgaccg ggccgccgac gggcaagggg gacgtgcga tctccgtcat cacgtccttc   12180
tcgggcgccg gttcggccag gcccgggcgg ccggccgccc ccagccgttc gagggcgaaa   12240
```

```
ccgccgccgt gcgacacgat ccggctgtcc gccgtcggat gcgcgtcgag cgtccgcgac    12300
caggccgcgg acagcacgtc gaggtcgagg tcgccctcga cctcgacggt gaccaccgcc    12360
cggctgcggt cgccgacgtg cagctcctca agtgggcaga ggggacggag ggagtcgggc    12420
atcggttgtg ctcctcgggt cgttcggtcg ggcccgccat cggggagggg cccgccggaa    12480
gtgcgcggtg tcgcgcgtca gccggtggct gccgcgtagt ggctcagggg gatcgacggg    12540
gaacggccac ggcgccggag caccggaccg ggccgacggc cgggcgcccg gccggggccc    12600
gccgaagtgg cgggcgcgtg atgacgccgc cggggtccgc tgggggccgg accggccgtc    12660
gggccgttct cgccgtccgg acccggccgg agcggcgggc gccgtgccgg tgccgcctcg    12720
ggcgccgggg cgtcgcgggg ccggccggtt gccggtccgt ggcgccgccg gattccgcct    12780
cgtgcggggg gctgcccatg ggggccgggc cggtcatccg gccgccacct ccgcccgttc    12840
ccctccgccg gcccccgcga gacgcgcctc gaccgccttc gcaatcacct cgatcgggcc    12900
ggcgtcggtc agggcgtagt gggagcaggc gagaggaacc tcctcgaagg tgccggtggt    12960
gaacgggcgc caggacgcgg cccggtcggc gatcccgccc gcgacctccg gttcgtcgtc    13020
ggcgacttcg gtggccgaga cgaagaggat gtcggcgcgc agccgttccg gaaccagatc    13080
gggggcgatc cgcagattgt tgcggaccac cttcgccacg gtgatcgcct cctcacgcgt    13140
gagcgtgccc ggcaccgcct cggggtcccg gcgggaggag tcgagcagcg cgagcgacgc    13200
gtcgaccgtg gccggcgcgg gcatggtcaa gccggccagc cgcaggacga gggcggcggc    13260
ctgcgcctcg accgcctcgc cctccagcgc cgccgcgtcc ggctgcggcg tgtcgagcat    13320
ggtcagcagc gcgacctcct cgccggccgc ctccagggcg gcggccaggc ggtgggcgac    13380
ggcgccgccg aacgaccagc ccagcaggtg gtacgggccg tggggctgga cggcccggat    13440
ccgttccagg ccgtcccgga tcacgtcctc ggcgcgcccg gcggcgggaa gggcgccgtc    13500
caggccaagg gcctggaggc cgtacaccgg gcggcgcggg tcgaggtgcg gcagcagccc    13560
cgtgtagcgc caggcgacgc cgctgaccgg gtgcacgcag aacagcggcg gcagatcccc    13620
cgcggcccgc atcggcagca tgggggcgaa cgcctcctgc ccgacggccc cgccgcgccc    13680
ggcgcggtcg agcagtccgg cgatcgtcgg cgtggcgagc agggccgcgg ccggcacgtc    13740
gagcacgccc gcggtgcgca ggcgcccgcc gagcagcacg gcgcgcatcg aatcgccgcc    13800
gaggtcgaag aagttgtcgt cgagcccgat gccgtcgaca ccgagcacgg cctcccactc    13860
ggccgccacg gcccgctccg cgtcggtgcc cggcggcacg tgcggcacgg ccagcggcgg    13920
acgcgggacg cggcgcgagg cgcggtcgcc ggcgcggtcg tcggatgcgc cgtgcggggc    13980
cgtggtcgcc cgggcgccgg gggcgtcgat ccagtgccgg tcgcgggcga aggcgtagcc    14040
gggcaggtcg gcagggacc gccggggcag tcgggtgccc tcctccgacg cgtcgccggg    14100
cgggacgatg tccacctcgg ccccggcggt ccacaggtgc gcgagcgcct ccgcccgcac    14160
ccggccgtcg ggcccggtcg ccgcgcgtg gcgcatcacc gggacggtga cgggctccgg    14220
gccgccgtcg tcgacggccg cggccagccg cgacaggacg tccccggc cgatctcgac     14280 gaggaccggg cccgcgcccc cggcggaggc ggcgcgcagc gtccgcaccc cgtcggcgaa    14340
gcggaccgtg ccgcgcgtgt gcgccaccca gtgctccacc gaggtggcct gctcggcggt    14400
gacccacgtg ccggtgacgt tggtgatgta cgggacgcgc ggctcgcgca ggtcgacgcc    14460
gcggaaggcg gcgccaggt cgtccaggac cgggtcgagc atcgaggagt gggcggcggc    14520
gggcagccgc agccgccggt gggtgacgcc gtcggcgacg agccgctcga ccagcgcgtc    14580
```

```
gacggcctcc accggtccgc ccaccgtgca cgaggacggc gagttgaccg ccgccaggga    14640
caacccaccg tccaggagcg ggaggacgtc ccgctcgggc agcgccacgc cgaccgccgc    14700
cccgcccgcc gagatcatca gccggacgcg ggtgaccagc agcggcagca tctcctccag    14760
ggtcatcacc cccgcgaggc acgccgccac gtactcgccc agggagtgcc ccatcagcgc    14820
gccgggccgg accccggaag ccgccagcga ggcggccaag gcgtactcga ccaccgcgag    14880
cgcgcacatc gactccacgc tgaagtggtc ggcccgctcg tggagcgtga cgcggatgtc    14940
gtggtccagg accggctgaa ggatggcggc gcaccggtcg acggcctcgc ggtaggcggg    15000
gtcgtcgcgg tacagctccg cgcccatccc cacgtactgg gtgccaccgc cgggcagcag    15060
gaagaccacc tccggcgcac tctccgcccc ggccgccggg accgtcgcgg cggccagcgc    15120
ccgcgctgcg tccgccgcgg tcgccgccgc gaccgcgcgc cggtggggcc ccgggcgccg    15180
ggcgcgcagg gcgcgcgcca cctcggtcac ggacagttcc gggttgtcct ccaagtggcg    15240
cccgaggcgg ctcagttggc cggcgagtcc gtcgcgggtg cgtgccgaca ccggcagtac    15300
ggtccagccg ggcgcctctt ccgccggccc gatgggtacc ggcaggcgcg gtgcctcctc    15360
caggacgacg tgggcgttgg tgcccccgac cccgaaggcg ctcaccgcgg cgcgcagcgg    15420
gccgtcggcc gtccacggct ccagcgccgt cgagacgcgc aacgggccgc tcgcgaagtc    15480
gatgaggggg ttcggggcgt cgtggtgcac cgtgggcggc acggcccggt gctcgagcgc    15540
gaggacggtc ttgatgatgc cggcgatccc ggccgccgcg ccgaggtggc cgatgttgcc    15600
cttgaccgag ccgagcgcgc agtaccccg ccggtcggtg gactcccgga acgcctcggt    15660
gagggccgcg acctcgatcg ggtcgccgag gcgcgtggcg gtcccgtggg cctcgacgta    15720
cgtcaccgag ccggcgtcga cgccggccgc cacctgggcg gccacgatga cctccgcctg    15780
cccggccggg ctcggggccg agaaaccgac cttgcgccgg ccgtcgttgt tgatcgcgga    15840
accccggatg acggcccgga tccggtcgcc gtccgccagc gcgtcggaca gccggcgcag    15900
gacgaggacg ccggccccgt cgccgttgaa cgtgcccgcc gcgtccgcgg cgaacggccg    15960
gcacgccccg tcggggagag gcgggccgtc gggcacgtgg cggtacccga gcatcgcctg    16020
cggatccacc gacaccgcgc cgaccacggc gatgtcgcac gcgtacgcgg ccagcgcctc    16080
gctggcggtg tgcacggcga cgagcgcggt cgagcaggcc gtgttcatcg agacgctcgg    16140
gcccgtcagc tccaggtcgt acgacagccg agtggcgagc gtgccaaggg agttggcggt    16200
ggccgcgtgg atcagaccca cggaggcggg ctcgccggcg tgccgcgggt gcacgttgta    16260
ggagtagtag cggctgtcgc cggcgcccgc gtagaccccg acgacgcggt cgccgtggcc    16320
gtccgcgtac cccgcgtcct ccagcgcgtg gtaggcggtc tccaggagca cccgctgctg    16380
cgggtcgatg agttcggcct cggccgggcc gtagccgaag aacgcggcgt cgaagcggtc    16440
ggcgtcgggc agcaccgccg ccacgcggac cagggacggg tcctccaggt ccgccggatc    16500
gccccggccg gccaggaact cctcctccgt cacctcccgg acgccctgcc ggccctcgct    16560
cagcagcgcc cagaactcct ccagcgtgtt cgcgcccggg aaccggccgg ccatcccgac    16620
gacggccagc ggctccgtcg ccatgtcctc attcagcatg cgatgcctcc tcttggccct    16680
gctggcctgg ctggtcctgc tgaccccttcc ggccttcgg gccttcccg ttccgctggg    16740 cgcgcgccgc gagccggcgg cgggcctgct cgcgggtggc gccgagggcg ctcccggccg    16800
ctgcggagcc gccgtcctcc tcgccgccgg cctccggcc gtcgcccggc gccgtgatgt    16860
cccgccggcc cgccaagtgc ccggcgagcg accgcgcgtt gggatgggcg aacaggtcga    16920
ccaccgtcag cgcgccgccc agggcctcgt tcagctcggc ctgggcccgc accagcagca    16980
```

```
gcgaatgccc gcccaggtcg aagaagttgt ccccggaccc cacccgctcg cggcccagca   17040
cccgccgcca gacggcgagg acggtctcct ccagcacgcg gacgcggtcg ccgccggccg   17100
cgccggaagc cgcgctcccc tcggcggcgg acgccgccga ggacgcggcc cggacgaccg   17160
cgccgtgccc ggcgacgccg ccgcaggcgc gcgccgcggc ggccacgcc gcctcgtgca    17220 gcccgccgat gtcggcgccc tcctccaact ccacccgggc ggcgagccga tggcgcggcc   17280
gggcgggcgc gtccaccagc cgccggacgc cgtccgccgt ccggtccgcg ccgatgagta   17340
ccaccggctc gtcgaggccg cgggcgaggt cgaacgagcg cagggccgac tccacgtcga   17400
gtgcccggta ccgcgcgtc tccccgaggg ccgccagctc gtcgccctcg ctcatccccg    17460
tgtcccgcca gctgctccac gccagcgact gggcgtccag ccccgcgcc cgctgacgga    17520 cggccagcgc gtcgaggaag cgcacgccg ccgcgtaagg ggcgccgaac gcggcccga     17580 aggtgccgtt gaccgaggag aaggagacga acgaccggac cgggtgccgg ccgcgagcc   17640 ggtccaggac gcacgccccg ccgatcttgg ccgcggtcgc cgcgcgccag gccgccgggt   17700
cgaggtcggc cgccgcccgc cgttcgatcg tcccggcgag gtggaggatc ccggtcagcg   17760
gggccgacca ggcgtccgtc gcggcggcca cggccgcgtc cagcgccgcc tcgtcggtga   17820
cgtcggcggc cgcgtagcgg acctccccga gctcgcgcag ccgccgcagc accgccgcgg   17880
cgcgggcgcg agcgtcatcc gcggccgggt ccccggccgg cagcggggtg cggccgacca   17940
ggagcagccg taccccgggc tcggtggtga gcaggtgctc ggcgaggtgg ccgcgacgc    18000 cgcccagccc gcccgtcacc aggacgacgc cgtcgccgta ggcggggacg gtgaccgact   18060
cgggcaccgg tacaggggcc agccggcgca ccaggcgccc ccgtcccgc cggcacacct    18120 cggcgtcggc cggagcgacc gcgagttccg cggcgatcag cgccgccacg tcgtccggct   18180
ccccgtcgcc cggcacggcc agcgtgcccg cggacaggcc gggacgctcg tcccgcagcg   18240
agggcaggag cccggcgagg gtcgcgtgcg gcaggtcccc gccggtgacg caccgcaggt   18300
cgacggcgtg gcccgcgtgg tcggggcgg ccagcgcccg ggccagggcc aggaccgagg    18360
cggcgccgga ccgctgggcg tcgagcaccc cgccggcgtc caggtcgcgg ccggacggct   18420
ccagcggccc gaggtgcacg acgcgctccg gacggcggtc gtcggccgcc agccggtcga   18480
gcagcgccgc gaagtcggac gcctcgtcgg ggcggaccgt gtaccgggcc gcgtcccgcc   18540
gcccgaagcc cgtaccggcc accgctgtcg tggcgcgtcc gccctcccgg cgcaccaggg   18600
cggcgagccg ctcggcgacc cccgcacccc gcggccccgc cgccacgatc agcacggacg   18660
tgccggccgg gggagcggtg gccgggcgcg tcaccggcga ccagacggga cgcaggaacc   18720
agtgcggaac cgtcgccgcc gtcccgagca gcacctcggc ggcgcgcgcc accgcgtcga   18780
actcaccggc ctcgaaccgc ttgcgcagct cgtccgctg gatcttgccg atctcggtct    18840
tcgggatcac cgccgtctcg acgggcagca cgtgcgcggg cgccacgccg acctcgcggg   18900
ccaccttgcc ccggatcgcc cgcagcgcgg ccgccgcgg ctccccggag tcgtgcccgg    18960
gggccaggtg cacgaacagc gcgagctggt cggtggcggc cgaggcgtcc gtacggaccg   19020
cgaccgccgc ggtgaacgag cgcaccacca ccggcagttc ctcgacgcac gcctctatct   19080
cgtgactgaa gtggttgacg ccgttgacga tgatgacgtc cttggcgcgc ccggtgatgt   19140
acagctcgcc gtcgcgcagg aacgccaggt cgccggtgtc gaaccagccg tcggcggtga   19200
acgcctcggc gttggccgcc gcgttgtcgt ggtagcccga cgtcaccgag gcgcgcggga   19260
cctggaagcg gccgacctcg ccctccggca gcagccgcag ctcctcgtcg accacgcgca   19320
```

```
tcgcgaaccc ggggtacggc cgcccgcagc tgacgaaggt ctcgtcgccg ccgggcggcg    19380
gctgcgggtc gaggaccgtg tccgtgacca cggagcacgt ctcggacatg ccccagccgg    19440
ggtgcatcac gtcggacggc agcccgtgcg gcgccagggc ctgcaggaac cggcggttgg    19500
tcgcgccgac gacgacctcg cccgcgttca tgatcagccg tacgggggag aggtcccact    19560
cccggccggc gagccggccg gcctgctcgg cgacgaggcc gaaggcgaag ttcggcgccc    19620
acgtgacgct gacgcgccac cggtccgcca gctcccacca gcgcagcggg tcctccagca    19680
cccagcccgt cggggcgtgc acctgccggg cgccgaggta gacgtcgcgc aggtggaaca    19740
tcaccacacc ggtgacgtgg tcgagcggga tccagttcag cgagacgtcg tgctcggtca    19800
gggagttggc cgccgccgcg gcgacggccc ggctcagcac gttgccgtgc gtcagccgca    19860
ccgccttcgg aagtcccgtg ctgccggagg tgagcagcat gagcagcagg tcgtcggggc    19920
gtgcctgatg ccagtcgcgg tccggggcgg ccgcgcgcag ggcgtccacg gtcacgatgc    19980
gggggtccgg ccactcccgg cgggccgcga gctccgccag gccgtcggca cggtccgcgg    20040
aggtgacgac gaccggccgg cccagcatgc gccagacgcc gtcgagcttg ttcacggccg    20100
ccgagtcggt ggcgtacgtg ggcggcacgg tgagcgggac gacggtgacc ccggcggcga    20160
tcgcgcccca gagcgcggcc acgaagtcct cggtgtcgtc gcactgcagg accacctggt    20220
cgccggcgcg caggcccagg gcccgcagcc cgcccaggac ccgctcggcc tcctcgatca    20280
gcgaggcgta cgagcgccgg ctctcggtgc cgtccgcgcg cacgtgcacg atctcggcgt    20340
ggtcgccgcc cgccgcggcg cggcgcaggg cctcgggcca gccgccgacc tccgccgggg    20400
gcagcggcgg gccctcggag agcgacacgc gcggtccgc ttggtgaacg gcggccggtc    20460
cggcggtggc cgccacggta cgcgggcggg tcgccggccg gagcgcctcc agcccctcgg    20520
ggacgtcctc gcgcccgacc gccgccgccc gtacgccggt cacggccgcg agagcggcgc    20580
gccagccgtc ggcggcggtg tcgtcgacga ccggcagccg gtgcagcgcg ccacgtcga    20640
ggtcgccggc ggcggtgcgc gggaggacgg tcacggccgt cacccggggt gccccgtcgc    20700
cgccttcgtc cgcgaggagc cggcgcgcgt cgtcgtccgc gcccggtcgc gcggggacga    20760
cccagacgac cggaccgccg tcggagggcc gggtgaccgc gacgtccgcg acggcggaca    20820
gggagcgcac acggctctcc agcgccgcgt cgtcggacac cgcctcgggt gcggcgtccc    20880
gcccggcgag caggccgtcc gggacgaggt cgccgaggcg cgcccccggg gcggccgcgg    20940
cccgggcgag gacggtgacc aggccctcgg cgagcaggcg cgcggtgctc gggtcgaaca    21000
ggtcgcgggc gaactcgacg tgacaggtca gaccgccggg cgccgagccg tcgtccccga    21060
cgtgctcggt gatgtcgaag aacaggtcga acttcgcggt acccgtcgcg ctgggccgca    21120
gcggcaccgg cgggccgccc agcgacaccg ccgcggcgg gttgttctgc agcgccagca    21180
tcaccgtgaa cagcggatga cgccccggca cgcgcggcgg gttgaccagc tccaccacct    21240
gctcgaacgg caggtcctcg tgcgcccagg cggcccggtc ggcctcctgg acgcgagcca    21300
gcaactcggc gacggccggc gagccggagg tgtcggtgcg cagcacgacg gtgttggtca    21360
ccagccccac cacgtcgtcg agcgcctggt cgtgccgccc ggcgaccggg gtgccgatcg    21420
ccagatccgt accggcgccg aggccggtga gcagggcggc gacgcccgcg tgcagcaccg    21480
tgaacaggct gacgccgtgc gcccgcgcca gctcccgcag ggccgcgtgg gccaccggac    21540
cgacggccag gtcgacggcg ccgcccggc cggtcggccg ggcgggccgc ggccggtcga    21600
acggcagcgc ggtctcctcc ggcagccccc gcagcgcggg gctccagaac tcctcgtcgc    21660
gccgggcggc ggcgccggcc gggtcgagcc ggtcgcgctg ccagagcacg tagtcggcga    21720
```

-continued

```
actgcaccgg gagcggcgcg agttcgggag cccggccggc ggcgcgcgcc gcgtacgccg    21780
cggtgaggtc ctcggccagc ggccgcagcg accagccgtc ggcgaccagg tggtgcagta    21840
gcaggacgag cgtgcgctcg ccgtccgccg gtccgtacag gccggcccgc aggcccggct    21900
cccgggtgat gtccagccgg cgtcgggcgg cggcctcgac gtgcgccccg atctcctcgg    21960
cggggcagtc gacgacgtgc agcggcacgg ccgccggttc ccggacctcc tggtacggca    22020
cgccggcctc ggccgggaag accgtgcgca ggctctcgtg gcgggcggcg acgtcgccca    22080
gcgcggcggc gagcgcgtcg gcgtccacgc ggttcggcag ggggagcacc agcgggatgt    22140
tgtacgtcgg cccgtcgtcg agccggtcca ggaaccacag gccccgctgg gccggggaca    22200
gcagcaggcg ctcgggccgg ccggccgggc gcaaggggt gcgcgcgggc ggtgcggtgg     22260
tcagccgggc ggcgaggccc gccgcgcagc gggcggcgaa cacgtcggcc acgccgatct    22320
cgacaccgaa ccgggcgcgg atcatcgtgg cggcgcgtgc ggcggtcagc gaatggccgc    22380
cggcggtgaa gaagtcgtcg tccggcccga tccgttcgat ccccagcacc tcggcgagga    22440
tctcggtgag cgcccgctcc tcggggccgt cgggctcccg cgcggcggcc gtgggctccg    22500
gcggctccgg gagcgcgtcc cggtcgagct tgccgttggc ggtggtgggg agctcggcga    22560
gggggacgac ggccgtgggg accatgtgct cgggcagccg ggcggcgagg tggtcgtgcc    22620
agcgccgggc gcgggcctcg aagccgtctt ccccgtcctt ctccgccggg gcggggacga    22680
cccaggcgac gagccggggc ccgccgcgc ggtcgtcacg ggtgccgacc accgccgcgg     22740
cgacctccgg gtgctcggtc agcacggcct cgatctcgcc cagctcgacc cggaagcccc    22800
ggatcttgac ctggtggtcc aggcgtccga ggaactccag cgccgcggag ggcagccgcc    22860
gtaccaggtc gccggtgcgg tagcgccggc ccgccgccgg gtcctccggg aagcgctcgg    22920
cggtgaggtc cggccgcccg aggtagccga cggcgagctg gtcgcccgcg atgtacagct    22980
cgccgggctc gccgggcggt accggtgccc ccaggggtc gagcacgtcc agccgggtgt     23040
tccagacggc gcggccgatc ggcaccgtgg cgcccggcgc ccgtcgcgc agcggccacc     23100 agctcacgtc gatcgcggcc tcggtcgggc cgtagaggtt gaagacctcc gcgccggtga    23160
cctcctcggc ccgccgcgcc gcctcggtcg gcagggcctc gccgctgcac aggatccgcc    23220
gcagcgcgcg aggccgggcg gcggccggct cgccgagata ggcgacgagc atcgacggga    23280
cgaagtgggc ggtcgtgatg cccgcctcgt cgatcgccgc ggcgacccgc gccgggtcgc    23340
gctgcgcgcc gggggccggc aggaccagcg tcgccccgct gatcaagggc cagaagaact    23400
cccagacgga gacgtcgaac gcgcagctgg tcttctgcag cacccggtcg cccggggccca    23460 ggccgaaccg gtcctgggtc cacaacagcc ggttgacgac ggcccggtgg gcgacggcga    23520
cgcccttggg gcggccggtc gagcccgagg tgtggatgac gtaggccagg tcgtcgggc     23580 cgggaccggc cggggccgcg cccgtgccgt cggcccgcag ggcgaggacg tcgacgacgt    23640
tcagctccgc cggcagcgcg acgggcgcgg gtccggcggt gaggaccgcg acgggccgga    23700
cgtcctccag gacggcggcg agccgggccg gcgggtggtc gaggtccagc ggcgcgtagg    23760
ccgcgccggt ccgcagcacc gccagcaggc tcacgaccag ggccgtcgaa cgcggctggg    23820
cgaccgcgac gatcgtcccc ggacccgcgc cgagcccggc gaggccacgg ccagccggt    23880 ccacccgctc gccgagttca cggtaggtga gctccggcga gccgtcggcg ggcaccagcg    23940
ctacggcgtc cggcgtccgc gcgatctgct cggcgacgag ccggtccagg gtggtgacgg    24000
gtaccgggtg ggcggtgtcg gcgtcggcgg ccagtgtgcg gtgctcggcc tcgtcgagca    24060
```

```
ggtcgactcc ggcgagcgtg gtctcggggt cggcggtcac cgcgtccaac aggcgtatga   24120
aacggcgcag ttcgctgtcg gaccaggcgg ggtcgtcggg ggcgtcgtcc acctggagtg   24180
cgcggacgcg gtcctcgccg aggaccgccg tcacggcggg gccggtcgcg ggagccgcgg   24240
agacgaggtg cagcgccgcg tcgcggtccg gtgtcccggc ccaccgtgcg acggtcacgg   24300
acgggccgga tacgcgcccg tccgccgtcg cgcggtggcc gcgcccgtcc tggaccgcgg   24360
cgacggtctc cgcgagcgtc gtggtgcccg tgaggtccag cggcagcggg acggggtgc   24420 catcggcggc cgggacgtac agctcgaccg cgccgctccc acggcggcga gcggtgaaca   24480
tcgcgacggc ggctgccacg aaatcccgta tccctacccc gagttcgcgg gatccttcca   24540
tcatccggcg gccgagcgcg gccgggaccg cgatctcgcg gtgccgggag ccggagccgg   24600
cgggccggga atcggccgcg acgtccgcga cgtccgcgac gtccgcgagg ccgtccggcg   24660
ccccggcgag cgcggcgacg cgccgggcca gggccggcgc ggcgcgctcg tcggactcgg   24720
gaccgcccgt acgccggaac cacaggtggt gctccggtcc gagcgcgagc accgcgtggc   24780
cgcaggccgt cgcggccggg cgcgccagct cggcccgcat ccaggccagg gccgcgccgg   24840
ccgggtcgct ctcaccggag agatcgacga attcggccgg cccgcatggc gcgccctcgc   24900
cgtccgccga cgtgtccgcc gacccgcccg ccggtccgga cgccgcttcc cccatccggcc   24960 cgtccaccgg cccgtccacc agcccgtacg ccgcatcgcg caccgcgcgg acgcccgccg   25020 gcggaggcc ctcgcggtcg accggccccc ggaggtccag gtagtggccg gtgtcgtaga   25080
tcggccccac cgctcccagg tcgtcgacgg ccgtgtcggg gccggcctcg gcgagcgcgc   25140
ccagcaggcg cccgagcccg cggccgtgcg ccagcgccgt cggcgcgtcg taccggaggg   25200
cgttggcctc gacctccagg gtggtcagct cgccgtcctc ggcgaggtcc acgacgaacg   25260
cgatgtcgtc gacgggcccg ggggagaggt ccacgaccgg gaggcgccgg cccaggagcc   25320
cgatcgtggt gtcgtaactc ttgatgttga cctgggcggt ggtgaactcg gactcgtcgg   25380
tgacgcgccc gaggtcccgg cggatgtcct cgacgcggta ccgcccgtgg cggcgcagct   25440
cccgcatcgc cttccgcagc cgggcgacca gcgtgccgac cgtgtcgccg tccgcgaccc   25500
gtacccgcag cggcagcacg ttgacggtgg tcgaggcag gcgcgcggcc gcgccgcccc   25560
gcagggccag cggcagggcg aggacgacgt cggcggcacc ggtcacccgg tgctggtaga   25620
cggcggtggc ggcgatcgcc aggtccgcgg tcgtggccga gaggctctcg gcgagccggg   25680
cgaggccggc cggatcgggc agcacgtcga cgcgcgcctt cagcggcgcg ccgcgcgccg   25740
gctccggagg cgtgccggac aggcttaccg ggggcgggag ttcggcgagt gcgtccagcc   25800
agtaggcgcg gtcccgcggc atccggtcgc ccgcccggta cccggcctcc tcgtccaggt   25860 acgcccgag gccgccgaag gcgggctcac ccggtgaccc gcccgtgcgc agcgcttcgt   25920
ggatctcctc gatccgccgc aggaccagcg agaacccgta gccgtcgagg agcatgtggt   25980
ggcagcggtg gaaccacagg gccccgccct gccaccggaa caggacctcc cgcgccaacg   26040 gccgcccac aggcggctgt tcgaggtcgg cgcgcatccg cgccagggcg acggcctccg   26100
ggtcgggccg cccggagagg tcgacgacct ccacgcgggg tgccgtgccg gtcccgcgct   26160
ggacggggac gtcgccgtcc gcgcccacct cgaccgcgag cccccacacc tcgccgaggg   26220
cccgctcgac cgcgcgcgcg aaccgctccg ggtcgacctc ggcgggcagc cgcacgtact   26280
ggcctgtggt gaagaccggg ttggaggtgt cacgctgctg ggcgaaccag atcccggcct   26340
gcggggcggt cagcggacac gagtcggcag cacggtcggg catggatgca ccttccacgt   26400
cgttgcggtg tgatcttcca cgtcgttggg gggagttcga gccggcgccg ggtgtgacgg   26460
```

-continued

```
caccagacga gtcggcaccg ggcgggacgg cccggcccgg gagcgcgtca gcccgccgcc   26520
gcggctccgg tccgcgagtc ccgcacgatc tcccaccact cctcggggt cggccgttcg    26580 aggaagtcgg ccaggggcgc ggtcaccccg gccgcgcgcc accgcccgat cagccgggtg   26640
agcgtcaccg agtcgagacc gagctcgaac aggttgtcgt ccgggaggag ttcctcgtcc   26700
tccatgccgg ccgtcgcggt cagggtcgtc agcagcgcgt cgaacgtctc ggggacgtcg   26760
atggtgtggg gcttcatgcg cgccacgcta atgacgcgga tctagggatt tcctcagatg   26820
tggtccgccg cggccggccg gccgggcgcg gcgaacggca ggggagcggg ccccgcggca   26880
cccagcacga tgtcggcgag gaggtccccg acggcggcgg cgtgcttgaa tccgtagccg   26940
ttgcaccccc cggccagcac gacccggggg tcggccgggg aggcgccgag cacgaactgc   27000 ccgtcggcg tcgtcgtgat cccgcagtgc aggatccgcg acggtacgcg ccccaccccg    27060
gggacggcgg tggcgagcac ctcgccgagc cgctcccagg gcctgctcgg gacggcggga   27120
gcgccgagtt cgggatcgta cgggtccggg tccgcccct gctcgatgcc gagcttgacg    27180
tgcccggggt cgccgtcgcc ctggccccag atgacggtgt ccgcgtcgat ctcccgcatg   27240
aacaccggga acagctcgcg gcggaacagc gccgggtcgc cgctcggcgg gaaccacgtc   27300
atcggcaggt ggacggagcg gacgcccagg ccggggggcga agtccggcag ccagcacccg   27360
ggcgtgagga cgacccggcc ggcgaccagg tcgcgcccgg cggtgcggac ccgtacgccg   27420
ccgccctccg gctcgacgcc gagcacctcg gtgccgcgga gcacggtggc cccgccgcgc   27480
tccgccagct cgaccgcggc gcggaccgag tcctcggccc gcaggacgcc cgccgagggc   27540
tcccacacgc ccacgtgtcc ttcggggatg ccggcgtgcc ccgggaagcg ggccgagacc   27600
tcggccggtt cgaggacctc gaccgcgacg ccgtgcgcct cggccgaggc gatggtgccg   27660
ccggccagcc ggccgtcgcg cgggccgatg agcaggcccc cggtgttctc gaagagccgg   27720
cggcccgtgc ccgcctccag ctcgcgccac agctccagcg aacgccgggc caccggcacg   27780
agggcctcgt tctccaggca ggtctcgcgg aacatgcggt gaccgccgtg cgaggacccg   27840
cgggcgtgcg cgatgtcgaa ccgctcgacc cccaccgccc ggacaccgcg ggcggcgagc   27900
cgccacagcg tcatggcccc ccagatcccc aggccgacca ccaccacgtc ggggcgggcg   27960
gggtcgtgcg accggtcgac ggacatcttc gctacctcct gggaaccaag cgggaattga   28020
ctgagagtca gggcgagaac tgaccgaacg tcaggcagcc gcgaaccgcg gcgcgatctc   28080
ggcggcgaac tcggcgaccg cccaccgcgc ctgctccagt ggcgtcacgc cgttgttcat   28140
gtgcaggctg acgtcacgt cgccgcccac ccgctcgcgc acccgctcca gctgctcggt   28200
gatgtcgccg gtggtgccga tcagcacctt gtcctgctcc cacgacttgc gcaggtcgga   28260
ggaggcgacc ttgtcggcga gcttctcgta ccccgggtac tgcgcggtcg cggcgccctg   28320
ccagctcttg acggcgccgc tcatcttgtc caggtagttg gactccgccg cctcggccgc   28380
ccgccaggcg ctgtcgcgt cccggtccag gtagcagctg tacttgacct ggatgcgcgg   28440
cgcgcggtcc gggtggtggg cggcgaaggc ctcgcggtag gccgcgagca tctccgcgaa   28500
ctgctcaccg ctggtgatgg tcggcacgat ctgcaggttg tgcccctcgc ggccggcggc   28560
ggcgcaggac tcggcgctgg acgccgaggc gacgaacagc ggaggatgcg gcgtctggtg   28620
cgggcgcggg gtgagcgtca ccgacccgaa gcggtggaac tcgccctcga agaccacgtc   28680
cgtcccggtc cagagcgcga cgaaggcccg cagcgcctcg gtgaagcgcg cccggctctc   28740
ctccatcgac acctcgaacg ccgtgaactc gtgcggcagg aaggcccgtc cgacgccgac   28800
```

-continued

```
gtcgacccgg ccgccgctca gctggtccag catcgccagc cgcccggcca gcttgagcgg   28860
gtggtcgaag gcgggatga ccgcgccggt ggtgatgcgc agccgctcgg tacgcgcggc   28920
gatggccgag agcaggacca ccgggtcggg gctgtacccc ccgtagggcc cgaggtggtg   28980
ctcgaccacc tggacgtgct cgtagcccag ccggtcggcg tcgacggcga gggccaggca   29040
gtcgtcgaag tagtcgtgcg gcgccttgtc ccgctcgtcg agcgcgggga agaaggtcag   29100
accgaaatcc atgggctccc caaggtgag aagtgaggtg ggtcggagcc ggagcctagg   29160
cggggaggac tggggagatc cctagacatc cgttggtaga caagggccgt cggcgggagt   29220
cggactcccg ccgtccttgc cgaccttcga aggaccccca gcgtgtcgaa tcggatgagc   29280
agcgaagtac ccgagatcag ggtcagcgac gagcgggtca accgcacgct caccgcggtc   29340
aacgcccggg cggccgagca cgaccggtcg ctattcgagc aggtgcgcga ctcgctggcg   29400
gtcgcggtgc cgccggaggc gggcacgctg atgtaccagc tcgtgcgcgc cacccgggcc   29460
gccaaggtgg tggagctggg gatgtcgctc ggcgtctcca cggtctacct cgccgccgcc   29520
gtgcgcgaca acggggcga ggggcgggtc tacacgaccg agatcgacga ggcgaagatc   29580
aagcagggcc gcgccaccct ggccgacgcc ggcgtcgccg acctcgtcga ggtgctggag   29640
ggcgacgcgc tccagaccct ggactcggtg cccgacggcg tccagttcgt cctgctcgac   29700
ggctggaacg agagctacct gcgggtgatg aagatcctgg agcccaagct cgcgccgggc   29760
gccctcgtgc tcgccgacga cgtcaacctc ttcggcgagg gctgcgtgga cttcctggag   29820
tacgtccgcg accccgcgaa cggctacctg tccgtcaact tcccgatggg cgagggcctg   29880
gagctcagca tgcgcgtggg ctgagcgccc gcggtaccg ggcgtgcggc ccgtccgcac   29940
gcccggccag gaaccgacag gaaccgaaag gaagaccatg acggaactgc gtgacgcggt   30000
gctgcgtggc gcgtccccg aggaactgct gcgcgccccc ctcccggcca cctacccggc   30060
cgcccacctg cgcgccgagg acgtcggcat gttcgacggc acggacggcg accgcgacgt   30120
gcgcaagtcg gtgccgtgg gccaggtgcc gctgccgag atcgcgcccg acgaggtcct   30180
gatcgcggtc atggccgccg cggtcaacta caactccgtg tggtcggcga cgttcctgcc   30240
gatgccgacc ttccgcttcc tcgagaagta cgcccgccag ggcggctggg cagcacgcca   30300
cgaccagccc taccacgtga tcggctccga ctgctcgggc gtcgtcgtgc gcgtcggctc   30360
cggcgtgcgc cggtggcggg tcggcgacca cgtggtgatc cacccggtgc acgtggacga   30420
ccagggcgcc gccacccacg acgacgccat gatggacgac cagcagcgcg cctgggggta   30480
cgagaccaac ttcggcgcct tcggcgagta cgccgtcgcc cgcgcagcc aactggtcgc   30540 caagcccggc cacttgacgt gggaggagtc ggcggcgaac acgctgtgca ccaccacgtc   30600
gtaccgcatg ctcgtcgggg cgcacggcgc ccggatgaag cagggggacg tggtcctggt   30660
ctggggcgcg gcgggcggcc tggggacgta cgccgtgcag ttggtcaaga acggcggcgg   30720
tatccccgtc gccgtcgtca gctcgccccg gaaggcggag gcggtccgcc ggctgggctg   30780
cgagcacgtc atcgaccgca ccgaactcgg gctcaccggc gacccctcgg gcgacttcga   30840
cgccgtgcgg gagatcggca gcggctgggg cgcccgcatc cgcgaactcg ccggccgcga   30900
ccccgacatc gtcttcgagc acaccggccg ggccaccttc gccctctcgg tgttcgtcgt   30960
ccgccgcggc ggcaccgtcg tcacctgcgg atccagctcg ggctaccggc acctgtacga   31020
caaccggtac ctgtgatga agctgaacac cgtcatcggc agccacgcg gaaacctgca   31080 ggaagccacc gagagcaccc gcctgatcgc ctccggcgcg atcgttccgg cgctctccga   31140
ggtccacccc ttcgaggacg tggccgaggc gatgcggcgg gtccagctca acgagcacgt   31200
```

```
cggcaaggtc gtcgtcctgt gccaggcccc caccgccggc ctgggcgtga ccgacccgga      31260
gctgcgggaa cggctggggg aggagcggac ggcacccctg ctgcgggact ccgcctga       31318

<210> SEQ ID NO 2
<211> LENGTH: 681
<212> TYPE: DNA
<213> ORGANISM: Streptoverticillium
<220> FEATURE:
<221> NAME/KEY: CDS
<222> LOCATION: (1)..(681)

<400> SEQUENCE: 2 atg agt tcc ttg gcg acc ccc acc ccc act ctc gag ggc ctc ctc acg       48
Met Ser Ser Leu Ala Thr Pro Thr Pro Thr Leu Glu Gly Leu Leu Thr
1               5                   10                  15 aca ccg gcg gcg cag cac gcc gaa gca cac ccc ccg ctc cac cgg ccg       96
Thr Pro Ala Ala Gln His Ala Glu Ala His Pro Pro Leu His Arg Pro
            20                  25                  30 ggc tcg gcc acg gcc tgc ctc gac cgg ggc ctg gtc ctc cgg cag gcg      144
Gly Ser Ala Thr Ala Cys Leu Asp Arg Gly Leu Val Leu Arg Gln Ala
        35                  40                  45 gac gag gag ttc ttc cgc cgg ttc ggc ggc tcg gcc ccg cgc ctc gtc      192
Asp Glu Glu Phe Phe Arg Arg Phe Gly Gly Ser Ala Pro Arg Leu Val
50                  55                  60 ggc cgg tcc ttc acc gag ctg gtg cac ccc ggc tgc cgg gag ccc ctg      240
Gly Arg Ser Phe Thr Glu Leu Val His Pro Gly Cys Arg Glu Pro Leu
65                  70                  75                  80 ctg cgg cag ttc gcc ggg ctc acc gag ggc cgg cgc gac cgg ttc ggc      288
Leu Arg Gln Phe Ala Gly Leu Thr Glu Gly Arg Arg Asp Arg Phe Gly
                85                  90                  95 acc gag gtc atc gcg gtg ggc ccg gac ggc acc ccg ttc cgg acc gac      336
Thr Glu Val Ile Ala Val Gly Pro Asp Gly Thr Pro Phe Arg Thr Asp
            100                 105                 110 ctg acg gcg ctg gcg gta cgc ggc gga acc ccc gac atc tcg gcc gtc      384
Leu Thr Ala Leu Ala Val Arg Gly Gly Thr Pro Asp Ile Ser Ala Val
        115                 120                 125 tgg ctg acg ctg gcg gcg gcc ggc gag acc gcg cag ccc gcc gcc gcg      432
Trp Leu Thr Leu Ala Ala Ala Gly Glu Thr Ala Gln Pro Ala Ala Ala
130                 135                 140 acg ccc cgc aag aag atc ctc agc gag atc gac gcc cgc atc ctc gaa      480
Thr Pro Arg Lys Lys Ile Leu Ser Glu Ile Asp Ala Arg Ile Leu Glu
145                 150                 155                 160 ggc atc gcg gcc ggt gtc tcc acc gtc ccc ctg gcc gca cgc ctg tat      528
Gly Ile Ala Ala Gly Val Ser Thr Val Pro Leu Ala Ala Arg Leu Tyr
                165                 170                 175 ctg agc cgg cag ggg gtc gag tac cac gtg aag agc ctg ttc cgg cag      576
Leu Ser Arg Gln Gly Val Glu Tyr His Val Lys Ser Leu Phe Arg Gln
            180                 185                 190 ctc cgc gtg ccc aac cgg gcc gcg ctc gtc tcc cgc gcc tac tcc atg      624
Leu Arg Val Pro Asn Arg Ala Ala Leu Val Ser Arg Ala Tyr Ser Met
        195                 200                 205 ggc ctg ctc aag gtg ggg acc tgg ccg ccc aag gtg gcg ccg gac ttc      672
Gly Leu Leu Lys Val Gly Thr Trp Pro Pro Lys Val Ala Pro Asp Phe
210                 215                 220 gtc aag tga                                                           681
Val Lys
225

<210> SEQ ID NO 3
<211> LENGTH: 226
```

<212> TYPE: PRT
<213> ORGANISM: Streptoverticillium

<400> SEQUENCE: 3

Met Ser Ser Leu Ala Thr Pro Thr Pro Thr Leu Glu Gly Leu Leu Thr
1               5                   10                  15

Thr Pro Ala Ala Gln His Ala Glu Ala His Pro Pro Leu His Arg Pro
            20                  25                  30

Gly Ser Ala Thr Ala Cys Leu Asp Arg Gly Leu Val Leu Arg Gln Ala
        35                  40                  45

Asp Glu Glu Phe Phe Arg Arg Phe Gly Gly Ser Ala Pro Arg Leu Val
    50                  55                  60

Gly Arg Ser Phe Thr Glu Leu Val His Pro Gly Cys Arg Glu Pro Leu
65                  70                  75                  80

Leu Arg Gln Phe Ala Gly Leu Thr Glu Gly Arg Arg Asp Arg Phe Gly
                85                  90                  95

Thr Glu Val Ile Ala Val Gly Pro Asp Gly Thr Pro Phe Arg Thr Asp
            100                 105                 110

Leu Thr Ala Leu Ala Val Arg Gly Gly Thr Pro Asp Ile Ser Ala Val
        115                 120                 125

Trp Leu Thr Leu Ala Ala Ala Gly Glu Thr Ala Gln Pro Ala Ala Ala
    130                 135                 140

Thr Pro Arg Lys Lys Ile Leu Ser Glu Ile Asp Ala Arg Ile Leu Glu
145                 150                 155                 160

Gly Ile Ala Ala Gly Val Ser Thr Val Pro Leu Ala Ala Arg Leu Tyr
                165                 170                 175

Leu Ser Arg Gln Gly Val Glu Tyr His Val Lys Ser Leu Phe Arg Gln
            180                 185                 190

Leu Arg Val Pro Asn Arg Ala Ala Leu Val Ser Arg Ala Tyr Ser Met
        195                 200                 205

Gly Leu Leu Lys Val Gly Thr Trp Pro Pro Lys Val Ala Pro Asp Phe
    210                 215                 220

Val Lys
225

<210> SEQ ID NO 4
<211> LENGTH: 1887
<212> TYPE: DNA
<213> ORGANISM: Streptoverticillium
<220> FEATURE:
<221> NAME/KEY: CDS
<222> LOCATION: (1)..(1887)

<400> SEQUENCE: 4

| | |
|---|---:|
| atg ccg cac ccg acc acg cgc acc gcc ccg cac tcc gcc gcc ggt ggg<br>Met Pro His Pro Thr Thr Arg Thr Ala Pro His Ser Ala Ala Gly Gly<br>1               5                   10                  15 | 48 |
| acc acc gcc ggg gag acc tcg tca ccg ctg ttc gcg ccc gcc cgg acc<br>Thr Thr Ala Gly Glu Thr Ser Ser Pro Leu Phe Ala Pro Ala Arg Thr<br>            20                  25                  30 | 96 |
| gtc cgg cgg gac cgg ccg gac ggg acc gtg ctc ctc tcg tcg gcg cag<br>Val Arg Arg Asp Arg Pro Asp Gly Thr Val Leu Leu Ser Ser Ala Gln<br>        35                  40                  45 | 144 |
| ccg ctg ggg gtg tat ccc gcc tcc gtg acc gac cat ctc cgc acc tgg<br>Pro Leu Gly Val Tyr Pro Ala Ser Val Thr Asp His Leu Arg Thr Trp<br>    50                  55                  60 | 192 |
| gcc cag gcc ggg ccc gac cgc ccg ctg gtc gcc gag cgc ggg gcc gac<br>Ala Gln Ala Gly Pro Asp Arg Pro Leu Val Ala Glu Arg Gly Ala Asp | 240 |

```
                65                  70                  75                  80
ggc cgg tgg ggg cac cgc acg tac ggc gag gtg ctg gcg gcg gcg gag        288
Gly Arg Trp Gly His Arg Thr Tyr Gly Glu Val Leu Ala Ala Ala Glu
                    85                  90                  95 gcg gtc ggg cag gcg ctg ctc gac cgc ggg ctg tcg gcg cgg ccg            336
Ala Val Gly Gln Ala Leu Leu Asp Arg Gly Leu Ser Ala Arg Arg Pro
                100                 105                 110 ctg atg gtc ctg tcc ggc aac tcc acc ggg cac ctg ctg atg acg ctc        384
Leu Met Val Leu Ser Gly Asn Ser Thr Gly His Leu Leu Met Thr Leu
                115                 120                 125 ggc gcg ctg agc gcc ggg atc ccg gtg gcg ccg gtc agc gtc gcc tac        432
Gly Ala Leu Ser Ala Gly Ile Pro Val Ala Pro Val Ser Val Ala Tyr
                130                 135                 140 tcc ctg ctg agc cgg gac cac gcg cgg atc cgg gcg atc gcg gaa ctg        480
Ser Leu Leu Ser Arg Asp His Ala Arg Ile Arg Ala Ile Ala Glu Leu
145                 150                 155                 160 ctg cgg ccg ggc gcg gtg tac gcc gag gac gcc ggg ccg ttc ggt ccc        528
Leu Arg Pro Gly Ala Val Tyr Ala Glu Asp Ala Gly Pro Phe Gly Pro
                165                 170                 175 gcg ctg gcc gcg gcg ggc ggt gga gcc atc gtc gtg gcg gcg cgg ggc        576
Ala Leu Ala Ala Ala Gly Gly Gly Ala Ile Val Val Ala Ala Arg Gly
                180                 185                 190 ggg ccg gcg gag cac tcg ctg gac gcc ctg ctg cgt acg gtg ccg ggc        624
Gly Pro Ala Glu His Ser Leu Asp Ala Leu Leu Arg Thr Val Pro Gly
                195                 200                 205 cgc gcg ttc gag gcg gcc cgt gcg ggc gtc acg agc gcg acg gtc gcg        672
Arg Ala Phe Glu Ala Ala Arg Ala Gly Val Thr Ser Ala Thr Val Ala
                210                 215                 220 aag gtc ctc ttc acg tcg ggc tcg acg gga gcg ccg aag ggc gtc gtc        720
Lys Val Leu Phe Thr Ser Gly Ser Thr Gly Ala Pro Lys Gly Val Val
225                 230                 235                 240 acc acg cac ggc atg ctc tgt gcc aac cag cgg atg atg cgg cag gtg        768
Thr Thr His Gly Met Leu Cys Ala Asn Gln Arg Met Met Arg Gln Val
                245                 250                 255 tgg ccg ttc ctg gcc ggg gag cgg ccg gtg ctg ctg gac tgg ctg ccg        816
Trp Pro Phe Leu Ala Gly Glu Arg Pro Val Leu Leu Asp Trp Leu Pro
                260                 265                 270 tgg agc cac acc ttc ggc ggc aac cac aac gtg aac ctg gtg ctg gcc        864
Trp Ser His Thr Phe Gly Gly Asn His Asn Val Asn Leu Val Leu Ala
                275                 280                 285 aac ggc ggc act ctg tac ctc gac gac ggc cgc ccg acc ccg gag ctg        912
Asn Gly Gly Thr Leu Tyr Leu Asp Asp Gly Arg Pro Thr Pro Glu Leu
                290                 295                 300 ttc ggg cgc acc ctg gcc aac ctg cgc gag gtc tcc ccg acc ctg gcg        960
Phe Gly Arg Thr Leu Ala Asn Leu Arg Glu Val Ser Pro Thr Leu Ala
305                 310                 315                 320 ttc aac gtc ccg gcc ggg tac gcg cgg ctc gtc ccc gcc ctg gag cgc        1008
Phe Asn Val Pro Ala Gly Tyr Ala Arg Leu Val Pro Ala Leu Glu Arg
                325                 330                 335 gac cgg gag ctg gcg gag cgg ttc ttc gcc cgg ctg cgg ctc gtc ttc        1056
Asp Arg Glu Leu Ala Glu Arg Phe Phe Ala Arg Leu Arg Leu Val Phe
                340                 345                 350 aac gcg gcg gcg gcg ctg gcc ccg gcc ctg cgc gaa cgg ctc cgg gcg        1104
Asn Ala Ala Ala Ala Leu Ala Pro Ala Leu Arg Glu Arg Leu Arg Ala
                355                 360                 365 ctg ggc cgc gaa gtg acc ggg cgg gac gtg ccg gtg acg ggc tcg tgg        1152
Leu Gly Arg Glu Val Thr Gly Arg Asp Val Pro Val Thr Gly Ser Trp
                370                 375                 380 ggc gcc acc gag acc tcg ccg gcg tcc acc agc gcg cac ttc ccg ttc        1200
```

```
Gly Ala Thr Glu Thr Ser Pro Ala Ser Thr Ser Ala His Phe Pro Phe
385                 390                 395                 400 acc gac ccg cgg tgc atc ggc gtg ccg ctg ccg ggg gtg gag ctg aag      1248
Thr Asp Pro Arg Cys Ile Gly Val Pro Leu Pro Gly Val Glu Leu Lys
                405                 410                 415 ctc gta ccg gcg gag ggt gac ggc tac gag gtc cgg gtg cgc ggc ccg      1296
Leu Val Pro Ala Glu Gly Asp Gly Tyr Glu Val Arg Val Arg Gly Pro
            420                 425                 430 cac gtg acg ccc ggc tac ctc ggc cgc ccg gac ctc gac gcg cgc gcc      1344
His Val Thr Pro Gly Tyr Leu Gly Arg Pro Asp Leu Asp Ala Arg Ala
        435                 440                 445 ttc gac gag gag ggc tac tac cgg ccg gga gac gcc gtc gcg ttc gcc      1392
Phe Asp Glu Glu Gly Tyr Tyr Arg Pro Gly Asp Ala Val Ala Phe Ala
    450                 455                 460 gac ccc ggc gac gcg ggc gcg ggg ctg gtg ttc cgg ggc cgg ctg acc      1440
Asp Pro Gly Asp Ala Gly Ala Gly Leu Val Phe Arg Gly Arg Leu Thr
465                 470                 475                 480 gag gac ttc aag ctg tcc acc ggt acg ttc gtg cac gtc gaa gcc gtg      1488
Glu Asp Phe Lys Leu Ser Thr Gly Thr Phe Val His Val Glu Ala Val
                485                 490                 495 cgc ggc gcg ctg ctt tcg gcc gcg ccg gtc ctc tcc gac gcg gtg atc      1536
Arg Gly Ala Leu Leu Ser Ala Ala Pro Val Leu Ser Asp Ala Val Ile
            500                 505                 510 acc ggg gag cac cgg gac gcg gtc tgc gcg ctg gcg tgg ctc gac ccg      1584
Thr Gly Glu His Arg Asp Ala Val Cys Ala Leu Ala Trp Leu Asp Pro
        515                 520                 525 gcc gag gcc gag cgg ctg ctc ggc cgg cgg ccg gcc gcg gac ggc ggg      1632
Ala Glu Ala Glu Arg Leu Leu Gly Arg Arg Pro Ala Ala Asp Gly Gly
    530                 535                 540 gtg ctg tac tcc gac gcg ctg gcc gcc cac ctc ggc gcg gca ctg gag      1680
Val Leu Tyr Ser Asp Ala Leu Ala Ala His Leu Gly Ala Ala Leu Glu
545                 550                 555                 560 cga ctc aac cgg ggc gcc ggg tcc gcg tcc cgg gtc cag cgg ctg ctg      1728
Arg Leu Asn Arg Gly Ala Gly Ser Ala Ser Arg Val Gln Arg Leu Leu
                565                 570                 575 gtg ctc gcg gac ccg ccc gac ctg gac gcg ggc gag atc acc gac aag      1776
Val Leu Ala Asp Pro Pro Asp Leu Asp Ala Gly Glu Ile Thr Asp Lys
            580                 585                 590 ggc tac gtc aac cag cgc cgg gtg ctg gcc gcc cgc gcg ccg ctg gtc      1824
Gly Tyr Val Asn Gln Arg Arg Val Leu Ala Ala Arg Ala Pro Leu Val
        595                 600                 605 gcc cgg ctg cac gcg gac ccc gcg ccg cga cac gtc atc acc ccg cgg      1872
Ala Arg Leu His Ala Asp Pro Ala Pro Arg His Val Ile Thr Pro Arg
    610                 615                 620 tcc ggg ctc act tga                                                  1887
Ser Gly Leu Thr
625

<210> SEQ ID NO 5
<211> LENGTH: 628
<212> TYPE: PRT
<213> ORGANISM: Streptoverticillium

<400> SEQUENCE: 5

Met Pro His Pro Thr Thr Arg Ala Pro His Ser Ala Ala Gly Gly
1               5                   10                  15

Thr Thr Ala Gly Glu Thr Ser Ser Pro Leu Phe Ala Pro Ala Arg Thr
                20                  25                  30

Val Arg Arg Asp Arg Pro Asp Gly Thr Val Leu Leu Ser Ala Gln
            35                  40                  45
```

-continued

```
Pro Leu Gly Val Tyr Pro Ala Ser Val Thr Asp His Leu Arg Thr Trp
 50                  55                  60
Ala Gln Ala Gly Pro Asp Arg Pro Leu Val Ala Glu Arg Gly Ala Asp
 65                  70                  75                  80
Gly Arg Trp Gly His Arg Thr Tyr Gly Glu Val Leu Ala Ala Ala Glu
                 85                  90                  95
Ala Val Gly Gln Ala Leu Leu Asp Arg Gly Leu Ser Ala Arg Arg Pro
            100                 105                 110
Leu Met Val Leu Ser Gly Asn Ser Thr Gly His Leu Leu Met Thr Leu
        115                 120                 125
Gly Ala Leu Ser Ala Gly Ile Pro Val Ala Pro Val Ser Val Ala Tyr
130                 135                 140
Ser Leu Leu Ser Arg Asp His Ala Arg Ile Arg Ala Ile Ala Glu Leu
145                 150                 155                 160
Leu Arg Pro Gly Ala Val Tyr Ala Glu Asp Ala Gly Pro Phe Gly Pro
                165                 170                 175
Ala Leu Ala Ala Ala Gly Gly Ala Ile Val Val Ala Ala Arg Gly
            180                 185                 190
Gly Pro Ala Glu His Ser Leu Asp Ala Leu Leu Arg Thr Val Pro Gly
        195                 200                 205
Arg Ala Phe Glu Ala Ala Arg Ala Gly Val Thr Ser Ala Thr Val Ala
210                 215                 220
Lys Val Leu Phe Thr Ser Gly Ser Thr Gly Ala Pro Lys Gly Val Val
225                 230                 235                 240
Thr Thr His Gly Met Leu Cys Ala Asn Gln Arg Met Met Arg Gln Val
                245                 250                 255
Trp Pro Phe Leu Ala Gly Glu Arg Pro Val Leu Leu Asp Trp Leu Pro
            260                 265                 270
Trp Ser His Thr Phe Gly Gly Asn His Asn Val Asn Leu Val Leu Ala
        275                 280                 285
Asn Gly Gly Thr Leu Tyr Leu Asp Asp Gly Arg Pro Thr Pro Glu Leu
290                 295                 300
Phe Gly Arg Thr Leu Ala Asn Leu Arg Glu Val Ser Pro Thr Leu Ala
305                 310                 315                 320
Phe Asn Val Pro Ala Gly Tyr Ala Arg Leu Val Pro Ala Leu Glu Arg
                325                 330                 335
Asp Arg Glu Leu Ala Glu Arg Phe Phe Ala Arg Leu Arg Leu Val Phe
            340                 345                 350
Asn Ala Ala Ala Ala Leu Ala Pro Ala Leu Arg Glu Arg Leu Arg Ala
        355                 360                 365
Leu Gly Arg Glu Val Thr Gly Arg Asp Val Pro Val Thr Gly Ser Trp
370                 375                 380
Gly Ala Thr Glu Thr Ser Pro Ala Ser Thr Ser Ala His Phe Pro Phe
385                 390                 395                 400
Thr Asp Pro Arg Cys Ile Gly Val Pro Leu Pro Gly Val Glu Leu Lys
                405                 410                 415
Leu Val Pro Ala Glu Gly Asp Gly Tyr Glu Val Arg Val Arg Gly Pro
            420                 425                 430
His Val Thr Pro Gly Tyr Leu Gly Arg Pro Asp Leu Asp Ala Arg Ala
        435                 440                 445
Phe Asp Glu Glu Gly Tyr Tyr Arg Pro Gly Asp Ala Val Ala Phe Ala
450                 455                 460
```

```
Asp Pro Gly Asp Ala Gly Ala Gly Leu Val Phe Arg Gly Arg Leu Thr
465                 470                 475                 480

Glu Asp Phe Lys Leu Ser Thr Gly Thr Phe Val His Val Glu Ala Val
            485                 490                 495

Arg Gly Ala Leu Leu Ser Ala Ala Pro Val Leu Ser Asp Ala Val Ile
        500                 505                 510

Thr Gly Glu His Arg Asp Ala Val Cys Ala Leu Ala Trp Leu Asp Pro
    515                 520                 525

Ala Glu Ala Glu Arg Leu Leu Gly Arg Arg Pro Ala Asp Gly Gly
    530                 535                 540

Val Leu Tyr Ser Asp Ala Leu Ala Ala His Leu Gly Ala Ala Leu Glu
545                 550                 555                 560

Arg Leu Asn Arg Gly Ala Gly Ser Ala Ser Arg Val Gln Arg Leu Leu
            565                 570                 575

Val Leu Ala Asp Pro Pro Asp Leu Asp Ala Gly Glu Ile Thr Asp Lys
        580                 585                 590

Gly Tyr Val Asn Gln Arg Arg Val Leu Ala Ala Arg Ala Pro Leu Val
    595                 600                 605

Ala Arg Leu His Ala Asp Pro Ala Pro Arg His Val Ile Thr Pro Arg
610                 615                 620

Ser Gly Leu Thr
625

<210> SEQ ID NO 6
<211> LENGTH: 1611
<212> TYPE: DNA
<213> ORGANISM: Streptoverticillium
<220> FEATURE:
<221> NAME/KEY: CDS
<222> LOCATION: (1)..(1611)

<400> SEQUENCE: 6 atg gcc tcg ccc acc gac gac acc acc atc gag ctg gac ggc cac agc    48
Met Ala Ser Pro Thr Asp Asp Thr Thr Ile Glu Leu Asp Gly His Ser
1               5                  10                  15 ctc tcg ctg cgg gcc gtg cgg cgg gtc gcg acc cag ccg ggc aag cag    96
Leu Ser Leu Arg Ala Val Arg Arg Val Ala Thr Gln Pro Gly Lys Gln
            20                  25                  30 aga atc gcc ctc gcg gcg gcc gcg gcc gag cgc atg acg gcg tcg cgg   144
Arg Ile Ala Leu Ala Ala Ala Ala Ala Glu Arg Met Thr Ala Ser Arg
        35                  40                  45 gag gcc acg gag cgg atc gtc gcc tcc ggc atc ccg atc tac ggg gtg   192
Glu Ala Thr Glu Arg Ile Val Ala Ser Gly Ile Pro Ile Tyr Gly Val
50                  55                  60 acg acc ggc ttc ggc gac agc agc ggc cgc cag gtc agc gcc gac aag   240
Thr Thr Gly Phe Gly Asp Ser Ser Gly Arg Gln Val Ser Ala Asp Lys
65                  70                  75                  80 gcc ggg gcg ctg caa cgg aac ctg ctc cgc ttc ctg cgg gtc ggc acc   288
Ala Gly Ala Leu Gln Arg Asn Leu Leu Arg Phe Leu Arg Val Gly Thr
                85                  90                  95 ggg gac atg gca ccc gac gag gtc gtc cgc gcc acc atg ctg atc cgc   336
Gly Asp Met Ala Pro Asp Glu Val Val Arg Ala Thr Met Leu Ile Arg
            100                 105                 110 gcc aac agt gcc gcg cgg ggc aac tcc ggc atc cgc acg gcg ccg gtg   384
Ala Asn Ser Ala Ala Arg Gly Asn Ser Gly Ile Arg Thr Ala Pro Val
        115                 120                 125 gag ctg atc ctg tca ctg ctg gag aag gac ctg ctg ccg cag ata ccg   432
Glu Leu Ile Leu Ser Leu Leu Glu Lys Asp Leu Leu Pro Gln Ile Pro
130                 135                 140
```

```
                                                      -continued gag cgc ggt tcg gtc ggc gcc agc ggc gac ctc gcg ccg ctc ggc tac    480
Glu Arg Gly Ser Val Gly Ala Ser Gly Asp Leu Ala Pro Leu Gly Tyr
145                 150                 155                 160 ctc gcc gcc gcg ctc acc ggc gag ggc acc ctg cgc agc cag ggc cgg    528
Leu Ala Ala Ala Leu Thr Gly Glu Gly Thr Leu Arg Ser Gln Gly Arg
                165                 170                 175 gcg ctc gac gcg ggc gag gcc atc cgg gcc tgc ggc ctc gcg ccc gtc    576
Ala Leu Asp Ala Gly Glu Ala Ile Arg Ala Cys Gly Leu Ala Pro Val
            180                 185                 190 acg ctc cgg gcc aag gag ggg ctg gcg ctc gtc aac ggg acg tcc ttc    624
Thr Leu Arg Ala Lys Glu Gly Leu Ala Leu Val Asn Gly Thr Ser Phe
        195                 200                 205 atg gcc gcc tac gcc gcc ctg gcg gtc gcc gag gcg gcc gag ctg gcg    672
Met Ala Ala Tyr Ala Ala Leu Ala Val Ala Glu Ala Ala Glu Leu Ala
    210                 215                 220 tgg gcg gcc gag ctg tgc acc gtg ctg tcg acg gag gtc cgg cgc agc    720
Trp Ala Ala Glu Leu Cys Thr Val Leu Ser Thr Glu Val Arg Arg Ser
225                 230                 235                 240 agc cgc gac cag ttc acc gcg ttc ccg cac gag cac aag ccg cac ccc    768
Ser Arg Asp Gln Phe Thr Ala Phe Pro His Glu His Lys Pro His Pro
                245                 250                 255 ggc cag ctc gcg agc gcc gcg aac gtc cac cgg atg ctg ggc gac tcc    816
Gly Gln Leu Ala Ser Ala Ala Asn Val His Arg Met Leu Gly Asp Ser
            260                 265                 270 ccc gcc gtg gtc gcc gac acc gat ctc gtg ggc ccc ggt tcg agc gag    864
Pro Ala Val Val Ala Asp Thr Asp Leu Val Gly Pro Gly Ser Ser Glu
        275                 280                 285 gag cgc cgg tac gtc gag ctg gag cgc cgc atc cag gac ccg tac tcg    912
Glu Arg Arg Tyr Val Glu Leu Glu Arg Arg Ile Gln Asp Pro Tyr Ser
    290                 295                 300 atc cgg tgc gcg ccg cac gtc gtc ggc gtg ctg cgg gac acg ctc ggc    960
Ile Arg Cys Ala Pro His Val Val Gly Val Leu Arg Asp Thr Leu Gly
305                 310                 315                 320 tgg gcc gag gac tgg ctg acc acc gag atc aac tcc tcg aac gac aac   1008
Trp Ala Glu Asp Trp Leu Thr Thr Glu Ile Asn Ser Ser Asn Asp Asn
                325                 330                 335 ccg ctc ttc gag gcg gcc acc gac acc gtc cac tac agc ggc aac ttc   1056
Pro Leu Phe Glu Ala Ala Thr Asp Thr Val His Tyr Ser Gly Asn Phe
            340                 345                 350 tac ggc ggg cac gtc gcc cag gcg gcg cag gcg gtc tcc gcc gcc gtg   1104
Tyr Gly Gly His Val Ala Gln Ala Ala Gln Ala Val Ser Ala Ala Val
        355                 360                 365 gcc ggg gtc gcc gac ctg ctc gac cgc cag ctg gcg atc ctg gtg gac   1152
Ala Gly Val Ala Asp Leu Leu Asp Arg Gln Leu Ala Ile Leu Val Asp
    370                 375                 380 gac aag ttc agc atc ggc ctc acc ccg aac ctg gtc gtc ccg gtc ggt   1200
Asp Lys Phe Ser Ile Gly Leu Thr Pro Asn Leu Val Val Pro Val Gly
385                 390                 395                 400 ccc gac gac ccg gag gca ggg ctg cac cac ggg ttc aag ggc gcg cag   1248
Pro Asp Asp Pro Glu Ala Gly Leu His His Gly Phe Lys Gly Ala Gln
                405                 410                 415 atc gcc gcg tcc gcg ctg acc gcc gag gcg ctg cac ctg acg atg ccc   1296
Ile Ala Ala Ser Ala Leu Thr Ala Glu Ala Leu His Leu Thr Met Pro
            420                 425                 430 gtg agc tcg ttc tcc cgt tcg acc gag gcg cac aac cag gac aag gtg   1344
Val Ser Ser Phe Ser Arg Ser Thr Glu Ala His Asn Gln Asp Lys Val
        435                 440                 445 agc atg ggc acc atc gcc gcg cgg cac gcg cac acg gtg gtc cgg ctg   1392
Ser Met Gly Thr Ile Ala Ala Arg His Ala His Thr Val Val Arg Leu
```

```
                    450                 455                 460
acg agc cag gtc acc gcc atc cac ctg ctc gcc ctg tgc cag gcc gcg       1440
Thr Ser Gln Val Thr Ala Ile His Leu Leu Ala Leu Cys Gln Ala Ala
465                 470                 475                 480 gac ctc acc ggg gtc ggg cgg ctg ggg agc gcg acc cgg gcc gcg cac       1488
Asp Leu Thr Gly Val Gly Arg Leu Gly Ser Ala Thr Arg Ala Ala His
                485                 490                 495 acg ctc gtc cgc ggg tac tcg ccg ttc ctc tcc gcc gac cgg ccg ctg       1536
Thr Leu Val Arg Gly Tyr Ser Pro Phe Leu Ser Ala Asp Arg Pro Leu
            500                 505                 510 gac gcc gac atc gag acc gtc gcc gcc ctg ctg cgc gcg ggc gag ctc       1584
Asp Ala Asp Ile Glu Thr Val Ala Ala Leu Leu Arg Ala Gly Glu Leu
        515                 520                 525 cgc cgc gcg gtc gag cgg cac gtc tga                                   1611
Arg Arg Ala Val Glu Arg His Val
        530                 535

<210> SEQ ID NO 7
<211> LENGTH: 536
<212> TYPE: PRT
<213> ORGANISM: Streptoverticillium

<400> SEQUENCE: 7

Met Ala Ser Pro Thr Asp Asp Thr Thr Ile Glu Leu Asp Gly His Ser
1               5                   10                  15

Leu Ser Leu Arg Ala Val Arg Arg Val Ala Thr Gln Pro Gly Lys Gln
            20                  25                  30

Arg Ile Ala Leu Ala Ala Ala Ala Glu Arg Met Thr Ala Ser Arg
        35                  40                  45

Glu Ala Thr Glu Arg Ile Val Ala Ser Gly Ile Pro Ile Tyr Gly Val
    50                  55                  60

Thr Thr Gly Phe Gly Asp Ser Ser Gly Arg Gln Val Ser Ala Asp Lys
65              70                  75                  80

Ala Gly Ala Leu Gln Arg Asn Leu Leu Arg Phe Leu Arg Val Gly Thr
            85                  90                  95

Gly Asp Met Ala Pro Asp Glu Val Val Arg Ala Thr Met Leu Ile Arg
        100                 105                 110

Ala Asn Ser Ala Ala Arg Gly Asn Ser Gly Ile Arg Thr Ala Pro Val
    115                 120                 125

Glu Leu Ile Leu Ser Leu Leu Glu Lys Asp Leu Leu Pro Gln Ile Pro
130                 135                 140

Glu Arg Gly Ser Val Gly Ala Ser Gly Asp Leu Ala Pro Leu Gly Tyr
            150                 155                 160
145

Leu Ala Ala Ala Leu Thr Gly Glu Gly Thr Leu Arg Ser Gln Gly Arg
        165                 170                 175

Ala Leu Asp Ala Gly Glu Ala Ile Arg Ala Cys Gly Leu Ala Pro Val
    180                 185                 190

Thr Leu Arg Ala Lys Glu Gly Leu Ala Leu Val Asn Gly Thr Ser Phe
        195                 200                 205

Met Ala Ala Tyr Ala Ala Leu Ala Val Ala Glu Ala Ala Glu Leu Ala
    210                 215                 220

Trp Ala Ala Glu Leu Cys Thr Val Leu Ser Thr Glu Val Arg Arg Ser
225                 230                 235                 240

Ser Arg Asp Gln Phe Thr Ala Phe Pro His Glu His Lys Pro His Pro
            245                 250                 255

Gly Gln Leu Ala Ser Ala Ala Asn Val His Arg Met Leu Gly Asp Ser
```

```
                    260                 265                 270
Pro Ala Val Val Ala Asp Thr Asp Leu Val Gly Pro Gly Ser Ser Glu
            275                 280                 285

Glu Arg Arg Tyr Val Glu Leu Glu Arg Arg Ile Gln Asp Pro Tyr Ser
        290                 295                 300

Ile Arg Cys Ala Pro His Val Val Gly Val Leu Arg Asp Thr Leu Gly
305                 310                 315                 320

Trp Ala Glu Asp Trp Leu Thr Thr Glu Ile Asn Ser Ser Asn Asp Asn
                325                 330                 335

Pro Leu Phe Glu Ala Ala Thr Asp Thr Val His Tyr Ser Gly Asn Phe
            340                 345                 350

Tyr Gly Gly His Val Ala Gln Ala Ala Gln Ala Val Ser Ala Ala Val
        355                 360                 365

Ala Gly Val Ala Asp Leu Leu Asp Arg Gln Leu Ala Ile Leu Val Asp
        370                 375                 380

Asp Lys Phe Ser Ile Gly Leu Thr Pro Asn Leu Val Val Pro Val Gly
385                 390                 395                 400

Pro Asp Asp Pro Glu Ala Gly Leu His His Gly Phe Lys Gly Ala Gln
                405                 410                 415

Ile Ala Ala Ser Ala Leu Thr Ala Glu Ala Leu His Leu Thr Met Pro
            420                 425                 430

Val Ser Ser Phe Ser Arg Ser Thr Glu Ala His Asn Gln Asp Lys Val
        435                 440                 445

Ser Met Gly Thr Ile Ala Ala Arg His Ala His Thr Val Val Arg Leu
        450                 455                 460

Thr Ser Gln Val Thr Ala Ile His Leu Leu Ala Leu Cys Gln Ala Ala
465                 470                 475                 480

Asp Leu Thr Gly Val Gly Arg Leu Gly Ser Ala Thr Arg Ala Ala His
                485                 490                 495

Thr Leu Val Arg Gly Tyr Ser Pro Phe Leu Ser Ala Arg Pro Leu
            500                 505                 510

Asp Ala Asp Ile Glu Thr Val Ala Ala Leu Leu Arg Ala Gly Glu Leu
        515                 520                 525

Arg Arg Ala Val Glu Arg His Val
        530                 535

<210> SEQ ID NO 8
<211> LENGTH: 183
<212> TYPE: DNA
<213> ORGANISM: Streptoverticillium
<220> FEATURE:
<221> NAME/KEY: CDS
<222> LOCATION: (1)..(183)

<400> SEQUENCE: 8 gtg ccc ctg atc cag gtc agc ctc tac gaa gac cgc ctc acg ccc gag     48
Val Pro Leu Ile Gln Val Ser Leu Tyr Glu Asp Arg Leu Thr Pro Glu
1               5                  10                  15 acc cgc cgc gcc ctg atc ggg gag ctc acc gag gcg gcg gtc cgc gcc     96
Thr Arg Arg Ala Leu Ile Gly Glu Leu Thr Glu Ala Ala Val Arg Ala
            20                  25                  30 ctc ggc ccc gag tgc cgc gac gtg acg tgg gtg acg ctc cag ggc atc    144
Leu Gly Pro Glu Cys Arg Asp Val Thr Trp Val Thr Leu Gln Gly Ile
        35                  40                  45 ccc cgc gac cag tgg ggc atc ggc gga acg ccc ggc tga                 183
Pro Arg Asp Gln Trp Gly Ile Gly Gly Thr Pro Gly
    50                  55                  60
```

<210> SEQ ID NO 9
<211> LENGTH: 60
<212> TYPE: PRT
<213> ORGANISM: Streptoverticillium

<400> SEQUENCE: 9

```
Val Pro Leu Ile Gln Val Ser Leu Tyr Glu Asp Arg Leu Thr Pro Glu
 1               5                  10                  15

Thr Arg Arg Ala Leu Ile Gly Glu Leu Thr Glu Ala Ala Val Arg Ala
             20                  25                  30

Leu Gly Pro Glu Cys Arg Asp Val Thr Trp Val Thr Leu Gln Gly Ile
         35                  40                  45

Pro Arg Asp Gln Trp Gly Ile Gly Gly Thr Pro Gly
     50                  55                  60
```

<210> SEQ ID NO 10
<211> LENGTH: 1137
<212> TYPE: DNA
<213> ORGANISM: Streptoverticillium
<220> FEATURE:
<221> NAME/KEY: CDS
<222> LOCATION: (1)..(1137)

<400> SEQUENCE: 10

```
atg ggc ccg gtg cgc gag gag ttc gag cgg gcc ttc gcc cgg cac gtc      48
Met Gly Pro Val Arg Glu Glu Phe Glu Arg Ala Phe Ala Arg His Val
 1               5                  10                  15 ggc gcc gcg cac gcc ctg acg gtc acc agc ggg acg gtc gcg ctg gag      96
Gly Ala Ala His Ala Leu Thr Val Thr Ser Gly Thr Val Ala Leu Glu
             20                  25                  30 atc gcg atc cgg ctg ctc gac ctg cgg gcc ggg gac gag gtc gtc gtg     144
Ile Ala Ile Arg Leu Leu Asp Leu Arg Ala Gly Asp Glu Val Val Val
         35                  40                  45 acg ccg cag acg tac cac gcc acc gcg cag ccg ctg ctc gcg acc gag     192
Thr Pro Gln Thr Tyr His Ala Thr Ala Gln Pro Leu Leu Ala Thr Glu
     50                  55                  60 gca acg gtg cga ttc tgc gac gtg gag ccg ggc agc ctc aac atg gac     240
Ala Thr Val Arg Phe Cys Asp Val Glu Pro Gly Ser Leu Asn Met Asp
 65                  70                  75                  80 ccg gac gcg ctg gag act ctc gtc aac gag cgc acg aag gcc gtc atc     288
Pro Asp Ala Leu Glu Thr Leu Val Asn Glu Arg Thr Lys Ala Val Ile
                 85                  90                  95 ctc gtc cac tac ggc ggc aac ccc gcc gac atg gac cgg atc acc gcc     336
Leu Val His Tyr Gly Gly Asn Pro Ala Asp Met Asp Arg Ile Thr Ala
            100                 105                 110 atc gcg cac gcg cac ggc gcc ctc gtg gtg gag gac tgc gcg cac gcg     384
Ile Ala His Ala His Gly Ala Leu Val Val Glu Asp Cys Ala His Ala
        115                 120                 125 atc ggc gcc gag tac cgg ggc cgc cgc ccc ggc gcg ctc ggc gac ctg     432
Ile Gly Ala Glu Tyr Arg Gly Arg Arg Pro Gly Ala Leu Gly Asp Leu
    130                 135                 140 tcc tgc ttc agc ttc cag gcg tcc aag aac atc acc acc ctc ggc gag     480
Ser Cys Phe Ser Phe Gln Ala Ser Lys Asn Ile Thr Thr Leu Gly Glu
145                 150                 155                 160 ggc ggc atg gtg tgc acc ccg tcg ccc gaa ctg gcc cgc agg atc gac     528
Gly Gly Met Val Cys Thr Pro Ser Pro Glu Leu Ala Arg Arg Ile Asp
                165                 170                 175 cgg atc cgg tcg aac gcg gtg gac ggc acc ttc acc tcg tcc gcg cac     576
Arg Ile Arg Ser Asn Ala Val Asp Gly Thr Phe Thr Ser Ser Ala His
            180                 185                 190
```

```
cgc cgg ccc ccc gcg gcg ctg ccg tgg atg gcg tac gcc gac tac gcc      624
Arg Arg Pro Pro Ala Ala Leu Pro Trp Met Ala Tyr Ala Asp Tyr Ala
        195                 200                 205 tac cgg gag gac tgc acg ggg ctg cgg ggc agc ggg acc aac gcc gcg      672
Tyr Arg Glu Asp Cys Thr Gly Leu Arg Gly Ser Gly Thr Asn Ala Ala
    210                 215                 220 ctc tcc gag gcc gcc tgc gcg gtg ggc ctg gtg cag ctg gaa cgg ctg      720
Leu Ser Glu Ala Ala Cys Ala Val Gly Leu Val Gln Leu Glu Arg Leu
225                 230                 235                 240 ccg gag ttc gtc gcc cgc cgg gcg atc gcc gcg gaa ctc gac gcg          768
Pro Glu Phe Val Ala Arg Arg Ala Ile Ala Ala Glu Leu Asp Ala
                245                 250                 255 gtg tgc cgc cgc ttc gac gtc cgg ccg ctg acc gcc gcg ccc gac gcg      816
Val Cys Arg Arg Phe Asp Val Arg Pro Leu Thr Ala Ala Pro Asp Ala
            260                 265                 270 gtg cac ccg tac cac ctc tac acc gcg ctc gtc ccc ggc gac gga cgc      864
Val His Pro Tyr His Leu Tyr Thr Ala Leu Val Pro Gly Asp Gly Arg
        275                 280                 285 cgc gac cgc gtg ctg gac gcc ctg caa cgc tcc ggt acc ccc gcc cag      912
Arg Asp Arg Val Leu Asp Ala Leu Gln Arg Ser Gly Thr Pro Ala Gln
    290                 295                 300 ttg cgc tac cac ccg gtg cac ctg ctg ccc gag tgg cgg ctg cgc ggg      960
Leu Arg Tyr His Pro Val His Leu Leu Pro Glu Trp Arg Leu Arg Gly
305                 310                 315                 320 cac ggc gag ggc gag tgc ccg gtc gcc gaa cgc ctg tgg ttc ggc gag     1008
His Gly Glu Gly Glu Cys Pro Val Ala Glu Arg Leu Trp Phe Gly Glu
                325                 330                 335 cac ctc aac ctg ccc tgc cac ccc gcc atg acc gat cgc cag gtc gag     1056
His Leu Asn Leu Pro Cys His Pro Ala Met Thr Asp Arg Gln Val Glu
            340                 345                 350 acc ctc ggc gcc aac ctg gcc gcc gcg ctg agt ggc cgg gaa gca ccc     1104
Thr Leu Gly Ala Asn Leu Ala Ala Ala Leu Ser Gly Arg Glu Ala Pro
        355                 360                 365 gcc cga cga gag aag gaa ccc tcg tgc ccc tga                         1137
Ala Arg Arg Glu Lys Glu Pro Ser Cys Pro
    370                 375

<210> SEQ ID NO 11
<211> LENGTH: 378
<212> TYPE: PRT
<213> ORGANISM: Streptoverticillium

<400> SEQUENCE: 11

Met Gly Pro Val Arg Glu Glu Phe Glu Arg Ala Phe Ala Arg His Val
1               5                   10                  15

Gly Ala Ala His Ala Leu Thr Val Thr Ser Gly Thr Val Ala Leu Glu
            20                  25                  30

Ile Ala Ile Arg Leu Leu Asp Leu Arg Ala Gly Asp Glu Val Val Val
        35                  40                  45

Thr Pro Gln Thr Tyr His Ala Thr Ala Gln Pro Leu Leu Ala Thr Glu
    50                  55                  60

Ala Thr Val Arg Phe Cys Asp Val Glu Pro Gly Ser Leu Asn Met Asp
65                  70                  75                  80

Pro Asp Ala Leu Glu Thr Leu Val Asn Glu Arg Thr Lys Ala Val Ile
                85                  90                  95

Leu Val His Tyr Gly Gly Asn Pro Ala Asp Met Asp Arg Ile Thr Ala
            100                 105                 110

Ile Ala His Ala His Gly Ala Leu Val Val Glu Asp Cys Ala His Ala
```

```
            115                 120                 125
Ile Gly Ala Glu Tyr Arg Gly Arg Arg Pro Gly Ala Leu Gly Asp Leu
    130                 135                 140

Ser Cys Phe Ser Phe Gln Ala Ser Lys Asn Ile Thr Thr Leu Gly Glu
145                 150                 155                 160

Gly Gly Met Val Cys Thr Pro Ser Pro Glu Leu Ala Arg Arg Ile Asp
                165                 170                 175

Arg Ile Arg Ser Asn Ala Val Asp Gly Thr Phe Thr Ser Ser Ala His
            180                 185                 190

Arg Arg Pro Pro Ala Ala Leu Pro Trp Met Ala Tyr Ala Asp Tyr Ala
        195                 200                 205

Tyr Arg Glu Asp Cys Thr Gly Leu Arg Gly Ser Gly Thr Asn Ala Ala
    210                 215                 220

Leu Ser Glu Ala Ala Cys Ala Val Gly Leu Val Gln Leu Glu Arg Leu
225                 230                 235                 240

Pro Glu Phe Val Ala Arg Arg Ala Ile Ala Ala Glu Leu Asp Ala
                245                 250                 255

Val Cys Arg Arg Phe Asp Val Arg Pro Leu Thr Ala Ala Pro Asp Ala
                260                 265                 270

Val His Pro Tyr His Leu Tyr Thr Ala Leu Val Pro Gly Asp Gly Arg
            275                 280                 285

Arg Asp Arg Val Leu Asp Ala Leu Gln Arg Ser Gly Thr Pro Ala Gln
    290                 295                 300

Leu Arg Tyr His Pro Val His Leu Leu Pro Glu Trp Arg Leu Arg Gly
305                 310                 315                 320

His Gly Glu Gly Glu Cys Pro Val Ala Glu Arg Leu Trp Phe Gly Glu
                325                 330                 335

His Leu Asn Leu Pro Cys His Pro Ala Met Thr Asp Arg Gln Val Glu
            340                 345                 350

Thr Leu Gly Ala Asn Leu Ala Ala Ala Leu Ser Gly Arg Glu Ala Pro
        355                 360                 365

Ala Arg Arg Glu Lys Glu Pro Ser Cys Pro
    370                 375

<210> SEQ ID NO 12
<211> LENGTH: 1686
<212> TYPE: DNA
<213> ORGANISM: Streptoverticillium
<220> FEATURE:
<221> NAME/KEY: CDS
<222> LOCATION: (1)..(1686)

<400> SEQUENCE: 12 atg cct ctt ctc gat gga ctc gat gga ctc gat ggt ttc gtc ccc tgg      48
Met Pro Leu Leu Asp Gly Leu Asp Gly Leu Asp Gly Phe Val Pro Trp
1               5                  10                  15 ccg gcc gag acc gcg gag cgc tac cgg gcc gac ggc acc tgg gcc ggt      96
Pro Ala Glu Thr Ala Glu Arg Tyr Arg Ala Asp Gly Thr Trp Ala Gly
            20                  25                  30 gag ccc ctg ggc gag ctg ctg cgt tcc cag gcc gcg cgc acc ccg gac     144
Glu Pro Leu Gly Glu Leu Leu Arg Ser Gln Ala Ala Arg Thr Pro Asp
        35                  40                  45 aac gtg gct ctg atc gac ggg gag cgg tcc ttc acc tac gcc gcc ctc     192
Asn Val Ala Leu Ile Asp Gly Glu Arg Ser Phe Thr Tyr Ala Ala Leu
    50                  55                  60 gac cgg tgg gcc gac cgc ctg gcc gcc ggg ttc tcg gcc gcc ggc ctg     240
Asp Arg Trp Ala Asp Arg Leu Ala Ala Gly Phe Ser Ala Ala Gly Leu
```

```
           65                  70                  75                  80
cgg gcg ggc gac cgg gcc gtg ctc caa ctg ccc aac gtc gcc gag cac          288
Arg Ala Gly Asp Arg Ala Val Leu Gln Leu Pro Asn Val Ala Glu His
                85                  90                  95 gtg gcg gtg tcg ttc gcc ttc ttc cgc atc ggt gtg ctg ccg gtc ttc          336
Val Ala Val Ser Phe Ala Phe Phe Arg Ile Gly Val Leu Pro Val Phe
            100                 105                 110 acg ctg ccc aac cac cgc atg gcg gag ctg gac cac atc tgc ggc ctg          384
Thr Leu Pro Asn His Arg Met Ala Glu Leu Asp His Ile Cys Gly Leu
        115                 120                 125 acc ggg gcg agc gcc tac gtg acc ctc gac cgg ttc ctg ggg ttc gac          432
Thr Gly Ala Ser Ala Tyr Val Thr Leu Asp Arg Phe Leu Gly Phe Asp
    130                 135                 140 cac cgc ggg ctg gcc cgg tcc ctg cgc gag cgg cac gcg tcg ctc cgg          480
His Arg Gly Leu Ala Arg Ser Leu Arg Glu Arg His Ala Ser Leu Arg
145                 150                 155                 160 cac gtg ttc gtg gtc ggc gac ccc ggg gag ttc gcc ccg ctt ccc gag          528
His Val Phe Val Val Gly Asp Pro Gly Glu Phe Ala Pro Leu Pro Glu
                165                 170                 175 gcg gag acg ccc ctg gac ccg gcc ggc gcg acc ggt ccc gac gcg tcg          576
Ala Glu Thr Pro Leu Asp Pro Ala Gly Ala Thr Gly Pro Asp Ala Ser
            180                 185                 190 gac gtg gcc ttc ttc ctg ctg tcc ggc ggc acc acg gcg ctg ccg aag          624
Asp Val Ala Phe Phe Leu Leu Ser Gly Gly Thr Thr Ala Leu Pro Lys
        195                 200                 205 ctc atc ccg cgg acg cac gac gac tac ctg tac cag gcc cgt acc gcc          672
Leu Ile Pro Arg Thr His Asp Asp Tyr Leu Tyr Gln Ala Arg Thr Ala
    210                 215                 220 gcc ggg atc tgc gag tac tcc gag gac acc cgc tac ctc gcc acc ctg          720
Ala Gly Ile Cys Glu Tyr Ser Glu Asp Thr Arg Tyr Leu Ala Thr Leu
225                 230                 235                 240 ccg atc gcc ttc aac ttc acg tgg ggc tgc ccg ggt gtg gtc ggg gtg          768
Pro Ile Ala Phe Asn Phe Thr Trp Gly Cys Pro Gly Val Val Gly Val
                245                 250                 255 ttc gcc aac ggg ggc gcc gtg gtg ctg agc acc gtg ccc gac ccc cag          816
Phe Ala Asn Gly Gly Ala Val Val Leu Ser Thr Val Pro Asp Pro Gln
            260                 265                 270 gtg tgc ttc ccg ctc atc gcc cgg cac ggg gtc acc acg acg tcg gtc          864
Val Cys Phe Pro Leu Ile Ala Arg His Gly Val Thr Thr Thr Ser Val
        275                 280                 285 gtg ccg acg atc gcg cac tcc tgg atc gcc gcc gcc gac ggg cgc cgg          912
Val Pro Thr Ile Ala His Ser Trp Ile Ala Ala Ala Asp Gly Arg Arg
    290                 295                 300 gag gag ctg gcg acg ctg gag ctg gtg cag gtc ggc agc gcg gtg gtg          960
Glu Glu Leu Ala Thr Leu Glu Leu Val Gln Val Gly Ser Ala Val Val
305                 310                 315                 320 cac cgg tcg ctc gcc gag gag gtc gga ccg gcg ctg acg gcc cgt ctc         1008
His Arg Ser Leu Ala Glu Glu Val Gly Pro Ala Leu Thr Ala Arg Leu
                325                 330                 335 cag cag gtg ttc ggg atg tcc gag ggc ctg ctg tgc ctc acg cgc cgc         1056
Gln Gln Val Phe Gly Met Ser Glu Gly Leu Leu Cys Leu Thr Arg Arg
            340                 345                 350 gag gac gcg ccc gag acc gtc ctc acc acc cag ggc cgg ccc atc tcc         1104
Glu Asp Ala Pro Glu Thr Val Leu Thr Thr Gln Gly Arg Pro Ile Ser
        355                 360                 365 ccc cac gac gaa ctg cgg gtg gtg gac gcg gcg ggc gac gag gtg gcg         1152
Pro His Asp Glu Leu Arg Val Val Asp Ala Ala Gly Asp Glu Val Ala
    370                 375                 380 gcc ggc ggg acg ggc gag ctg ctc acc cgg ggc ccg tac acc ctg cgc         1200
Ala Gly Gly Thr Gly Glu Leu Leu Thr Arg Gly Pro Tyr Thr Leu Arg
```

```
Ala Gly Gly Thr Gly Glu Leu Leu Thr Arg Gly Pro Tyr Thr Leu Arg
385                 390                 395                 400 ggc tac tac cgg gcc gag gag cac aac gcc ggg gcg ttc acc ccg gac    1248
Gly Tyr Tyr Arg Ala Glu Glu His Asn Ala Gly Ala Phe Thr Pro Asp
                405                 410                 415 ggc ttc tac cgc acc ggc gac ctg gtg cgg atc acc gac gac ggc ggc    1296
Gly Phe Tyr Arg Thr Gly Asp Leu Val Arg Ile Thr Asp Asp Gly Gly
                420                 425                 430 gtc gtg gtg atg ggc cgc gcg aag gac gtc atc gtc cgc ggc ggc gac    1344
Val Val Val Met Gly Arg Ala Lys Asp Val Ile Val Arg Gly Gly Asp
                435                 440                 445 aag gtg tcc gcc ccc gag ctg gag ggc cac ctc acc ggc cac gag cgg    1392
Lys Val Ser Ala Pro Glu Leu Glu Gly His Leu Thr Gly His Glu Arg
450                 455                 460 atc gac cag gcc gcc gtg gtg ccg atg gcc gac gcc gtc ctc ggc gag    1440
Ile Asp Gln Ala Ala Val Val Pro Met Ala Asp Ala Val Leu Gly Glu
465                 470                 475                 480 cgc acc tgc gcc gtg atc atc ccg gtc ggc acg ccg ccg acc ctg ggc    1488
Arg Thr Cys Ala Val Ile Ile Pro Val Gly Thr Pro Pro Thr Leu Gly
                485                 490                 495 gag ctg cgc cgc tac ctg cgc gac cgc ggg ctg gcg tcc tac aag ttc    1536
Glu Leu Arg Arg Tyr Leu Arg Asp Arg Gly Leu Ala Ser Tyr Lys Phe
            500                 505                 510 ccc gac cgg gtc gtg tgc gtc gag gcg ttc ccc aag agc ggc ctc ggc    1584
Pro Asp Arg Val Val Cys Val Glu Ala Phe Pro Lys Ser Gly Leu Gly
                515                 520                 525 aag gtc gac aag aag cgc ctc gtg gcc gac ctc ggc ctc gac gcg ccg    1632
Lys Val Asp Lys Lys Arg Leu Val Ala Asp Leu Gly Leu Asp Ala Pro
530                 535                 540 ccg ggc ccg gac gcc gcc ggg tcc gac ccc gag ccg gcc ggt gcc cgc    1680
Pro Gly Pro Asp Ala Ala Gly Ser Asp Pro Glu Pro Ala Gly Ala Arg
545                 550                 555                 560 tcg tga                                                             1686
Ser

<210> SEQ ID NO 13
<211> LENGTH: 561
<212> TYPE: PRT
<213> ORGANISM: Streptoverticillium

<400> SEQUENCE: 13

Met Pro Leu Leu Asp Gly Leu Asp Gly Leu Asp Gly Phe Val Pro Trp
1               5                   10                  15

Pro Ala Glu Thr Ala Glu Arg Tyr Arg Ala Asp Gly Thr Trp Ala Gly
                20                  25                  30

Glu Pro Leu Gly Glu Leu Leu Arg Ser Gln Ala Ala Arg Thr Pro Asp
            35                  40                  45

Asn Val Ala Leu Ile Asp Gly Glu Arg Ser Phe Thr Tyr Ala Ala Leu
        50                  55                  60

Asp Arg Trp Ala Asp Arg Leu Ala Ala Gly Phe Ser Ala Ala Gly Leu
65                  70                  75                  80

Arg Ala Gly Asp Arg Ala Val Leu Gln Leu Pro Asn Val Ala Glu His
                85                  90                  95

Val Ala Val Ser Phe Ala Phe Phe Arg Ile Gly Val Leu Pro Val Phe
                100                 105                 110

Thr Leu Pro Asn His Arg Met Ala Glu Leu Asp His Ile Cys Gly Leu
            115                 120                 125

Thr Gly Ala Ser Ala Tyr Val Thr Leu Asp Arg Phe Leu Gly Phe Asp
```

```
                130                 135                 140
His Arg Gly Leu Ala Arg Ser Leu Arg Glu Arg His Ala Ser Leu Arg
145                 150                 155                 160

His Val Phe Val Val Gly Asp Pro Gly Glu Phe Ala Pro Leu Pro Glu
                165                 170                 175

Ala Glu Thr Pro Leu Asp Pro Ala Gly Ala Thr Gly Pro Asp Ala Ser
                180                 185                 190

Asp Val Ala Phe Phe Leu Leu Ser Gly Thr Thr Ala Leu Pro Lys
                195                 200                 205

Leu Ile Pro Arg Thr His Asp Asp Tyr Leu Tyr Gln Ala Arg Thr Ala
210                 215                 220

Ala Gly Ile Cys Glu Tyr Ser Glu Asp Thr Arg Tyr Leu Ala Thr Leu
225                 230                 235                 240

Pro Ile Ala Phe Asn Phe Thr Trp Gly Cys Pro Gly Val Val Gly Val
                245                 250                 255

Phe Ala Asn Gly Gly Ala Val Val Leu Ser Thr Val Pro Asp Pro Gln
                260                 265                 270

Val Cys Phe Pro Leu Ile Ala Arg His Gly Val Thr Thr Ser Val
                275                 280                 285

Val Pro Thr Ile Ala His Ser Trp Ile Ala Ala Asp Gly Arg Arg
                290                 295                 300

Glu Glu Leu Ala Thr Leu Glu Leu Val Gln Val Gly Ser Ala Val Val
305                 310                 315                 320

His Arg Ser Leu Ala Glu Glu Val Gly Pro Ala Leu Thr Ala Arg Leu
                325                 330                 335

Gln Gln Val Phe Gly Met Ser Glu Gly Leu Leu Cys Leu Thr Arg Arg
                340                 345                 350

Glu Asp Ala Pro Glu Thr Val Leu Thr Thr Gln Gly Arg Pro Ile Ser
                355                 360                 365

Pro His Asp Glu Leu Arg Val Val Asp Ala Ala Gly Asp Glu Val Ala
                370                 375                 380

Ala Gly Gly Thr Gly Glu Leu Leu Thr Arg Gly Pro Tyr Thr Leu Arg
385                 390                 395                 400

Gly Tyr Tyr Arg Ala Glu Glu His Asn Ala Gly Ala Phe Thr Pro Asp
                405                 410                 415

Gly Phe Tyr Arg Thr Gly Asp Leu Val Arg Ile Thr Asp Asp Gly Gly
                420                 425                 430

Val Val Val Met Gly Arg Ala Lys Asp Val Ile Val Arg Gly Gly Asp
                435                 440                 445

Lys Val Ser Ala Pro Glu Leu Glu Gly His Leu Thr Gly His Glu Arg
                450                 455                 460

Ile Asp Gln Ala Ala Val Val Pro Met Ala Asp Ala Val Leu Gly Glu
465                 470                 475                 480

Arg Thr Cys Ala Val Ile Ile Pro Val Gly Thr Pro Thr Leu Gly
                485                 490                 495

Glu Leu Arg Arg Tyr Leu Arg Asp Arg Gly Leu Ala Ser Tyr Lys Phe
                500                 505                 510

Pro Asp Arg Val Val Cys Val Glu Ala Phe Pro Lys Ser Gly Leu Gly
                515                 520                 525

Lys Val Asp Lys Lys Arg Leu Val Ala Asp Leu Gly Leu Asp Ala Pro
                530                 535                 540

Pro Gly Pro Asp Ala Ala Gly Ser Asp Pro Glu Pro Ala Gly Ala Arg
545                 550                 555                 560
```

Ser

```
<210> SEQ ID NO 14
<211> LENGTH: 1248
<212> TYPE: DNA
<213> ORGANISM: Streptoverticillium
<220> FEATURE:
<221> NAME/KEY: CDS
<222> LOCATION: (1)..(1248)

<400> SEQUENCE: 14
```

| | | | | | | | | | | | | | | | | |
|---|---|---|---|---|---|---|---|---|---|---|---|---|---|---|---|---|
| atg | acc | gtc | gac | gag | gct | tcg | gcg | cac | gag | ggc | cgc | ctg | ccg | gcc | ttc | 48 |
| Met | Thr | Val | Asp | Glu | Ala | Ser | Ala | His | Glu | Gly | Arg | Leu | Pro | Ala | Phe | |
| 1 | | | | 5 | | | | | 10 | | | | | 15 | | |
| gag | gtg | ttc | gac | cag | ggc | ttc | aag | acc | gat | ccg | tac | ccg | tgg | tac | cgc | 96 |
| Glu | Val | Phe | Asp | Gln | Gly | Phe | Lys | Thr | Asp | Pro | Tyr | Pro | Trp | Tyr | Arg | |
| | | | 20 | | | | | 25 | | | | | 30 | | | |
| aag | ctg | cgc | gag | gcg | gcg | ccg | atc | cac | cgg | gta | cgg | atg | acc | ctg | ggc | 144 |
| Lys | Leu | Arg | Glu | Ala | Ala | Pro | Ile | His | Arg | Val | Arg | Met | Thr | Leu | Gly | |
| | | 35 | | | | | 40 | | | | | 45 | | | | |
| gcg | gac | gtg | tgg | ctg | gtg | acc | ggc | tac | gag | ctg | gcg | aag | acc | gtg | ctc | 192 |
| Ala | Asp | Val | Trp | Leu | Val | Thr | Gly | Tyr | Glu | Leu | Ala | Lys | Thr | Val | Leu | |
| 50 | | | | | 55 | | | | | 60 | | | | | | |
| gcg | gac | ggc | cgg | ttc | tcc | aag | atg | acc | gtc | aac | gcc | gag | cgc | gcg | tgg | 240 |
| Ala | Asp | Gly | Arg | Phe | Ser | Lys | Met | Thr | Val | Asn | Ala | Glu | Arg | Ala | Trp | |
| 65 | | | | | 70 | | | | | 75 | | | | | 80 | |
| cgc | tcc | ctg | gag | ctc | atc | ccg | gac | gac | ccc | gac | gcc | ctg | gtc | aac | cgg | 288 |
| Arg | Ser | Leu | Glu | Leu | Ile | Pro | Asp | Asp | Pro | Asp | Ala | Leu | Val | Asn | Arg | |
| | | | | 85 | | | | | 90 | | | | | 95 | | |
| atg | ctg | ctg | atg | agc | gat | ccg | ccc | gac | cac | gag | cgc | ctc | cgc | cgc | ctg | 336 |
| Met | Leu | Leu | Met | Ser | Asp | Pro | Pro | Asp | His | Glu | Arg | Leu | Arg | Arg | Leu | |
| | | | | 100 | | | | | 105 | | | | | 110 | | |
| gtg | tcc | cgg | gcg | ttc | acg | gcg | cgc | tcg | atg | gag | gcg | atg | cgg | ccc | cgc | 384 |
| Val | Ser | Arg | Ala | Phe | Thr | Ala | Arg | Ser | Met | Glu | Ala | Met | Arg | Pro | Arg | |
| | | 115 | | | | | 120 | | | | | 125 | | | | |
| atc | gcc | gag | gtc | gcc | gac | gaa | ctc | gtc | gca | cgg | ttc | gcc | ggc | cgg | ggc | 432 |
| Ile | Ala | Glu | Val | Ala | Asp | Glu | Leu | Val | Ala | Arg | Phe | Ala | Gly | Arg | Gly | |
| | 130 | | | | | 135 | | | | | 140 | | | | | |
| cgc | gtc | gac | ctc | atc | cgc | gag | ttc | gcg | ttc | ccg | ctg | ccc | gcc | atg | atc | 480 |
| Arg | Val | Asp | Leu | Ile | Arg | Glu | Phe | Ala | Phe | Pro | Leu | Pro | Ala | Met | Ile | |
| 145 | | | | | 150 | | | | | 155 | | | | | 160 | |
| atc | tgc | gat | ctg | ctc | ggc | gtc | ccc | gcc | gaa | cac | cgc | acc | cgg | ttc | gag | 528 |
| Ile | Cys | Asp | Leu | Leu | Gly | Val | Pro | Ala | Glu | His | Arg | Thr | Arg | Phe | Glu | |
| | | | | 165 | | | | | 170 | | | | | 175 | | |
| gag | tac | ctg | cgg | ctg | ctc | tgc | ctg | gcc | gaa | ccc | gag | gac | gtc | cac | cgg | 576 |
| Glu | Tyr | Leu | Arg | Leu | Leu | Cys | Leu | Ala | Glu | Pro | Glu | Asp | Val | His | Arg | |
| | | | | 180 | | | | | 185 | | | | | 190 | | |
| atg | ccc | gcc | gtc | ttc | gcc | gaa | ctc | acg | gcg | gaa | ctc | gcc | gag | ttg | gtc | 624 |
| Met | Pro | Ala | Val | Phe | Ala | Glu | Leu | Thr | Ala | Glu | Leu | Ala | Glu | Leu | Val | |
| | | 195 | | | | | 200 | | | | | 205 | | | | |
| gag | cgc | aag | cgg | gcc | gag | ccc | gac | ggg | cac | ctg | ctc | tcc | gcg | ctg | gtc | 672 |
| Glu | Arg | Lys | Arg | Ala | Glu | Pro | Asp | Gly | His | Leu | Leu | Ser | Ala | Leu | Val | |
| | 210 | | | | | 215 | | | | | 220 | | | | | |
| ggg | atc | cgg | gac | ggc | agc | gac | cgg | ctc | acc | gac | gac | gaa | ctg | gtc | tcc | 720 |
| Gly | Ile | Arg | Asp | Gly | Ser | Asp | Arg | Leu | Thr | Asp | Asp | Glu | Leu | Val | Ser | |
| 225 | | | | | 230 | | | | | 235 | | | | | 240 | |
| atg | gcc | ttc | cag | ctc | atg | tac | ggc | gcc | cag | gac | acc | acc | gtc | aac | ctc | 768 |
| Met | Ala | Phe | Gln | Leu | Met | Tyr | Gly | Ala | Gln | Asp | Thr | Thr | Val | Asn | Leu | |
| | | | | 245 | | | | | 250 | | | | | 255 | | |
| atc | ggc | aac | ggc | atg | ctc | gcc | ctg | ctg | gac | aac | ccc | gcc | gcc | atg | gcc | 816 |

```
Ile Gly Asn Gly Met Leu Ala Leu Leu Asp Asn Pro Ala Ala Met Ala
            260                 265                 270 gaa ctg cgg gag aac ccg gag ctc atc ccg ggc gcc gtc gag gag atc      864
Glu Leu Arg Glu Asn Pro Glu Leu Ile Pro Gly Ala Val Glu Glu Ile
                275                 280                 285 ctc cgc ttc gac ccg ccg gtg gag acc gcc acc ccg cgg tac gcc ctg      912
Leu Arg Phe Asp Pro Pro Val Glu Thr Ala Thr Pro Arg Tyr Ala Leu
        290                 295                 300 gaa ccg ctc gac gtc ggc ggg atg cgc gtg gag aag ggc ggg gtc gtg      960
Glu Pro Leu Asp Val Gly Gly Met Arg Val Glu Lys Gly Gly Val Val
305                 310                 315                 320 ctc gtc tcc ctc gcg agc gcc tcc cgc gac ccc ggg cag ttc gag gac     1008
Leu Val Ser Leu Ala Ser Ala Ser Arg Asp Pro Gly Gln Phe Glu Asp
                325                 330                 335 ccc gac gtc ttc gac atc cac cgc gag gtg cgc gga cag ctc gcg ttc     1056
Pro Asp Val Phe Asp Ile His Arg Glu Val Arg Gly Gln Leu Ala Phe
                340                 345                 350 ggg cac ggg ctg cac tac tgc ctc ggg gcc gtg atg gcc cgc gtg aag     1104
Gly His Gly Leu His Tyr Cys Leu Gly Ala Val Met Ala Arg Val Lys
        355                 360                 365 ggc gag gtc gcc ctg cgg gcc ctg ctg tgc ggc ctg gac gac ctg cgc     1152
Gly Glu Val Ala Leu Arg Ala Leu Leu Cys Gly Leu Asp Asp Leu Arg
370                 375                 380 ccg gac gag gac gcc gaa ccg ctc gcg cgc cac gcc ggg ttc atc atg     1200
Pro Asp Glu Asp Ala Glu Pro Leu Ala Arg His Ala Gly Phe Ile Met
385                 390                 395                 400 cgc ggg ctg aag gcg ctc ccc gtc cgc ttc acc ccg cgc gcc gcg tga     1248
Arg Gly Leu Lys Ala Leu Pro Val Arg Phe Thr Pro Arg Ala Ala
                405                 410                 415

<210> SEQ ID NO 15
<211> LENGTH: 415
<212> TYPE: PRT
<213> ORGANISM: Streptoverticillium

<400> SEQUENCE: 15

Met Thr Val Asp Glu Ala Ser Ala His Glu Gly Arg Leu Pro Ala Phe
1               5                   10                  15

Glu Val Phe Asp Gln Gly Phe Lys Thr Asp Pro Tyr Pro Trp Tyr Arg
                20                  25                  30

Lys Leu Arg Glu Ala Ala Pro Ile His Arg Val Arg Met Thr Leu Gly
            35                  40                  45

Ala Asp Val Trp Leu Val Thr Gly Tyr Glu Leu Ala Lys Thr Val Leu
        50                  55                  60

Ala Asp Gly Arg Phe Ser Lys Met Thr Val Asn Ala Glu Arg Ala Trp
65                  70                  75                  80

Arg Ser Leu Glu Leu Ile Pro Asp Pro Asp Ala Leu Val Asn Arg
                85                  90                  95

Met Leu Leu Met Ser Asp Pro Asp His Glu Arg Leu Arg Arg Leu
                100                 105                 110

Val Ser Arg Ala Phe Thr Ala Arg Ser Met Glu Ala Met Arg Pro Arg
            115                 120                 125

Ile Ala Glu Val Ala Asp Glu Leu Val Ala Arg Phe Ala Gly Arg Gly
        130                 135                 140

Arg Val Asp Leu Ile Arg Glu Phe Ala Phe Pro Leu Pro Ala Met Ile
145                 150                 155                 160

Ile Cys Asp Leu Leu Gly Val Pro Ala Glu His Arg Thr Arg Phe Glu
                165                 170                 175
```

Glu Tyr Leu Arg Leu Leu Cys Leu Ala Glu Pro Asp Val His Arg
            180                 185                 190

Met Pro Ala Val Phe Ala Glu Leu Thr Ala Glu Leu Ala Glu Leu Val
        195                 200                 205

Glu Arg Lys Arg Ala Glu Pro Asp Gly His Leu Leu Ser Ala Leu Val
210                 215                 220

Gly Ile Arg Asp Gly Ser Asp Arg Leu Thr Asp Asp Glu Leu Val Ser
225                 230                 235                 240

Met Ala Phe Gln Leu Met Tyr Gly Ala Gln Asp Thr Thr Val Asn Leu
                245                 250                 255

Ile Gly Asn Gly Met Leu Ala Leu Leu Asp Asn Pro Ala Ala Met Ala
            260                 265                 270

Glu Leu Arg Glu Asn Pro Glu Leu Ile Pro Gly Ala Val Glu Glu Ile
        275                 280                 285

Leu Arg Phe Asp Pro Pro Val Glu Thr Ala Thr Pro Arg Tyr Ala Leu
    290                 295                 300

Glu Pro Leu Asp Val Gly Gly Met Arg Val Glu Lys Gly Gly Val Val
305                 310                 315                 320

Leu Val Ser Leu Ala Ser Ala Ser Arg Asp Pro Gly Gln Phe Glu Asp
                325                 330                 335

Pro Asp Val Phe Asp Ile His Arg Glu Val Arg Gly Gln Leu Ala Phe
            340                 345                 350

Gly His Gly Leu His Tyr Cys Leu Gly Ala Val Met Ala Arg Val Lys
        355                 360                 365

Gly Glu Val Ala Leu Arg Ala Leu Leu Cys Gly Leu Asp Leu Arg
    370                 375                 380

Pro Asp Glu Asp Ala Glu Pro Leu Ala Arg His Ala Gly Phe Ile Met
385                 390                 395                 400

Arg Gly Leu Lys Ala Leu Pro Val Arg Phe Thr Pro Arg Ala Ala
                405                 410                 415

<210> SEQ ID NO 16
<211> LENGTH: 546
<212> TYPE: DNA
<213> ORGANISM: Streptoverticillium
<220> FEATURE:
<221> NAME/KEY: CDS
<222> LOCATION: (1)..(546)

<400> SEQUENCE: 16

| | | |
|---|---|---|
| atg gcc gac ctg ctc ctc ccc ggc gtc ctc gaa gcg gcc gac cgc ccg<br>Met Ala Asp Leu Leu Leu Pro Gly Val Leu Glu Ala Ala Asp Arg Pro<br>1               5                   10                  15 | 48 | |
| ttc gtc ttc tac ggc cac tcg ctc ggc gcg cgc gtc gcc tac gag acg<br>Phe Val Phe Tyr Gly His Ser Leu Gly Ala Arg Val Ala Tyr Glu Thr<br>            20                  25                  30 | 96 | |
| gcc cac cgc ctc gcg gac acc ggc cgg ccg ctg ccc gcc gcg ctc tgc<br>Ala His Arg Leu Ala Asp Thr Gly Arg Pro Leu Pro Ala Ala Leu Cys<br>        35                  40                  45 | 144 | |
| gtc tcc ggg gcg ccc gcc ccg gcc ctc ggc gtc cac acc ccg tgc cac<br>Val Ser Gly Ala Pro Ala Pro Ala Leu Gly Val His Thr Pro Cys His<br>    50                  55                  60 | 192 | |
| gac cag ccc cgc gcg gaa ttc ctc cgc acc ctg cgg gcg atg ggc ggc<br>Asp Gln Pro Arg Ala Glu Phe Leu Arg Thr Leu Arg Ala Met Gly Gly<br>65                  70                  75                  80 | 240 | |
| gtc gcc ccg gag gtg ctc gcc gac gag gag ctg tgc gac tac gtc ctg<br>Val Ala Pro Glu Val Leu Ala Asp Glu Glu Leu Cys Asp Tyr Val Leu | 288 | |

```
                        85                  90                  95
ccg gtc atc cgc gcc gac atg cgg gcc gcc gag aca tac cgg cca ccg       336
Pro Val Ile Arg Ala Asp Met Arg Ala Ala Glu Thr Tyr Arg Pro Pro
            100                 105                 110 cgc cgg acc ccg ctg cgc aca ccg atc agg gcg ctc gcc gga cgg gac       384
Arg Arg Thr Pro Leu Arg Thr Pro Ile Arg Ala Leu Ala Gly Arg Asp
            115                 120                 125 gac ccc cgg gtg ccg gtg gag cac gtg cgg cgg tgg tcg gac gag gcc       432
Asp Pro Arg Val Pro Val Glu His Val Arg Arg Trp Ser Asp Glu Ala
130                 135                 140 ggt ggg gag ttc cgc tgc acg gtc ttc gag gga ggc cac ttc ttc ttc       480
Gly Gly Glu Phe Arg Cys Thr Val Phe Glu Gly Gly His Phe Phe Phe
145                 150                 155                 160 cgt gac cac ccg tcg gag gtc gcc gcg gtg ttg gac ggc ctg ctg cgg       528
Arg Asp His Pro Ser Glu Val Ala Ala Val Leu Asp Gly Leu Leu Arg
                165                 170                 175 gaa gtc gcc ggg gga tag                                               546
Glu Val Ala Gly Gly
            180

<210> SEQ ID NO 17
<211> LENGTH: 181
<212> TYPE: PRT
<213> ORGANISM: Streptoverticillium

<400> SEQUENCE: 17

Met Ala Asp Leu Leu Leu Pro Gly Val Leu Ala Ala Asp Arg Pro
1               5                   10                  15

Phe Val Phe Tyr Gly His Ser Leu Gly Ala Arg Val Ala Tyr Glu Thr
                20                  25                  30

Ala His Arg Leu Ala Asp Thr Gly Arg Pro Leu Pro Ala Ala Leu Cys
            35                  40                  45

Val Ser Gly Ala Pro Ala Pro Ala Leu Gly Val His Thr Pro Cys His
        50                  55                  60

Asp Gln Pro Arg Ala Glu Phe Leu Arg Thr Leu Arg Ala Met Gly Gly
65                  70                  75                  80

Val Ala Pro Glu Val Leu Ala Asp Glu Leu Cys Asp Tyr Val Leu
                85                  90                  95

Pro Val Ile Arg Ala Asp Met Arg Ala Ala Glu Thr Tyr Arg Pro Pro
            100                 105                 110

Arg Arg Thr Pro Leu Arg Thr Pro Ile Arg Ala Leu Ala Gly Arg Asp
            115                 120                 125

Asp Pro Arg Val Pro Val Glu His Val Arg Arg Trp Ser Asp Glu Ala
        130                 135                 140

Gly Gly Glu Phe Arg Cys Thr Val Phe Glu Gly Gly His Phe Phe Phe
145                 150                 155                 160

Arg Asp His Pro Ser Glu Val Ala Ala Val Leu Asp Gly Leu Leu Arg
                165                 170                 175

Glu Val Ala Gly Gly
            180

<210> SEQ ID NO 18
<211> LENGTH: 531
<212> TYPE: DNA
<213> ORGANISM: Streptoverticillium
<220> FEATURE:
<221> NAME/KEY: CDS
<222> LOCATION: (1)..(531)
```

<400> SEQUENCE: 18

```
atg gac ccg gtg acc ctt cgg acc gac cgc ctg gtg ctg cgg gcc ttc      48
Met Asp Pro Val Thr Leu Arg Thr Asp Arg Leu Val Leu Arg Ala Phe
1               5                   10                  15 acg cct gcc gac gtg gat gcg gtg tac gag gcc tgc cag gac gag gac      96
Thr Pro Ala Asp Val Asp Ala Val Tyr Glu Ala Cys Gln Asp Glu Asp
                20                  25                  30 atc cag ctc tac acc ccg gtg ccg gtg ccg tac ctg cgt gcg gac gcg     144
Ile Gln Leu Tyr Thr Pro Val Pro Val Pro Tyr Leu Arg Ala Asp Ala
            35                  40                  45 gag aag ctc gtc ggc gag aag ctg ccc gcc cag tgg gcc gcg gac gag     192
Glu Lys Leu Val Gly Glu Lys Leu Pro Ala Gln Trp Ala Ala Asp Glu
    50                  55                  60 gac tac acc ttc ggc gcg ttc cgc gag gac acc ggc gcc ctg gcc ggc     240
Asp Tyr Thr Phe Gly Ala Phe Arg Glu Asp Thr Gly Ala Leu Ala Gly
65                  70                  75                  80 tcg tac tgc ctg acc cgc gtc agc cgc ggc gtc tgg gag ctc ggc tac     288
Ser Tyr Cys Leu Thr Arg Val Ser Arg Gly Val Trp Glu Leu Gly Tyr
                85                  90                  95 tgg gcg gtc aag gag cag cgc ggt cac ggg tat tcg gtg gag gcc gcc     336
Trp Ala Val Lys Glu Gln Arg Gly His Gly Tyr Ser Val Glu Ala Ala
                100                 105                 110 cga gcc ctg tgc gac tgg gga tgg gcc acg ctc gac gtg cac cgc atc     384
Arg Ala Leu Cys Asp Trp Gly Trp Ala Thr Leu Asp Val His Arg Ile
            115                 120                 125 gag tgg tgg gcc atg gtc ggg aac gcc ggc tcg cgt gcc gtc gcc gag     432
Glu Trp Trp Ala Met Val Gly Asn Ala Gly Ser Arg Ala Val Ala Glu
        130                 135                 140 aga ctc ggc ttc acc gtc gag ggg aca ctg cgc aag cgc ggc atc gcc     480
Arg Leu Gly Phe Thr Val Glu Gly Thr Leu Arg Lys Arg Gly Ile Ala
145                 150                 155                 160 aac gac ggc gta ccg cac gac tgg tgg gtg ggc gga ctg ctg cgg ccc     528
Asn Asp Gly Val Pro His Asp Trp Trp Val Gly Gly Leu Leu Arg Pro
                165                 170                 175 tga                                                                 531
```

<210> SEQ ID NO 19
<211> LENGTH: 176
<212> TYPE: PRT
<213> ORGANISM: Streptoverticillium

<400> SEQUENCE: 19

```
Met Asp Pro Val Thr Leu Arg Thr Asp Arg Leu Val Leu Arg Ala Phe
1               5                   10                  15

Thr Pro Ala Asp Val Asp Ala Val Tyr Glu Ala Cys Gln Asp Glu Asp
                20                  25                  30

Ile Gln Leu Tyr Thr Pro Val Pro Val Pro Tyr Leu Arg Ala Asp Ala
            35                  40                  45

Glu Lys Leu Val Gly Glu Lys Leu Pro Ala Gln Trp Ala Ala Asp Glu
        50                  55                  60

Asp Tyr Thr Phe Gly Ala Phe Arg Glu Asp Thr Gly Ala Leu Ala Gly
65                  70                  75                  80

Ser Tyr Cys Leu Thr Arg Val Ser Arg Gly Val Trp Glu Leu Gly Tyr
                85                  90                  95

Trp Ala Val Lys Glu Gln Arg Gly His Gly Tyr Ser Val Glu Ala Ala
                100                 105                 110

Arg Ala Leu Cys Asp Trp Gly Trp Ala Thr Leu Asp Val His Arg Ile
            115                 120                 125
```

Glu Trp Trp Ala Met Val Gly Asn Ala Gly Ser Arg Ala Val Ala Glu
    130                 135                 140

Arg Leu Gly Phe Thr Val Glu Gly Thr Leu Arg Lys Arg Gly Ile Ala
145                 150                 155                 160

Asn Asp Gly Val Pro His Asp Trp Trp Val Gly Gly Leu Leu Arg Pro
                165                 170                 175

<210> SEQ ID NO 20
<211> LENGTH: 777
<212> TYPE: DNA
<213> ORGANISM: Streptoverticillium
<220> FEATURE:
<221> NAME/KEY: CDS
<222> LOCATION: (1)..(777)

<400> SEQUENCE: 20

| | |
|---|---:|
| atg tca gat ccg acc gac cgc atc gcc ctg gtg acc ggg gcc ggc cgc<br>Met Ser Asp Pro Thr Asp Arg Ile Ala Leu Val Thr Gly Ala Gly Arg<br>1               5                   10                  15 | 48 |
| ggc atc ggc cgt gcc gtc gcc gtc cgc ctc gcc gcg gag ggc gcg ctg<br>Gly Ile Gly Arg Ala Val Ala Val Arg Leu Ala Ala Glu Gly Ala Leu<br>                20                  25                  30 | 96 |
| gtc gcc gtc cac tac gga cgg gac gac gaa gcc gcg cgg tcg acg gtg<br>Val Ala Val His Tyr Gly Arg Asp Asp Glu Ala Ala Arg Ser Thr Val<br>            35                  40                  45 | 144 |
| cgg gag atc cgc gaa ggc ggg tcg gcc ttc ccc gtc cgc gcg gag<br>Arg Glu Ile Arg Glu Ala Gly Gly Ser Ala Phe Pro Val Arg Ala Glu<br>50                  55                  60 | 192 |
| ttc ggc gag ctc ggc gcc ctc gac gag ctg tgg cgc ggt tac gac gag<br>Phe Gly Glu Leu Gly Ala Leu Asp Glu Leu Trp Arg Gly Tyr Asp Glu<br>65                  70                  75                  80 | 240 |
| ggc gtc gcc gcc gtc cgc ggc ggc tcg ggt ccc gcg ccg gtg gac atc<br>Gly Val Ala Ala Val Arg Gly Gly Ser Gly Pro Ala Pro Val Asp Ile<br>                85                  90                  95 | 288 |
| ctc gtg aac aac gcc ggg atc acc gtc ccg cgt ggc gta cgg gac ctc<br>Leu Val Asn Asn Ala Gly Ile Thr Val Pro Arg Gly Val Arg Asp Leu<br>            100                 105                 110 | 336 |
| gaa gag gcc gac tgg gac cgg ctg ttc gcg gtc aac gcc aag gcc ccg<br>Glu Glu Ala Asp Trp Asp Arg Leu Phe Ala Val Asn Ala Lys Ala Pro<br>        115                 120                 125 | 384 |
| ttc ttc ctg gtg cag ggc gcg ctg ccg cgg ctg cgc gac ggg ggc cgg<br>Phe Phe Leu Val Gln Gly Ala Leu Pro Arg Leu Arg Asp Gly Gly Arg<br>130                 135                 140 | 432 |
| atc gtc aac gtc acc acc gcc gcg acc cgg gtg gcg atg ccg gtg atc<br>Ile Val Asn Val Thr Thr Ala Ala Thr Arg Val Ala Met Pro Val Ile<br>145                 150                 155                 160 | 480 |
| gcc gcg tac acc atg acc aag gcg gcg ctg gag acc ttc acc gtc gac<br>Ala Ala Tyr Thr Met Thr Lys Ala Ala Leu Glu Thr Phe Thr Val Asp<br>                165                 170                 175 | 528 |
| ctc gcc ctg gag ctg ggg ccg cgc ggc atc acc gtc aac gcg gtc gcc<br>Leu Ala Leu Glu Leu Gly Pro Arg Gly Ile Thr Val Asn Ala Val Ala<br>            180                 185                 190 | 576 |
| ccg ggg tac acc gac acc gac atc aac ccg gac atg aag gtg ccc gcc<br>Pro Gly Tyr Thr Asp Thr Asp Ile Asn Pro Asp Met Lys Val Pro Ala<br>        195                 200                 205 | 624 |
| cag cgc gag gcc atg gcc gcc acc acc gca ctc cac cgg gtc ggt acg<br>Gln Arg Glu Ala Met Ala Ala Thr Thr Ala Leu His Arg Val Gly Thr<br>210                 215                 220 | 672 |
| ccc ggc gag gtc gcc gac gtc gtc gcc tac ctg gcg gga ccg ggc ggc<br>Pro Gly Glu Val Ala Asp Val Val Ala Tyr Leu Ala Gly Pro Gly Gly | 720 |

```
                225                 230                 235                 240
cgc tgg gtc acc ggg cag cgc atc gag gcg tcg ggg ggc gtc cgg ctc       768
Arg Trp Val Thr Gly Gln Arg Ile Glu Ala Ser Gly Gly Val Arg Leu
                245                 250                 255 gga ctc tag                                                           777
Gly Leu <210> SEQ ID NO 21
<211> LENGTH: 258
<212> TYPE: PRT
<213> ORGANISM: Streptoverticillium

<400> SEQUENCE: 21

Met Ser Asp Pro Thr Asp Arg Ile Ala Leu Val Thr Gly Ala Gly Arg
1               5                   10                  15

Gly Ile Gly Arg Ala Val Ala Val Arg Leu Ala Ala Glu Gly Ala Leu
            20                  25                  30

Val Ala Val His Tyr Gly Arg Asp Asp Glu Ala Ala Arg Ser Thr Val
        35                  40                  45

Arg Glu Ile Arg Glu Ala Gly Gly Ser Ala Phe Pro Val Arg Ala Glu
    50                  55                  60

Phe Gly Glu Leu Gly Ala Leu Asp Glu Leu Trp Arg Gly Tyr Asp Glu
65                  70                  75                  80

Gly Val Ala Ala Val Arg Gly Gly Ser Gly Pro Ala Pro Val Asp Ile
                85                  90                  95

Leu Val Asn Asn Ala Gly Ile Thr Val Pro Arg Gly Val Arg Asp Leu
            100                 105                 110

Glu Glu Ala Asp Trp Asp Arg Leu Phe Ala Val Asn Ala Lys Ala Pro
        115                 120                 125

Phe Phe Leu Val Gln Gly Ala Leu Pro Arg Leu Arg Asp Gly Gly Arg
    130                 135                 140

Ile Val Asn Val Thr Thr Ala Ala Thr Arg Val Ala Met Pro Val Ile
145                 150                 155                 160

Ala Ala Tyr Thr Met Thr Lys Ala Ala Leu Glu Thr Phe Thr Val Asp
                165                 170                 175

Leu Ala Leu Glu Leu Gly Pro Arg Gly Ile Thr Val Asn Ala Val Ala
            180                 185                 190

Pro Gly Tyr Thr Asp Thr Asp Ile Asn Pro Asp Met Lys Val Pro Ala
        195                 200                 205

Gln Arg Glu Ala Met Ala Ala Thr Thr Ala Leu His Arg Val Gly Thr
    210                 215                 220

Pro Gly Glu Val Ala Asp Val Val Ala Tyr Leu Ala Gly Pro Gly Gly
225                 230                 235                 240

Arg Trp Val Thr Gly Gln Arg Ile Glu Ala Ser Gly Gly Val Arg Leu
                245                 250                 255

Gly Leu

<210> SEQ ID NO 22
<211> LENGTH: 1302
<212> TYPE: DNA
<213> ORGANISM: Streptoverticillium
<220> FEATURE:
<221> NAME/KEY: CDS
<222> LOCATION: (1)..(1302)

<400> SEQUENCE: 22 atg ccc gac tcc ctc cgt ccc ctc tgc cca ctt gag gag ctg cac gtc    48
```

```
Met Pro Asp Ser Leu Arg Pro Leu Cys Pro Leu Glu Glu Leu His Val
1               5                   10                  15 ggc gac cgc agc cgg gcg gtg gtc acc gtc gag gtc gag ggc gac ctc         96
Gly Asp Arg Ser Arg Ala Val Val Thr Val Glu Val Glu Gly Asp Leu
            20                  25                  30 gac ctc gac gtg ctg tcc gcg gcc tgg tcg cgg acg ctc gac gcg cat        144
Asp Leu Asp Val Leu Ser Ala Ala Trp Ser Arg Thr Leu Asp Ala His
        35                  40                  45 ccg acg gcg gac agc cgg atc gtg tcg cac ggc ggc ggt ttc gcc ctc        192
Pro Thr Ala Asp Ser Arg Ile Val Ser His Gly Gly Gly Phe Ala Leu
    50                  55                  60 gaa cgg ctg ggg gcg gcc ggc cgc ccg ggc ctg gcc gaa ccg gcg ccc        240
Glu Arg Leu Gly Ala Ala Gly Arg Pro Gly Leu Ala Glu Pro Ala Pro
65                  70                  75                  80 gag aag gac gtg atg acg gag atc gcc acg tcc ccc ttg ccc gtc ggc        288
Glu Lys Asp Val Met Thr Glu Ile Ala Thr Ser Pro Leu Pro Val Gly
                85                  90                  95 ggc ccg gtc gcg cgg ctg tcg acg gcc gcg cgg ggc tcg gac acg gtc        336
Gly Pro Val Ala Arg Leu Ser Thr Ala Ala Arg Gly Ser Asp Thr Val
            100                 105                 110 gtg ggg ctc gtc gtg gac cac gtg gtg acc gac ggc acc agc gcc ctc        384
Val Gly Leu Val Val Asp His Val Val Thr Asp Gly Thr Ser Ala Leu
        115                 120                 125 acc ctc cac acg gaa ctc tgg cgg cac tac gcc gcg gtg ctg gcc ggc        432
Thr Leu His Thr Glu Leu Trp Arg His Tyr Ala Ala Val Leu Ala Gly
    130                 135                 140 gaa ccg gcc cgc ccg gcg gcg acc gcg tgg ccg gcc ccg gtg tcg gag        480
Glu Pro Ala Arg Pro Ala Ala Thr Ala Trp Pro Ala Pro Val Ser Glu
145                 150                 155                 160 cgg ctg ccg gcc gtg tcc ggg gac gcc gtc gcg gcg ctg ctc gcc gag        528
Arg Leu Pro Ala Val Ser Gly Asp Ala Val Ala Ala Leu Leu Ala Glu
                165                 170                 175 cgc ctg gaa cag gcg cgc gac cgt ccg ccg gcg cag ttg ccg tac gtg        576
Arg Leu Glu Gln Ala Arg Asp Arg Pro Pro Ala Gln Leu Pro Tyr Val
            180                 185                 190 gag gcg ggc ggg gac ggt gcg ccg ccg gcc ggg cgg cag ccg gtg cac        624
Glu Ala Gly Gly Asp Gly Ala Pro Pro Ala Gly Arg Gln Pro Val His
        195                 200                 205 aac gtc cgc gtc gcc ctg tcc gcc gac agg acc ggc gaa ctc gcg gcg        672
Asn Val Arg Val Ala Leu Ser Ala Asp Arg Thr Gly Glu Leu Ala Ala
    210                 215                 220 ggc gca cgg agg ttg ggc acc tcg gtg cac ggc gtg acc gcc gcg gcg        720
Gly Ala Arg Arg Leu Gly Thr Ser Val His Gly Val Thr Ala Ala Ala
225                 230                 235                 240 ctg ctc ctg gcg ata cgg gag gag ctc ggc ggt tcc ggt acc gcc gcc        768
Leu Leu Leu Ala Ile Arg Glu Glu Leu Gly Gly Ser Gly Thr Ala Ala
                245                 250                 255 ctc ggc tgc ttc tcg ccc gtg gac ctg cgc tcc cgg gtc gag ccc ccg        816
Leu Gly Cys Phe Ser Pro Val Asp Leu Arg Ser Arg Val Glu Pro Pro
            260                 265                 270 gcg gcg gcc ggc gtg atg ctg ccg ctg gtc tcg ggg ttc ccg gac gtg        864
Ala Ala Ala Gly Val Met Leu Pro Leu Val Ser Gly Phe Pro Asp Val
        275                 280                 285 gtg gac gtc gcg ccg ggc gag ggc ccg gag cac gtg ggt ccg ctg gcg        912
Val Asp Val Ala Pro Gly Glu Gly Pro Glu His Val Gly Pro Leu Ala
    290                 295                 300 cgc cgg gtc acc gag ggg ctg cgc ggc gcc ctg gcc ggc gac ggc tgg        960
Arg Arg Val Thr Glu Gly Leu Arg Gly Ala Leu Ala Gly Asp Gly Trp
305                 310                 315                 320
```

```
                                                                    -continued gcc gtg gag acc gct ctg ctc gcc cgc ctc gtc gac cac ccg gag ctg    1008
Ala Val Glu Thr Ala Leu Leu Ala Arg Leu Val Asp His Pro Glu Leu
            325                 330                 335 ctg gcc acc acc gtg atc gtg tcg aac atg ggc cgg atc gcc ggc ccg    1056
Leu Ala Thr Thr Val Ile Val Ser Asn Met Gly Arg Ile Ala Gly Pro
        340                 345                 350 gtg tcc ccg ccc ggg ctg cgg ctg cgc gac acc cgg ctg acg gcc gga    1104
Val Ser Pro Pro Gly Leu Arg Leu Arg Asp Thr Arg Leu Thr Ala Gly
    355                 360                 365 cgc gag gac tac ggc ccc ggg ttc ggg cag ggt ccg ctc ttc gcc tgt    1152
Arg Glu Asp Tyr Gly Pro Gly Phe Gly Gln Gly Pro Leu Phe Ala Cys
370                 375                 380 gtc agc acc gtg gac ggc gcg ttc tcg ctg gag atc ccg tac acc ccc    1200
Val Ser Thr Val Asp Gly Ala Phe Ser Leu Glu Ile Pro Tyr Thr Pro
385                 390                 395                 400 gtc tgc tcc ccg ccc gcc cag atc gag cgg gtg cgg gcg cgg acg ctg    1248
Val Cys Ser Pro Pro Ala Gln Ile Glu Arg Val Arg Ala Arg Thr Leu
                405                 410                 415 gcg acg ctg gag cgg gtc gcg gac gcc ggg gcg cgt gcc gcg ctg tcc    1296
Ala Thr Leu Glu Arg Val Ala Asp Ala Gly Ala Arg Ala Ala Leu Ser
            420                 425                 430 gtc tga                                                             1302
Val

<210> SEQ ID NO 23
<211> LENGTH: 433
<212> TYPE: PRT
<213> ORGANISM: Streptoverticillium

<400> SEQUENCE: 23

Met Pro Asp Ser Leu Arg Pro Leu Cys Pro Leu Glu Glu Leu His Val
1               5                   10                  15

Gly Asp Arg Ser Arg Ala Val Val Thr Val Glu Val Glu Gly Asp Leu
            20                  25                  30

Asp Leu Asp Val Leu Ser Ala Ala Trp Ser Arg Thr Leu Asp Ala His
        35                  40                  45

Pro Thr Ala Asp Ser Arg Ile Val Ser His Gly Gly Gly Phe Ala Leu
    50                  55                  60

Glu Arg Leu Gly Ala Ala Gly Arg Pro Gly Leu Ala Glu Pro Ala Pro
65                  70                  75                  80

Glu Lys Asp Val Met Thr Glu Ile Ala Thr Ser Pro Leu Pro Val Gly
                85                  90                  95

Gly Pro Val Ala Arg Leu Ser Thr Ala Ala Arg Gly Ser Asp Thr Val
            100                 105                 110

Val Gly Leu Val Val Asp His Val Val Thr Asp Gly Thr Ser Ala Leu
        115                 120                 125

Thr Leu His Thr Glu Leu Trp Arg His Tyr Ala Ala Val Leu Ala Gly
    130                 135                 140

Glu Pro Ala Arg Pro Ala Ala Thr Ala Trp Pro Ala Val Ser Glu
145                 150                 155                 160

Arg Leu Pro Ala Val Ser Gly Asp Ala Val Ala Ala Leu Leu Ala Glu
                165                 170                 175

Arg Leu Glu Gln Ala Arg Asp Arg Pro Pro Ala Gln Leu Pro Tyr Val
            180                 185                 190

Glu Ala Gly Gly Asp Gly Ala Pro Pro Ala Gly Arg Gln Pro Val His
        195                 200                 205

Asn Val Arg Val Ala Leu Ser Ala Asp Arg Thr Gly Glu Leu Ala Ala
```

```
                    210                 215                 220
Gly Ala Arg Arg Leu Gly Thr Ser Val His Gly Val Thr Ala Ala
225                 230                 235                 240

Leu Leu Leu Ala Ile Arg Glu Glu Leu Gly Gly Ser Gly Thr Ala Ala
                245                 250                 255

Leu Gly Cys Phe Ser Pro Val Asp Leu Arg Ser Arg Val Glu Pro Pro
            260                 265                 270

Ala Ala Ala Gly Val Met Leu Pro Leu Val Ser Gly Phe Pro Asp Val
        275                 280                 285

Val Asp Val Ala Pro Gly Glu Gly Pro Glu His Val Gly Pro Leu Ala
    290                 295                 300

Arg Arg Val Thr Glu Gly Leu Arg Gly Ala Leu Ala Gly Asp Gly Trp
305                 310                 315                 320

Ala Val Glu Thr Ala Leu Leu Ala Arg Leu Val Asp His Pro Glu Leu
                325                 330                 335

Leu Ala Thr Thr Val Ile Val Ser Asn Met Gly Arg Ile Ala Gly Pro
            340                 345                 350

Val Ser Pro Pro Gly Leu Arg Leu Arg Asp Thr Arg Leu Thr Ala Gly
        355                 360                 365

Arg Glu Asp Tyr Gly Pro Gly Phe Gly Gln Gly Pro Leu Phe Ala Cys
    370                 375                 380

Val Ser Thr Val Asp Gly Ala Phe Ser Leu Glu Ile Pro Tyr Thr Pro
385                 390                 395                 400

Val Cys Ser Pro Pro Ala Gln Ile Glu Arg Val Arg Ala Arg Thr Leu
                405                 410                 415

Ala Thr Leu Glu Arg Val Ala Asp Ala Gly Ala Arg Ala Ala Leu Ser
            420                 425                 430

Val

<210> SEQ ID NO 24
<211> LENGTH: 3831
<212> TYPE: DNA
<213> ORGANISM: Streptoverticillium
<220> FEATURE:
<221> NAME/KEY: CDS
<222> LOCATION: (1)..(3831)

<400> SEQUENCE: 24 atg gcg acg gag ccg ctg gcc gtc gtc ggg atg gcc ggc cgg ttc ccg    48
Met Ala Thr Glu Pro Leu Ala Val Val Gly Met Ala Gly Arg Phe Pro
1               5                   10                  15 ggc gcg aac acg ctg gag gag ttc tgg gcg ctg ctg agc gag ggc cgg    96
Gly Ala Asn Thr Leu Glu Glu Phe Trp Ala Leu Leu Ser Glu Gly Arg
            20                  25                  30 cag ggc gtc cgg gag gtg acg gag gag gag ttc ctg gcc gcc ggg ggc    144
Gln Gly Val Arg Glu Val Thr Glu Glu Glu Phe Leu Ala Ala Gly Gly
        35                  40                  45 gat ccg gcg gac ctg gag gac ccg tcc ctg gtc cgc gtg gcg gcg gtg    192
Asp Pro Ala Asp Leu Glu Asp Pro Ser Leu Val Arg Val Ala Ala Val
    50                  55                  60 ctg ccc gac gcc gac cgc ttc gac gcc gcg ttc ttc ggc tac ggc ccg    240
Leu Pro Asp Ala Asp Arg Phe Asp Ala Ala Phe Phe Gly Tyr Gly Pro
65                  70                  75                  80 gcc gag gcc gaa ctc atc gac ccg cag cag cgg gtg ctc ctg gag acc    288
Ala Glu Ala Glu Leu Ile Asp Pro Gln Gln Arg Val Leu Leu Glu Thr
                85                  90                  95 gcc tac cac gcg ctg gag gac gcg ggg tac gcg gac ggc cac ggc gac    336
```

|     |     |     |     |     |     |     |     |     |     |     |     |     |     |
|-----|-----|-----|-----|-----|-----|-----|-----|-----|-----|-----|-----|-----|-----|
| Ala | Tyr | His | Ala | Leu | Glu | Asp | Ala | Gly | Tyr | Ala | Asp | Gly | His | Gly | Asp |
|     |     |     | 100 |     |     |     | 105 |     |     |     | 110 |     |     |

```
cgc gtc gtc ggg gtc tac gcg ggc gcc ggc gac agc cgc tac tac tcc       384
Arg Val Val Gly Val Tyr Ala Gly Ala Gly Asp Ser Arg Tyr Tyr Ser
            115                 120                 125 tac aac gtg cac ccg cgg cac gcc ggc gag ccc gcc tcc gtg ggt ctg       432
Tyr Asn Val His Pro Arg His Ala Gly Glu Pro Ala Ser Val Gly Leu
        130                 135                 140 atc cac gcg gcc acc gcc aac tcc ctt ggc acg ctc gcc act cgg ctg       480
Ile His Ala Ala Thr Ala Asn Ser Leu Gly Thr Leu Ala Thr Arg Leu
145                 150                 155                 160 tcg tac gac ctg gag ctg acg ggc ccg agc gtc tcg atg aac acg gcc       528
Ser Tyr Asp Leu Glu Leu Thr Gly Pro Ser Val Ser Met Asn Thr Ala
                165                 170                 175 tgc tcc acc gcg ctc gtc gcc gtg cac acc gcc agc gag gcg ctg gcc       576
Cys Ser Thr Ala Leu Val Ala Val His Thr Ala Ser Glu Ala Leu Ala
            180                 185                 190 gcg tac gcg tgc gac atc gcc gtg gtc ggc gcg gtg tcg gtg gat ccg       624
Ala Tyr Ala Cys Asp Ile Ala Val Val Gly Ala Val Ser Val Asp Pro
        195                 200                 205 cag gcg atg ctc ggg tac cgc cac gtg ccc gac ggc ccg ctc tcc ccc       672
Gln Ala Met Leu Gly Tyr Arg His Val Pro Asp Gly Pro Leu Ser Pro
    210                 215                 220 gac ggg gcg tgc cgg ccg ttc gcc gcg gac gcg gcg ggc acg ttc aac       720
Asp Gly Ala Cys Arg Pro Phe Ala Ala Asp Ala Ala Gly Thr Phe Asn
225                 230                 235                 240 ggc gac ggg gcc ggc gtc ctc gtc ctg cgc cgg ctg tcc gac gcg ctg       768
Gly Asp Gly Ala Gly Val Leu Val Leu Arg Arg Leu Ser Asp Ala Leu
                245                 250                 255 gcg gac ggc gac cgg atc cgg gcc gtc atc cgg ggt tcc gcg atc aac       816
Ala Asp Gly Asp Arg Ile Arg Ala Val Ile Arg Gly Ser Ala Ile Asn
            260                 265                 270 aac gac ggc cgg cgc aag gtc ggt ttc tcg gcc ccg agc ccg gcc ggg       864
Asn Asp Gly Arg Arg Lys Val Gly Phe Ser Ala Pro Ser Pro Ala Gly
        275                 280                 285 cag gcg gag gtc atc gtg gcc gcc cag gtg gcg gcc ggc gtc gac gcc       912
Gln Ala Glu Val Ile Val Ala Ala Gln Val Ala Ala Gly Val Asp Ala
    290                 295                 300 ggc tcg gtg acg tac gtc gag gcc cac ggg acc gcc acg cgc ctc ggc       960
Gly Ser Val Thr Tyr Val Glu Ala His Gly Thr Ala Thr Arg Leu Gly
305                 310                 315                 320 gac ccg atc gag gtc gcg gcc ctc acc gag gcg ttc cgg gag tcc acc      1008
Asp Pro Ile Glu Val Ala Ala Leu Thr Glu Ala Phe Arg Glu Ser Thr
                325                 330                 335 gac cgg cgg ggg tac tgc gcg ctc ggc tcg gtc aag ggc aac atc ggc      1056
Asp Arg Arg Gly Tyr Cys Ala Leu Gly Ser Val Lys Gly Asn Ile Gly
            340                 345                 350 cac ctc ggc gcg gcg gcc ggg atc gcc ggc atc atc aag acc gtc ctc      1104
His Leu Gly Ala Ala Ala Gly Ile Ala Gly Ile Ile Lys Thr Val Leu
        355                 360                 365 gcg ctc gag cac cgg gcc gtg ccc ccg acg gtg cac cac gac gcc ccg      1152
Ala Leu Glu His Arg Ala Val Pro Pro Thr Val His His Asp Ala Pro
    370                 375                 380 aac ccc ctc atc gac ttc gcg agc ggc ccg ttc cgc gtc tcg acg gcg      1200
Asn Pro Leu Ile Asp Phe Ala Ser Gly Pro Phe Arg Val Ser Thr Ala
385                 390                 395                 400 ctg gag ccg tgg acg gcc gac ggc ccg ctg cgc gcc gcg gtg agc gcc      1248
Leu Glu Pro Trp Thr Ala Asp Gly Pro Leu Arg Ala Ala Val Ser Ala
                405                 410                 415
```

```
ttc ggg gtc ggg ggc acc aac gcc cac gtc gtc ctg gag gag gca ccg      1296
Phe Gly Val Gly Gly Thr Asn Ala His Val Val Leu Glu Glu Ala Pro
            420                 425                 430 cgc ctg ccg gta ccc atc ggg ccg gcg gaa gag gcg ccc ggc tgg acc      1344
Arg Leu Pro Val Pro Ile Gly Pro Ala Glu Glu Ala Pro Gly Trp Thr
            435                 440                 445 gta ctg ccg gtg tcg gca cgc acc cgc gac gga ctc gcc ggc caa ctg      1392
Val Leu Pro Val Ser Ala Arg Thr Arg Asp Gly Leu Ala Gly Gln Leu
450                 455                 460 agc cgc ctc ggg cgc cac ttg gag gac aac ccg gaa ctg tcc gtg acc      1440
Ser Arg Leu Gly Arg His Leu Glu Asp Asn Pro Glu Leu Ser Val Thr
465                 470                 475                 480 gag gtg gcg cgc gcc ctg cgc gcc cgg cgc ccg ggg ccc cac cgg cgc      1488
Glu Val Ala Arg Ala Leu Arg Ala Arg Arg Pro Gly Pro His Arg Arg
                485                 490                 495 gcg gtc gcg gcg gcg acc gcg gcg gac gca gcg cgg gcg ctg gcc gcc      1536
Ala Val Ala Ala Ala Thr Ala Ala Asp Ala Ala Arg Ala Leu Ala Ala
                500                 505                 510 gcg acg gtc ccg gcg gcc ggg gcg gag agt gcg ccg gag gtg gtc ttc      1584
Ala Thr Val Pro Ala Ala Gly Ala Glu Ser Ala Pro Glu Val Val Phe
            515                 520                 525 ctg ctg ccc ggc ggt ggc acc cag tac gtg ggg atg ggc gcg gag ctg      1632
Leu Leu Pro Gly Gly Gly Thr Gln Tyr Val Gly Met Gly Ala Glu Leu
530                 535                 540 tac cgc gac gac ccc gcc tac cgc gag gcc gtc gac cgg tgc gcc gcc      1680
Tyr Arg Asp Asp Pro Ala Tyr Arg Glu Ala Val Asp Arg Cys Ala Ala
545                 550                 555                 560 atc ctt cag ccg gtc ctg gac cac gac atc cgc gtc acg ctc cac gag      1728
Ile Leu Gln Pro Val Leu Asp His Asp Ile Arg Val Thr Leu His Glu
                565                 570                 575 cgg gcc gac cac ttc agc gtg gag tcg atg tgc gcg ctc gcg gtg gtc      1776
Arg Ala Asp His Phe Ser Val Glu Ser Met Cys Ala Leu Ala Val Val
                580                 585                 590 gag tac gcc ttg gcc gcc tcg ctg gcg gct tcc ggg gtc cgg ccc ggc      1824
Glu Tyr Ala Leu Ala Ala Ser Leu Ala Ala Ser Gly Val Arg Pro Gly
            595                 600                 605 gcg ctg atg ggg cac tcc ctg ggc gag tac gtg gcg gcg tgc ctc gcg      1872
Ala Leu Met Gly His Ser Leu Gly Glu Tyr Val Ala Ala Cys Leu Ala
610                 615                 620 ggg gtg atg acc ctg gag gag atg ctg ccg ctg ctg gtc acc cgc gtc      1920
Gly Val Met Thr Leu Glu Glu Met Leu Pro Leu Leu Val Thr Arg Val
625                 630                 635                 640 cgg ctg atg atc tcg gcg ggc ggg gcg gcg gtc ggc gtg gcg ctg ccc      1968
Arg Leu Met Ile Ser Ala Gly Gly Ala Ala Val Gly Val Ala Leu Pro
                645                 650                 655 gag cgg gac gtc ctc ccg ctc ctg gac ggt ggg ttg tcc ctg gcg gcg      2016
Glu Arg Asp Val Leu Pro Leu Leu Asp Gly Gly Leu Ser Leu Ala Ala
                660                 665                 670 gtc aac tcg ccg tcc tcg tgc acg gtg ggc gga ccg gtg gag gcc gtc      2064
Val Asn Ser Pro Ser Ser Cys Thr Val Gly Gly Pro Val Glu Ala Val
            675                 680                 685 gac gcg ctg gtc gag cgg ctc gtc gcc gac ggc gtc acc cac cgg cgg      2112
Asp Ala Leu Val Glu Arg Leu Val Ala Asp Gly Val Thr His Arg Arg
690                 695                 700 ctg cgg ctg ccc gcc gcc gcc cac tcc tcg atg ctc gac ccg gtc ctg      2160
Leu Arg Leu Pro Ala Ala Ala His Ser Ser Met Leu Asp Pro Val Leu
705                 710                 715                 720 gac gac ctg gcc gcc gcc ttc cgc ggc gtc gac ctg cgc gag ccg cgc      2208
Asp Asp Leu Ala Ala Ala Phe Arg Gly Val Asp Leu Arg Glu Pro Arg
                725                 730                 735
```

-continued

| | |
|---|---|
| gtc ccg tac atc acc aac gtc acc ggc acg tgg gtc acc gcc gag cag<br>Val Pro Tyr Ile Thr Asn Val Thr Gly Thr Trp Val Thr Ala Glu Gln<br>740                        745                     750 | 2256 |
| gcc acc tcg gtg gag cac tgg gtg gcg cac acg cgc ggc acg gtc cgc<br>Ala Thr Ser Val Glu His Trp Val Ala His Thr Arg Gly Thr Val Arg<br>       755                        760                     765 | 2304 |
| ttc gcc gac ggg gtg cgg acg ctg cgc gcc gcc tcc gcc ggg ggc gcg<br>Phe Ala Asp Gly Val Arg Thr Leu Arg Ala Ala Ser Ala Gly Gly Ala<br>770                        775                     780 | 2352 |
| ggc ccg gtc ctc gtc gag atc ggc ccg ggg gac gtc ctg tcg cgg ctg<br>Gly Pro Val Leu Val Glu Ile Gly Pro Gly Asp Val Leu Ser Arg Leu<br>785                        790                     795                     800 | 2400 |
| gcc gcg gcc gtc gac gac ggc ggc ccg gag ccc gtc acc gtc ccg gtg<br>Ala Ala Ala Val Asp Asp Gly Gly Pro Glu Pro Val Thr Val Pro Val<br>                       805                        810                     815 | 2448 |
| atg cgc cac gcg cgg gcg acc ggg ccc gac ggc cgg gtg cgg gcg gag<br>Met Arg His Ala Arg Ala Thr Gly Pro Asp Gly Arg Val Arg Ala Glu<br>                  820                        825                     830 | 2496 |
| gcg ctc gcg cac ctg tgg acc gcc ggg gcc gag gtg gac atc gtc ccg<br>Ala Leu Ala His Leu Trp Thr Ala Gly Ala Glu Val Asp Ile Val Pro<br>835                        840                     845 | 2544 |
| ccc ggc gac gcg tcg gag gag ggc acc cga ctg ccc cgg cgg tcc ctg<br>Pro Gly Asp Ala Ser Glu Glu Gly Thr Arg Leu Pro Arg Arg Ser Leu<br>850                        855                     860 | 2592 |
| ccc gac ctg ccc ggc tac gcc ttc gcc cgc gac cgg cac tgg atc gac<br>Pro Asp Leu Pro Gly Tyr Ala Phe Ala Arg Asp Arg His Trp Ile Asp<br>865                        870                     875                     880 | 2640 |
| gcc ccc ggc gcc cgg gcg acc acg gcc ccg cac ggc gca tcc gac gac<br>Ala Pro Gly Ala Arg Ala Thr Thr Ala Pro His Gly Ala Ser Asp Asp<br>                       885                        890                     895 | 2688 |
| cgc gcc ggc gac cgc gcc tcg cgc cgc gtc ccg cgt ccg ccg ctg gcc<br>Arg Ala Gly Asp Arg Ala Ser Arg Arg Val Pro Arg Pro Pro Leu Ala<br>                  900                        905                     910 | 2736 |
| gtg ccg cac gtg ccg ccg ggc acc gac gcg gag cgg gcc gtg gcg gcc<br>Val Pro His Val Pro Pro Gly Thr Asp Ala Glu Arg Ala Val Ala Ala<br>915                        920                     925 | 2784 |
| gag tgg gag gcc gtg ctc ggt gtc gac ggc atc ggg ctc gac gac aac<br>Glu Trp Glu Ala Val Leu Gly Val Asp Gly Ile Gly Leu Asp Asp Asn<br>930                        935                     940 | 2832 |
| ttc ttc gac ctc ggc ggc gat tcg atg cgc gcc gtg ctc ctc ggc ggg<br>Phe Phe Asp Leu Gly Gly Asp Ser Met Arg Ala Val Leu Leu Gly Gly<br>945                        950                     955                     960 | 2880 |
| cgc ctg cgc acc gcg ggc gtg ctc gac gtg ccg gcc gcg gcc ctg ctc<br>Arg Leu Arg Thr Ala Gly Val Leu Asp Val Pro Ala Ala Ala Leu Leu<br>                       965                        970                     975 | 2928 |
| gcc acg ccg acg atc gcc gga ctg ctc gac cgc gcc ggg cgc ggc ggg<br>Ala Thr Pro Thr Ile Ala Gly Leu Leu Asp Arg Ala Gly Arg Gly Gly<br>                  980                        985                     990 | 2976 |
| gcc gtc ggg cag gag gcg ttc gcc ccc atg ctg ccg atg cgg gcc gcg<br>Ala Val Gly Gln Glu Ala Phe Ala Pro Met Leu Pro Met Arg Ala Ala<br>995                        1000                     1005 | 3024 |
| ggg gat ctg ccg ccg ctg ttc tgc gtg cac ccg gtc agc ggc gtc<br>Gly Asp Leu Pro Pro Leu Phe Cys Val His Pro Val Ser Gly Val<br>                       1010                     1015                     1020 | 3069 |
| gcc tgg cgc tac acg ggg ctg ctg ccg cac ctc gac ccg cgc cgc<br>Ala Trp Arg Tyr Thr Gly Leu Leu Pro His Leu Asp Pro Arg Arg<br>1025                     1030                     1035 | 3114 |
| ccg gtg tac ggc ctc cag gcc ctt ggc ctg gac ggc gcc ctt ccc<br>Pro Val Tyr Gly Leu Gln Ala Leu Gly Leu Asp Gly Ala Leu Pro | 3159 |

-continued

```
                1040                1045                1050
gcc gcc ggg cgc gcc gag gac gtg atc cgg gac ggc ctg gaa cgg          3204
Ala Ala Gly Arg Ala Glu Asp Val Ile Arg Asp Gly Leu Glu Arg
        1055                1060                1065 atc cgg gcc gtc cag ccc cac ggc ccg tac cac ctg ctg ggc tgg          3249
Ile Arg Ala Val Gln Pro His Gly Pro Tyr His Leu Leu Gly Trp
    1070                1075                1080 tcg ttc ggc ggc gcc gtc gcc cac cgc ctg gcc gcc gcc ctg gag          3294
Ser Phe Gly Gly Ala Val Ala His Arg Leu Ala Ala Ala Leu Glu
1085                1090                1095 gcg gcc ggc gag gag gtc gcg ctg ctg acc atg ctc gac acg ccg          3339
Ala Ala Gly Glu Glu Val Ala Leu Leu Thr Met Leu Asp Thr Pro
        1100                1105                1110 cag ccg gac gcg gcg gcg ctg gag ggc gag gcg gtc gag gcg cag          3384
Gln Pro Asp Ala Ala Ala Leu Glu Gly Glu Ala Val Glu Ala Gln
    1115                1120                1125 gcc gcc gcc ctc gtc ctg cgg ctg gcc ggc ttg acc atg ccc gcg          3429
Ala Ala Ala Leu Val Leu Arg Leu Ala Gly Leu Thr Met Pro Ala
1130                1135                1140 ccg gcc acg gtc gac gcg tcg ctc gcg ctg ctc gac tcc tcc cgc          3474
Pro Ala Thr Val Asp Ala Ser Leu Ala Leu Leu Asp Ser Ser Arg
        1145                1150                1155 cgg gac ccc gag gcg gtg ccg ggc acg ctc acg cgt gag gag gcg          3519
Arg Asp Pro Glu Ala Val Pro Gly Thr Leu Thr Arg Glu Glu Ala
    1160                1165                1170 atc acc gtg gcg aag gtg gtc cgc aac aat ctg cgg atc gcc ccc          3564
Ile Thr Val Ala Lys Val Val Arg Asn Asn Leu Arg Ile Ala Pro
1175                1180                1185 gat ctg gtt ccg gaa cgg ctg cgc gcc gac atc ctc ttc gtc tcg          3609
Asp Leu Val Pro Glu Arg Leu Arg Ala Asp Ile Leu Phe Val Ser
        1190                1195                1200 gcc acc gaa gtc gcc gac gac gaa ccg gag gtc gcg ggc ggg atc          3654
Ala Thr Glu Val Ala Asp Asp Glu Pro Glu Val Ala Gly Gly Ile
    1205                1210                1215 gcc gac cgg gcc gcg tcc tgg cgc ccg ttc acc acc ggc acc ttc          3699
Ala Asp Arg Ala Ala Ser Trp Arg Pro Phe Thr Thr Gly Thr Phe
1220                1225                1230 gag gag gtt cct ctc gcc tgc tcc cac tac gcc ctg acc gac gcc          3744
Glu Glu Val Pro Leu Ala Cys Ser His Tyr Ala Leu Thr Asp Ala
        1235                1240                1245 ggc ccg atc gag gtg att gcg aag gcg gtc gag gcg cgt ctc gcg          3789
Gly Pro Ile Glu Val Ile Ala Lys Ala Val Glu Ala Arg Leu Ala
    1250                1255                1260 ggg gcc ggc gga ggg gaa cgg gcg gag gtg gcg gcc gga tga              3831
Gly Ala Gly Gly Gly Glu Arg Ala Glu Val Ala Ala Gly
1265                1270                1275
```

<210> SEQ ID NO 25
<211> LENGTH: 1276
<212> TYPE: PRT
<213> ORGANISM: Streptoverticillium

<400> SEQUENCE: 25

Met Ala Thr Glu Pro Leu Ala Val Val Gly Met Ala Gly Arg Phe Pro
1               5                   10                  15

Gly Ala Asn Thr Leu Glu Glu Phe Trp Ala Leu Leu Ser Glu Gly Arg
            20                  25                  30

Gln Gly Val Arg Glu Val Thr Glu Glu Glu Phe Leu Ala Ala Gly Gly
        35                  40                  45

```
Asp Pro Ala Asp Leu Glu Asp Pro Ser Leu Val Arg Val Ala Ala Val
 50                  55                  60
Leu Pro Asp Ala Asp Arg Phe Asp Ala Ala Phe Phe Gly Tyr Gly Pro
 65                  70                  75                  80
Ala Glu Ala Glu Leu Ile Asp Pro Gln Gln Arg Val Leu Leu Glu Thr
                 85                  90                  95
Ala Tyr His Ala Leu Glu Asp Ala Gly Tyr Ala Asp Gly His Gly Asp
                100                 105                 110
Arg Val Val Gly Val Tyr Ala Gly Ala Gly Asp Ser Arg Tyr Tyr Ser
            115                 120                 125
Tyr Asn Val His Pro Arg His Ala Gly Glu Pro Ala Ser Val Gly Leu
130                 135                 140
Ile His Ala Ala Thr Ala Asn Ser Leu Gly Thr Leu Ala Thr Arg Leu
145                 150                 155                 160
Ser Tyr Asp Leu Glu Leu Thr Gly Pro Ser Val Ser Met Asn Thr Ala
                165                 170                 175
Cys Ser Thr Ala Leu Val Ala Val His Thr Ala Ser Glu Ala Leu Ala
                180                 185                 190
Ala Tyr Ala Cys Asp Ile Ala Val Val Gly Ala Val Ser Val Asp Pro
                195                 200                 205
Gln Ala Met Leu Gly Tyr Arg His Val Pro Asp Gly Pro Leu Ser Pro
            210                 215                 220
Asp Gly Ala Cys Arg Pro Phe Ala Ala Asp Ala Ala Gly Thr Phe Asn
225                 230                 235                 240
Gly Asp Gly Ala Gly Val Leu Val Leu Arg Arg Leu Ser Asp Ala Leu
                245                 250                 255
Ala Asp Gly Asp Arg Ile Arg Ala Val Ile Arg Gly Ser Ala Ile Asn
                260                 265                 270
Asn Asp Gly Arg Arg Lys Val Gly Phe Ser Ala Pro Ser Pro Ala Gly
            275                 280                 285
Gln Ala Glu Val Ile Val Ala Ala Gln Val Ala Ala Gly Val Asp Ala
            290                 295                 300
Gly Ser Val Thr Tyr Val Glu Ala His Gly Thr Ala Thr Arg Leu Gly
305                 310                 315                 320
Asp Pro Ile Glu Val Ala Ala Leu Thr Glu Ala Phe Arg Glu Ser Thr
                325                 330                 335
Asp Arg Arg Gly Tyr Cys Ala Leu Gly Ser Val Lys Gly Asn Ile Gly
            340                 345                 350
His Leu Gly Ala Ala Ala Gly Ile Ala Gly Ile Ile Lys Thr Val Leu
            355                 360                 365
Ala Leu Glu His Arg Ala Val Pro Pro Thr Val His His Asp Ala Pro
370                 375                 380
Asn Pro Leu Ile Asp Phe Ala Ser Gly Pro Phe Arg Val Ser Thr Ala
385                 390                 395                 400
Leu Glu Pro Trp Thr Ala Asp Gly Pro Leu Arg Ala Ala Val Ser Ala
                405                 410                 415
Phe Gly Val Gly Gly Thr Asn Ala His Val Val Leu Glu Glu Ala Pro
                420                 425                 430
Arg Leu Pro Val Pro Ile Gly Pro Ala Glu Glu Ala Pro Gly Trp Thr
            435                 440                 445
Val Leu Pro Val Ser Ala Arg Thr Arg Asp Gly Leu Ala Gly Gln Leu
450                 455                 460
Ser Arg Leu Gly Arg His Leu Glu Asp Asn Pro Glu Leu Ser Val Thr
```

```
            465                 470                 475                 480
        Glu Val Ala Arg Ala Leu Arg Ala Arg Arg Pro Gly Pro His Arg Arg
                        485                 490                 495
        Ala Val Ala Ala Ala Thr Ala Ala Asp Ala Ala Arg Ala Leu Ala Ala
                        500                 505                 510
        Ala Thr Val Pro Ala Ala Gly Ala Glu Ser Ala Pro Glu Val Val Phe
                        515                 520                 525
        Leu Leu Pro Gly Gly Gly Thr Gln Tyr Val Gly Met Gly Ala Glu Leu
                        530                 535                 540
        Tyr Arg Asp Asp Pro Ala Tyr Arg Glu Ala Val Asp Arg Cys Ala Ala
        545                 550                 555                 560
        Ile Leu Gln Pro Val Leu Asp His Asp Ile Arg Val Thr Leu His Glu
                        565                 570                 575
        Arg Ala Asp His Phe Ser Val Glu Ser Met Cys Ala Leu Ala Val Val
                        580                 585                 590
        Glu Tyr Ala Leu Ala Ala Ser Leu Ala Ala Ser Gly Val Arg Pro Gly
                        595                 600                 605
        Ala Leu Met Gly His Ser Leu Gly Glu Tyr Val Ala Ala Cys Leu Ala
                        610                 615                 620
        Gly Val Met Thr Leu Glu Glu Met Leu Pro Leu Leu Val Thr Arg Val
        625                 630                 635                 640
        Arg Leu Met Ile Ser Ala Gly Gly Ala Ala Val Gly Val Ala Leu Pro
                        645                 650                 655
        Glu Arg Asp Val Leu Pro Leu Leu Asp Gly Gly Leu Ser Leu Ala Ala
                        660                 665                 670
        Val Asn Ser Pro Ser Ser Cys Thr Val Gly Gly Pro Val Glu Ala Val
                        675                 680                 685
        Asp Ala Leu Val Glu Arg Leu Val Ala Asp Gly Val Thr His Arg Arg
                        690                 695                 700
        Leu Arg Leu Pro Ala Ala Ala His Ser Ser Met Leu Asp Pro Val Leu
        705                 710                 715                 720
        Asp Asp Leu Ala Ala Ala Phe Arg Gly Val Asp Leu Arg Glu Pro Arg
                        725                 730                 735
        Val Pro Tyr Ile Thr Asn Val Thr Gly Thr Trp Val Thr Ala Glu Gln
                        740                 745                 750
        Ala Thr Ser Val Glu His Trp Val Ala His Thr Arg Gly Thr Val Arg
                        755                 760                 765
        Phe Ala Asp Gly Val Arg Thr Leu Arg Ala Ala Ser Ala Gly Gly Ala
        770                 775                 780
        Gly Pro Val Leu Val Glu Ile Gly Pro Gly Asp Val Leu Ser Arg Leu
        785                 790                 795                 800
        Ala Ala Ala Val Asp Asp Gly Gly Pro Glu Pro Val Thr Val Pro Val
                        805                 810                 815
        Met Arg His Ala Arg Ala Thr Gly Pro Asp Gly Arg Val Arg Ala Glu
                        820                 825                 830
        Ala Leu Ala His Leu Trp Thr Ala Gly Ala Glu Val Asp Ile Val Pro
                        835                 840                 845
        Pro Gly Asp Ala Ser Glu Glu Gly Thr Arg Leu Pro Arg Arg Ser Leu
                        850                 855                 860
        Pro Asp Leu Pro Gly Tyr Ala Phe Ala Arg Asp Arg His Trp Ile Asp
        865                 870                 875                 880
        Ala Pro Gly Ala Arg Ala Thr Thr Ala Pro His Gly Ala Ser Asp Asp
                        885                 890                 895
```

Arg Ala Gly Asp Arg Ala Ser Arg Arg Val Pro Arg Pro Leu Ala
            900                 905                 910

Val Pro His Val Pro Pro Gly Thr Asp Ala Glu Arg Ala Val Ala Ala
            915                 920                 925

Glu Trp Glu Ala Val Leu Gly Val Asp Gly Ile Gly Leu Asp Asp Asn
        930                 935                 940

Phe Phe Asp Leu Gly Gly Asp Ser Met Arg Ala Val Leu Leu Gly Gly
945                 950                 955                 960

Arg Leu Arg Thr Ala Gly Val Leu Asp Val Pro Ala Ala Ala Leu Leu
                965                 970                 975

Ala Thr Pro Thr Ile Ala Gly Leu Leu Asp Arg Ala Gly Arg Gly Gly
            980                 985                 990

Ala Val Gly Gln Glu Ala Phe Ala Pro Met Leu Pro Met Arg Ala Ala
            995                 1000                1005

Gly Asp Leu Pro Pro Leu Phe Cys Val His Pro Val Ser Gly Val
        1010                1015                1020

Ala Trp Arg Tyr Thr Gly Leu Leu Pro His Leu Asp Pro Arg Arg
        1025                1030                1035

Pro Val Tyr Gly Leu Gln Ala Leu Gly Leu Asp Gly Ala Leu Pro
        1040                1045                1050

Ala Ala Gly Arg Ala Glu Asp Val Ile Arg Asp Gly Leu Glu Arg
        1055                1060                1065

Ile Arg Ala Val Gln Pro His Gly Pro Tyr His Leu Leu Gly Trp
        1070                1075                1080

Ser Phe Gly Gly Ala Val Ala His Arg Leu Ala Ala Ala Leu Glu
        1085                1090                1095

Ala Ala Gly Glu Glu Val Ala Leu Leu Thr Met Leu Asp Thr Pro
        1100                1105                1110

Gln Pro Asp Ala Ala Ala Leu Glu Gly Glu Ala Val Glu Ala Gln
        1115                1120                1125

Ala Ala Ala Leu Val Leu Arg Leu Ala Gly Leu Thr Met Pro Ala
        1130                1135                1140

Pro Ala Thr Val Asp Ala Ser Leu Ala Leu Leu Asp Ser Ser Arg
        1145                1150                1155

Arg Asp Pro Glu Ala Val Pro Gly Thr Leu Thr Arg Glu Glu Ala
        1160                1165                1170

Ile Thr Val Ala Lys Val Val Arg Asn Asn Leu Arg Ile Ala Pro
        1175                1180                1185

Asp Leu Val Pro Glu Arg Leu Arg Ala Asp Ile Leu Phe Val Ser
        1190                1195                1200

Ala Thr Glu Val Ala Asp Asp Glu Pro Glu Val Ala Gly Gly Ile
        1205                1210                1215

Ala Asp Arg Ala Ala Ser Trp Arg Pro Phe Thr Thr Gly Thr Phe
        1220                1225                1230

Glu Glu Val Pro Leu Ala Cys Ser His Tyr Ala Leu Thr Asp Ala
        1235                1240                1245

Gly Pro Ile Glu Val Ile Ala Lys Ala Val Glu Ala Arg Leu Ala
        1250                1255                1260

Gly Ala Gly Gly Gly Glu Arg Ala Glu Val Ala Ala Gly
        1265                1270                1275

<210> SEQ ID NO 26
<211> LENGTH: 9735

```
<212> TYPE: DNA
<213> ORGANISM: Streptoverticillium
<220> FEATURE:
<221> NAME/KEY: CDS
<222> LOCATION: (1)..(9735)

<400> SEQUENCE: 26
```

| | | | | | | | | | | | | | | | | |
|---|---|---|---|---|---|---|---|---|---|---|---|---|---|---|---|---|
| atg | ccc | gac | cgt | gct | gcc | gac | tcg | tgt | ccg | ctg | acc | gcc | ccg | cag | gcc | 48 |
| Met | Pro | Asp | Arg | Ala | Ala | Asp | Ser | Cys | Pro | Leu | Thr | Ala | Pro | Gln | Ala | |
| 1 | | | | 5 | | | | 10 | | | | | 15 | | | |
| ggg | atc | tgg | ttc | gcc | cag | cag | cgt | gac | acc | tcc | aac | ccg | gtc | ttc | acc | 96 |
| Gly | Ile | Trp | Phe | Ala | Gln | Gln | Arg | Asp | Thr | Ser | Asn | Pro | Val | Phe | Thr | |
| | | | 20 | | | | | 25 | | | | | 30 | | | |
| aca | ggc | cag | tac | gtg | cgg | ctg | ccc | gcc | gag | gtc | gac | ccg | gag | cgg | ttc | 144 |
| Thr | Gly | Gln | Tyr | Val | Arg | Leu | Pro | Ala | Glu | Val | Asp | Pro | Glu | Arg | Phe | |
| | | 35 | | | | | 40 | | | | | 45 | | | | |
| gcg | cgc | gcg | gtc | gag | cgg | gcc | ctc | ggc | gag | gtg | tgg | ggg | ctc | gcg | gtc | 192 |
| Ala | Arg | Ala | Val | Glu | Arg | Ala | Leu | Gly | Glu | Val | Trp | Gly | Leu | Ala | Val | |
| | 50 | | | | | 55 | | | | | 60 | | | | | |
| gag | gtg | ggc | gcg | gac | ggc | gac | gtc | ccc | gtc | cag | cgc | ggg | acc | ggc | acg | 240 |
| Glu | Val | Gly | Ala | Asp | Gly | Asp | Val | Pro | Val | Gln | Arg | Gly | Thr | Gly | Thr | |
| 65 | | | | | 70 | | | | | 75 | | | | | 80 | |
| gca | ccc | cgc | gtg | gag | gtc | gtc | gac | ctc | tcc | ggg | cgg | ccc | gac | ccg | gag | 288 |
| Ala | Pro | Arg | Val | Glu | Val | Val | Asp | Leu | Ser | Gly | Arg | Pro | Asp | Pro | Glu | |
| | | | | 85 | | | | | 90 | | | | | 95 | | |
| gcc | gtc | gcc | ctg | gcg | cgg | atg | cgc | gcc | gac | ctc | gaa | cag | ccg | cct | gtg | 336 |
| Ala | Val | Ala | Leu | Ala | Arg | Met | Arg | Ala | Asp | Leu | Glu | Gln | Pro | Pro | Val | |
| | | | 100 | | | | | 105 | | | | | 110 | | | |
| ggg | cgg | ccg | ttg | gcg | cgg | gag | gtc | ctg | ttc | cgg | tgg | cag | ggc | ggg | gcc | 384 |
| Gly | Arg | Pro | Leu | Ala | Arg | Glu | Val | Leu | Phe | Arg | Trp | Gln | Gly | Gly | Ala | |
| | | 115 | | | | | 120 | | | | | 125 | | | | |
| ctg | tgg | ttc | cac | cgc | tgc | cac | cac | atg | ctc | ctc | gac | ggc | tac | ggg | ttc | 432 |
| Leu | Trp | Phe | His | Arg | Cys | His | His | Met | Leu | Leu | Asp | Gly | Tyr | Gly | Phe | |
| | 130 | | | | | 135 | | | | | 140 | | | | | |
| tcg | ctg | gtc | ctg | cgg | cgg | atc | gag | gag | atc | cac | gaa | gcg | ctg | cgc | acg | 480 |
| Ser | Leu | Val | Leu | Arg | Arg | Ile | Glu | Glu | Ile | His | Glu | Ala | Leu | Arg | Thr | |
| 145 | | | | | 150 | | | | | 155 | | | | | 160 | |
| ggc | ggg | tca | ccg | ggt | gag | ccc | gcc | ttc | ggc | ggc | ctc | ggg | gcg | tac | ctg | 528 |
| Gly | Gly | Ser | Pro | Gly | Glu | Pro | Ala | Phe | Gly | Gly | Leu | Gly | Ala | Tyr | Leu | |
| | | | | 165 | | | | | 170 | | | | | 175 | | |
| gac | gag | gag | gcc | ggg | tac | cgg | gcg | ggc | gac | cgg | atg | ccg | cgg | gac | cgc | 576 |
| Asp | Glu | Glu | Ala | Gly | Tyr | Arg | Ala | Gly | Asp | Arg | Met | Pro | Arg | Asp | Arg | |
| | | | 180 | | | | | 185 | | | | | 190 | | | |
| gcc | tac | tgg | ctg | gac | gca | ctc | gcc | gaa | ctc | ccg | ccc | ccg | gta | agc | ctg | 624 |
| Ala | Tyr | Trp | Leu | Asp | Ala | Leu | Ala | Glu | Leu | Pro | Pro | Pro | Val | Ser | Leu | |
| | | 195 | | | | | 200 | | | | | 205 | | | | |
| tcc | ggc | acg | cct | ccg | gag | ccg | gcg | cgc | ggc | gcg | ccg | ctg | aag | gcg | cgc | 672 |
| Ser | Gly | Thr | Pro | Pro | Glu | Pro | Ala | Arg | Gly | Ala | Pro | Leu | Lys | Ala | Arg | |
| | 210 | | | | | 215 | | | | | 220 | | | | | |
| gtc | gac | gtg | ctg | ccc | gat | ccg | gcc | ggc | ctc | gcc | cgg | ctc | gcc | gag | agc | 720 |
| Val | Asp | Val | Leu | Pro | Asp | Pro | Ala | Gly | Leu | Ala | Arg | Leu | Ala | Glu | Ser | |
| 225 | | | | | 230 | | | | | 235 | | | | | 240 | |
| ctc | tcg | gcc | acg | acc | gcg | gac | ctg | gcg | atc | gcc | gcc | acc | gcc | gtc | tac | 768 |
| Leu | Ser | Ala | Thr | Thr | Ala | Asp | Leu | Ala | Ile | Ala | Ala | Thr | Ala | Val | Tyr | |
| | | | | 245 | | | | | 250 | | | | | 255 | | |
| cag | cac | cgg | gtg | acc | ggt | gcc | gcc | gac | gtc | gtc | ctc | gcc | ctg | ccg | ctg | 816 |
| Gln | His | Arg | Val | Thr | Gly | Ala | Ala | Asp | Val | Val | Leu | Ala | Leu | Pro | Leu | |
| | | | 260 | | | | | 265 | | | | | 270 | | | |
| gcc | ctg | cgg | ggc | ggc | gcg | gcc | gcg | cgc | ctg | ccc | tcg | acc | acc | gtc | aac | 864 |
| Ala | Leu | Arg | Gly | Gly | Ala | Ala | Ala | Arg | Leu | Pro | Ser | Thr | Thr | Val | Asn | |
| | | 275 | | | | | 280 | | | | | 285 | | | | |

```
gtg ctg ccg ctg cgg gta cgg gtc gcg gac ggc gac acg gtc ggc acg       912
Val Leu Pro Leu Arg Val Arg Val Ala Asp Gly Asp Thr Val Gly Thr
    290             295                 300 ctg gtc gcc cgg ctg cgg aag gcg atg cgg gag ctg cgc cgc cac ggg       960
Leu Val Ala Arg Leu Arg Lys Ala Met Arg Glu Leu Arg Arg His Gly
305                 310                 315                 320 cgg tac cgc gtc gag gac atc cgc cgg gac ctc ggg cgc gtc acc gac      1008
Arg Tyr Arg Val Glu Asp Ile Arg Arg Asp Leu Gly Arg Val Thr Asp
                325                 330                 335 gag tcc gag ttc acc acc gcc cag gtc aac atc aag agt tac gac acc      1056
Glu Ser Glu Phe Thr Thr Ala Gln Val Asn Ile Lys Ser Tyr Asp Thr
            340                 345                 350 acg atc ggg ctc ctg ggc cgg cgc ctc ccg gtc gtg gac ctc tcc ccc      1104
Thr Ile Gly Leu Leu Gly Arg Arg Leu Pro Val Val Asp Leu Ser Pro
        355                 360                 365 ggg ccc gtc gac gac atc gcg ttc gtc gtg gac ctc gcc gag gac ggc      1152
Gly Pro Val Asp Asp Ile Ala Phe Val Val Asp Leu Ala Glu Asp Gly
    370                 375                 380 gag ctg acc acc ctg gag gtc gag gcc aac gcc ctc cgg tac gac gcg      1200
Glu Leu Thr Thr Leu Glu Val Glu Ala Asn Ala Leu Arg Tyr Asp Ala
385                 390                 395                 400 ccg acg gcg ctg gcg cac ggc cgc ggg ctc ggg cgc ctg ctg ggc gcg      1248
Pro Thr Ala Leu Ala His Gly Arg Gly Leu Gly Arg Leu Leu Gly Ala
                405                 410                 415 ctc gcc gag gcc ggc ccc gac acg gcc gtc gac gac ctg gga gcg gtg      1296
Leu Ala Glu Ala Gly Pro Asp Thr Ala Val Asp Asp Leu Gly Ala Val
            420                 425                 430 ggg ccg atc tac gac acc ggc cac tac ctg gac ctc cgg ggg ccg gtc      1344
Gly Pro Ile Tyr Asp Thr Gly His Tyr Leu Asp Leu Arg Gly Pro Val
        435                 440                 445 gac cgc gag ggc ctc cgc gcg gcg ggc gtc cgc gcg gtg cgc gat gcg      1392
Asp Arg Glu Gly Leu Arg Ala Ala Gly Val Arg Ala Val Arg Asp Ala
    450                 455                 460 gcg tac ggg ctg gtg gac ggg ccg gtg gac ggg ccg atg ggg gaa gcg      1440
Ala Tyr Gly Leu Val Asp Gly Pro Val Asp Gly Pro Met Gly Glu Ala
465                 470                 475                 480 gcg tcc gga ccg gcg ggc ggg tcg gcg gac acg tcg gcg gac ggc gag      1488
Ala Ser Gly Pro Ala Gly Gly Ser Ala Asp Thr Ser Ala Asp Gly Glu
                485                 490                 495 ggc gcg cca tgc ggg ccg gcc gaa ttc gtc gat ctc tcc ggt gag agc      1536
Gly Ala Pro Cys Gly Pro Ala Glu Phe Val Asp Leu Ser Gly Glu Ser
            500                 505                 510 gac ccg gcc ggc gcg gcc ctg gcc tgg atg cgg gcc gag ctg gcg cgc      1584
Asp Pro Ala Gly Ala Ala Leu Ala Trp Met Arg Ala Glu Leu Ala Arg
        515                 520                 525 ccg gcc gcg acg gcc tgc ggc cac gcg gtg ctc gcg ctc gga ccg gag      1632
Pro Ala Ala Thr Ala Cys Gly His Ala Val Leu Ala Leu Gly Pro Glu
    530                 535                 540 cac cac ctg tgg ttc cgg cgt acg ggc ggt ccc gag tcc gac gag cgc      1680
His His Leu Trp Phe Arg Arg Thr Gly Gly Pro Glu Ser Asp Glu Arg
545                 550                 555                 560 gcc gcg ccg gcc ctg gcc cgg cgc gtc gcc gcg ctc gcc ggg gcg ccg      1728
Ala Ala Pro Ala Leu Ala Arg Arg Val Ala Ala Leu Ala Gly Ala Pro
                565                 570                 575 gac ggc ctc gcg gac gtc gcg gac gtc gcg gac gtc gcg gcc gat tcc      1776
Asp Gly Leu Ala Asp Val Ala Asp Val Ala Asp Val Ala Ala Asp Ser
            580                 585                 590 cgg ccc gcc ggc tcc ggc tcc cgg cac cgc gag atc gcg gtc ccg gcc      1824
Arg Pro Ala Gly Ser Gly Ser Arg His Arg Glu Ile Ala Val Pro Ala
```

```
                   595                 600                 605
gcg ctc ggc cgc cgg atg atg gaa gga tcc cgc gaa ctc ggg gta ggg    1872
Ala Leu Gly Arg Arg Met Met Glu Gly Ser Arg Glu Leu Gly Val Gly
    610                 615                 620 ata cgg gat ttc gtg gca gcc gtc gcg atg ttc acc gct cgc cgc        1920
Ile Arg Asp Phe Val Ala Ala Val Ala Met Phe Thr Ala Arg Arg
625                 630                 635                 640 cgt ggg agc ggc gcg gtc gag ctg tac gtc ccg gcc gcc gat ggc acc    1968
Arg Gly Ser Gly Ala Val Glu Leu Tyr Val Pro Ala Ala Asp Gly Thr
                645                 650                 655 ccc gtc ccg ctg ccg ctg gac ctc acg ggc acc acg acg ctc gcg gag    2016
Pro Val Pro Leu Pro Leu Asp Leu Thr Gly Thr Thr Thr Leu Ala Glu
            660                 665                 670 acc gtc gcc gcg gtc cag gac ggg cgc ggc cac cgc gcg acg gcg gac    2064
Thr Val Ala Ala Val Gln Asp Gly Arg Gly His Arg Ala Thr Ala Asp
        675                 680                 685 ggg cgc gta tcc ggc ccg tcc gtg acc gtc gca cgg tgg gcc ggg aca    2112
Gly Arg Val Ser Gly Pro Ser Val Thr Val Ala Arg Trp Ala Gly Thr
    690                 695                 700 ccg gac cgc gac gcg gcg ctg cac ctc gtc tcc gcg gct ccc gcg acc    2160
Pro Asp Arg Asp Ala Ala Leu His Leu Val Ser Ala Ala Pro Ala Thr
705                 710                 715                 720 ggc ccc gcc gtg acg gcg gtc ctc ggc gag gac cgc gtc cgc gca ctc    2208
Gly Pro Ala Val Thr Ala Val Leu Gly Glu Asp Arg Val Arg Ala Leu
                725                 730                 735 cag gtg gac gac gcc ccc gac gac ccc gcc tgg tcc gac agc gaa ctg    2256
Gln Val Asp Asp Ala Pro Asp Asp Pro Ala Trp Ser Asp Ser Glu Leu
            740                 745                 750 cgc cgt ttc ata cgc ctg ttg gac gcg gtg acc gcc gac ccc gag acc    2304
Arg Arg Phe Ile Arg Leu Leu Asp Ala Val Thr Ala Asp Pro Glu Thr
        755                 760                 765 acg ctc gcc gga gtc gac ctc ctc gac gag gcc gag cac cgc aca ctg    2352
Thr Leu Ala Gly Val Asp Leu Leu Asp Glu Ala Glu His Arg Thr Leu
    770                 775                 780 gcc gcc gac gcc gac acc gcc cac ccg gta ccc gtc acc acc ctg gac    2400
Ala Ala Asp Ala Asp Thr Ala His Pro Val Pro Val Thr Thr Leu Asp
785                 790                 795                 800 cgg ctc gtc gcc gag cag atc gcg cgg acg ccg gac gcc gta gcg ctg    2448
Arg Leu Val Ala Glu Gln Ile Ala Arg Thr Pro Asp Ala Val Ala Leu
                805                 810                 815 gtg ccc gcc gac ggc tcg ccg gag ctc acc tac cgt gaa ctc ggc gag    2496
Val Pro Ala Asp Gly Ser Pro Glu Leu Thr Tyr Arg Glu Leu Gly Glu
            820                 825                 830 cgg gtg gac cgg ctg gcc cgt ggc ctc gcc ggg ctc ggc gcg ggt ccg    2544
Arg Val Asp Arg Leu Ala Arg Gly Leu Ala Gly Leu Gly Ala Gly Pro
        835                 840                 845 ggg acg atc gtc gcg gtc gcc cag ccg cgt tcg acg gcc ctg gtc gtg    2592
Gly Thr Ile Val Ala Val Ala Gln Pro Arg Ser Thr Ala Leu Val Val
    850                 855                 860 agc ctg ctg gcg gtg ctg cgg acc ggc gcg gcc tac gcg ccg ctg gac    2640
Ser Leu Leu Ala Val Leu Arg Thr Gly Ala Ala Tyr Ala Pro Leu Asp
865                 870                 875                 880 ctc gac cac ccg ccg gcc cgg ctc gcc gcc gtc ctg gag gac gtc cgg    2688
Leu Asp His Pro Pro Ala Arg Leu Ala Ala Val Leu Glu Asp Val Arg
                885                 890                 895 ccc gtc gcg gtc ctc acc gcc gga ccc gcg ccc gtc gcg ctg ccg gcg    2736
Pro Val Ala Val Leu Thr Ala Gly Pro Ala Pro Val Ala Leu Pro Ala
            900                 905                 910 gag ctg aac gtc gtc gac gtc ctc gcc ctg cgg gcc gac ggc acg ggc    2784
Glu Leu Asn Val Val Asp Val Leu Ala Leu Arg Ala Asp Gly Thr Gly
```

```
                Glu Leu Asn Val Val Asp Val Leu Ala Leu Arg Ala Asp Gly Thr Gly
                            915                 920                 925 gcg gcc ccg gcc ggt ccc ggc ccc gac gac ctg gcc tac gtc atc cac      2832
Ala Ala Pro Ala Gly Pro Gly Pro Asp Asp Leu Ala Tyr Val Ile His
            930                 935                 940 acc tcg ggc tcg acc ggc cgc ccc aag ggc gtc gcc gtc gcc cac cgg      2880
Thr Ser Gly Ser Thr Gly Arg Pro Lys Gly Val Ala Val Ala His Arg
945                 950                 955                 960 gcc gtc gtc aac cgg ctg ttg tgg acc cag gac cgg ttc ggc ctg ggc      2928
Ala Val Val Asn Arg Leu Leu Trp Thr Gln Asp Arg Phe Gly Leu Gly
                965                 970                 975 ccg ggc gac cgg gtg ctg cag aag acc agc tgc gcg ttc gac gtc tcc      2976
Pro Gly Asp Arg Val Leu Gln Lys Thr Ser Cys Ala Phe Asp Val Ser
            980                 985                 990 gtc tgg gag ttc ttc tgg ccc ttg atc agc ggg gcg acg ctg gtc ctg      3024
Val Trp Glu Phe Phe Trp Pro Leu Ile Ser Gly Ala Thr Leu Val Leu
        995                 1000                1005 ccg gcc ccc ggc gcg cag cgc gac ccg gcg cgg gtc gcc gcg gcg          3069
Pro Ala Pro Gly Ala Gln Arg Asp Pro Ala Arg Val Ala Ala Ala
    1010                1015                1020 atc gac gag gcg ggc atc acg acc gcc cac ttc gtc ccg tcg atg          3114
Ile Asp Glu Ala Gly Ile Thr Thr Ala His Phe Val Pro Ser Met
1025                1030                1035 ctc gtc gcc tat ctc ggc gag ccg gcc gcc gcg cgg cct cgc gcg          3159
Leu Val Ala Tyr Leu Gly Glu Pro Ala Ala Ala Arg Pro Arg Ala
    1040                1045                1050 ctg cgg cgg atc ctg tgc agc ggc gag gcc ctg ccg acc gag gcg          3204
Leu Arg Arg Ile Leu Cys Ser Gly Glu Ala Leu Pro Thr Glu Ala
    1055                1060                1065 gcg cgg cgg gcc gag gag gtc acc ggc gcg gag gtc ttc aac ctc          3249
Ala Arg Arg Ala Glu Glu Val Thr Gly Ala Glu Val Phe Asn Leu
    1070                1075                1080 tac ggc ccg acc gag gcc gcg atc gac gtg agc tgg tgg ccg ctg          3294
Tyr Gly Pro Thr Glu Ala Ala Ile Asp Val Ser Trp Trp Pro Leu
    1085                1090                1095 cgc gac ggc gcg ccg ggc gcc acg gtg ccg atc ggc cgc gcc gtc          3339
Arg Asp Gly Ala Pro Gly Ala Thr Val Pro Ile Gly Arg Ala Val
    1100                1105                1110 tgg aac acc cgg ctg gac gtg ctc gac ccc tgg ggg gca ccg gta          3384
Trp Asn Thr Arg Leu Asp Val Leu Asp Pro Trp Gly Ala Pro Val
    1115                1120                1125 ccg ccc ggc gag ccc ggc gag ctg tac atc gcg ggc gac cag ctc          3429
Pro Pro Gly Glu Pro Gly Glu Leu Tyr Ile Ala Gly Asp Gln Leu
    1130                1135                1140 gcc gtc ggc tac ctc ggg cgg ccg gac ctc acc gcc gag cgc ttc          3474
Ala Val Gly Tyr Leu Gly Arg Pro Asp Leu Thr Ala Glu Arg Phe
    1145                1150                1155 ccg gag gac ccg gcg gcg ggc cgg cgc tac cgc acc ggc gac ctg          3519
Pro Glu Asp Pro Ala Ala Gly Arg Arg Tyr Arg Thr Gly Asp Leu
    1160                1165                1170 gta cgg cgg ctg ccc tcc ggc gcg ctg gag ttc ctc gga cgc ctg          3564
Val Arg Arg Leu Pro Ser Gly Ala Leu Glu Phe Leu Gly Arg Leu
    1175                1180                1185 gac cac cag gtc aag atc cgg ggc ttc cgg gtc gag ctg ggc gag          3609
Asp His Gln Val Lys Ile Arg Gly Phe Arg Val Glu Leu Gly Glu
    1190                1195                1200 atc gag gcc gtg ctg acc gag cac ccg gag gtc gcc gcg gcg gtg          3654
Ile Glu Ala Val Leu Thr Glu His Pro Glu Val Ala Ala Ala Val
    1205                1210                1215
```

```
gtc ggc acc cgt gac gac cgc gcg ggc ggg ccc cgg ctc gtc gcc    3699
Val Gly Thr Arg Asp Asp Arg Ala Gly Gly Pro Arg Leu Val Ala
1220            1225                1230 tgg gtc gtc ccc gcc ccg gcg gag aag gac ggg gaa gac ggc ttc    3744
Trp Val Val Pro Ala Pro Ala Glu Lys Asp Gly Glu Asp Gly Phe
    1235            1240                1245 gag gcc cgc gcc cgg cgc tgg cac gac cac ctc gcc gcc cgg ctg    3789
Glu Ala Arg Ala Arg Arg Trp His Asp His Leu Ala Ala Arg Leu
1250            1255                1260 ccc gag cac atg gtc ccc acg gcc gtc gtc ccc ctc gcc gag ctc    3834
Pro Glu His Met Val Pro Thr Ala Val Val Pro Leu Ala Glu Leu
    1265            1270                1275 ccc acc acc gcc aac ggc aag ctc gac cgg gac gcg ctc ccg gag    3879
Pro Thr Thr Ala Asn Gly Lys Leu Asp Arg Asp Ala Leu Pro Glu
1280            1285                1290 ccg ccg gag ccc acg gcc gcc gcg cgg gag ccc gac ggc ccc gag    3924
Pro Pro Glu Pro Thr Ala Ala Ala Arg Glu Pro Asp Gly Pro Glu
    1295            1300                1305 gag cgg gcg ctc acc gag atc ctc gcc gag gtg ctg ggg atc gaa    3969
Glu Arg Ala Leu Thr Glu Ile Leu Ala Glu Val Leu Gly Ile Glu
1310            1315                1320 cgg atc ggg ccg gac gac gac ttc ttc acc gcc ggc ggc cat tcg    4014
Arg Ile Gly Pro Asp Asp Asp Phe Phe Thr Ala Gly Gly His Ser
    1325            1330                1335 ctg acc gcc gca cgc gcc gcc acg atg atc cgc gcc cgg ttc ggt    4059
Leu Thr Ala Ala Arg Ala Ala Thr Met Ile Arg Ala Arg Phe Gly
1340            1345                1350 gtc gag atc ggc gtg gcc gac gtg ttc gcc gcc cgc tgc gcg gcg    4104
Val Glu Ile Gly Val Ala Asp Val Phe Ala Ala Arg Cys Ala Ala
    1355            1360                1365 ggc ctc gcc gcc cgg ctg acc acc gca ccg ccc gcg cgc acc ccc    4149
Gly Leu Ala Ala Arg Leu Thr Thr Ala Pro Pro Ala Arg Thr Pro
1370            1375                1380 ttg cgc ccg gcc ggc cgg ccc gag cgc ctg ctg ctg tcc ccg gcc    4194
Leu Arg Pro Ala Gly Arg Pro Glu Arg Leu Leu Leu Ser Pro Ala
    1385            1390                1395 cag cgg ggc ctg tgg ttc ctg gac cgg ctc gac gac ggg ccg acg    4239
Gln Arg Gly Leu Trp Phe Leu Asp Arg Leu Asp Asp Gly Pro Thr
1400            1405                1410 tac aac atc ccg ctg gtg ctc ccc ctg ccg aac cgc gtg gac gcc    4284
Tyr Asn Ile Pro Leu Val Leu Pro Leu Pro Asn Arg Val Asp Ala
    1415            1420                1425 gac gcg ctc gcc gcc gcg ctg ggc gac gtc gcc gcc cgc cac gag    4329
Asp Ala Leu Ala Ala Ala Leu Gly Asp Val Ala Ala Arg His Glu
1430            1435                1440 agc ctg cgc acg gtc ttc ccg gcc gag gcc ggc gtg ccg tac cag    4374
Ser Leu Arg Thr Val Phe Pro Ala Glu Ala Gly Val Pro Tyr Gln
    1445            1450                1455 gag gtc cgg gaa ccg gcg gcc gtg ccg ctg cac gtc gtc gac tgc    4419
Glu Val Arg Glu Pro Ala Ala Val Pro Leu His Val Val Asp Cys
1460            1465                1470 ccc gcc gag gag atc ggg gcg cac gtc gag gcc gcc gcc cga cgc    4464
Pro Ala Glu Glu Ile Gly Ala His Val Glu Ala Ala Ala Arg Arg
    1475            1480                1485 cgg ctg gac atc acc cgg gag ccg ggc ctg cgg gcc ggc ctg tac    4509
Arg Leu Asp Ile Thr Arg Glu Pro Gly Leu Arg Ala Gly Leu Tyr
1490            1495                1500 gga ccg gcg gac ggc gag cgc acg ctc gtc ctg cta ctg cac cac    4554
Gly Pro Ala Asp Gly Glu Arg Thr Leu Val Leu Leu Leu His His
    1505            1510                1515
```

```
ctg gtc gcc gac ggc tgg tcg ctg cgg ccg ctg gcc gag gac ctc      4599
Leu Val Ala Asp Gly Trp Ser Leu Arg Pro Leu Ala Glu Asp Leu
1520            1525            1530 acc gcg gcg tac gcg gcg cgc gcc gcc ggc cgg gct ccc gaa ctc      4644
Thr Ala Ala Tyr Ala Ala Arg Ala Ala Gly Arg Ala Pro Glu Leu
1535            1540            1545 gcg ccg ctc ccg gtg cag ttc gcc gac tac gtg ctc tgg cag cgc      4689
Ala Pro Leu Pro Val Gln Phe Ala Asp Tyr Val Leu Trp Gln Arg
1550            1555            1560 gac cgg ctc gac ccg gcc ggc gcc gcc cgg cgc gac gag gag           4734
Asp Arg Leu Asp Pro Ala Gly Ala Ala Arg Arg Asp Glu Glu
1565            1570            1575 ttc tgg agc gcc gcg ctg cgg ggg ctg ccg gag gag acc gcg ctg      4779
Phe Trp Ser Ala Ala Leu Arg Gly Leu Pro Glu Glu Thr Ala Leu
1580            1585            1590 ccg ttc gac cgg ccg cgg ccc gcc cgg ccg acc ggc cgg ggc ggc      4824
Pro Phe Asp Arg Pro Arg Pro Ala Arg Pro Thr Gly Arg Gly Gly
1595            1600            1605 gcc gtc gac ctg gcc gtc ggt ccg gtg gcc cac gcg gcc ctg cgg      4869
Ala Val Asp Leu Ala Val Gly Pro Val Ala His Ala Ala Leu Arg
1610            1615            1620 gag ctg gcg cgg gcg cac ggc gtc agc ctg ttc acg gtg ctg cac      4914
Glu Leu Ala Arg Ala His Gly Val Ser Leu Phe Thr Val Leu His
1625            1630            1635 gcg ggc gtc gcc gcc ctg ctc acc ggc ctc ggc gcc ggt acg gat      4959
Ala Gly Val Ala Ala Leu Leu Thr Gly Leu Gly Ala Gly Thr Asp
1640            1645            1650 ctg gcg atc ggc acc ccg gtc gcc ggg cgg cac gac cag gcg ctc      5004
Leu Ala Ile Gly Thr Pro Val Ala Gly Arg His Asp Gln Ala Leu
1655            1660            1665 gac gac gtg gtg ggg ctg gtc acc aac acc gtc gtg ctg cgc acc      5049
Asp Asp Val Val Gly Leu Val Thr Asn Thr Val Val Leu Arg Thr
1670            1675            1680 gac acc tcc ggc tcg ccg gcc gtc gcc gag ttg ctg gct cgc gtc      5094
Asp Thr Ser Gly Ser Pro Ala Val Ala Glu Leu Leu Ala Arg Val
1685            1690            1695 cag gag gcc gac cgg gcc gcc tgg gcg cac gag gac ctg ccg ttc      5139
Gln Glu Ala Asp Arg Ala Ala Trp Ala His Glu Asp Leu Pro Phe
1700            1705            1710 gag cag gtg gtg gag ctg gtc aac ccg ccg cgc gtg ccg ggg cgt      5184
Glu Gln Val Val Glu Leu Val Asn Pro Pro Arg Val Pro Gly Arg
1715            1720            1725 cat ccg ctg ttc acg gtg atg ctg gcg ctg cag aac aac gcc gcc      5229
His Pro Leu Phe Thr Val Met Leu Ala Leu Gln Asn Asn Ala Ala
1730            1735            1740 gcg gcg gtg tcg ctg ggc ggc ccg ccg gtg ccg ctg cgg ccc agc      5274
Ala Ala Val Ser Leu Gly Gly Pro Pro Val Pro Leu Arg Pro Ser
1745            1750            1755 gcg acg ggt acc gcg aag ttc gac ctg ttc ttc gac atc acc gag      5319
Ala Thr Gly Thr Ala Lys Phe Asp Leu Phe Phe Asp Ile Thr Glu
1760            1765            1770 cac gtc ggg gac gac ggc tcg gcg ccc ggc ggt ctg acc tgt cac      5364
His Val Gly Asp Asp Gly Ser Ala Pro Gly Gly Leu Thr Cys His
1775            1780            1785 gtc gag ttc gcc cgc gac ctg ttc gac ccg agc acc gcg cgc ctg      5409
Val Glu Phe Ala Arg Asp Leu Phe Asp Pro Ser Thr Ala Arg Leu
1790            1795            1800 ctc gcc gag ggc ctg gtc acc gtc ctc gcc cgg gcc gcg gcc gcc      5454
Leu Ala Glu Gly Leu Val Thr Val Leu Ala Arg Ala Ala Ala Ala
```

-continued

| | | |
|---|---|---|
| ccg ggg gcg cgc ctc ggc gac ctc gtc ccg gac ggc ctg ctc gcc<br>Pro Gly Ala Arg Leu Gly Asp Leu Val Pro Asp Gly Leu Leu Ala<br>1820                                  1825                              1830 | | 5499 |
| ggg cgg gac gcc gca ccc gag gcg gtg tcc gac gac gcg gcg ctg<br>Gly Arg Asp Ala Ala Pro Glu Ala Val Ser Asp Asp Ala Ala Leu<br>1835                                  1840                            1845 | | 5544 |
| gag agc cgt gtg cgc tcc ctg tcc gcc gtc gcg gac gtc gcg gtc<br>Glu Ser Arg Val Arg Ser Leu Ser Ala Val Ala Asp Val Ala Val<br>1850                                  1855                            1860 | | 5589 |
| acc cgg ccc tcc gac ggc ggt ccg gtc gtc tgg gtc gtc ccc gcg<br>Thr Arg Pro Ser Asp Gly Gly Pro Val Val Trp Val Val Pro Ala<br>1865                                  1870                            1875 | | 5634 |
| cga ccg ggc gcg gac gac gac gcg cgc cgg ctc ctc gcg gac gaa<br>Arg Pro Gly Ala Asp Asp Asp Ala Arg Arg Leu Leu Ala Asp Glu<br>1880                                  1885                            1890 | | 5679 |
| ggc ggc gac ggg gca ccc cgg gtg acg gcc gtg acc gtc ctc ccg<br>Gly Gly Asp Gly Ala Pro Arg Val Thr Ala Val Thr Val Leu Pro<br>1895                                  1900                            1905 | | 5724 |
| cgc acc gcc gcc ggc gac ctc gac gtg gcc gcg ctg cac cgg ctg<br>Arg Thr Ala Ala Gly Asp Leu Asp Val Ala Ala Leu His Arg Leu<br>1910                                  1915                            1920 | | 5769 |
| ccg gtc gtc gac gac acc gcc gcc gac ggc tgg cgc gcc gct ctc<br>Pro Val Val Asp Asp Thr Ala Ala Asp Gly Trp Arg Ala Ala Leu<br>1925                                  1930                            1935 | | 5814 |
| gcg gcc gtg acc ggc gta cgg gcg gcg gcg gtc ggg cgc gag gac<br>Ala Ala Val Thr Gly Val Arg Ala Ala Ala Val Gly Arg Glu Asp<br>1940                                  1945                            1950 | | 5859 |
| gtc ccc gag ggg ctg gag gcg ctc cgg ccg gcg acc cgc ccg cgt<br>Val Pro Glu Gly Leu Glu Ala Leu Arg Pro Ala Thr Arg Pro Arg<br>1955                                  1960                            1965 | | 5904 |
| acc gtg gcg gcc acc gcc gga ccg gcc gcc gtt cac caa gcg gac<br>Thr Val Ala Ala Thr Ala Gly Pro Ala Ala Val His Gln Ala Asp<br>1970                                  1975                            1980 | | 5949 |
| cgc gcg ctg tcg ctc tcc gag ggc ccg ccg ctg ccc ccg gcg gag<br>Arg Ala Leu Ser Leu Ser Glu Gly Pro Pro Leu Pro Pro Ala Glu<br>1985                                  1990                            1995 | | 5994 |
| gtc ggc ggc tgg ccc gag gcc ctg cgc cgc gcc gcg gcg ggc ggc<br>Val Gly Gly Trp Pro Glu Ala Leu Arg Arg Ala Ala Ala Gly Gly<br>2000                                  2005                            2010 | | 6039 |
| gac cac gcc gag atc gtg cac gtg cgc gcg gac ggc acc gag agc<br>Asp His Ala Glu Ile Val His Val Arg Ala Asp Gly Thr Glu Ser<br>2015                                  2020                            2025 | | 6084 |
| cgg cgc tcg tac gcc tcg ctg atc gag gag gcc gag cgg gtc ctg<br>Arg Arg Ser Tyr Ala Ser Leu Ile Glu Glu Ala Glu Arg Val Leu<br>2030                                  2035                            2040 | | 6129 |
| ggc ggg ctg cgg gcc ctg ggc ctg cgc gcc ggc gac cag gtg gtc<br>Gly Gly Leu Arg Ala Leu Gly Leu Arg Ala Gly Asp Gln Val Val<br>2045                                  2050                            2055 | | 6174 |
| ctg cag tgc gac gac acc gag gac ttc gtg gcc gcg ctc tgg ggc<br>Leu Gln Cys Asp Asp Thr Glu Asp Phe Val Ala Ala Leu Trp Gly<br>2060                                  2065                            2070 | | 6219 |
| gcg atc gcc gcc ggg gtc acc gtc gtc ccg ctc acc gtg ccg ccc<br>Ala Ile Ala Ala Gly Val Thr Val Val Pro Leu Thr Val Pro Pro<br>2075                                  2080                            2085 | | 6264 |
| acg tac gcc acc gac tcg gcg gcc gtg aac aag ctc gac ggc gtc<br>Thr Tyr Ala Thr Asp Ser Ala Ala Val Asn Lys Leu Asp Gly Val<br>2090                                  2095                            2100 | | 6309 |
| tgg cgc atg ctg ggc cgg ccg gtc gtc gtc acc tcc gcg gac cgt | | 6354 |

```
Trp Arg Met Leu Gly Arg Pro Val Val Thr Ser Ala Asp Arg
    2105            2110            2115 gcc gac ggc ctg gcg gag ctc gcg gcc cgc cgg gag tgg ccg gac    6399
Ala Asp Gly Leu Ala Glu Leu Ala Ala Arg Arg Glu Trp Pro Asp
2120            2125            2130 ccc cgc atc gtg acc gtg gac gcc ctg cgc gcg gcc gcc ccg gac    6444
Pro Arg Ile Val Thr Val Asp Ala Leu Arg Ala Ala Ala Pro Asp
2135            2140            2145 cgc gac tgg cat cag gca cgc ccc gac gac ctg ctg ctc atg ctg    6489
Arg Asp Trp His Gln Ala Arg Pro Asp Asp Leu Leu Leu Met Leu
2150            2155            2160 ctc acc tcc ggc agc acg gga ctt ccg aag gcg gtg cgg ctg acg    6534
Leu Thr Ser Gly Ser Thr Gly Leu Pro Lys Ala Val Arg Leu Thr
2165            2170            2175 cac ggc aac gtg ctg agc cgg gcc gtc gcc gcg gcg gcc aac        6579
His Gly Asn Val Leu Ser Arg Ala Val Ala Ala Ala Ala Asn
2180            2185            2190 tcc ctg acc gag cac gac gtc tcg ctg aac tgg atc ccg ctc gac    6624
Ser Leu Thr Glu His Asp Val Ser Leu Asn Trp Ile Pro Leu Asp
2195            2200            2205 cac gtc acc ggt gtg gtg atg ttc cac ctg cgc gac gtc tac ctc    6669
His Val Thr Gly Val Val Met Phe His Leu Arg Asp Val Tyr Leu
2210            2215            2220 ggc gcc cgg cag gtg cac gcc ccg acg ggc tgg gtg ctg gag gac    6714
Gly Ala Arg Gln Val His Ala Pro Thr Gly Trp Val Leu Glu Asp
2225            2230            2235 ccg ctg cgc tgg tgg gag ctg gcg gac cgg tgg cgc gtc agc gtc    6759
Pro Leu Arg Trp Trp Glu Leu Ala Asp Arg Trp Arg Val Ser Val
2240            2245            2250 acg tgg gcg ccg aac ttc gcc ttc ggc ctc gtc gcc gag cag gcc    6804
Thr Trp Ala Pro Asn Phe Ala Phe Gly Leu Val Ala Glu Gln Ala
2255            2260            2265 ggc cgg ctc gcc ggc cgg gag tgg gac ctc tcc ccg gta cgg ctg    6849
Gly Arg Leu Ala Gly Arg Glu Trp Asp Leu Ser Pro Val Arg Leu
2270            2275            2280 atc atg aac gcg ggc gag gtc gtc gtc ggc gcg acc aac cgc cgg    6894
Ile Met Asn Ala Gly Glu Val Val Val Gly Ala Thr Asn Arg Arg
2285            2290            2295 ttc ctg cag gcc ctg gcg ccg cac ggg ctg ccg tcc gac gtg atg    6939
Phe Leu Gln Ala Leu Ala Pro His Gly Leu Pro Ser Asp Val Met
2300            2305            2310 cac ccc ggc tgg ggc atg tcc gag acg tgc tcc gtg gtc acg gac    6984
His Pro Gly Trp Gly Met Ser Glu Thr Cys Ser Val Val Thr Asp
2315            2320            2325 acg gtc ctc gac ccg cag ccg ccg ccc ggc ggc gac gag acc ttc    7029
Thr Val Leu Asp Pro Gln Pro Pro Pro Gly Gly Asp Glu Thr Phe
2330            2335            2340 gtc agc tgc ggg cgg ccg tac ccc ggg ttc gcg atg cgc gtg gtc    7074
Val Ser Cys Gly Arg Pro Tyr Pro Gly Phe Ala Met Arg Val Val
2345            2350            2355 gac gag gag ctg cgg ctg ctg ccg gag ggc gag gtc ggc cgc ttc    7119
Asp Glu Glu Leu Arg Leu Leu Pro Glu Gly Glu Val Gly Arg Phe
2360            2365            2370 cag gtc cgc ggc gcc tcg gtg acg tcg ggc tac cac gac aac gcg    7164
Gln Val Arg Gly Ala Ser Val Thr Ser Gly Tyr His Asp Asn Ala
2375            2380            2385 gcg gcc aac gcc gag gcg ttc acc gcc gac ggc tgg ttc gac acc    7209
Ala Ala Asn Ala Glu Ala Phe Thr Ala Asp Gly Trp Phe Asp Thr
2390            2395            2400
```

| | | | | | | | | | | | |
|---|---|---|---|---|---|---|---|---|---|---|---|
| ggc | gac | ctg | gcg | ttc | ctg | cgc | gac | ggc | gag | ctg | tac | atc | acc | ggg | 7254 |
| Gly | Asp | Leu | Ala | Phe | Leu | Arg | Asp | Gly | Glu | Leu | Tyr | Ile | Thr | Gly | |
| 2405 | | | | 2410 | | | | | 2415 | | | | | | |

| cgc | gcc | aag | gac | gtc | atc | atc | gtc | aac | ggc | gtc | aac | cac | ttc | agt | 7299 |
|---|---|---|---|---|---|---|---|---|---|---|---|---|---|---|---|
| Arg | Ala | Lys | Asp | Val | Ile | Ile | Val | Asn | Gly | Val | Asn | His | Phe | Ser | |
| 2420 | | | | 2425 | | | | | 2430 | | | | | | |

| cac | gag | ata | gag | gcg | tgc | gtc | gag | gaa | ctg | ccg | gtg | gtg | gtg | cgc | 7344 |
|---|---|---|---|---|---|---|---|---|---|---|---|---|---|---|---|
| His | Glu | Ile | Glu | Ala | Cys | Val | Glu | Glu | Leu | Pro | Val | Val | Val | Arg | |
| 2435 | | | | 2440 | | | | | 2445 | | | | | | |

| tcg | ttc | acc | gcg | gcg | gtc | gcg | gtc | cgt | acg | gac | gcc | tcg | gcc | gcc | 7389 |
|---|---|---|---|---|---|---|---|---|---|---|---|---|---|---|---|
| Ser | Phe | Thr | Ala | Ala | Val | Ala | Val | Arg | Thr | Asp | Ala | Ser | Ala | Ala | |
| 2450 | | | | 2455 | | | | | 2460 | | | | | | |

| acc | gac | cag | ctc | gcg | ctg | ttc | gtg | cac | ctg | gcc | ccc | ggg | cac | gac | 7434 |
|---|---|---|---|---|---|---|---|---|---|---|---|---|---|---|---|
| Thr | Asp | Gln | Leu | Ala | Leu | Phe | Val | His | Leu | Ala | Pro | Gly | His | Asp | |
| 2465 | | | | 2470 | | | | | 2475 | | | | | | |

| tcc | ggg | gag | gcc | gcg | gcg | gcc | gcg | ctg | cgg | gcg | atc | cgg | ggc | aag | 7479 |
|---|---|---|---|---|---|---|---|---|---|---|---|---|---|---|---|
| Ser | Gly | Glu | Ala | Ala | Ala | Ala | Ala | Leu | Arg | Ala | Ile | Arg | Gly | Lys | |
| 2480 | | | | 2485 | | | | | 2490 | | | | | | |

| gtg | gcc | cgc | gag | gtc | ggc | gtg | gcg | ccc | gcg | cac | gtg | ctg | ccc | gtc | 7524 |
|---|---|---|---|---|---|---|---|---|---|---|---|---|---|---|---|
| Val | Ala | Arg | Glu | Val | Gly | Val | Ala | Pro | Ala | His | Val | Leu | Pro | Val | |
| 2495 | | | | 2500 | | | | | 2505 | | | | | | |

| gag | acg | gcg | gtg | atc | ccg | aag | acc | gag | atc | ggc | aag | atc | cag | cgg | 7569 |
|---|---|---|---|---|---|---|---|---|---|---|---|---|---|---|---|
| Glu | Thr | Ala | Val | Ile | Pro | Lys | Thr | Glu | Ile | Gly | Lys | Ile | Gln | Arg | |
| 2510 | | | | 2515 | | | | | 2520 | | | | | | |

| acg | cag | ctg | cgc | aag | cgg | ttc | gag | gcc | ggt | gag | ttc | gac | gcg | gtg | 7614 |
|---|---|---|---|---|---|---|---|---|---|---|---|---|---|---|---|
| Thr | Gln | Leu | Arg | Lys | Arg | Phe | Glu | Ala | Gly | Glu | Phe | Asp | Ala | Val | |
| 2525 | | | | 2530 | | | | | 2535 | | | | | | |

| gcg | cgc | gcc | gcc | gag | gtg | ctg | ctc | ggg | acg | gcg | gcg | acg | gtt | ccg | 7659 |
|---|---|---|---|---|---|---|---|---|---|---|---|---|---|---|---|
| Ala | Arg | Ala | Ala | Glu | Val | Leu | Leu | Gly | Thr | Ala | Ala | Thr | Val | Pro | |
| 2540 | | | | 2545 | | | | | 2550 | | | | | | |

| cac | tgg | ttc | ctg | cgt | ccc | gtc | tgg | tcg | ccg | gtg | acg | cgc | ccg | gcc | 7704 |
|---|---|---|---|---|---|---|---|---|---|---|---|---|---|---|---|
| His | Trp | Phe | Leu | Arg | Pro | Val | Trp | Ser | Pro | Val | Thr | Arg | Pro | Ala | |
| 2555 | | | | 2560 | | | | | 2565 | | | | | | |

| acc | gct | ccc | ccg | gcc | ggc | acg | tcc | gtg | ctg | atc | gtg | gcg | gcg | ggg | 7749 |
|---|---|---|---|---|---|---|---|---|---|---|---|---|---|---|---|
| Thr | Ala | Pro | Pro | Ala | Gly | Thr | Ser | Val | Leu | Ile | Val | Ala | Ala | Gly | |
| 2570 | | | | 2575 | | | | | 2580 | | | | | | |

| ccg | cgg | ggt | gcg | ggg | gtc | gcc | gag | cgg | ctc | gcc | gcc | ctg | gtg | cgc | 7794 |
|---|---|---|---|---|---|---|---|---|---|---|---|---|---|---|---|
| Pro | Arg | Gly | Ala | Gly | Val | Ala | Glu | Arg | Leu | Ala | Ala | Leu | Val | Arg | |
| 2585 | | | | 2590 | | | | | 2595 | | | | | | |

| cgg | gag | ggc | gga | cgc | gcc | acg | aca | gcg | gtg | gcc | ggt | acg | ggc | ttc | 7839 |
|---|---|---|---|---|---|---|---|---|---|---|---|---|---|---|---|
| Arg | Glu | Gly | Gly | Arg | Ala | Thr | Thr | Ala | Val | Ala | Gly | Thr | Gly | Phe | |
| 2600 | | | | 2605 | | | | | 2610 | | | | | | |

| ggg | cgg | cgg | gac | gcg | gcc | cgg | tac | acg | gtc | cgc | ccc | gac | gag | gcg | 7884 |
|---|---|---|---|---|---|---|---|---|---|---|---|---|---|---|---|
| Gly | Arg | Arg | Asp | Ala | Ala | Arg | Tyr | Thr | Val | Arg | Pro | Asp | Glu | Ala | |
| 2615 | | | | 2620 | | | | | 2625 | | | | | | |

| tcc | gac | ttc | gcg | gcg | ctg | ctc | gac | cgg | ctg | gcg | gcc | gac | gac | cgc | 7929 |
|---|---|---|---|---|---|---|---|---|---|---|---|---|---|---|---|
| Ser | Asp | Phe | Ala | Ala | Leu | Leu | Asp | Arg | Leu | Ala | Ala | Asp | Asp | Arg | |
| 2630 | | | | 2635 | | | | | 2640 | | | | | | |

| cgt | ccg | gag | cgc | gtc | gtg | cac | ctc | ggg | ccg | ctg | gag | ccg | tcc | ggc | 7974 |
|---|---|---|---|---|---|---|---|---|---|---|---|---|---|---|---|
| Arg | Pro | Glu | Arg | Val | Val | His | Leu | Gly | Pro | Leu | Glu | Pro | Ser | Gly | |
| 2645 | | | | 2650 | | | | | 2655 | | | | | | |

| cgc | gac | ctg | gac | gcc | ggc | ggg | gtg | ctc | gac | gcc | cag | cgg | tcc | ggc | 8019 |
|---|---|---|---|---|---|---|---|---|---|---|---|---|---|---|---|
| Arg | Asp | Leu | Asp | Ala | Gly | Gly | Val | Leu | Asp | Ala | Gln | Arg | Ser | Gly | |
| 2660 | | | | 2665 | | | | | 2670 | | | | | | |

| gcc | gcc | tcg | gtc | ctg | gcc | ctg | gcc | cgg | gcg | ctg | gcc | gcc | ccc | gac | 8064 |
|---|---|---|---|---|---|---|---|---|---|---|---|---|---|---|---|
| Ala | Ala | Ser | Val | Leu | Ala | Leu | Ala | Arg | Ala | Leu | Ala | Ala | Pro | Asp | |
| 2675 | | | | 2680 | | | | | 2685 | | | | | | |

| cac | gcg | ggc | cac | gcc | gtc | gac | ctg | cgg | tgc | gtc | acc | ggc | ggg | gac | 8109 |
|---|---|---|---|---|---|---|---|---|---|---|---|---|---|---|---|
| His | Ala | Gly | His | Ala | Val | Asp | Leu | Arg | Cys | Val | Thr | Gly | Gly | Asp | |
| 2690 | | | | 2695 | | | | | 2700 | | | | | | |

| | | | | | | | | | | |
|---|---|---|---|---|---|---|---|---|---|---|
| ctg | ccg | cac | gcg | acc | ctc | gcc | ggg | ctc | ctg | ccc | tcg | ctg | cgg | gac | 8154 |
| Leu | Pro | His | Ala | Thr | Leu | Ala | Gly | Leu | Leu | Pro | Ser | Leu | Arg | Asp | |
| | 2705 | | | | 2710 | | | | | 2715 | | | | | |

| gag | cgt | ccc | ggc | ctg | tcc | gcg | ggc | acg | ctg | gcc | gtg | ccg | ggc | gac | 8199 |
| Glu | Arg | Pro | Gly | Leu | Ser | Ala | Gly | Thr | Leu | Ala | Val | Pro | Gly | Asp | |
| | 2720 | | | | 2725 | | | | | 2730 | | | | | |

| ggg | gag | ccg | gac | gac | gtg | gcg | gcg | ctg | atc | gcc | gcg | gaa | ctc | gcg | 8244 |
| Gly | Glu | Pro | Asp | Asp | Val | Ala | Ala | Leu | Ile | Ala | Ala | Glu | Leu | Ala | |
| | 2735 | | | | 2740 | | | | | 2745 | | | | | |

| gtc | gct | ccg | gcc | gac | gcc | gag | gtg | tgc | cgg | cgg | gac | ggc | ggg | cgc | 8289 |
| Val | Ala | Pro | Ala | Asp | Ala | Glu | Val | Cys | Arg | Arg | Asp | Gly | Gly | Arg | |
| | 2750 | | | | 2755 | | | | | 2760 | | | | | |

| ctg | gtg | cgc | cgg | ctg | gcc | cct | gta | ccg | gtg | ccc | gag | tcg | gtc | acc | 8334 |
| Leu | Val | Arg | Arg | Leu | Ala | Pro | Val | Pro | Val | Pro | Glu | Ser | Val | Thr | |
| | 2765 | | | | 2770 | | | | | 2775 | | | | | |

| gtc | ccc | gcc | tac | ggc | gac | ggc | gtc | gtc | ctg | gtg | acg | ggc | ggg | ctg | 8379 |
| Val | Pro | Ala | Tyr | Gly | Asp | Gly | Val | Val | Leu | Val | Thr | Gly | Gly | Leu | |
| | 2780 | | | | 2785 | | | | | 2790 | | | | | |

| ggc | ggc | gtc | gcg | gcc | cac | ctc | gcc | gag | cac | ctg | ctc | acc | acc | gag | 8424 |
| Gly | Gly | Val | Ala | Ala | His | Leu | Ala | Glu | His | Leu | Leu | Thr | Thr | Glu | |
| | 2795 | | | | 2800 | | | | | 2805 | | | | | |

| ccc | ggg | gta | cgg | ctg | ctc | ctg | gtc | ggc | cgc | acc | ccg | ctg | ccg | gcc | 8469 |
| Pro | Gly | Val | Arg | Leu | Leu | Leu | Val | Gly | Arg | Thr | Pro | Leu | Pro | Ala | |
| | 2810 | | | | 2815 | | | | | 2820 | | | | | |

| ggg | gac | ccg | gcc | gcg | gat | gac | gct | cgc | gcc | cgc | gcc | gcg | gcg | gtg | 8514 |
| Gly | Asp | Pro | Ala | Ala | Asp | Asp | Ala | Arg | Ala | Arg | Ala | Ala | Ala | Val | |
| | 2825 | | | | 2830 | | | | | 2835 | | | | | |

| ctg | cgg | cgg | ctg | cgc | gag | ctc | ggg | gag | gtc | cgc | tac | gcg | gcc | gcc | 8559 |
| Leu | Arg | Arg | Leu | Arg | Glu | Leu | Gly | Glu | Val | Arg | Tyr | Ala | Ala | Ala | |
| | 2840 | | | | 2845 | | | | | 2850 | | | | | |

| gac | gtc | acc | gac | gag | gcg | gcg | ctg | gac | gcg | gcc | gtg | gcc | gcc | gcg | 8604 |
| Asp | Val | Thr | Asp | Glu | Ala | Ala | Leu | Asp | Ala | Ala | Val | Ala | Ala | Ala | |
| | 2855 | | | | 2860 | | | | | 2865 | | | | | |

| acg | gac | gcc | tgg | tcg | gcc | ccg | ctg | acc | ggg | atc | ctc | cac | ctc | gcc | 8649 |
| Thr | Asp | Ala | Trp | Ser | Ala | Pro | Leu | Thr | Gly | Ile | Leu | His | Leu | Ala | |
| | 2870 | | | | 2875 | | | | | 2880 | | | | | |

| ggg | acg | atc | gaa | cgg | cgg | gcg | gcg | gcc | gac | ctc | gac | ccg | gcg | gcc | 8694 |
| Gly | Thr | Ile | Glu | Arg | Arg | Ala | Ala | Ala | Asp | Leu | Asp | Pro | Ala | Ala | |
| | 2885 | | | | 2890 | | | | | 2895 | | | | | |

| tgg | cgc | gcg | gcg | acc | gcg | gcc | aag | atc | ggc | ggg | gcg | tgc | gtc | ctg | 8739 |
| Trp | Arg | Ala | Ala | Thr | Ala | Ala | Lys | Ile | Gly | Gly | Ala | Cys | Val | Leu | |
| | 2900 | | | | 2905 | | | | | 2910 | | | | | |

| gac | cgg | ctc | gcg | gcc | cgg | cac | ccg | gtc | cgg | tcg | ttc | gtc | tcc | ttc | 8784 |
| Asp | Arg | Leu | Ala | Ala | Arg | His | Pro | Val | Arg | Ser | Phe | Val | Ser | Phe | |
| | 2915 | | | | 2920 | | | | | 2925 | | | | | |

| tcc | tcg | gtc | aac | ggc | acc | ttc | ggg | gcc | gcg | ttc | ggc | gcc | cct | tac | 8829 |
| Ser | Ser | Val | Asn | Gly | Thr | Phe | Gly | Ala | Ala | Phe | Gly | Ala | Pro | Tyr | |
| | 2930 | | | | 2935 | | | | | 2940 | | | | | |

| gcg | gcg | gcg | tgc | gcc | ttc | ctc | gac | gcg | ctg | gcc | gtc | cgt | cag | cgg | 8874 |
| Ala | Ala | Ala | Cys | Ala | Phe | Leu | Asp | Ala | Leu | Ala | Val | Arg | Gln | Arg | |
| | 2945 | | | | 2950 | | | | | 2955 | | | | | |

| gcg | cgg | ggg | ctg | gac | gcc | cag | tcg | ctg | gcg | tgg | agc | agc | tgg | cgg | 8919 |
| Ala | Arg | Gly | Leu | Asp | Ala | Gln | Ser | Leu | Ala | Trp | Ser | Ser | Trp | Arg | |
| | 2960 | | | | 2965 | | | | | 2970 | | | | | |

| gac | acg | ggg | atg | agc | gag | ggc | gac | gag | ctg | gcg | gcc | ctc | ggg | gag | 8964 |
| Asp | Thr | Gly | Met | Ser | Glu | Gly | Asp | Glu | Leu | Ala | Ala | Leu | Gly | Glu | |
| | 2975 | | | | 2980 | | | | | 2985 | | | | | |

| acg | cgc | ggc | tac | cgg | gca | ctc | gac | gtg | gag | tcg | gcc | ctg | cgc | tcg | 9009 |
| Thr | Arg | Gly | Tyr | Arg | Ala | Leu | Asp | Val | Glu | Ser | Ala | Leu | Arg | Ser | |

```
ttc gac ctc gcc cgc ggc ctc gac gag ccg gtg gta ctc atc ggc    9054
Phe Asp Leu Ala Arg Gly Leu Asp Glu Pro Val Val Leu Ile Gly
    3005                3010                3015 gcg gac cgg acg gcg gac ggc gtc cgg cgg ctg gtg gac gcg ccc    9099
Ala Asp Arg Thr Ala Asp Gly Val Arg Arg Leu Val Asp Ala Pro
    3020                3025                3030 gcc cgg ccg cgc cat cgg ctc gcc gcc cgg gtg gag ttg gag gag    9144
Ala Arg Pro Arg His Arg Leu Ala Ala Arg Val Glu Leu Glu Glu
    3035                3040                3045 ggc gcc gac atc ggc ggg ctg cac gag gcg gcc gtg gcc gcc gcg    9189
Gly Ala Asp Ile Gly Gly Leu His Glu Ala Ala Val Ala Ala Ala
    3050                3055                3060 gcg cgc gcc tgc ggc ggc gtc gcc ggg cac ggc gcg gtc gtc cgg    9234
Ala Arg Ala Cys Gly Gly Val Ala Gly His Gly Ala Val Val Arg
    3065                3070                3075 gcc gcg tcc tcg gcg gcg tcc gcc gcc gag ggg agc gcg gct tcc    9279
Ala Ala Ser Ser Ala Ala Ser Ala Ala Glu Gly Ser Ala Ala Ser
    3080                3085                3090 ggc gcg gcc ggc ggc gac cgc gtc cgc gtg ctg gag gag acc gtc    9324
Gly Ala Ala Gly Gly Asp Arg Val Arg Val Leu Glu Glu Thr Val
    3095                3100                3105 ctc gcc gtc tgg cgg cgg gtg ctg ggc cgc gag cgg gtg ggg tcc    9369
Leu Ala Val Trp Arg Arg Val Leu Gly Arg Glu Arg Val Gly Ser
    3110                3115                3120 ggg gac aac ttc ttc gac ctg ggc ggg cat tcg ctg ctg ctg gtg    9414
Gly Asp Asn Phe Phe Asp Leu Gly Gly His Ser Leu Leu Leu Val
    3125                3130                3135 cgg gcc cag gcc gag ctg aac gag gcc ctg ggc ggc gcg ctg acg    9459
Arg Ala Gln Ala Glu Leu Asn Glu Ala Leu Gly Gly Ala Leu Thr
    3140                3145                3150 gtg gtc gac ctg ttc gcc cat ccc aac gcg cgg tcg ctc gcc ggg    9504
Val Val Asp Leu Phe Ala His Pro Asn Ala Arg Ser Leu Ala Gly
    3155                3160                3165 cac ttg gcg ggc cgg cgg gac atc acg gcg ccg ggc gac ggc cgg    9549
His Leu Ala Gly Arg Arg Asp Ile Thr Ala Pro Gly Asp Gly Arg
    3170                3175                3180 gag gcc ggc ggc gag gag gac ggc ggc tcc gca gcg gcc ggg agc    9594
Glu Ala Gly Gly Glu Glu Asp Gly Gly Ser Ala Ala Ala Gly Ser
    3185                3190                3195 gcc ctc ggc gcc acc cgc gag cag gcc cgc cgc cgg ctc gcg gcg    9639
Ala Leu Gly Ala Thr Arg Glu Gln Ala Arg Arg Arg Leu Ala Ala
    3200                3205                3210 cgc gcc cag cgg aac ggg aag ggc ccg aag ggc cgg aag ggt cag    9684
Arg Ala Gln Arg Asn Gly Lys Gly Pro Lys Gly Arg Lys Gly Gln
    3215                3220                3225 cag gac cag cca ggc cag cag ggc caa gag gag gca tcg cat gct    9729
Gln Asp Gln Pro Gly Gln Gln Gly Gln Glu Glu Ala Ser His Ala
    3230                3235                3240 gaa tga                                                         9735
Glu

<210> SEQ ID NO 27
<211> LENGTH: 3244
<212> TYPE: PRT
<213> ORGANISM: Streptoverticillium

<400> SEQUENCE: 27

Met Pro Asp Arg Ala Ala Asp Ser Cys Pro Leu Thr Ala Pro Gln Ala
1               5                   10                  15
```

```
Gly Ile Trp Phe Ala Gln Gln Arg Asp Thr Ser Asn Pro Val Phe Thr
            20                  25                  30

Thr Gly Gln Tyr Val Arg Leu Pro Ala Glu Val Asp Pro Glu Arg Phe
        35                  40                  45

Ala Arg Ala Val Glu Arg Ala Leu Gly Glu Val Trp Gly Leu Ala Val
 50                  55                  60

Glu Val Gly Ala Asp Gly Asp Val Pro Val Gln Arg Gly Thr Gly Thr
 65                  70                  75                  80

Ala Pro Arg Val Glu Val Val Asp Leu Ser Gly Arg Pro Asp Pro Glu
                 85                  90                  95

Ala Val Ala Leu Ala Arg Met Arg Ala Asp Leu Glu Gln Pro Pro Val
            100                 105                 110

Gly Arg Pro Leu Ala Arg Glu Val Leu Phe Arg Trp Gln Gly Gly Ala
        115                 120                 125

Leu Trp Phe His Arg Cys His His Met Leu Leu Asp Gly Tyr Gly Phe
130                 135                 140

Ser Leu Val Leu Arg Arg Ile Glu Glu Ile His Glu Ala Leu Arg Thr
145                 150                 155                 160

Gly Gly Ser Pro Gly Glu Pro Ala Phe Gly Gly Leu Gly Ala Tyr Leu
                165                 170                 175

Asp Glu Glu Ala Gly Tyr Arg Ala Gly Asp Arg Met Pro Arg Asp Arg
            180                 185                 190

Ala Tyr Trp Leu Asp Ala Leu Ala Glu Leu Pro Pro Val Ser Leu
        195                 200                 205

Ser Gly Thr Pro Pro Glu Pro Ala Arg Gly Ala Pro Leu Lys Ala Arg
210                 215                 220

Val Asp Val Leu Pro Asp Pro Ala Gly Leu Ala Arg Leu Ala Glu Ser
225                 230                 235                 240

Leu Ser Ala Thr Thr Ala Asp Leu Ala Ile Ala Ala Thr Ala Val Tyr
                245                 250                 255

Gln His Arg Val Thr Gly Ala Ala Asp Val Val Leu Ala Leu Pro Leu
            260                 265                 270

Ala Leu Arg Gly Gly Ala Ala Arg Leu Pro Ser Thr Thr Val Asn
        275                 280                 285

Val Leu Pro Leu Arg Val Arg Val Ala Asp Gly Asp Thr Val Gly Thr
290                 295                 300

Leu Val Ala Arg Leu Arg Lys Ala Met Arg Glu Leu Arg Arg His Gly
305                 310                 315                 320

Arg Tyr Arg Val Glu Asp Ile Arg Arg Asp Leu Gly Arg Val Thr Asp
                325                 330                 335

Glu Ser Glu Phe Thr Thr Ala Gln Val Asn Ile Lys Ser Tyr Asp Thr
            340                 345                 350

Thr Ile Gly Leu Leu Gly Arg Arg Leu Pro Val Val Asp Leu Ser Pro
        355                 360                 365

Gly Pro Val Asp Asp Ile Ala Phe Val Val Asp Leu Ala Glu Asp Gly
370                 375                 380

Glu Leu Thr Thr Leu Glu Val Glu Ala Asn Ala Leu Arg Tyr Asp Ala
385                 390                 395                 400

Pro Thr Ala Leu Ala His Gly Arg Gly Leu Gly Arg Leu Leu Gly Ala
                405                 410                 415

Leu Ala Glu Ala Gly Pro Asp Thr Ala Val Asp Asp Leu Gly Ala Val
            420                 425                 430
```

```
Gly Pro Ile Tyr Asp Thr Gly His Tyr Leu Asp Leu Arg Gly Pro Val
            435                 440                 445

Asp Arg Glu Gly Leu Arg Ala Ala Gly Val Arg Ala Val Arg Asp Ala
450                 455                 460

Ala Tyr Gly Leu Val Asp Gly Pro Val Asp Gly Pro Met Gly Glu Ala
465                 470                 475                 480

Ala Ser Gly Pro Ala Gly Gly Ser Ala Asp Thr Ser Ala Asp Gly Glu
                485                 490                 495

Gly Ala Pro Cys Gly Pro Ala Glu Phe Val Asp Leu Ser Gly Glu Ser
                500                 505                 510

Asp Pro Ala Gly Ala Ala Leu Ala Trp Met Arg Ala Glu Leu Ala Arg
            515                 520                 525

Pro Ala Ala Thr Ala Cys Gly His Ala Val Leu Ala Leu Gly Pro Glu
            530                 535                 540

His His Leu Trp Phe Arg Arg Thr Gly Gly Pro Glu Ser Asp Glu Arg
545                 550                 555                 560

Ala Ala Pro Ala Leu Ala Arg Arg Val Ala Ala Leu Ala Gly Ala Pro
                565                 570                 575

Asp Gly Leu Ala Asp Val Ala Asp Val Ala Asp Val Ala Ala Asp Ser
            580                 585                 590

Arg Pro Ala Gly Ser Gly Ser Arg His Arg Glu Ile Ala Val Pro Ala
595                 600                 605

Ala Leu Gly Arg Arg Met Met Glu Gly Ser Arg Glu Leu Gly Val Gly
            610                 615                 620

Ile Arg Asp Phe Val Ala Ala Val Ala Met Phe Thr Ala Arg Arg
625                 630                 635                 640

Arg Gly Ser Gly Ala Val Glu Leu Tyr Val Pro Ala Ala Asp Gly Thr
                645                 650                 655

Pro Val Pro Leu Pro Leu Asp Leu Thr Gly Thr Thr Leu Ala Glu
                660                 665                 670

Thr Val Ala Ala Val Gln Asp Gly Arg Gly His Arg Ala Thr Ala Asp
            675                 680                 685

Gly Arg Val Ser Gly Pro Ser Val Thr Val Ala Arg Trp Ala Gly Thr
690                 695                 700

Pro Asp Arg Asp Ala Ala Leu His Leu Val Ser Ala Ala Pro Ala Thr
705                 710                 715                 720

Gly Pro Ala Val Thr Ala Val Leu Gly Glu Asp Arg Val Arg Ala Leu
                725                 730                 735

Gln Val Asp Asp Ala Pro Asp Pro Ala Trp Ser Asp Ser Glu Leu
            740                 745                 750

Arg Arg Phe Ile Arg Leu Leu Asp Ala Val Thr Ala Asp Pro Glu Thr
            755                 760                 765

Thr Leu Ala Gly Val Asp Leu Leu Asp Glu Ala Glu His Arg Thr Leu
770                 775                 780

Ala Ala Asp Ala Asp Thr Ala His Pro Val Pro Val Thr Thr Leu Asp
785                 790                 795                 800

Arg Leu Val Ala Glu Gln Ile Ala Arg Thr Pro Asp Ala Val Ala Leu
                805                 810                 815

Val Pro Ala Asp Gly Ser Pro Glu Leu Thr Tyr Arg Glu Leu Gly Glu
            820                 825                 830

Arg Val Asp Arg Leu Ala Arg Gly Leu Ala Gly Leu Gly Ala Gly Pro
835                 840                 845

Gly Thr Ile Val Ala Val Ala Gln Pro Arg Ser Thr Ala Leu Val Val
```

-continued

```
            850                 855                 860
Ser Leu Leu Ala Val Leu Arg Thr Gly Ala Ala Tyr Ala Pro Leu Asp
865                 870                 875                 880

Leu Asp His Pro Pro Ala Arg Leu Ala Ala Val Leu Glu Asp Val Arg
                885                 890                 895

Pro Val Ala Val Leu Thr Ala Gly Pro Ala Pro Val Ala Leu Pro Ala
                    900                 905                 910

Glu Leu Asn Val Val Asp Val Leu Ala Leu Arg Ala Asp Gly Thr Gly
                915                 920                 925

Ala Ala Pro Ala Gly Pro Gly Pro Asp Asp Leu Ala Tyr Val Ile His
            930                 935                 940

Thr Ser Gly Ser Thr Gly Arg Pro Lys Gly Val Ala Val Ala His Arg
945                 950                 955                 960

Ala Val Val Asn Arg Leu Leu Trp Thr Gln Asp Arg Phe Gly Leu Gly
                965                 970                 975

Pro Gly Asp Arg Val Leu Gln Lys Thr Ser Cys Ala Phe Asp Val Ser
                980                 985                 990

Val Trp Glu Phe Phe Trp Pro Leu Ile Ser Gly Ala Thr Leu Val Leu
            995                 1000                1005

Pro Ala  Pro Gly Ala Gln Arg  Asp Pro Ala Arg Val  Ala Ala Ala
    1010                1015                1020

Ile Asp  Glu Ala Gly Ile Thr  Thr Ala His Phe Val  Pro Ser Met
    1025                1030                1035

Leu Val  Ala Tyr Leu Gly Glu  Pro Ala Ala Ala Arg  Pro Arg Ala
    1040                1045                1050

Leu Arg  Arg Ile Leu Cys Ser  Gly Glu Ala Leu Pro  Thr Glu Ala
    1055                1060                1065

Ala Arg  Arg Ala Glu Glu Val  Thr Gly Ala Glu Val  Phe Asn Leu
    1070                1075                1080

Tyr Gly  Pro Thr Glu Ala Ala  Ile Asp Val Ser Trp  Trp Pro Leu
    1085                1090                1095

Arg Asp  Gly Ala Pro Gly Ala  Thr Val Pro Ile Gly  Arg Ala Val
    1100                1105                1110

Trp Asn  Thr Arg Leu Asp Val  Leu Asp Pro Trp Gly  Ala Pro Val
    1115                1120                1125

Pro Pro  Gly Glu Pro Gly Glu  Leu Tyr Ile Ala Gly  Asp Gln Leu
    1130                1135                1140

Ala Val  Gly Tyr Leu Gly Arg  Pro Asp Leu Thr Ala  Glu Arg Phe
    1145                1150                1155

Pro Glu  Asp Pro Ala Ala Gly  Arg Arg Tyr Arg Thr  Gly Asp Leu
    1160                1165                1170

Val Arg  Arg Leu Pro Ser Gly  Ala Leu Glu Phe Leu  Gly Arg Leu
    1175                1180                1185

Asp His  Gln Val Lys Ile Arg  Gly Phe Arg Val Glu  Leu Gly Glu
    1190                1195                1200

Ile Glu  Ala Val Leu Thr Glu  His Pro Glu Val Ala  Ala Ala Val
    1205                1210                1215

Val Gly  Thr Arg Asp Asp Arg  Ala Gly Gly Pro Arg  Leu Val Ala
    1220                1225                1230

Trp Val  Val Pro Ala Pro Ala  Glu Lys Asp Gly Glu  Asp Gly Phe
    1235                1240                1245

Glu Ala  Arg Ala Arg Arg Trp  His Asp His Leu Ala  Ala Arg Leu
    1250                1255                1260
```

```
Pro Glu His Met Val Pro Thr Ala Val Pro Leu Ala Glu Leu
    1265            1270            1275

Pro Thr Thr Ala Asn Gly Lys Leu Asp Arg Asp Ala Leu Pro Glu
    1280            1285            1290

Pro Pro Glu Pro Thr Ala Ala Arg Glu Pro Asp Gly Pro Glu
    1295            1300            1305

Glu Arg Ala Leu Thr Glu Ile Leu Ala Glu Val Leu Gly Ile Glu
    1310            1315            1320

Arg Ile Gly Pro Asp Asp Asp Phe Phe Thr Ala Gly Gly His Ser
    1325            1330            1335

Leu Thr Ala Ala Arg Ala Ala Thr Met Ile Arg Ala Arg Phe Gly
    1340            1345            1350

Val Glu Ile Gly Val Ala Asp Val Phe Ala Ala Arg Cys Ala Ala
    1355            1360            1365

Gly Leu Ala Ala Arg Leu Thr Thr Ala Pro Pro Ala Arg Thr Pro
    1370            1375            1380

Leu Arg Pro Ala Gly Arg Pro Glu Arg Leu Leu Leu Ser Pro Ala
    1385            1390            1395

Gln Arg Gly Leu Trp Phe Leu Asp Arg Leu Asp Asp Gly Pro Thr
    1400            1405            1410

Tyr Asn Ile Pro Leu Val Leu Pro Leu Pro Asn Arg Val Asp Ala
    1415            1420            1425

Asp Ala Leu Ala Ala Ala Leu Gly Asp Val Ala Ala Arg His Glu
    1430            1435            1440

Ser Leu Arg Thr Val Phe Pro Ala Glu Ala Gly Val Pro Tyr Gln
    1445            1450            1455

Glu Val Arg Glu Pro Ala Ala Val Pro Leu His Val Val Asp Cys
    1460            1465            1470

Pro Ala Glu Glu Ile Gly His Val Glu Ala Ala Ala Arg Arg
    1475            1480            1485

Arg Leu Asp Ile Thr Arg Glu Pro Gly Leu Arg Ala Gly Leu Tyr
    1490            1495            1500

Gly Pro Ala Asp Gly Glu Arg Thr Leu Val Leu Leu Leu His His
    1505            1510            1515

Leu Val Ala Asp Gly Trp Ser Leu Arg Pro Leu Ala Glu Asp Leu
    1520            1525            1530

Thr Ala Ala Tyr Ala Ala Arg Ala Ala Gly Arg Ala Pro Glu Leu
    1535            1540            1545

Ala Pro Leu Pro Val Gln Phe Ala Asp Tyr Val Leu Trp Gln Arg
    1550            1555            1560

Asp Arg Leu Asp Pro Ala Gly Ala Ala Ala Arg Arg Asp Glu Glu
    1565            1570            1575

Phe Trp Ser Ala Ala Leu Arg Gly Leu Pro Glu Glu Thr Ala Leu
    1580            1585            1590

Pro Phe Asp Arg Pro Arg Pro Ala Arg Pro Thr Gly Arg Gly Gly
    1595            1600            1605

Ala Val Asp Leu Ala Val Gly Pro Val Ala His Ala Ala Leu Arg
    1610            1615            1620

Glu Leu Ala Arg Ala His Gly Val Ser Leu Phe Thr Val Leu His
    1625            1630            1635

Ala Gly Val Ala Ala Leu Leu Thr Gly Leu Gly Ala Gly Thr Asp
    1640            1645            1650
```

```
Leu Ala Ile Gly Thr Pro Val Ala Gly Arg His Asp Gln Ala Leu
    1655                1660                1665

Asp Asp Val Val Gly Leu Val Thr Asn Thr Val Val Leu Arg Thr
    1670                1675                1680

Asp Thr Ser Gly Ser Pro Ala Val Ala Glu Leu Leu Ala Arg Val
    1685                1690                1695

Gln Glu Ala Asp Arg Ala Ala Trp Ala His Glu Asp Leu Pro Phe
    1700                1705                1710

Glu Gln Val Val Glu Leu Val Asn Pro Pro Arg Val Pro Gly Arg
    1715                1720                1725

His Pro Leu Phe Thr Val Met Leu Ala Leu Gln Asn Asn Ala Ala
    1730                1735                1740

Ala Ala Val Ser Leu Gly Gly Pro Pro Val Pro Leu Arg Pro Ser
    1745                1750                1755

Ala Thr Gly Thr Ala Lys Phe Asp Leu Phe Phe Asp Ile Thr Glu
    1760                1765                1770

His Val Gly Asp Asp Gly Ser Ala Pro Gly Gly Leu Thr Cys His
    1775                1780                1785

Val Glu Phe Ala Arg Asp Leu Phe Asp Pro Ser Thr Ala Arg Leu
    1790                1795                1800

Leu Ala Glu Gly Leu Val Thr Val Leu Ala Arg Ala Ala Ala Ala
    1805                1810                1815

Pro Gly Ala Arg Leu Gly Asp Leu Val Pro Asp Gly Leu Leu Ala
    1820                1825                1830

Gly Arg Asp Ala Ala Pro Glu Ala Val Ser Asp Ala Ala Leu
    1835                1840                1845

Glu Ser Arg Val Arg Ser Leu Ser Ala Val Ala Asp Val Ala Val
    1850                1855                1860

Thr Arg Pro Ser Asp Gly Gly Pro Val Val Trp Val Val Pro Ala
    1865                1870                1875

Arg Pro Gly Ala Asp Asp Ala Arg Arg Leu Leu Ala Asp Glu
    1880                1885                1890

Gly Gly Asp Gly Ala Pro Arg Val Thr Ala Val Thr Val Leu Pro
    1895                1900                1905

Arg Thr Ala Ala Gly Asp Leu Asp Val Ala Ala Leu His Arg Leu
    1910                1915                1920

Pro Val Val Asp Asp Thr Ala Ala Asp Gly Trp Arg Ala Ala Leu
    1925                1930                1935

Ala Ala Val Thr Gly Val Arg Ala Ala Ala Val Gly Arg Glu Asp
    1940                1945                1950

Val Pro Glu Gly Leu Glu Ala Leu Arg Pro Ala Thr Arg Pro Arg
    1955                1960                1965

Thr Val Ala Ala Thr Ala Gly Pro Ala Ala Val His Gln Ala Asp
    1970                1975                1980

Arg Ala Leu Ser Leu Ser Glu Gly Pro Pro Leu Pro Pro Ala Glu
    1985                1990                1995

Val Gly Gly Trp Pro Glu Ala Leu Arg Arg Ala Ala Ala Gly Gly
    2000                2005                2010

Asp His Ala Glu Ile Val His Val Arg Ala Asp Gly Thr Glu Ser
    2015                2020                2025

Arg Arg Ser Tyr Ala Ser Leu Ile Glu Glu Ala Glu Arg Val Leu
    2030                2035                2040

Gly Gly Leu Arg Ala Leu Gly Leu Arg Ala Gly Asp Gln Val Val
```

```
                  2045                2050                2055
Leu Gln Cys Asp Asp Thr Glu Asp Phe Val Ala Ala Leu Trp Gly
              2060                2065                2070
Ala Ile Ala Ala Gly Val Thr Val Val Pro Leu Thr Val Pro Pro
              2075                2080                2085
Thr Tyr Ala Thr Asp Ser Ala Ala Val Asn Lys Leu Asp Gly Val
              2090                2095                2100
Trp Arg Met Leu Gly Arg Pro Val Val Val Thr Ser Ala Asp Arg
              2105                2110                2115
Ala Asp Gly Leu Ala Glu Leu Ala Ala Arg Arg Glu Trp Pro Asp
              2120                2125                2130
Pro Arg Ile Val Thr Val Asp Ala Leu Arg Ala Ala Ala Pro Asp
              2135                2140                2145
Arg Asp Trp His Gln Ala Arg Pro Asp Asp Leu Leu Leu Met Leu
              2150                2155                2160
Leu Thr Ser Gly Ser Thr Gly Leu Pro Lys Ala Val Arg Leu Thr
              2165                2170                2175
His Gly Asn Val Leu Ser Arg Ala Val Ala Ala Ala Ala Ala Asn
              2180                2185                2190
Ser Leu Thr Glu His Asp Val Ser Leu Asn Trp Ile Pro Leu Asp
              2195                2200                2205
His Val Thr Gly Val Val Met Phe His Leu Arg Asp Val Tyr Leu
              2210                2215                2220
Gly Ala Arg Gln Val His Ala Pro Thr Gly Trp Val Leu Glu Asp
              2225                2230                2235
Pro Leu Arg Trp Trp Glu Leu Ala Asp Arg Trp Arg Val Ser Val
              2240                2245                2250
Thr Trp Ala Pro Asn Phe Ala Phe Gly Leu Val Ala Glu Gln Ala
              2255                2260                2265
Gly Arg Leu Ala Gly Arg Glu Trp Asp Leu Ser Pro Val Arg Leu
              2270                2275                2280
Ile Met Asn Ala Gly Glu Val Val Val Gly Ala Thr Asn Arg Arg
              2285                2290                2295
Phe Leu Gln Ala Leu Ala Pro His Gly Leu Pro Ser Asp Val Met
              2300                2305                2310
His Pro Gly Trp Gly Met Ser Glu Thr Cys Ser Val Val Thr Asp
              2315                2320                2325
Thr Val Leu Asp Pro Gln Pro Pro Gly Gly Asp Glu Thr Phe
              2330                2335                2340
Val Ser Cys Gly Arg Pro Tyr Pro Gly Phe Ala Met Arg Val Val
              2345                2350                2355
Asp Glu Glu Leu Arg Leu Leu Pro Glu Gly Glu Val Gly Arg Phe
              2360                2365                2370
Gln Val Arg Gly Ala Ser Val Thr Ser Gly Tyr His Asp Asn Ala
              2375                2380                2385
Ala Ala Asn Ala Glu Ala Phe Thr Ala Asp Gly Trp Phe Asp Thr
              2390                2395                2400
Gly Asp Leu Ala Phe Leu Arg Asp Gly Glu Leu Tyr Ile Thr Gly
              2405                2410                2415
Arg Ala Lys Asp Val Ile Ile Val Asn Gly Val Asn His Phe Ser
              2420                2425                2430
His Glu Ile Glu Ala Cys Val Glu Glu Leu Pro Val Val Val Arg
              2435                2440                2445
```

```
Ser Phe Thr Ala Ala Val Ala Val Arg Thr Asp Ala Ser Ala Ala
    2450            2455                2460

Thr Asp Gln Leu Ala Leu Phe Val His Leu Ala Pro Gly His Asp
    2465            2470                2475

Ser Gly Glu Ala Ala Ala Ala Leu Arg Ala Ile Arg Gly Lys
    2480            2485                2490

Val Ala Arg Glu Val Gly Val Ala Pro Ala His Val Leu Pro Val
    2495            2500                2505

Glu Thr Ala Val Ile Pro Lys Thr Glu Ile Gly Lys Ile Gln Arg
    2510            2515                2520

Thr Gln Leu Arg Lys Arg Phe Glu Ala Gly Glu Phe Asp Ala Val
    2525            2530                2535

Ala Arg Ala Ala Glu Val Leu Leu Gly Thr Ala Ala Thr Val Pro
    2540            2545                2550

His Trp Phe Leu Arg Pro Val Trp Ser Pro Val Thr Arg Pro Ala
    2555            2560                2565

Thr Ala Pro Pro Ala Gly Thr Ser Val Leu Ile Val Ala Ala Gly
    2570            2575                2580

Pro Arg Gly Ala Gly Val Ala Glu Arg Leu Ala Ala Leu Val Arg
    2585            2590                2595

Arg Glu Gly Gly Arg Ala Thr Thr Ala Val Ala Gly Thr Gly Phe
    2600            2605                2610

Gly Arg Arg Asp Ala Ala Arg Tyr Thr Val Arg Pro Asp Glu Ala
    2615            2620                2625

Ser Asp Phe Ala Ala Leu Leu Asp Arg Leu Ala Ala Asp Asp Arg
    2630            2635                2640

Arg Pro Glu Arg Val Val His Leu Gly Pro Leu Glu Pro Ser Gly
    2645            2650                2655

Arg Asp Leu Asp Ala Gly Gly Val Leu Asp Ala Gln Arg Ser Gly
    2660            2665                2670

Ala Ala Ser Val Leu Ala Leu Ala Arg Ala Leu Ala Ala Pro Asp
    2675            2680                2685

His Ala Gly His Ala Val Asp Leu Arg Cys Val Thr Gly Gly Asp
    2690            2695                2700

Leu Pro His Ala Thr Leu Ala Gly Leu Leu Pro Ser Leu Arg Asp
    2705            2710                2715

Glu Arg Pro Gly Leu Ser Ala Gly Thr Leu Ala Val Pro Gly Asp
    2720            2725                2730

Gly Glu Pro Asp Asp Val Ala Ala Leu Ile Ala Ala Glu Leu Ala
    2735            2740                2745

Val Ala Pro Ala Asp Ala Glu Val Cys Arg Arg Asp Gly Gly Arg
    2750            2755                2760

Leu Val Arg Arg Leu Ala Pro Val Pro Val Pro Glu Ser Val Thr
    2765            2770                2775

Val Pro Ala Tyr Gly Asp Gly Val Val Leu Val Thr Gly Gly Leu
    2780            2785                2790

Gly Gly Val Ala Ala His Leu Ala Glu His Leu Leu Thr Thr Glu
    2795            2800                2805

Pro Gly Val Arg Leu Leu Leu Val Gly Arg Thr Pro Leu Pro Ala
    2810            2815                2820

Gly Asp Pro Ala Ala Asp Asp Ala Arg Ala Arg Ala Ala Ala Val
    2825            2830                2835
```

```
Leu Arg Arg Leu Arg Glu Leu Gly Glu Val Arg Tyr Ala Ala Ala
    2840            2845                2850

Asp Val Thr Asp Glu Ala Ala Leu Asp Ala Ala Val Ala Ala Ala
    2855            2860                2865

Thr Asp Ala Trp Ser Ala Pro Leu Thr Gly Ile Leu His Leu Ala
    2870            2875                2880

Gly Thr Ile Glu Arg Arg Ala Ala Ala Asp Leu Asp Pro Ala Ala
    2885            2890                2895

Trp Arg Ala Ala Thr Ala Ala Lys Ile Gly Gly Ala Cys Val Leu
    2900            2905                2910

Asp Arg Leu Ala Ala Arg His Pro Val Arg Ser Phe Val Ser Phe
    2915            2920                2925

Ser Ser Val Asn Gly Thr Phe Gly Ala Ala Phe Gly Ala Pro Tyr
    2930            2935                2940

Ala Ala Ala Cys Ala Phe Leu Asp Ala Leu Ala Val Arg Gln Arg
    2945            2950                2955

Ala Arg Gly Leu Asp Ala Gln Ser Leu Ala Trp Ser Ser Trp Arg
    2960            2965                2970

Asp Thr Gly Met Ser Glu Gly Asp Glu Leu Ala Ala Leu Gly Glu
    2975            2980                2985

Thr Arg Gly Tyr Arg Ala Leu Asp Val Glu Ser Ala Leu Arg Ser
    2990            2995                3000

Phe Asp Leu Ala Arg Gly Leu Asp Glu Pro Val Val Leu Ile Gly
    3005            3010                3015

Ala Asp Arg Thr Ala Asp Gly Val Arg Arg Leu Val Asp Ala Pro
    3020            3025                3030

Ala Arg Pro Arg His Arg Leu Ala Ala Arg Val Glu Leu Glu Glu
    3035            3040                3045

Gly Ala Asp Ile Gly Gly Leu His Glu Ala Ala Val Ala Ala Ala
    3050            3055                3060

Ala Arg Ala Cys Gly Gly Val Ala Gly His Gly Ala Val Val Arg
    3065            3070                3075

Ala Ala Ser Ser Ala Ala Ser Ala Ala Glu Gly Ser Ala Ala Ser
    3080            3085                3090

Gly Ala Ala Gly Gly Asp Arg Val Arg Val Leu Glu Glu Thr Val
    3095            3100                3105

Leu Ala Val Trp Arg Arg Val Leu Gly Arg Glu Arg Val Gly Ser
    3110            3115                3120

Gly Asp Asn Phe Phe Asp Leu Gly Gly His Ser Leu Leu Leu Val
    3125            3130                3135

Arg Ala Gln Ala Glu Leu Asn Glu Ala Leu Gly Gly Ala Leu Thr
    3140            3145                3150

Val Val Asp Leu Phe Ala His Pro Asn Ala Arg Ser Leu Ala Gly
    3155            3160                3165

His Leu Ala Gly Arg Arg Asp Ile Thr Ala Pro Gly Asp Gly Arg
    3170            3175                3180

Glu Ala Gly Gly Glu Glu Asp Gly Gly Ser Ala Ala Ala Gly Ser
    3185            3190                3195

Ala Leu Gly Ala Thr Arg Glu Gln Ala Arg Arg Leu Ala Ala
    3200            3205                3210

Arg Ala Gln Arg Asn Gly Lys Gly Pro Lys Gly Arg Lys Gly Gln
    3215            3220                3225

Gln Asp Gln Pro Gly Gln Gln Gly Gln Glu Glu Ala Ser His Ala
```

Glu

<210> SEQ ID NO 28
<211> LENGTH: 1173
<212> TYPE: DNA
<213> ORGANISM: Streptoverticillium
<220> FEATURE:
<221> NAME/KEY: CDS
<222> LOCATION: (1)..(1173)

<400> SEQUENCE: 28

```
atg tcc gtc gac cgg tcg cac gac ccc gcc cgc ccc gac gtg gtg gtg         48
Met Ser Val Asp Arg Ser His Asp Pro Ala Arg Pro Asp Val Val Val
1               5                   10                  15 gtc ggc ctg ggg atc tgg ggg gcc atg acg ctg tgg cgg ctc gcc gcc         96
Val Gly Leu Gly Ile Trp Gly Ala Met Thr Leu Trp Arg Leu Ala Ala
            20                  25                  30 cgc ggt gtc cgg gcg gtg ggg gtc gag cgg ttc gac atc gcg cac gcc        144
Arg Gly Val Arg Ala Val Gly Val Glu Arg Phe Asp Ile Ala His Ala
        35                  40                  45 cgc ggg tcc tcg cac ggc ggt cac cgc atg ttc cgc gag acc tgc ctg        192
Arg Gly Ser Ser His Gly Gly His Arg Met Phe Arg Glu Thr Cys Leu
    50                  55                  60 gag aac gag gcc ctc gtg ccg gtg gcc cgg cgt tcg ctg gag ctg tgg        240
Glu Asn Glu Ala Leu Val Pro Val Ala Arg Arg Ser Leu Glu Leu Trp
65                  70                  75                  80 cgc gag ctg gag gcg ggc acg ggc cgc cgg ctc ttc gag aac acc ggg        288
Arg Glu Leu Glu Ala Gly Thr Gly Arg Arg Leu Phe Glu Asn Thr Gly
                85                  90                  95 ggc ctg ctc atc ggc ccg cgc gac ggc cgg ctg gcc ggc ggc acc atc        336
Gly Leu Leu Ile Gly Pro Arg Asp Gly Arg Leu Ala Gly Gly Thr Ile
            100                 105                 110 gcc tcg gcc gag gcg cac ggc gtc gcg gtc gag gtc ctc gaa ccg gcc        384
Ala Ser Ala Glu Ala His Gly Val Ala Val Glu Val Leu Glu Pro Ala
        115                 120                 125 gag gtc tcg gcc cgc ttc ccg ggg cac gcc ggc atc ccc gaa gga cac        432
Glu Val Ser Ala Arg Phe Pro Gly His Ala Gly Ile Pro Glu Gly His
    130                 135                 140 gtg ggc gtg tgg gag ccc tcg gcg ggc gtc ctg cgg gcc gag gac tcg        480
Val Gly Val Trp Glu Pro Ser Ala Gly Val Leu Arg Ala Glu Asp Ser
145                 150                 155                 160 gtc cgc gcc gcg gtc gag ctg gcg gag cgc ggc ggg gcc acc gtg ctc        528
Val Arg Ala Ala Val Glu Leu Ala Glu Arg Gly Gly Ala Thr Val Leu
                165                 170                 175 cgc ggc acc gag gtg ctc ggc gtc gag ccg gag ggc ggc ggc gta cgg        576
Arg Gly Thr Glu Val Leu Gly Val Glu Pro Glu Gly Gly Gly Val Arg
            180                 185                 190 gtc cgc acc gcc ggg cgc gac ctg gtc gcc ggc cgg gtc gtc ctc acg        624
Val Arg Thr Ala Gly Arg Asp Leu Val Ala Gly Arg Val Val Leu Thr
        195                 200                 205 ccc ggg tgc tgg ctg ccg gac ttc gcc ccc ggc ctg ggc gtc cgc tcc        672
Pro Gly Cys Trp Leu Pro Asp Phe Ala Pro Gly Leu Gly Val Arg Ser
    210                 215                 220 gtc cac ctg ccg atg acg tgg ttc ccg ccg agc ggc gac ccg gcg ctg        720
Val His Leu Pro Met Thr Trp Phe Pro Pro Ser Gly Asp Pro Ala Leu
225                 230                 235                 240 ttc cgc cgc gag ctg ttc ccg gtg ttc atg cgg gag atc gac gcg gac        768
Phe Arg Arg Glu Leu Phe Pro Val Phe Met Arg Glu Ile Asp Ala Asp
                245                 250                 255
```

```
acc gtc atc tgg ggc cag ggc gac ggc gac ccc ggg cac gtc aag ctc      816
Thr Val Ile Trp Gly Gln Gly Asp Gly Asp Pro Gly His Val Lys Leu
        260                 265                 270 ggc atc gag cag ggg gcg gac ccg gac ccg tac gat ccc gaa ctc ggc      864
Gly Ile Glu Gln Gly Ala Asp Pro Asp Pro Tyr Asp Pro Glu Leu Gly
            275                 280                 285 gct ccc gcc gtc ccg agc agg ccc tgg gag cgg ctc ggc gag gtg ctc      912
Ala Pro Ala Val Pro Ser Arg Pro Trp Glu Arg Leu Gly Glu Val Leu
    290                 295                 300 gcc acc gcc gtc ccc ggg gtg ggg cgc gta ccg tcg cgg atc ctg cac      960
Ala Thr Ala Val Pro Gly Val Gly Arg Val Pro Ser Arg Ile Leu His
305                 310                 315                 320 tgc ggg atc acg acg acc gcc gac ggg cag ttc gtg ctc ggc gcc tcc     1008
Cys Gly Ile Thr Thr Thr Ala Asp Gly Gln Phe Val Leu Gly Ala Ser
            325                 330                 335 ccg gcc gac ccc cgg gtc gtg ctg gcc ggg ggg tgc aac ggc tac gga     1056
Pro Ala Asp Pro Arg Val Val Leu Ala Gly Gly Cys Asn Gly Tyr Gly
        340                 345                 350 ttc aag cac gcc gcc gcc gtc ggg gac ctc ctc gcc gac atc gtg ctg     1104
Phe Lys His Ala Ala Ala Val Gly Asp Leu Leu Ala Asp Ile Val Leu
    355                 360                 365 ggt gcc gcg ggg ccc gct ccc ctg ccg ttc gcc gcg ccc ggc cgg ccg     1152
Gly Ala Ala Gly Pro Ala Pro Leu Pro Phe Ala Ala Pro Gly Arg Pro
370                 375                 380 gcc gcg gcg gac cac atc tga                                         1173
Ala Ala Ala Asp His Ile
385                 390

<210> SEQ ID NO 29
<211> LENGTH: 390
<212> TYPE: PRT
<213> ORGANISM: Streptoverticillium

<400> SEQUENCE: 29

Met Ser Val Asp Arg Ser His Asp Pro Ala Arg Pro Asp Val Val Val
1               5                   10                  15

Val Gly Leu Gly Ile Trp Gly Ala Met Thr Leu Trp Arg Leu Ala Ala
            20                  25                  30

Arg Gly Val Arg Ala Val Gly Val Glu Arg Phe Asp Ile Ala His Ala
        35                  40                  45

Arg Gly Ser Ser His Gly Gly His Arg Met Phe Arg Glu Thr Cys Leu
    50                  55                  60

Glu Asn Glu Ala Leu Val Pro Val Ala Arg Arg Ser Leu Glu Leu Trp
65                  70                  75                  80

Arg Glu Leu Glu Ala Gly Thr Gly Arg Arg Leu Phe Glu Asn Thr Gly
                85                  90                  95

Gly Leu Leu Ile Gly Pro Arg Asp Gly Arg Leu Ala Gly Gly Thr Ile
            100                 105                 110

Ala Ser Ala Glu Ala His Gly Val Ala Val Glu Val Leu Glu Pro Ala
        115                 120                 125

Glu Val Ser Ala Arg Phe Pro Gly His Ala Gly Ile Pro Glu Gly His
    130                 135                 140

Val Gly Val Trp Glu Pro Ser Ala Gly Val Leu Arg Ala Glu Asp Ser
145                 150                 155                 160

Val Arg Ala Ala Val Glu Leu Ala Glu Arg Gly Gly Ala Thr Val Leu
                165                 170                 175

Arg Gly Thr Glu Val Leu Gly Val Glu Pro Glu Gly Gly Gly Val Arg
            180                 185                 190
```

```
Val Arg Thr Ala Gly Arg Asp Leu Val Ala Gly Arg Val Val Leu Thr
        195                 200                 205

Pro Gly Cys Trp Leu Pro Asp Phe Ala Pro Gly Leu Gly Val Arg Ser
210                 215                 220

Val His Leu Pro Met Thr Trp Phe Pro Pro Ser Gly Asp Pro Ala Leu
225                 230                 235                 240

Phe Arg Arg Glu Leu Phe Pro Val Phe Met Arg Glu Ile Asp Ala Asp
                245                 250                 255

Thr Val Ile Trp Gly Gln Gly Asp Gly Asp Pro Gly His Val Lys Leu
            260                 265                 270

Gly Ile Glu Gln Gly Ala Asp Pro Asp Pro Tyr Asp Pro Glu Leu Gly
                275                 280                 285

Ala Pro Ala Val Pro Ser Arg Pro Trp Glu Arg Leu Gly Glu Val Leu
    290                 295                 300

Ala Thr Ala Val Pro Gly Val Gly Arg Val Pro Ser Arg Ile Leu His
305                 310                 315                 320

Cys Gly Ile Thr Thr Thr Ala Asp Gly Gln Phe Val Leu Gly Ala Ser
                325                 330                 335

Pro Ala Asp Pro Arg Val Val Leu Ala Gly Gly Cys Asn Gly Tyr Gly
                340                 345                 350

Phe Lys His Ala Ala Ala Val Gly Asp Leu Leu Ala Asp Ile Val Leu
            355                 360                 365

Gly Ala Ala Gly Pro Ala Pro Leu Pro Phe Ala Pro Gly Arg Pro
370                 375                 380

Ala Ala Ala Asp His Ile
385                 390

<210> SEQ ID NO 30
<211> LENGTH: 1062
<212> TYPE: DNA
<213> ORGANISM: Streptoverticillium
<220> FEATURE:
<221> NAME/KEY: CDS
<222> LOCATION: (1)..(1062)

<400> SEQUENCE: 30 atg gat ttc ggt ctg acc ttc ttc ccc gcg ctc gac gag cgg gac aag      48
Met Asp Phe Gly Leu Thr Phe Phe Pro Ala Leu Asp Glu Arg Asp Lys
1               5                   10                  15 gcg ccg cac gac tac ttc gac gac tgc ctg gcc ctc gcc gtc gac gcc      96
Ala Pro His Asp Tyr Phe Asp Asp Cys Leu Ala Leu Ala Val Asp Ala
                20                  25                  30 gac cgg ctg ggc tac gag cac gtc cag gtg gtc gag cac cac ctc ggg     144
Asp Arg Leu Gly Tyr Glu His Val Gln Val Val Glu His His Leu Gly
            35                  40                  45 ccc tac ggg ggg tac agc ccc gac ccg gtg gtc ctg ctc tcg gcc atc     192
Pro Tyr Gly Gly Tyr Ser Pro Asp Pro Val Val Leu Leu Ser Ala Ile
        50                  55                  60 gcc gcg cgt acc gag cgg ctg cgc atc acc acc ggc gcg gtc atc ccc     240
Ala Ala Arg Thr Glu Arg Leu Arg Ile Thr Thr Gly Ala Val Ile Pro
65                  70                  75                  80 gcc ttc gac cac ccg ctc aag ctg gcc ggg cgg ctg gcg atg ctg gac     288
Ala Phe Asp His Pro Leu Lys Leu Ala Gly Arg Leu Ala Met Leu Asp
                85                  90                  95 cag ctg agc ggc ggc cgg gtc gac gtc ggc gtc gga cgg gcc ttc ctg     336
Gln Leu Ser Gly Gly Arg Val Asp Val Gly Val Gly Arg Ala Phe Leu
                100                 105                 110
```

```
ccg cac gag ttc acg gcg ttc gag gtg tcg atg gag gag agc cgg gcg    384
Pro His Glu Phe Thr Ala Phe Glu Val Ser Met Glu Glu Ser Arg Ala
        115                 120                 125 cgc ttc acc gag gcg ctg cgg gcc ttc gtc gcg ctc tgg acc ggg acg    432
Arg Phe Thr Glu Ala Leu Arg Ala Phe Val Ala Leu Trp Thr Gly Thr
130                 135                 140 gac gtg gtc ttc gag ggc gag ttc cac cgc ttc ggg tcg gtg acg ctc    480
Asp Val Val Phe Glu Gly Glu Phe His Arg Phe Gly Ser Val Thr Leu
145                 150                 155                 160 acc ccg cgc ccg cac cag acg ccg cat cct ccg ctg ttc gtc gcc tcg    528
Thr Pro Arg Pro His Gln Thr Pro His Pro Pro Leu Phe Val Ala Ser
                165                 170                 175 gcg tcc agc gcc gag tcc tgc gcc gcc gcc ggc cgc gag ggg cac aac    576
Ala Ser Ser Ala Glu Ser Cys Ala Ala Ala Gly Arg Glu Gly His Asn
            180                 185                 190 ctg cag atc gtg ccg acc atc acc agc ggt gag cag ttc gcg gag atg    624
Leu Gln Ile Val Pro Thr Ile Thr Ser Gly Glu Gln Phe Ala Glu Met
        195                 200                 205 ctc gcg gcc tac cgc gag gcc ttc gcc gcc cac cac ccg gac cgc gcg    672
Leu Ala Ala Tyr Arg Glu Ala Phe Ala Ala His His Pro Asp Arg Ala
210                 215                 220 ccg cgc atc cag gtc aag tac agc tgc tac ctg gac cgg gac cgc gac    720
Pro Arg Ile Gln Val Lys Tyr Ser Cys Tyr Leu Asp Arg Asp Arg Asp
225                 230                 235                 240 agc gcc tgg cgg gcg gcc gag gcg gcg gag tcc aac tac ctg gac aag    768
Ser Ala Trp Arg Ala Ala Glu Ala Ala Glu Ser Asn Tyr Leu Asp Lys
                245                 250                 255 atg agc ggc gcc gtc aag agc tgg cag ggc gcc gcg acc gcg cag tac    816
Met Ser Gly Ala Val Lys Ser Trp Gln Gly Ala Ala Thr Ala Gln Tyr
            260                 265                 270 ccg ggg tac gag aag ctc gcc gac aag gtc gcc tcc tcc gac ctg cgc    864
Pro Gly Tyr Glu Lys Leu Ala Asp Lys Val Ala Ser Ser Asp Leu Arg
        275                 280                 285 aag tcg tgg gag cag gac aag gtg ctg atc ggc acc acc ggc gac atc    912
Lys Ser Trp Glu Gln Asp Lys Val Leu Ile Gly Thr Thr Gly Asp Ile
290                 295                 300 acc gag cag ctg gag cgg gtg cgc gag cgg gtg ggc ggc gac gtg acc    960
Thr Glu Gln Leu Glu Arg Val Arg Glu Arg Val Gly Gly Asp Val Thr
305                 310                 315                 320 gtc agc ctg cac atg aac aac ggc gtg acg cca ctg gag cag gcg cgg    1008
Val Ser Leu His Met Asn Asn Gly Val Thr Pro Leu Glu Gln Ala Arg
                325                 330                 335 tgg gcg gtc gcc gag ttc gcc gcc gag atc gcg ccg cgg ttc gcg gct    1056
Trp Ala Val Ala Glu Phe Ala Ala Glu Ile Ala Pro Arg Phe Ala Ala
            340                 345                 350 gcc tga                                                            1062
Ala

<210> SEQ ID NO 31
<211> LENGTH: 353
<212> TYPE: PRT
<213> ORGANISM: Streptoverticillium

<400> SEQUENCE: 31

Met Asp Phe Gly Leu Thr Phe Phe Pro Ala Leu Asp Glu Arg Asp Lys
1               5                   10                  15

Ala Pro His Asp Tyr Phe Asp Asp Cys Leu Ala Leu Ala Val Asp Ala
            20                  25                  30

Asp Arg Leu Gly Tyr Glu His Val Gln Val Val Glu His His Leu Gly
        35                  40                  45
```

```
Pro Tyr Gly Gly Tyr Ser Pro Asp Pro Val Val Leu Leu Ser Ala Ile
    50              55                  60

Ala Ala Arg Thr Glu Arg Leu Arg Ile Thr Thr Gly Ala Val Ile Pro
65              70                  75                  80

Ala Phe Asp His Pro Leu Lys Leu Ala Gly Arg Leu Ala Met Leu Asp
                85                  90                  95

Gln Leu Ser Gly Gly Arg Val Asp Val Gly Val Gly Arg Ala Phe Leu
                100                 105                 110

Pro His Glu Phe Thr Ala Phe Glu Val Ser Met Glu Glu Ser Arg Ala
            115                 120                 125

Arg Phe Thr Glu Ala Leu Arg Ala Phe Val Ala Leu Trp Thr Gly Thr
    130                 135                 140

Asp Val Val Phe Glu Gly Glu Phe His Arg Phe Gly Ser Val Thr Leu
145                 150                 155                 160

Thr Pro Arg Pro His Gln Thr Pro His Pro Leu Phe Val Ala Ser
                165                 170                 175

Ala Ser Ser Ala Glu Ser Cys Ala Ala Ala Gly Arg Glu Gly His Asn
                180                 185                 190

Leu Gln Ile Val Pro Thr Ile Thr Ser Gly Glu Gln Phe Ala Glu Met
        195                 200                 205

Leu Ala Ala Tyr Arg Glu Ala Phe Ala Ala His His Pro Asp Arg Ala
    210                 215                 220

Pro Arg Ile Gln Val Lys Tyr Ser Cys Tyr Leu Asp Arg Asp Arg Asp
225                 230                 235                 240

Ser Ala Trp Arg Ala Ala Glu Ala Glu Ser Asn Tyr Leu Asp Lys
                245                 250                 255

Met Ser Gly Ala Val Lys Ser Trp Gln Gly Ala Ala Thr Ala Gln Tyr
            260                 265                 270

Pro Gly Tyr Glu Lys Leu Ala Asp Lys Val Ala Ser Ser Asp Leu Arg
    275                 280                 285

Lys Ser Trp Glu Gln Asp Lys Val Leu Ile Gly Thr Thr Gly Asp Ile
290                 295                 300

Thr Glu Gln Leu Glu Arg Val Arg Glu Arg Val Gly Gly Asp Val Thr
305                 310                 315                 320

Val Ser Leu His Met Asn Asn Gly Val Thr Pro Leu Glu Gln Ala Arg
                325                 330                 335

Trp Ala Val Ala Glu Phe Ala Ala Glu Ile Ala Pro Arg Phe Ala Ala
            340                 345                 350

Ala

<210> SEQ ID NO 32
<211> LENGTH: 630
<212> TYPE: DNA
<213> ORGANISM: Streptoverticillium
<220> FEATURE:
<221> NAME/KEY: CDS
<222> LOCATION: (1)..(630)

<400> SEQUENCE: 32 atg agc agc gaa gta ccc gag atc agg gtc agc gac gag cgg gtc aac     48
Met Ser Ser Glu Val Pro Glu Ile Arg Val Ser Asp Glu Arg Val Asn
1               5                   10                  15 cgc acg ctc acc gcg gtc aac gcc cgg gcg gcc gag cac gac cgg tcg     96
Arg Thr Leu Thr Ala Val Asn Ala Arg Ala Ala Glu His Asp Arg Ser
                20                  25                  30
```

| | | |
|---|---|---|
| cta ttc gag cag gtg cgc gac tcg ctg gcg gtc gcg gtg ccg ccg gag<br>Leu Phe Glu Gln Val Arg Asp Ser Leu Ala Val Ala Val Pro Pro Glu<br>35 40 45 | | 144 |
| gcg ggc acg ctg atg tac cag ctc gtg cgc gcc acc cgg gcc gcc aag<br>Ala Gly Thr Leu Met Tyr Gln Leu Val Arg Ala Thr Arg Ala Ala Lys<br>50 55 60 | | 192 |
| gtg gtg gag ctg ggg atg tcg ctc ggc gtc tcc acg gtc tac ctc gcc<br>Val Val Glu Leu Gly Met Ser Leu Gly Val Ser Thr Val Tyr Leu Ala<br>65 70 75 80 | | 240 |
| gcc gcc gtg cgc gac aac ggg ggc gag ggg cgg gtc tac acg acc gag<br>Ala Ala Val Arg Asp Asn Gly Gly Glu Gly Arg Val Tyr Thr Thr Glu<br>85 90 95 | | 288 |
| atc gac gag gcg aag atc aag cag ggc cgc gcc acc ctg gcc gac gcc<br>Ile Asp Glu Ala Lys Ile Lys Gln Gly Arg Ala Thr Leu Ala Asp Ala<br>100 105 110 | | 336 |
| ggc gtc gcc gac ctc gtg gag gtg ctg gag ggc gac gcg ctc cag acc<br>Gly Val Ala Asp Leu Val Glu Val Leu Glu Gly Asp Ala Leu Gln Thr<br>115 120 125 | | 384 |
| ctg gac tcg gtg ccc gac ggc gtc cag ttc gtc ctg ctc gac ggc tgg<br>Leu Asp Ser Val Pro Asp Gly Val Gln Phe Val Leu Leu Asp Gly Trp<br>130 135 140 | | 432 |
| aac gag agc tac ctg cgg gtg atg aag atc ctg gag ccc aag ctc gcg<br>Asn Glu Ser Tyr Leu Arg Val Met Lys Ile Leu Glu Pro Lys Leu Ala<br>145 150 155 160 | | 480 |
| ccg ggc gcc ctc gtg ctc gcc gac gac gtc aac ctc ttc ggc gag ggc<br>Pro Gly Ala Leu Val Leu Ala Asp Asp Val Asn Leu Phe Gly Glu Gly<br>165 170 175 | | 528 |
| tgc gtg gac ttc ctg gag tac gtc cgc gac ccc gcg aac ggc tac ctg<br>Cys Val Asp Phe Leu Glu Tyr Val Arg Asp Pro Ala Asn Gly Tyr Leu<br>180 185 190 | | 576 |
| tcc gtc aac ttc ccg atg ggc gag ggc ctg gag ctc agc atg cgc gtg<br>Ser Val Asn Phe Pro Met Gly Glu Gly Leu Glu Leu Ser Met Arg Val<br>195 200 205 | | 624 |
| ggc tga<br>Gly | | 630 |

<210> SEQ ID NO 33
<211> LENGTH: 209
<212> TYPE: PRT
<213> ORGANISM: Streptoverticillium

<400> SEQUENCE: 33

Met Ser Ser Glu Val Pro Glu Ile Arg Val Ser Asp Glu Arg Val Asn
1               5                   10                  15

Arg Thr Leu Thr Ala Val Asn Ala Arg Ala Ala Glu His Asp Arg Ser
                20                  25                  30

Leu Phe Glu Gln Val Arg Asp Ser Leu Ala Val Ala Val Pro Pro Glu
            35                  40                  45

Ala Gly Thr Leu Met Tyr Gln Leu Val Arg Ala Thr Arg Ala Ala Lys
        50                  55                  60

Val Val Glu Leu Gly Met Ser Leu Gly Val Ser Thr Val Tyr Leu Ala
65                  70                  75                  80

Ala Ala Val Arg Asp Asn Gly Gly Glu Gly Arg Val Tyr Thr Thr Glu
                85                  90                  95

Ile Asp Glu Ala Lys Ile Lys Gln Gly Arg Ala Thr Leu Ala Asp Ala
                100                 105                 110

Gly Val Ala Asp Leu Val Glu Val Leu Glu Gly Asp Ala Leu Gln Thr
            115                 120                 125

```
Leu Asp Ser Val Pro Asp Gly Val Gln Phe Val Leu Leu Asp Gly Trp
130                 135                 140

Asn Glu Ser Tyr Leu Arg Val Met Lys Ile Leu Glu Pro Lys Leu Ala
145                 150                 155                 160

Pro Gly Ala Leu Val Leu Ala Asp Asp Val Asn Leu Phe Gly Glu Gly
                165                 170                 175

Cys Val Asp Phe Leu Glu Tyr Val Arg Asp Pro Ala Asn Gly Tyr Leu
            180                 185                 190

Ser Val Asn Phe Pro Met Gly Gly Leu Glu Leu Ser Met Arg Val
        195                 200                 205

Gly

<210> SEQ ID NO 34
<211> LENGTH: 1341
<212> TYPE: DNA
<213> ORGANISM: Streptoverticillium
<220> FEATURE:
<221> NAME/KEY: CDS
<222> LOCATION: (1)..(1341)

<400> SEQUENCE: 34 atg acg gaa ctg cgt gac gcg gtg ctg cgt ggc gcg tcc ccc gag gaa      48
Met Thr Glu Leu Arg Asp Ala Val Leu Arg Gly Ala Ser Pro Glu Glu
1               5                   10                  15 ctg ctg cgc gcc ccc ctc ccg gcc acc tac cgg gcc gcc cac ctg cgc      96
Leu Leu Arg Ala Pro Leu Pro Ala Thr Tyr Arg Ala Ala His Leu Arg
            20                  25                  30 gcc gag gac gtc ggc atg ttc gac ggc acg gac ggc gac cgc gac gtg      144
Ala Glu Asp Val Gly Met Phe Asp Gly Thr Asp Gly Asp Arg Asp Val
        35                  40                  45 cgc aag tcg gtg gcc gtg ggc cag gtg ccg ctg ccc gag atc gcg ccc      192
Arg Lys Ser Val Ala Val Gly Gln Val Pro Leu Pro Glu Ile Ala Pro
50                  55                  60 gac gag gtc ctg atc gcg gtc atg gcc gcc gcg gtc aac tac aac tcc      240
Asp Glu Val Leu Ile Ala Val Met Ala Ala Ala Val Asn Tyr Asn Ser
65                  70                  75                  80 gtg tgg tcg gcg acg ttc ctg ccg atg ccg acc ttc cgc ttc ctc gag      288
Val Trp Ser Ala Thr Phe Leu Pro Met Pro Thr Phe Arg Phe Leu Glu
                85                  90                  95 aag tac gcc cgc cag ggc ggc tgg gca gca cgc cac gac cag ccc tac      336
Lys Tyr Ala Arg Gln Gly Gly Trp Ala Ala Arg His Asp Gln Pro Tyr
            100                 105                 110 cac gtg atc ggc tcc gac tgc tcg ggc gtc gtc gtg cgc gtc ggc tcc      384
His Val Ile Gly Ser Asp Cys Ser Gly Val Val Val Arg Val Gly Ser
        115                 120                 125 ggc gtg cgc cgg tgg cgg gtc ggc gac cac gtg gtg atc cac ccg gtg      432
Gly Val Arg Arg Trp Arg Val Gly Asp His Val Val Ile His Pro Val
130                 135                 140 cac gtg gac gac cag ggc gcc gcc acc cac gac gac gcc atg atg gac      480
His Val Asp Asp Gln Gly Ala Ala Thr His Asp Asp Ala Met Met Asp
145                 150                 155                 160 gac cag cag cgc gcc tgg ggg tac gag acc aac ttc ggc gcc ttc ggc      528
Asp Gln Gln Arg Ala Trp Gly Tyr Glu Thr Asn Phe Gly Ala Phe Gly
                165                 170                 175 gag tac gcc gtc gcc cgc gcc agc caa ctg gtc gcc aag ccc ggc cac      576
Glu Tyr Ala Val Ala Arg Ala Ser Gln Leu Val Ala Lys Pro Gly His
            180                 185                 190 ttg acg tgg gag gag tcg gcg gcg aac acg ctg tgc acc acc acg tcg      624
Leu Thr Trp Glu Glu Ser Ala Ala Asn Thr Leu Cys Thr Thr Thr Ser
        195                 200                 205
```

```
tac cgc atg ctc gtc ggg gcg cac ggc gcc cgg atg aag cag ggg gac      672
Tyr Arg Met Leu Val Gly Ala His Gly Ala Arg Met Lys Gln Gly Asp
        210                 215                 220 gtg gtc ctg gtc tgg ggc gcg gcg ggc ggc ctg ggg acg tac gcc gtg      720
Val Val Leu Val Trp Gly Ala Ala Gly Gly Leu Gly Thr Tyr Ala Val
225                 230                 235                 240 cag ttg gtc aag aac ggc ggc ggt atc ccc gtc gcc gtc gtc agc tcg      768
Gln Leu Val Lys Asn Gly Gly Gly Ile Pro Val Ala Val Val Ser Ser
            245                 250                 255 ccc gcg aag gcg gag gcg gtc cgc cgg ctg ggc tgc gag cac gtc atc      816
Pro Ala Lys Ala Glu Ala Val Arg Arg Leu Gly Cys Glu His Val Ile
        260                 265                 270 gac cgc acc gaa ctc ggg ctc acc ggc gac ccc tcg ggc gac ttc gac      864
Asp Arg Thr Glu Leu Gly Leu Thr Gly Asp Pro Ser Gly Asp Phe Asp
    275                 280                 285 gcc gtg cgg gag atc ggc aag cgg ctg ggc gcc cgc atc cgc gaa ctc      912
Ala Val Arg Glu Ile Gly Lys Arg Leu Gly Ala Arg Ile Arg Glu Leu
        290                 295                 300 gcc ggc cgc gac ccc gac atc gtc ttc gag cac acc ggc cgg gcc acc      960
Ala Gly Arg Asp Pro Asp Ile Val Phe Glu His Thr Gly Arg Ala Thr
305                 310                 315                 320 ttc gcc ctc tcg gtg ttc gtc gtc cgc cgc ggc ggc acc gtc gtc acc     1008
Phe Ala Leu Ser Val Phe Val Val Arg Arg Gly Gly Thr Val Val Thr
            325                 330                 335 tgc gga tcc agc tcg ggc tac cgg cac ctg tac gac aac cgg tac ctg     1056
Cys Gly Ser Ser Ser Gly Tyr Arg His Leu Tyr Asp Asn Arg Tyr Leu
        340                 345                 350 tgg atg aag ctg aac acc gtc atc ggc agc cac ggc gga aac ctg cag     1104
Trp Met Lys Leu Asn Thr Val Ile Gly Ser His Gly Gly Asn Leu Gln
    355                 360                 365 gaa gcc acc gag agc acc cgc ctg atc gcc tcc ggc gcg atc gtt ccg     1152
Glu Ala Thr Glu Ser Thr Arg Leu Ile Ala Ser Gly Ala Ile Val Pro
        370                 375                 380 gcg ctc tcc gag gtc cac ccc ttc gag gac gtg gcc gag gcg atg cgg     1200
Ala Leu Ser Glu Val His Pro Phe Glu Asp Val Ala Glu Ala Met Arg
385                 390                 395                 400 cgg gtc cag ctc aac gag cac gtc ggc aag gtc gtc gtc ctg tgc cag     1248
Arg Val Gln Leu Asn Glu His Val Gly Lys Val Val Val Leu Cys Gln
            405                 410                 415 gcc ccc acc gcc ggc ctg ggc gtg acc gac ccg gag ctg cgg gaa cgg     1296
Ala Pro Thr Ala Gly Leu Gly Val Thr Asp Pro Glu Leu Arg Glu Arg
        420                 425                 430 ctg ggg gag gag cgg acg gca ccc ctg ctg cgg gac tcc gcc tga         1341
Leu Gly Glu Glu Arg Thr Ala Pro Leu Leu Arg Asp Ser Ala
    435                 440                 445

<210> SEQ ID NO 35
<211> LENGTH: 446
<212> TYPE: PRT
<213> ORGANISM: Streptoverticillium

<400> SEQUENCE: 35

Met Thr Glu Leu Arg Asp Ala Val Leu Arg Gly Ala Ser Pro Glu Glu
1               5                   10                  15

Leu Leu Arg Ala Pro Leu Pro Ala Thr Tyr Arg Ala Ala His Leu Arg
            20                  25                  30

Ala Glu Asp Val Gly Met Phe Asp Gly Thr Asp Gly Asp Arg Asp Val
        35                  40                  45

Arg Lys Ser Val Ala Val Gly Gln Val Pro Leu Pro Glu Ile Ala Pro
```

```
                50                  55                  60
Asp Glu Val Leu Ile Ala Val Met Ala Ala Val Asn Tyr Asn Ser
 65                  70                  75                  80

Val Trp Ser Ala Thr Phe Leu Pro Met Pro Thr Phe Arg Phe Leu Glu
                 85                  90                  95

Lys Tyr Ala Arg Gln Gly Gly Trp Ala Ala Arg His Asp Gln Pro Tyr
                100                 105                 110

His Val Ile Gly Ser Asp Cys Ser Gly Val Val Arg Val Gly Ser
                115                 120                 125

Gly Val Arg Arg Trp Arg Val Gly Asp His Val Ile His Pro Val
                130                 135                 140

His Val Asp Asp Gln Gly Ala Ala Thr His Asp Asp Ala Met Met Asp
145                 150                 155                 160

Asp Gln Gln Arg Ala Trp Gly Tyr Glu Thr Asn Phe Gly Ala Phe Gly
                165                 170                 175

Glu Tyr Ala Val Ala Arg Ala Ser Gln Leu Val Ala Lys Pro Gly His
                180                 185                 190

Leu Thr Trp Glu Glu Ser Ala Ala Asn Thr Leu Cys Thr Thr Thr Ser
                195                 200                 205

Tyr Arg Met Leu Val Gly Ala His Gly Ala Arg Met Lys Gln Gly Asp
                210                 215                 220

Val Val Leu Val Trp Gly Ala Ala Gly Leu Gly Thr Tyr Ala Val
225                 230                 235                 240

Gln Leu Val Lys Asn Gly Gly Gly Ile Pro Val Ala Val Val Ser Ser
                245                 250                 255

Pro Ala Lys Ala Glu Ala Val Arg Arg Leu Gly Cys Glu His Val Ile
                260                 265                 270

Asp Arg Thr Glu Leu Gly Leu Thr Gly Asp Pro Ser Gly Asp Phe Asp
                275                 280                 285

Ala Val Arg Glu Ile Gly Lys Arg Leu Gly Ala Arg Ile Arg Glu Leu
                290                 295                 300

Ala Gly Arg Asp Pro Asp Ile Val Phe Glu His Thr Gly Arg Ala Thr
305                 310                 315                 320

Phe Ala Leu Ser Val Phe Val Arg Arg Gly Thr Val Val Thr
                325                 330                 335

Cys Gly Ser Ser Ser Gly Tyr Arg His Leu Tyr Asp Asn Arg Tyr Leu
                340                 345                 350

Trp Met Lys Leu Asn Thr Val Ile Gly Ser His Gly Gly Asn Leu Gln
                355                 360                 365

Glu Ala Thr Glu Ser Thr Arg Leu Ile Ala Ser Gly Ala Ile Val Pro
                370                 375                 380

Ala Leu Ser Glu Val His Pro Phe Glu Asp Val Ala Glu Ala Met Arg
385                 390                 395                 400

Arg Val Gln Leu Asn Glu His Val Gly Lys Val Val Leu Cys Gln
                405                 410                 415

Ala Pro Thr Ala Gly Leu Gly Val Thr Asp Pro Glu Leu Arg Glu Arg
                420                 425                 430

Leu Gly Glu Glu Arg Thr Ala Pro Leu Leu Arg Asp Ser Ala
                435                 440                 445
```

```
<210> SEQ ID NO 36
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 36
ggggcagcct gctcggcgag                                              20

<210> SEQ ID NO 37
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 37
ggtgagctcc ccgatcaggg                                              20

<210> SEQ ID NO 38
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 38
gcgctcgtac gcctcgctga t                                            21

<210> SEQ ID NO 39
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 39
cgggctcggt ggtgagcagg                                              20

<210> SEQ ID NO 40
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 40
gtccgtggcg ccgccggatt                                              20

<210> SEQ ID NO 41
<211> LENGTH: 59
<212> TYPE: DNA
<213> ORGANISM: Artificial
<220> FEATURE:
<223> OTHER INFORMATION: Artificially synthesized primer sequence

<400> SEQUENCE: 41
gtcaccgtcc ccgcctacgg cgacggcgtc gtcctggtga ttccggggat ccgtcgacc   59

<210> SEQ ID NO 42
<211> LENGTH: 58
<212> TYPE: DNA
<213> ORGANISM: Artificial
<220> FEATURE:
```

<223> OTHER INFORMATION: Artificially synthesized primer sequence

<400> SEQUENCE: 42
ggtcgcgggc gaaggcgtag ccgggcaggt cgggcaggat gtaggctgga gctgcttc    58

<210> SEQ ID NO 43
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 43
cgtgaccgag gtggcgcg    18

<210> SEQ ID NO 44
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 44
gtcgtcggat gcgccgtgcg    20

<210> SEQ ID NO 45
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 45
gcaccttcat gtccgggttg    20

<210> SEQ ID NO 46
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 46
atcgccgcgt acaccatgac    20

<210> SEQ ID NO 47
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 47
cgaaggtccg gttgatggtg    20

<210> SEQ ID NO 48
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 48
atcgctgcga caccctggag    20

UK-2 BIOSYNTHETIC GENE AND METHOD FOR IMPROVING UK-2 PRODUCTIVITY USING THE SAME

BACKGROUND OF THE INVENTION

1. Field of the Invention

The present invention relates to a gene necessary for biosynthesis of UK-2 which is a compound useful for rice blast control agents and the like (hereinafter referred to as a "UK-2 biosynthetic gene") and a method for improving UK-2 productivity. More specifically, the present invention relates to a UK-2 biosynthetic gene, a vector in which the UK-2 biosynthetic gene is inserted, a transformant in which the vector is introduced, a method for determining UK-2 productivity by detecting the presence of the UK-2 biosynthetic gene, a bacterium in which the presence of the UK-2 biosynthetic gene is detected by the method, a bacterium comprising the UK-2 biosynthetic gene inserted in a genome thereof, a bacterium in which one or two or more copies of the UK-2 biosynthetic gene are present per cell, and methods for producing UK-2 and a UK-2A derivative by utilizing these bacteria and so forth.

2. Related Background Art

UK-2 is a compound produced as a secondary metabolite by actinobacteria, and shows strong antifungal actions similar to antimycin against various fungi including filamentous fungi and yeasts. Further, since having low cytotoxicity to culture cells, UK-2 has been found to be useful for rice blast control agents, agricultural and horticultural fungicides, and medical antifungal agents (Japanese Examined Patent Application Publication No. Hei 07-233165 and International Publication No. WO1999/11127). Moreover, it has been revealed that there naturally exists four analogues, UK-2A to D, based on the difference in structure of their side chains (Ueki M., et al., Journal of antibiotics, Jul. 25, 1996, vol. 49, no. 7, pp. 639 to 643).

UK-2 is produced by culturing actinobacteria (bacteria and the like belonging to the genus *Streptoverticillium*) and then collecting UK-2 therefrom. However, generally, the amount of UK-2 (all UK-2 factors) produced by microorganisms isolated from nature is very small. Accordingly, in order to use the target (UK-2) industrially at low cost, the productivity has to be improved.

The productivity of the target is improved through investigations on the methods for culturing the microorganisms producing the target, investigations on the medium components, improvement in fermentation conditions by addition of the precursor, and improvement in the bacterial strain utilizing ultraviolet irradiation- or chemical mutagen-induced mutation. Furthermore, in addition to these methods, the productivity has been improved recently by utilizing gene recombination.

A general method for improving the productivity by gene recombination is that including the enhancing of expression of a gene necessary for biosynthesis of the target. For example, International Publication No. WO2001/018179 discloses that this method improves the productivity of µF-1022 in Agonomycetales.

However, when this method is utilized, it is essential to isolate the gene necessary for biosynthesis of the target or the gene synthesized using known techniques, and also to establish the transformation method for microorganisms producing the target (producing microorganisms). Since the UK-2 biosynthetic gene is yet to be elucidated, the transformation using the UK-2 biosynthetic gene cannot be performed. The productivity cannot be improved by gene recombination.

SUMMARY OF INVENTION

The present invention has been made in view of the above-described problems in the conventional techniques. An object of the present invention is to provide a transformant having high UK-2 productivity, obtained by isolating a gene necessary for biosynthesis of UK-2 followed by introduction of the gene. Moreover, another object is to produce a large amount of UK-2 at low cost using the transformant. And a further object is to provide a method for determining UK-2 productivity by detecting the presence of the gene.

UK-2 has a characteristic hydroxypicolinic acid skeleton. Meanwhile, a compound called virginiamycin also has a hydroxypicolinic acid skeleton. Further, it has been revealed that VisA (L-lysine 2-aminotransferase) and VisB (3-hydroxypicolinic acid AMP ligase) are involved in the biosynthesis of virginiamycin (Namwat W., et al, Journal of Bacteriology, September 2002, vol. 184, no. 17, pp. 4811 to 4818).

Thus, in order to achieve the above objects, the present inventors first prepared the genomic DNA library of *Streptoverticillium* sp. 3-7, which produces UK-2, and comprehensively determined the base sequence of the genomic DNA of the strain. Then, a homology analysis was conducted between the amino acid sequence of a putative protein encoded by the genomic DNA and the amino acid sequences of VisA and VisB to thus find out a genomic site where genes whose products have a high homology with these two amino acid sequences are consecutively located. Furthermore, it was found out that a gene encoding a protein having a homology with a non-ribosomal peptide synthetase (NRPS) and a gene encoding a protein having a homology with a polyketide synthase (PKS) were located near the site.

These enzymes are thought to be necessary to form the UK-2 skeleton. In addition, the secondary metabolite genes of actinobacteria form clusters. Accordingly, the genomic region is expected to be a UK-2 biosynthetic gene cluster.

Then, based on the thus-obtained information on the base sequences of the genes expected to be encoding the enzymes necessary for biosynthesis of UK-2, a probe was prepared. By colony hybridization using the probe, DNAs expected to be in the UK-2 biosynthetic gene cluster (i.e., DNAs contained in the genomic region) were successfully isolated from the above-described genomic DNA library. Moreover, the DNAs were used to prepare *Streptoverticillium* sp. 3-7 in which the genes present in the genomic region were disrupted. The strain was found not to produce UK-2. It was verified that the genomic region was the UK-2 biosynthetic gene cluster. Further, *Streptoverticillium* sp. 3-7 was transformed by introduction of a vector in which the isolated UK-2 biosynthetic gene cluster was inserted. It was found out also that the UK-2 productivity by the transformant was improved about 10 to 60 times or more in comparison with that of the parental strain. Furthermore, it was confirmed that 2 copies of the UK-2 biosynthetic gene cluster were present per cell in these transformants, respectively.

Specifically, the present invention relates to a UK-2 biosynthetic gene, a vector in which the UK-2 biosynthetic gene is inserted, a transformant in which the vector is introduced, and methods for producing UK-2 and the like by utilizing the transformant. More specifically, the present invention provides the followings.

<1> An isolated nucleic acid that induces UK-2 biosynthesis and improves UK-2 productivity, the nucleic acid is at least one nucleic acid selected from the group consisting of the following (a) to (q):

(a) a nucleic acid encoding a protein comprising an amino acid sequence of SEQ ID NO: 3, a nucleic acid encoding a protein comprising an amino acid sequence of SEQ ID NO: 3 in which one or more amino acids are substituted, deleted, added and/or inserted, a nucleic acid encoding an amino acid sequence having a homology of 95% or more with an amino acid sequence of SEQ ID NO: 3, or a nucleic acid hybridizing under stringent conditions to a nucleic acid comprising a base sequence of SEQ ID NO: 2;

(b) a nucleic acid encoding a protein comprising an amino acid sequence of SEQ ID NO: 5, a nucleic acid encoding a protein comprising an amino acid sequence of SEQ ID NO: 5 in which one or more amino acids are substituted, deleted, added and/or inserted, a nucleic acid encoding an amino acid sequence having a homology of 95% or more with an amino acid sequence of SEQ ID NO: 5, or a nucleic acid hybridizing under stringent conditions to a nucleic acid comprising a base sequence of SEQ ID NO: 4;

(c) a nucleic acid encoding a protein comprising an amino acid sequence of SEQ ID NO: 7, a nucleic acid encoding a protein comprising an amino acid sequence of SEQ ID NO: 7 in which one or more amino acids are substituted, deleted, added and/or inserted, a nucleic acid encoding an amino acid sequence having a homology of 95% or more with an amino acid sequence of SEQ ID NO: 7, or a nucleic acid hybridizing under stringent conditions to a nucleic acid comprising a base sequence of SEQ ID NO: 6;

(d) a nucleic acid encoding a protein comprising an amino acid sequence of SEQ ID NO: 9, a nucleic acid encoding a protein comprising an amino acid sequence of SEQ ID NO: 9 in which one or more amino acids are substituted, deleted, added and/or inserted, a nucleic acid encoding an amino acid sequence having a homology of 95% or more with an amino acid sequence of SEQ ID NO: 9, or a nucleic acid hybridizing under stringent conditions to a nucleic acid comprising a base sequence of SEQ ID NO: 8;

(e) a nucleic acid encoding a protein comprising an amino acid sequence of SEQ ID NO: 11, a nucleic acid encoding a protein comprising an amino acid sequence of SEQ ID NO: 11 in which one or more amino acids are substituted, deleted, added and/or inserted, a nucleic acid encoding an amino acid sequence having a homology of 95% or more with an amino acid sequence of SEQ ID NO: 11, or a nucleic acid hybridizing under stringent conditions to a nucleic acid comprising a base sequence of SEQ ID NO: 10;

(f) a nucleic acid encoding a protein comprising an amino acid sequence of SEQ ID NO: 13, a nucleic acid encoding a protein comprising an amino acid sequence of SEQ ID NO: 13 in which one or more amino acids are substituted, deleted, added and/or inserted, a nucleic acid encoding an amino acid sequence having a homology of 95% or more with an amino acid sequence of SEQ ID NO: 13, or a nucleic acid hybridizing under stringent conditions to a nucleic acid comprising a base sequence of SEQ ID NO: 12;

(g) a nucleic acid encoding a protein comprising an amino acid sequence of SEQ ID NO: 15, a nucleic acid encoding a protein comprising an amino acid sequence of SEQ ID NO: 15 in which one or more amino acids are substituted, deleted, added and/or inserted, a nucleic acid encoding an amino acid sequence having a homology of 95% or more with an amino acid sequence of SEQ ID NO: 15, or a nucleic acid hybridizing under stringent conditions to a nucleic acid comprising a base sequence of SEQ ID NO: 14;

(h) a nucleic acid encoding a protein comprising an amino acid sequence of SEQ ID NO: 17, a nucleic acid encoding a protein comprising an amino acid sequence of SEQ ID NO: 17 in which one or more amino acids are substituted, deleted, added and/or inserted, a nucleic acid encoding an amino acid sequence having a homology of 95% or more with an amino acid sequence of SEQ ID NO: 17, or a nucleic acid hybridizing under stringent conditions to a nucleic acid comprising a base sequence of SEQ ID NO: 16;

(i) a nucleic acid encoding a protein comprising an amino acid sequence of SEQ ID NO: 19, a nucleic acid encoding a protein comprising an amino acid sequence of SEQ ID NO: 19 in which one or more amino acids are substituted, deleted, added and/or inserted, a nucleic acid encoding an amino acid sequence having a homology of 95% or more with an amino acid sequence of SEQ ID NO: 19, or a nucleic acid hybridizing under stringent conditions to a nucleic acid comprising a base sequence of SEQ ID NO: 18;

(j) a nucleic acid encoding a protein comprising an amino acid sequence of SEQ ID NO: 21, a nucleic acid encoding a protein comprising an amino acid sequence of SEQ ID NO: 21 in which one or more amino acids are substituted, deleted, added and/or inserted, a nucleic acid encoding an amino acid sequence having a homology of 95% or more with an amino acid sequence of SEQ ID NO: 21, or a nucleic acid hybridizing under stringent conditions to a nucleic acid comprising a base sequence of SEQ ID NO: 20;

(k) a nucleic acid encoding a protein comprising an amino acid sequence of SEQ ID NO: 23, a nucleic acid encoding a protein comprising an amino acid sequence of SEQ ID NO: 23 in which one or more amino acids are substituted, deleted, added and/or inserted, a nucleic acid encoding an amino acid sequence having a homology of 95% or more with an amino acid sequence of SEQ ID NO: 23, or a nucleic acid hybridizing under stringent conditions to a nucleic acid comprising a base sequence of SEQ ID NO: 22;

(l) a nucleic acid encoding a protein comprising an amino acid sequence of SEQ ID NO: 25, a nucleic acid encoding a protein comprising an amino acid sequence of SEQ ID NO: 25 in which one or more amino acids are substituted, deleted, added and/or inserted, a nucleic acid encoding an amino acid sequence having a homology of 95% or more with an amino acid sequence of SEQ ID NO: 25, or a nucleic acid hybridizing under stringent conditions to a nucleic acid comprising a base sequence of SEQ ID NO: 24;

(m) a nucleic acid encoding a protein comprising an amino acid sequence of SEQ ID NO: 27, a nucleic acid encoding a protein comprising an amino acid sequence of SEQ ID NO: 27 in which one or more amino acids are substituted, deleted, added and/or inserted, a nucleic acid encoding an amino acid sequence having a homology of 95% or more with an amino acid sequence of SEQ ID NO: 27, or a nucleic acid hybridizing under stringent conditions to a nucleic acid comprising a base sequence of SEQ ID NO: 26;

(n) a nucleic acid encoding a protein comprising an amino acid sequence of SEQ ID NO: 29, a nucleic acid encoding a protein comprising an amino acid sequence of SEQ ID NO: 29 in which one or more amino acids are substituted, deleted, added and/or inserted, a nucleic acid encoding an amino acid sequence having a homology of 95% or more with an amino acid sequence of SEQ ID NO: 29, or a nucleic acid hybridizing under stringent conditions to a nucleic acid comprising a base sequence of SEQ ID NO: 28;

(o) a nucleic acid encoding a protein comprising an amino acid sequence of SEQ ID NO: 31, a nucleic acid encoding a protein comprising an amino acid sequence of SEQ ID NO: 31 in which one or more amino acids are substituted, deleted, added and/or inserted, a nucleic acid encoding an amino acid sequence having a homology of 95% or more with an amino acid sequence of SEQ ID NO: 31, or a nucleic acid hybridizing under stringent conditions to a nucleic acid comprising a base sequence of SEQ ID NO: 30;

(p) a nucleic acid encoding a protein comprising an amino acid sequence of SEQ ID NO: 33, a nucleic acid encoding a protein comprising an amino acid sequence of SEQ ID NO: 33 in which one or more amino acids are substituted, deleted, added and/or inserted, a nucleic acid encoding an amino acid sequence having a homology of 95% or more with an amino acid sequence of SEQ ID NO: 33, or a nucleic acid hybridizing under stringent conditions to a nucleic acid comprising a base sequence of SEQ ID NO: 32; and (q) a nucleic acid encoding a protein comprising an amino acid sequence of SEQ ID NO: 35, a nucleic acid encoding a protein comprising an amino acid sequence of SEQ ID NO: 35 in which one or more amino acids are substituted, deleted, added and/or inserted, a nucleic acid encoding an amino acid sequence having a homology of 95% or more with an amino acid sequence of SEQ ID NO: 35, or a nucleic acid hybridizing under stringent conditions to a nucleic acid comprising a base sequence of SEQ ID NO: 34.

<2> The nucleic acid according to <1>, comprising all the nucleic acids of (a) to (q).

<3> The nucleic acid according to <2>, comprising a base sequence of SEQ ID NO: 1.

<4> A vector in which the nucleic acid according to any one of <1> to <3> is inserted, for inducing UK-2 biosynthesis and improving UK-2 productivity.

<5> A method for determining UK-2 productivity, comprising detecting, in a test bacterium, the presence of a nucleic acid comprising a base sequence of the nucleic acid according to any one of <1> to <3> or a base sequence complementary to the sequence.

<6> The method according to <5>, wherein a method for detecting the presence of the nucleic acid is a PCR method.

<7> The method in <5>, wherein the PCR method is a method in which the nucleic acid is amplified using a primer comprising a base sequence of SEQ ID NO: 45 and a primer comprising a base sequence of SEQ ID NO: 46.

<8> A bacterium in which UK-2 biosynthesis is induced and UK-2 productivity is improved, and in which the presence of the nucleic acid comprising the base sequence of the nucleic acid according to any one of <1> to <3> or the base sequence complementary to the sequence is detected by the method according to any one of <5> to <7>.

<9> A bacterium in which UK-2 biosynthesis is induced and UK-2 productivity is improved by introducing the vector according to <4>.

<10> A bacterium in which UK-2 biosynthesis is induced and UK-2 productivity is improved, and in which the nucleic acid according to any one of <1> to <3> is inserted in a genome thereof.

<11> A bacterium in which one or two or more copies of a nucleic acid comprising a base sequence of the nucleic acid according to any one of <1> to <3> are present per cell.

<12> The bacterium according to any one of <8> to <11>, which is any one of *Streptoverticillium*, *Streptomyces*, *Escherichia coli*, *Bacillus subtilis*, yeasts, filamentous fungi and *Corynebacterium glutamicum*.

<13> A method for producing UK-2, comprising the step of: culturing the bacterium according to any one of <8> to <12>, and collecting UK-2 from a culture of the bacterium.

<14> A method for producing a derivative of UK-2, comprising the steps of:
culturing the bacterium according to any one of <8> to <12>, and collecting UK-2 from a culture of the bacterium; and
synthesizing a derivative of UK-2 represented by any one of the following formulae (1) from the collected UK-2

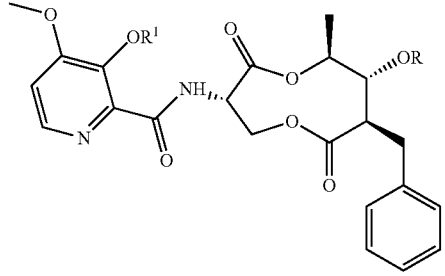

(1)

[in the formula (1),

R represents any one of a 2-methylpropanoyl group, a trans-2-methyl-2-butenoyl group, a 3-methylbutanoyl group and a 2-methylbutanoyl group.

$R^1$ represents any one of a $C_{1-6}$ alkyl group, a benzyl group, a $C_{1-10}$ alkylcarbonyl group (the $C_{1-10}$ alkylcarbonyl group may be substituted with any one of a carboxyl group, a benzyloxycarbonyl group, a $C_{1-4}$ alkyloxycarbonyl group and benzyloxycarbonylamino group), a benzoyl group, a $C_{1-4}$ alkyloxycarbonyl group, a $(C_{1-4})$ alkyloxycarbonyl $(C_{1-4})$ alkyl group, a benzyloxycarbonyl $(C_{1-4})$ alkyl group may be substituted with a nitro group, a $C_{1-6}$ alkylsulfonyl, di$(C_{1-6})$ alkylphosphoryl group, a diphenylphosphory group and a substituent represented by the following formula (2);

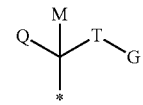

(2)

(in the formula (2),

Q is selected from the group consisting of H, $CH_3$, $CH_2CH_3$, $CF_3$, Ph, $CH=CH_2$ and a cyclopropyl.

M is selected from the group consisting of H, $CH_3$, $CH_2CH_3$, $CF_3$, Ph, $CH=CH_2$ and a cyclopropyl.

T is selected from the group consisting of O, OC(O), OC(O)O, S, SC(O), SC(O)O and a substituent represented by the following formula (3);

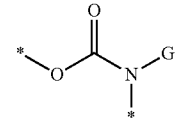

(3)

G is selected from the group consisting of H, $C_{1-6}$ alkyl group, a $C_{1-6}$ alkyloxy $C_{1-6}$ alkyl group, a $C_{2-6}$ alkenyl group, a $C_{2-6}$ alkynyl group, a $C_{3-6}$ cycloalkyl group, an aryl group and a heteroaryl group.

G and M may form an isobenzofuran ring optionally having an oxo group.

M and Q may form a 3-8 membered carbocyclicsystem.].

<15> A method for producing a derivative of UK-2A, comprising the steps of:

culturing the bacterium according to any one of <8> to <12>, and collecting UK-2A from a culture of the bacterium; and synthesizing a derivative of UK-2A represented by any one of the following formulae (4) to (7) from the collected UK-2A.

(4)

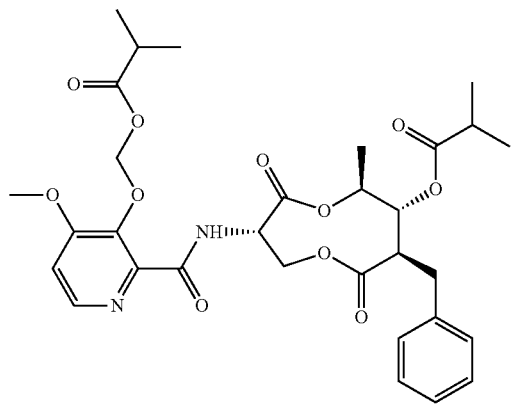

(5)

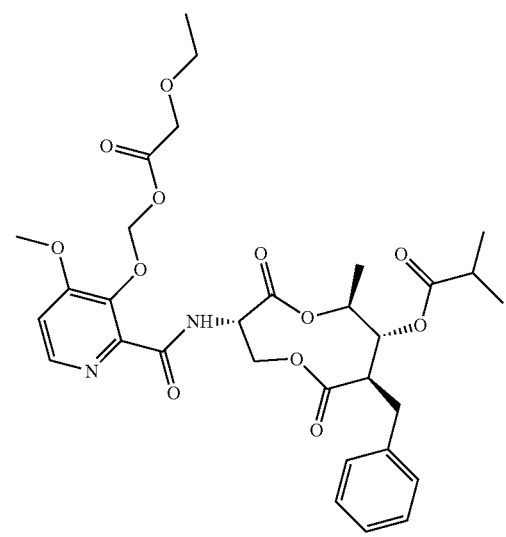

(6)

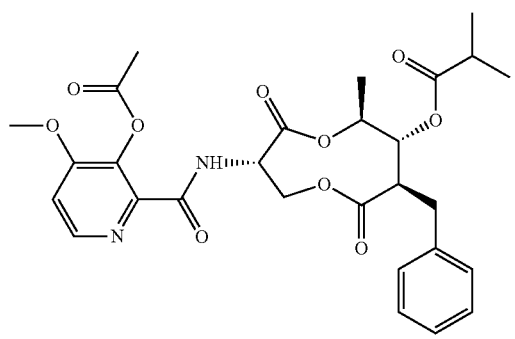

-continued (7)

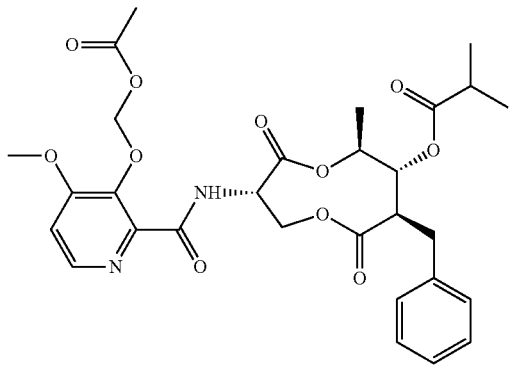

Note that, as used herein, the term "acyl" shall mean a residue RCO— provided by removing OH from a carboxylic acid R—COOH, wherein R represents a hydrocarbon group. As used herein, the term "aryl" shall mean phenyl or naphthyl. As used herein, the term "heteroaryl" shall mean any 5 or 6 membered aromatic ring, containing one or more heteroatoms, where such heteroatoms are selected from the group consisting of O, N, and S, and where the remaining atoms of the aromatic ring are carbon atoms. Suitable examples include, but are not limited to a pyridine, a pyridazine, a pyrimidine, a pyrazine, a pyrrole, a pyrazole, an imidazole, a furan, a thiophene, an oxazole, an isoxazole, a thiazole, an isothiazole, a quinoline, a quinoxoline and a thiadiazole.

The present invention makes it possible to provide a transformant having high UK-2 productivity by introducing a UK-2 biosynthetic gene into a host cell such as a bacterium. Further, mass production of UK-2 at low cost is also possible using the transformant. Moreover, it is also made possible to provide a method for determining UK-2 productivity by detecting the presence of the gene.

DETAILED DESCRIPTION OF THE PREFERRED EMBODIMENTS

UK-2 Biosynthetic Gene

The present invention provides a UK-2 biosynthetic gene. As described in Examples later, the present inventors have isolated, as novel UK-2 biosynthetic genes, genes shown in Table 2 from a genomic DNA of *Streptoverticillium* sp. 3-7.

Thus, one embodiment of the UK-2 biosynthetic gene of the present invention is an "isolated nucleic acid that induces UK-2 biosynthesis and improves UK-2 productivity, the nucleic acid is a nucleic acid encoding a protein comprising an amino acid sequence of SEQ ID NO: 3, 5, 7, 9, 11, 13, 15, 17, 19, 21, 23, 25, 27, 29, 31, 33 or 35," and typically an "isolated nucleic acid that induces UK-2 biosynthesis and improves UK-2 productivity, the nucleic acid is a nucleic acid comprising a base sequence of SEQ ID NO: 2, 4, 6, 8, 10, 12, 14, 16, 18, 20, 22, 24, 26, 28, 30, 32 or 34."

In the present invention, the phrase "improvement in UK-2 productivity" and related phrases mean not only improvement in UK-2 productivity that a bacterium or the like naturally has, but also the acquisition of a UK-2 production ability by a bacterium or the like that does not naturally have the UK-2 production ability.

In the present invention, the term "isolation" and related terms mean an artificial treatment which allows the nucleic acid to exist under a condition different from the originally existing condition. The UK-2 biosynthetic gene of the present invention can be isolated, for example, by first synthesizing an appropriate primer on the basis of the information on the base sequence of SEQ ID NO: 2, 4, 6, 8, 10, 12, 14, 16, 18, 20, 22, 24, 26, 28, 30, 32 or 34, and then carrying out PCR using the primer with a template of the genomic DNA of *Streptoverticillium* sp. 3-7. Alternatively, as described in Example later, the UK-2 biosynthetic gene of the present invention can also be isolated from a genomic DNA library or cDNA library of *Streptoverticillium* sp. 3-7 by carrying out colony hybridization using the amplification product obtained by the PCR as a probe. Besides, the UK-2 biosynthetic gene of the present invention can also be prepared by total chemical synthesis based on the base sequence information.

In the present invention, "UK-2" is a compound represented by the following formula (8):

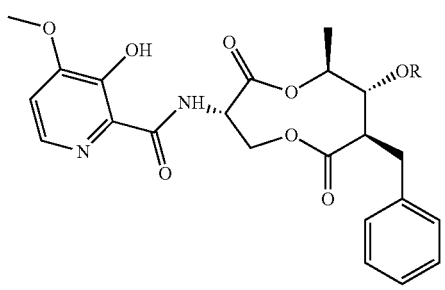

(8)

wherein R represents a linear or branched saturated aliphatic acyl group or a linear or branched unsaturated aliphatic acyl group. Preferably, "UK-2" is a compound wherein R is an isobutyryl group (2-methylpropanoyl group) (UK-2A), a compound wherein R is a tigloyl group (trans-2-methyl-2-butenoyl group) (UK-2B), a compound wherein R is an isovaleryl group (3-methylbutanoyl group) (UK-2C) and a compound wherein R is a 2-methylbutanoyl group (UK-2D).

Moreover, in the present invention, the "UK-2 biosynthetic gene" is a gene encoding a protein having an activity capable of inducing UK-2 biosynthesis. The "activity capable of inducing UK-2 biosynthesis" can be evaluated by, for example, a method described in Example 9 later. Specifically, after a nucleic acid for encoding the test protein is inserted into a vector which is subjected to introduction or the like into a host cell (for example, *Streptoverticillium* sp. 3-7), the amount of UK-2 produced in the host cell is measured by forced expression of the test protein in the host cell. If the amount produced is larger than that in a host cell in which the test protein is not expressed, it can be evaluated that the test protein has an activity capable of inducing UK-2 biosynthesis.

In the state of the art, if the information on the base sequence of the UK-2 biosynthetic gene is available, those skilled in the art can modify the base sequence and obtain a nucleic acid encoding a protein involved in UK-2 biosynthesis, although the amino acid sequence of the protein is different from one that is encoded from the base sequence. Meanwhile, in nature also, the amino acid sequence of a protein to be encoded may undergo mutation by a mutation of the base sequence. Thus, another embodiment of the UK-2 biosynthetic gene of the present invention is an "isolated nucleic acid that is a nucleic acid encoding a protein comprising an amino acid sequence of SEQ ID NO: 3, 5, 7, 9, 11, 13, 15, 17, 19, 21, 23, 25, 27, 29, 31, 33 or 35 in which one or more amino acids are substituted, deleted, added and/or inserted." Here, "more than one" refers to the number of amino acids modified in a protein involved in UK-2 biosynthesis after the modification, provided that the protein still has an activity of inducing UK-2 biosynthesis. The number is normally 1 to 50, preferably 1 to 40, and more preferably 1 to several (for example, 1 to 20, 1 to 10, 1 to 8, and 1 to 4).

Those skilled in the art can prepare the nucleic acid encoding such a variant by known methods such as site-directed mutagenesis on the basis of the information on the base sequence of the UK-2 biosynthetic gene.

Further, in the state of the art, if the information on the base sequence of the UK-2 biosynthetic gene is available, those skilled in the art can obtain nucleic acids (homologous genes) encoding a protein having an activity of inducing UK-2 biosynthesis from strains other than *Streptoverticillium* sp. 3-7 and other bacteria by a hybridization technique or a polymerase chain reaction (PCR) technique. Thus, another embodiment of the UK-2 biosynthetic gene of the present invention is an "isolated nucleic acid that is a nucleic acid hybridizing under stringent conditions to a nucleic acid comprising a base sequence of SEQ ID NO: 2, 4, 6, 8, 10, 12, 14, 16, 18, 20, 22, 24, 26, 28, 30, 32 or 34."

To isolate such a homologous gene, normally a hybridization reaction is carried out under stringent conditions. The "stringent conditions" mean that under which the membrane washing procedure following the hybridization is carried out at high temperature in a solution having a low salt concentration. The "stringent conditions" include washing conditions, for example, at a 2×SSC concentration (1×SSC: 15 mM trisodium citrate, 150 mM sodium chloride) in a 0.5% SDS solution at 60° C. for 20 minutes. Additionally, the hybridization can be carried out, for example, according to a method described in the instruction attached to known ECL Direct DNA/RNA Labeling and Detection System (manufactured by Amersham Pharmacia Biotech Inc.).

Moreover, the protein encoded by the homologous gene obtained by such a method normally has a high homology with an amino acid sequence of SEQ ID NO: 3, 5, 7, 9, 11, 13, 15, 17, 19, 21, 23, 25, 27, 29, 31, 33 or 35. Thus, another embodiment of the UK-2 biosynthetic gene of the present invention is an "isolated nucleic acid that is a nucleic acid encoding an amino acid sequence having a homology of 95% or more with an amino acid sequence of SEQ ID NO: 3, 5, 7, 9, 11, 13, 15, 17, 19, 21, 23, 25, 27, 29, 31, 33 or 35."

The homology of the sequences can be determined using, for example, a program of BLASTX (amino acid level) from NCBI.

As described in Examples later, the UK-2 biosynthetic gene of the present invention can be used for preparing a transformant having high UK-2 productivity, and can also be used effectively for screening for the UK-2 biosynthetic gene cluster.

In preparing such a transformant and screening for the UK-2 biosynthetic gene cluster, the use of the above-described UK-2 biosynthetic genes in combination is preferable to the individual use of the UK-2 biosynthetic genes. The number of the UK-2 biosynthetic genes in combination is not particularly limited, as long as the UK-2 biosynthesis can be induced by the combination. For example, the number is 2 or larger, preferably 5 or larger, further preferably 10 or larger, and more preferably 15 or larger. The number of the UK-2 biosynthetic genes in combination is most preferably 17 because the UK-2 productivity in the transformant can be significantly improved.

The UK-2 biosynthetic genes in combination may exist as a single nucleic acid or as separate nucleic acids.

The present invention provides a "nucleic acid comprising a base sequence of SEQ ID NO: 1" as a single nucleic acid (UK-2 biosynthetic gene cluster) comprising the 17 UK-2 biosynthetic genes. The locations of open reading frames (ORFs) of the genes in the nucleic acid comprising the base sequence of SEQ ID NO: 1 are as shown in Table 1 described later.

As described in Example later, the "nucleic acid comprising the base sequence of SEQ ID NO: 1" can be isolated by first synthesizing an appropriate primer on the basis of the information on the base sequence of the UK-2 biosynthetic gene, and the like, and then carrying out PCR using the primer with a template of a cosmid genomic DNA library of *Streptoverticillium* sp. 3-7 prepared independently, followed by colony hybridization using the obtained amplification product as a probe.

<Vector>

The present invention provides a vector in which the UK-2 biosynthetic gene of the present invention is inserted. The vector of the present invention can be constructed based on a self-replicating vector, i.e., for example, a plasmid which exists as an extrachromosomal element, and which replicates independently of the replication of the chromosome. Alternatively, the vector of the present invention may be replicated together with the chromosome of a host cell such as a bacterium, after introduced into the host cell and incorporated into the genome thereof. As a procedure and a method for constructing the vector of the present invention, any procedure and method commonly used in the field of genetic engineering can be used.

Those skilled in the art can select as appropriate the vector of the present invention from known vectors according to the type of the host cell to be introduced. Examples of the known vectors include cosmid vectors (SuperCos 1 cosmid vector and the like), phage vectors, pUC based plasmids (pCR2.1-TOPO plasmid vector and the like), pBluescript based plasmids, and pBR322 plasmids.

To express the protein encoded by the UK-2 biosynthetic gene of the present invention in the host cell, the "vector" of the present invention preferably comprises, in addition to the gene, a DNA sequence for regulating the expression, a marker gene for selecting the transformed host cell, and the like.

Examples of the "DNA sequence for regulating the expression" include a promoter, an enhancer and a terminator. The example also includes a lactose operon capable of inducing expression of the gene located downstream by addition of isopropyl-β-D-thiogalactopyranoside (IPTG) to the bacteria. The vector of the present invention can be constructed, for example, by operably ligating a promoter and a terminator respectively upstream and downstream of the UK-2 biosynthetic gene of the present invention.

The "marker gene" can be selected as appropriate according to the method for selecting the transformed host cell (transformant). For example, a gene encoding drug resistance or a gene complementing the auxotrophy can be used. In a case where the host cell used is a bacterium, examples of the marker gene include an ampicilin resistance gene, a kanamycin resistance gene, and a tetracycline resistance gene. Particularly, in a case of an actinobacterium, the examples include an apramycin resistance gene, a thiostrepton resistance gene, a hygromycin resistance gene, a kanamycin resistance gene, a streptomycin resistance gene, a viomycin resistance gene, and the like. In a case of a yeast, the examples include a tryptophan biosynthetase gene (TRP1), a uracil biosynthesis gene (URA3), a leucine biosynthesis gene (LEU2), and the like. In a case of a mold, the examples include a hygromycin resistance gene, a bialaphos resistance gene, a bleomycin resistance gene, an aureobasidin resistance gene, and the like. In a case of a plant, the examples include a kanamycin resistance gene, a bialaphos resistance gene, and the like.

<Transformant etc.>

The present invention provides a transformant in which the vector of the present invention is introduced (for example, a bacterium in which UK-2 biosynthesis is induced and UK-2 productivity is improved by introducing the vector of the present invention).

Moreover, the present invention provides a transformant in which UK-2 biosynthesis is induced and UK-2 productivity is improved, and in which the UK-2 biosynthetic gene of the present invention is inserted in a genome thereof.

The host cell which is transformed by the introduction of the vector of the present invention or the host cell in the genome of which the UK-2 biosynthetic gene of the present invention is not particularly limited. Examples thereof include actinobacteria, *Escherichia coli, Bacillus subtilis*, yeasts, filamentous fungi, *Corynebacterium glutamicum*, plant cells, insect cells, and animal cells. From the viewpoint of UK-2 productivity, actinobacteria are preferable, bacteria belonging to the genus *Streptoverticillium* and bacteria belonging to the genus *Streptomyces* are more preferably, bacteria belonging to the genus *Streptoverticillium* are even more preferably, and *Streptoverticillium* sp. 3-7 is particularly preferable.

The method for introducing the vector of the present invention into the host cell is not particularly limited. It can be selected and employed as appropriate by those skilled in the art from known transformation methods such as conjugal transfer, phage transduction, a calcium ion method, a lithium ion method, an electroporation method, a PEG method, an *Agrobacterium* method, and a particle gun method, depending on the type of the host cell under test. Moreover, in a case where the vector comprising the "marker gene" is introduced to the host cell, the transformant of the present invention can be efficiently prepared by culturing in a medium to which an antibiotic corresponding to the drug resistance gene is added or in a medium which is deficient in a nutrient corresponding to the gene complementing the auxotrophy.

Further, the present invention provides a bacterium in which UK-2 biosynthesis is induced and UK-2 productivity is improved by improvement in fermentation conditions, mutation induction, or the like. Furthermore, it has been revealed as described in Examples later that comprising at least two copies of the UK-2 biosynthetic gene of the present invention induces UK-2 biosynthesis and significantly improves UK-2 productivity. Thus, the present invention also provides a bacterium in which one or two or more copies of the UK-2 biosynthetic gene of the present invention are present per cell. From the viewpoint of UK-2 productivity, such bacteria are preferably actinobacteria, more preferably bacteria belonging to the genus *Streptoverticillium* and bacteria belonging to the genus *Streptomyces*, and further preferably bacteria belonging to the genus *Streptoverticillium*. Additionally, from the viewpoint of UK-2 productivity, the number of copies of the UK-2 biosynthetic gene of the present invention per cell is preferably two or larger. Note that the number of copies of the UK-2 biosynthetic gene of the present invention per cell can be identified, for example, by a PCR method as described in Examples later.

<Method for Determining UK-2 Productivity>

The present inventors have isolated and identified genes necessary for biosynthesis of UK-2, and therefore have made it possible to determine UK-2 productivity by detecting the presence of the genes. Thus, the present invention also provides a method for determining UK-2 productivity, comprising detecting, in a test bacterium, the presence of a nucleic acid comprising a base sequence of the UK-2 biosynthetic gene of the present invention or a base sequence complementary to the sequence.

In the method of the present invention, the "test bacterium" is not particularly limited. Examples thereof include actinobacteria (bacteria belonging to the genus *Streptoverticillium*, bacteria belonging to the genus *Streptomyces*, and the like), *Escherichia coli*, *Bacillus subtilis*, yeasts, filamentous fungi, and *Corynebacterium glutamicum*.

In the method for determining UK-2 productivity of the present invention, the base sequence of the UK-2 biosynthetic gene of the present invention to be detected, that is, the base sequence of the nucleic acid of the present invention, is a base sequence of at least one nucleic acid selected from the group consisting of the above-described (a) to (q).

The nucleic acid and so forth can be detected directly by targeting a genomic DNA including the nucleic acid and so forth or a transcription product from the genomic DNA. Alternatively, the nucleic acid and so forth can also be detected indirectly by targeting a translation product from the transcription product (a protein encoded by the UK-2 biosynthetic gene of the present invention). Further, the detection of the nucleic acid and so forth can employ any of known methods. In a case of targeting the genomic DNA, it is possible to employ, for example, an in situ hybridization (ISH) method, a genomic PCR method, a direct sequencing method, a southern blotting method, and an analysis method using a genome microarray. In a case of targeting the transcription product, it is possible to employ, for example, a PCR method, a direct sequencing method, a northern blotting method, a dot plot method, and an analysis method using a cDNA microarray. In a case of targeting the translation product, examples of the known methods include immunological methods using an antibody against a protein encoded by the UK-2 biosynthetic gene of the present invention (a western blotting method, an ELISA method, flow cytometry, immunohistochemical staining, imaging cytometry, radioimmunoassay, immunoprecipitation, an analysis method using an antibody array, and the like). Among these methods, preferable is a PCR method, and more preferable is a PCR method in which the nucleic acid is amplified using a primer comprising a base sequence of SEQ ID NO: 45 and a primer comprising a base sequence of SEQ ID NO: 46.

Additionally, in the method of the present invention, from the viewpoint of achieving more accurate determination of UK-2 productivity, it is preferable to detect the presence of multiple nucleic acids (the UK-2 biosynthetic genes of the present invention) described above, rather than detecting the presence of one of the nucleic acids. The number of the nucleic acids to be detected is, for example, two or larger, preferably five or larger, more preferably 10 or larger, and even more preferably 15 or larger. Detecting all of the 17 nucleic acids is particularly preferable, and detecting a single nucleic acid comprising all the 17 nucleic acids (the nucleic acid comprising the base sequence of SEQ ID NO: 1) is the most preferable. Furthermore, besides the entire length of the nucleic acid, a portion thereof is targeted in a normal practice for detecting the presence of the nucleic acid. Thus, in the method of the present invention also, the detection of the nucleic acid and so forth may be detection of a portion of the nucleic acid and so forth. Those skilled in the art can select as appropriate the length of the portion of the nucleic acid to be detected by the method of the present invention, depending on the detection method.

Then, if the presence of the nucleic acid in the test bacterium can be detected by such a method, the test bacterium is determined to have UK-2 productivity. Additionally, the method of the present invention may further comprises culturing the test bacterium in which the presence of the nucleic acid can be detected, in conditions that allow UK-2 to be produced.

In addition, the present invention also provides a bacterium in which UK-2 biosynthesis is induced and UK-2 productivity is improved, and in which the presence of the nucleic acid comprising the base sequence of the nucleic acid of the present invention or the base sequence complementary to the sequence is detected by the method for determining UK-2 productivity of the present invention. From the viewpoint of UK-2 productivity, such bacteria are preferably actinobacteria, more preferably bacteria belonging to the genus *Streptoverticillium* and bacteria belonging to the genus *Streptomyces*, and even more preferably bacteria belonging to the genus *Streptoverticillium*.

Note that, as used herein, the above-described bacteria and so forth having the UK-2 biosynthetic gene of the present invention, that is, the bacterium in which UK-2 biosynthesis is induced and UK-2 productivity is improved, and in which the presence of the nucleic acid is detected by the method for determining UK-2 productivity of the present invention, the transformant in which UK-2 biosynthesis is induced and UK-2 productivity is improved by introducing the vector of the present invention, the transformant in which UK-2 biosynthesis is induced and UK-2 productivity is improved, and in which the UK-2 biosynthetic gene of the present invention is inserted in a genome thereof, the bacterium in which one or two or more copies of the UK-2 biosynthetic gene of the present invention are present per cell, and the bacterium in which UK-2 biosynthesis is induced and UK-2 productivity is improved by improvement in fermentation conditions, mutation induction, or the like, are hereinafter collectively referred to as "bacteria etc. of the present invention."

<Method for Producing UK-2>

The present invention provides a method for producing UK-2, comprising the step of:

culturing the bacteria etc. of the present invention, and collecting UK-2 from a culture of the bacteria etc.

The bacteria etc. can be cultured by selecting the medium, the culture condition, and the like as appropriate according to a conventional method. As the medium, commonly used components can be used. For example, as the carbon source, it is possible to use glucose, sucrose, cellulose, starch syrup, dextrin, starch, glycerol, molasses, animal and vegetable oils, or the like. Moreover, as the nitrogen source, it is possible to use soybean flour, wheat germ, pharmamedia, corn steep liquor, cottonseed meal, broth, peptone, polypeptone, malt extract, yeast extract, ammonium sulfate, sodium nitrate, urea, or the like. Besides, if necessary, it is effective to add inorganic salts which can produce sodium, potassium, calcium, magnesium, cobalt, chlorine, phosphoric acid, sulfuric acid and other ions; examples of the inorganic salts include potassium chloride, calcium carbonate, dipotassium hydrogen phosphate, magnesium sulfate, monopotassium phosphate, zinc sulfate, manganese sulfate, and copper sulfate. Additionally, if necessary, it is also possible to add various vitamins such as thiamine (thiamine hydrochloride and the like), amino acids such as glutamic acid (sodium glutamate and the like) and asparagine (DL-asparagine and the like), trace nutrients such as nucleotide, and selective drugs such as antibiotics. Further, organic and inorganic substances to promote growth of the bacterium and the UK-2 production can be added as appropriate. The pH of the medium is not particularly limited, and may be adjusted according to the type of the bacteria etc. to be cultured. For example, the pH is approximately 6 to 8.

Those skilled in the art can select and set as appropriate the culture conditions according to the type of the bacteria etc. to be cultured, the type of the medium to be used, and so forth. For example, the culture method can be selected from known culture methods such as a shaking culture method under an aerobic condition, an aerated and agitated culture method and an aerobic submerged culture method. The aerated and agitated culture method is preferable. An appropriate culture temperature is 15° C. to 40° C. In many cases, the culture temperature is set around 26° C. to 37° C. Moreover, the culture period is preferably 2 days to 25 days when the maximum accumulation of UK-2 is achieved.

In the present invention, the "culture" refers to a medium obtained by culturing the bacteria etc. of the present invention, the medium containing the proliferated bacteria etc., a secretion and a metabolite of the bacteria etc., and the like. The culture also includes a dilution and a concentrate of these.

In the culture, UK-2 is accumulated in both of the bacteria etc. and the medium. Thus, an example of the method for collecting UK-2 from the medium of the culture is an extraction method using an organic solvent such as ethyl acetate, chloroform, and dichloromethane which do not mix with water freely, and which are capable of effectively extracting UK-2. Meanwhile, from the bacteria etc. of the culture, for example, UK-2 can be collected by extraction, with an organic solvent such as acetone, on the bacteria etc. which has been obtained by means such as filtration or centrifugation. Further, UK-2 can be collected by extraction in the same way as the above-described extraction from the medium, after the bacteria etc. of the culture has been disrupted using glass beads or the like.

Moreover, in collecting UK-2 from the culture, UK-2 can be isolated and purified by subjecting a thus-prepared extraction fraction such as organic solvent to known purification techniques such as solvent transfer dissolution, normal-phase and reverse-phase chromatographies, gel filtration chromatography, and crystallization in combination.

<Method for Producing UK-2 Derivative>

As described above, the present invention makes mass production of UK-2 at low cost possible. Accordingly, mass production of UK-2 derivatives at low cost is also made possible using UK-2 obtained by the production method of the present invention as the material thereof.

Thus, the present invention can also provide a method for producing a derivative of UK-2, comprising the steps of:

culturing the bacteria etc. of the present invention, and collecting UK-2 (UK-2A, UK-2B, UK-2C or UK-2D) from a culture of the bacteria etc.; and synthesizing a derivative of UK-2 represented by any one of the following formulae (1) from the collected UK-2

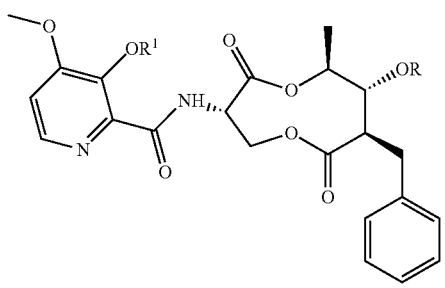

[in the formula (1),

R represents any one of a 2-methylpropanoyl group, a trans-2-methyl-2-butenoyl group, a 3-methylbutanoyl group and a 2-methylbutanoyl group.

$R^1$ represents any one of a $C_{1-6}$ alkyl group, a benzyl group, a $C_{1-10}$ alkylcarbonyl group (the $C_{1-10}$ alkylcarbonyl group may be substituted with any one of a carboxyl group, a benzyloxycarbonyl group, a $C_{1-4}$ alkyloxycarbonyl group and benzyloxycarbonylamino group), a benzoyl group, a $C_{1-4}$ alkyloxycarbonyl group, a $(C_{1-4})$ alkyloxycarbonyl $(C_{1-4})$ alkyl group, a benzyloxycarbonyl $(C_{1-4})$ alkyl group may be substituted with a nitro group, a $C_{1-6}$ alkylsulfonyl, di($C_{1-6}$) alkylphosphoryl group, a diphenyl phosphory group and a substituent represented by the following formula (2);

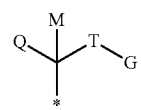

(in the formula (2),

Q is selected from the group consisting of H, $CH_3$, $CH_2CH_3$, $CF_3$, Ph, $CH=CH_2$ and a cyclopropyl.

M is selected from the group consisting of H, $CH_3$, $CH_2CH_3$, $CF_3$, Ph, $CH=CH_2$ and a cyclopropyl.

T is selected from the group consisting of O, OC(O), OC(O)O, S, SC(O), SC(O)O and a substituent represented by the following formula (3);

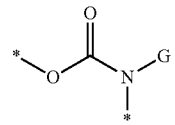

G is selected from the group consisting of H, $C_{1-6}$ alkyl group, a $C_{1-6}$ alkyloxy $C_{2-6}$ alkyl group, a $C_{2-6}$ alkenyl group, a $C_{2-6}$ alkynyl group, a $C_{3-6}$ cycloalkyl group, an aryl group and a heteroaryl group.

G and M may form an isobenzofuran ring optionally having an oxo group.

M and Q may form a 3-8 membered carbocyclic system.].

In the substituent represented by the formula (2), the alkyl group, the alkynyl group, the alkenyl group, the cycloalkyl group, the aryl group and the heteroaryl group may be substituted with at least one substituent selected from the group consisting of the following substituent groups;

a $C_{1-6}$ alkyl group, a $C_{2-6}$ alkenyl group, a $C_{2-6}$ alkynyl group, a $C_{3-6}$ cycloalkyl group, a $C_{5-6}$ cycloalkenyl group, an aryl group, a heteroaryl group, a halogen atom, a nitro group, a hydroxy group, a cyano group, a $C_{1-6}$ alkoxy group, a $C_{2-6}$ alkenoxy group, a $C_{3-6}$ cycloalkoxy group, an aryloxy group, a heteroaryloxy group, an acyloxy group, a $C_{1-6}$ alkylacyloxy group, a $C_{3-6}$ cycloalkylacyloxy group, an arylacyloxy group, a heteroarylacyloxy group, a $C_{1-6}$ alkyloxyacyl group, a $C_{3-6}$ cycloalkyloxyacyl group, an aryloxyacyl group, a heteroaryloxyacyl group, a $C_{1-6}$ alkylacyl group, a $C_{3-6}$ cycloalkylacyl group, an arylacyl group, a heteroarylacyl group, a $C_{1-6}$ alkylacylamino group, a $C_{3-6}$ cycloalkylacylamino group, an arylacylamino group, a heteroarylacylamino group, a $C_{1-6}$ alkylaminoacyl group, a $C_{3-6}$ cycloalkylaminoacyl group, an arylaminoacyl group, a heteroarylaminoacyl group, a $C_{1-6}$ alkylthio group, a $C_{3-6}$ cycloalkylthio group, an arylthio group, a heteroarylthio group, a $C_{1-6}$ alkylsulfonyl group, a $C_{3-6}$ cycloalkylsulfonyl group, an arylsulfonyl group, a heteroarylsulfonyl group, a $C_{1-6}$ alkylsulfinyl group, a $C_{3-6}$ cycloalkylsulfinyl group, an arylsulfinyl group, a heteroarylsulfinyl group and —C(NOR$^x$)R$^Y$ wherein R$^Y$ and R$^x$ are independently any one of H, a $C_{1-6}$ alkyl group, a $C_{2-6}$ alkenyl group, a $C_{3-6}$ cycloalkyl group, an aryl group and a heteroaryl group in which any alkyl or cycloalkyl containing substituent may be substituted with one or more halogens.

Note that, the substituent may also be substituted with at least one substituent selected from the group consisting of the following substituent groups;

a $C_{1-6}$ alkyl group, a $C_{2-6}$ alkenyl group, a $C_{2-6}$ alkynyl group, a $C_{3-6}$ cycloalkyl group, a $C_{5-6}$ cycloalkenyl group, an aryl group, a heteroaryl group, a halogen atom, a nitro group, a hydroxy group, a cyano group, a $C_{1-6}$ alkoxy group, a $C_{2-6}$ alkenoxy group, a $C_{3-6}$ cycloalkoxy group, an aryloxy group, a heteroaryloxy group, an acyloxy group, a $C_{1-6}$ alkylacyloxy group, a $C_{3-6}$ cycloalkylacyloxy group, an arylacyloxy group, a heteroarylacyloxy group, a $C_{1-6}$ alkyloxyacyl group, a $C_{3-6}$ cycloalkyloxyacyl group, an aryloxyacyl group, a heteroaryloxyacyl group, a $C_{1-6}$ alkylacyl group, a $C_{3-6}$ cycloalkylacyl group, an arylacyl group, a heteroarylacyl group, a $C_{1-6}$ alkylacylamino group, a $C_{3-6}$ cycloalkylacylamino group, an arylacylamino group, a heteroarylacylamino group, a $C_{1-6}$ alkylaminoacyl group, a $C_{3-6}$ cycloalkylaminoacyl group, an arylaminoacyl group, a heteroarylaminoacyl group, a $C_{1-6}$ alkylthio group, a $C_{3-6}$ cycloalkylthio group, an arylthio group, a heteroarylthio group, a $C_{1-6}$ alkylsulfonyl group, a $C_{3-6}$ cycloalkylsulfonyl group, an arylsulfonyl group, a heteroarylsulfonyl group, a $C_{1-6}$ alkylsulfinyl group, a $C_{3-6}$ cycloalkylsulfinyl group, an arylsulfinyl group, a heteroarylsulfinyl group and —C(NOR$^x$)R$^Y$ wherein R$^Y$ and R$^x$ are independently any one of H, a $C_{1-6}$ alkyl group, a $C_{2-6}$ alkenyl group, a $C_{3-6}$ cycloalkyl group, an aryl group and a heteroaryl group in which any alkyl or cycloalkyl containing substituent may be substituted with one or more halogens.

In addition, the present invention can also provide a method for producing a UK-2A derivative, comprising the steps of:

culturing the bacteria etc. of the present invention, and collecting UK-2A from a culture of the bacteria etc.; and synthesizing a UK-2A derivative represented by any one of the following formulae (4) to (7) from the collected UK-2A.

(4)
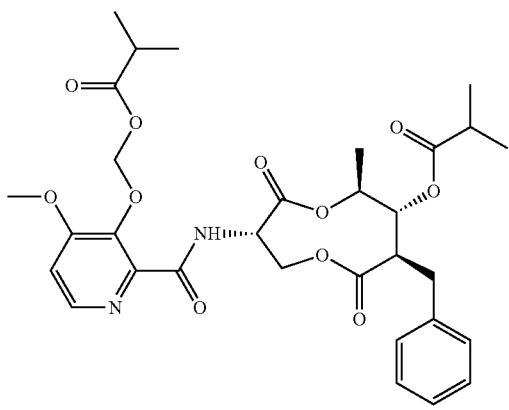

(5)
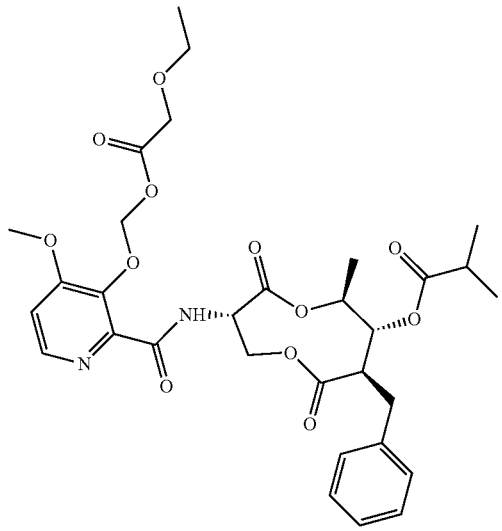

(6)
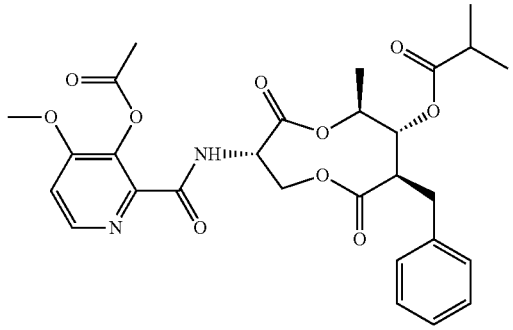

(7)
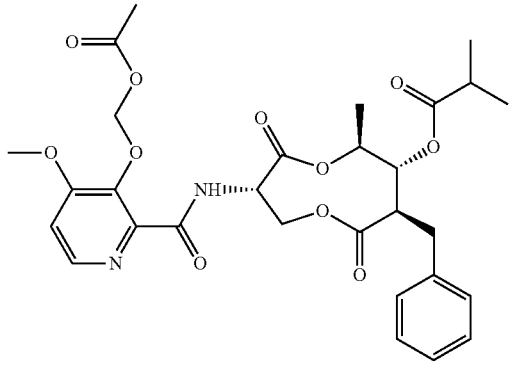

In collecting UK-2A, UK-2B, UK-2C or UK-2D from the culture, UK-2A, UK-2B, UK-2C or UK-2D can be isolated and purified, for example, as described above, by subjecting the extraction fraction such as organic solvent to known purification techniques such as solvent transfer dissolution, normal-phase and reverse-phase chromatographies, gel filtration chromatography, and crystallization in combination. More specifically, the extraction fraction such as organic solvent is concentrated under reduced pressure. The resultant is transferred to and dissolved in chloroform, and subjected to silica gel chromatography, which is then eluted stepwise with chloroform/methanol. Thus, a fraction which contains UK-2A and UK-2D at a ratio of approximately 3:1, and which also contains trace amounts of UK-2B and UK-2C can be obtained. Further, the fraction is treated by reverse-phase high performance liquid chromatography (HPLC) using a C-18 column, and thus UK-2A, UK-2B, UK-2C or UK-2D can be isolated (see Japanese Examined Patent Application Publication No. Hei 07-233165).

Then, the derivative of UK-2A, UK-2B, UK-2C or UK-2D represented by any one of the formulae (1) and (4) to (7) can be synthesized using UK-2A, UK-2B, UK-2C or UK-2D thus collected as the material thereof by, for example, the synthesis method described in International Publication No. 2003/035617 or International Publication No. 1999/40081.

EXAMPLES

Hereinafter, the present invention will be more specifically described based on Example. However, the present invention is not to be limited to Examples below.

Note that the microorganism described in the present Examples is deposited as follows. *Streptoverticillium* sp. 3-7 was deposited at International Patent Organism Depositary, National Institute of Advanced Industrial Science and Technology (Central 6, 1-1-1, Higashi, Tsukuba, Ibaraki, postal code 305-8566, Japan) on November 9, Heisei 23 (2011) under the accession number of FERM BP-11437. Incidentally, the deposit of the patent microorganisms by International Patent Organism Depositary, National Institute of Advanced Industrial Science and Technology (former name: IPOD) was succeeded by National Institute of Technology and Evaluation (NITE, #122, 2-5-8 Kazusakamatari, Kisarazu-shi, Chiba, postal code 292-0818) on April, 2012.

*Streptoverticillium* sp. 3-7 was established from SAM 2084 strain described in Japanese Examined Patent Application Publication No. Hei 07-233165, which was artificially mutated through a single ultraviolet irradiation by the present inventors. The SAM 2084 strain is a UK-2-producing bacterial strain obtained from soil in Kyoto prefecture of Japan and identified under the international deposit number FERM BP-6446.

Example 1

Preparation of Genomic DNA Library

To isolate genes necessary for biosynthesis of UK-2, first, the genomic DNA library of *Streptoverticillium* sp. 3-7 capable of producing UK-2 was prepared by a method described below.

*Streptoverticillium* sp. 3-7 was inoculated into 50 ml of modified YEME (0.3% Difco yeast extract, 0.5% Difco bacto peptone, 0.3% Oxoid malt extract, 3.0% sucrose, 1.0% glucose, 5 mmol/L $MgCl_2.6H_2O$) and shake-cultured at 220 rpm at 30° C. for 18 hours. After the culturing was complete, the bacterial cells were collected by centrifugation at 7500 rpm for 10 minutes. From the bacterial cells thus obtained, the genomic DNA was prepared employing the salting out method [see "Practical *Streptomyces* Genetics," The John Innes Foundation, (UK), Norwich, 2000].

The obtained genomic DNA was partially digested with a restriction enzyme MboI, and then treated with alkaline phosphatase to dephosphorylate the terminal of the DNA. This DNA fragment was ligated to a commercially available cosmid vector SuperCos1 (manufactured by Stratagene Corporation) which had been subjected in advance to digestion with a restriction enzyme XbaI, an alkaline phosphatase treatment for dephosphorylation and further digestion with a restriction enzyme BamHI. Thus, a recombinant cosmid vector was prepared. This recombinant cosmid vector was subjected to in vitro packaging using MAXPLAX Lambda Packaging Extracts manufactured by Epicentre Biotechnologies. *Escherichia coli* XLI-Blue MRA was infected therewith to prepare the cosmid genomic DNA library.

Example 2

Estimation of UK-2 Biosynthetic Gene

Based on the genomic DNA prepared by the method described in Example 1, construction of the mate-pair library for Roche GS FLX Titanium sequencer was entrusted to Genaris, Inc. Then, this sequencer was used to determine the sequence. Separately from this, based on the genomic DNA, the fragment library for this sequencer was constructed. Then, this sequencer was used to determine the sequence. The sequence obtained from the mate-pair library and the sequence obtained from the fragment library were co-assembled together to obtain the contig sequence and the scaffold sequence.

UK-2 has a characteristic 3-hydroxypicolinic acid skeleton. Meanwhile, virginiamycin also has a hydroxypicolinic acid skeleton. Two genes (visA, visB) involved in the biosynthesis of virginiamycin have been disclosed (see Namwat W., et al, Journal of Bacteriology, September 2002, vol. 184, no. 17, pp. 4811 to 4818). Thus, a homology analysis was conducted between the amino acid sequence of the proteins encoded by these two genes and the proposed amino acid sequence obtained from the genome of the UK-2 producing bacterium to examine the existence of genes involved in formation of the hydroxypicolinic acid skeleton. Tables 1 and 2 show the obtained result.

TABLE 1

| ORF name | SEQ ID NO: | Location in base sequence of SEQ ID NO: 1 | ORF direction | Protein encoded by ORF SEQ ID NO: | The number of amino acid residues |
|---|---|---|---|---|---|
| ORF1 | 2 | 1-681 | + | 3 | 226 |
| ORF2 | 4 | 674-2560 | − | 5 | 628 |
| ORF3 | 6 | 2590-4200 | − | 7 | 536 |
| ORF4 | 8 | 4377-4559 | − | 9 | 60 |
| ORF5 | 10 | 4550-5686 | − | 11 | 378 |
| ORF6 | 12 | 5800-7485 | − | 13 | 561 |
| ORF7 | 14 | 7637-8884 | + | 15 | 415 |
| ORF8 | 16 | 9109-9654 | + | 17 | 181 |
| ORF9 | 18 | 9671-10201 | − | 19 | 176 |
| ORF10 | 20 | 10302-11078 | − | 21 | 258 |
| ORF11 | 22 | 11121-12422 | − | 23 | 433 |
| ORF12 | 24 | 12814-16644 | − | 25 | 1276 |
| ORF13 | 26 | 16649-26383 | − | 27 | 3244 |
| ORF14 | 28 | 26814-27986 | − | 29 | 390 |
| ORF15 | 30 | 28051-29112 | − | 31 | 353 |
| ORF16 | 32 | 29275-29904 | + | 33 | 209 |
| ORF17 | 34 | 29978-31318 | + | 35 | 446 |

TABLE 2

| | | Known protein having high homology with protein encoded by ORF | | | | |
|---|---|---|---|---|---|---|
| ORF name | SEQ ID NO: | Protein name | Species | GenBank accession number | Homology (%) | Putative functional protein to be encoded by ORF |
| ORF1 | 2 | LuxR family transcriptional regulator | *Streptomyces Avermitilis* | NP_821584.1 | 60 | Transcriptional regulator |
| ORF2 | 4 | Long-chain-fatty-acid--CoA ligase | *Pseudonocardia Dioxanivorans* | YP_004335893.1 | 53 | Long-chain fatty-acid-CoA ligase |

TABLE 2-continued

Known protein having high homology with protein encoded by ORF

| ORF name | SEQ ID NO: | Protein name | Species | GenBank accession number | Homology (%) | Putative functional protein to be encoded by ORF |
|---|---|---|---|---|---|---|
| ORF3 | 6 | Histidine ammonia-lyase | Rubrobacter Xylanophilus | YP_644511.1 | 55 | Phenylalanine/histidine ammonia-lyase |
| ORF4 | 8 | 4-oxalocrotonate tautomerase | Streptomyces pristinaespiralis | CBW45760.1 | 47 | 4-oxalocrotonate tautomerase |
| ORF5 | 10 | L-lysin 2-aminotransferase | Streptomyces pristinaespiralis | ZP_06913862.1 | 58 | L-Lysine 2-aminotransferase |
| ORF6 | 12 | 3-hydroxypicolinic acid: AMP ligase | Streptomyces Pyridomyceticus | AEF33098.1 | 60 | 3-hydroxypicolinic acid AMP ligase |
| ORF7 | 14 | Cytochrome P450 | Streptomyces Albus | ZP_06593022.1 | 46 | Cytochrome P450 |
| ORF8 | 16 | Thioesterase type II | Verrucosispora Maris | YP_004406133.1 | 41 | Thioesterase |
| ORF9 | 18 | Ribosomal-protein-serine acetyltransferase | Streptomyces Hygroscopicus | ZP_07300520.1 | 90 | Acetyltransferase |
| ORF10 | 20 | Oxidoreductase, short-chain dehydrogenase/reductase | Streptomyces Griseoflavus | ZP_07314911.1 | 58 | Short chain dehydrogenase |
| ORF11 | 22 | Putative polyketide associated protein | Streptomyces Ambofaciens | CAJ89364.1 | 40 | Condensation domain protein |
| ORF12 | 24 | Putative polyketide synthase related protein | Streptomyces Ambofaciens | CAJ89362.1 | 58 | Polyketide synthase |
| ORF13 | 26 | Putative peptide synthetase | Streptomyces Ambofaciens | CAJ89363.1 | 52 | Non-ribosomal peptidesynthetase |
| ORF14 | 28 | Sarcosine oxidase | Streptomyces Griseoflavus | ZP_07310135.1 | 49 | N-methyltryptophan oxidase |
| ORF15 | 30 | Favin-dependent oxidoreductase | Streptomyces Pyridomyceticus | AEF33076.1 | 53 | Flavin-dependent oxidoreductase |
| ORF16 | 32 | O-methyltransferase | Mycobacterium Marinum | YP_001848635.1 | 52 | O-methyltransferase |
| ORF17 | 34 | Crotonyl-CoA reductase | Streptomyces Hygroscopicus | AAR32675.1 | 67 | Crotonyl-CoA reductase |

As a result of the examination, the position where genes having a high homology with VisA and VisB were consecutively located was found out as a single position on the genome derived from *Streptoverticillium* sp. 3-7 (see Table 1). Moreover, it was found out that genes associated with a non-ribosomal peptide synthetase (NRPS) and a polyketide synthase (PKS) which were thought to be necessary to form the UK-2 skeleton were located near these genes (see Table 2). A region around the genes was expected to be a UK-2 biosynthetic gene cluster because the secondary metabolite genes of actinobacteria form a cluster. Further, there is an alignment between the genes (ORFs) located in the UK-2 biosynthetic gene cluster and putative functions of proteins encoded by the respective genes as follows.

ORF1 is a gene potentially involved in the regulation of the biosynthetic gene cluster. ORF5, ORF6, ORF7, and ORF16 are genes involved in the biosynthesis of the 3-hydroxypicolinic acid skeleton. ORF2, ORF3, and ORF17 are genes involved in the biosynthesis of a benzylmalonic acid skeleton. ORF13 is a gene involved in the biosynthesis of a picolinic acid skeleton, serine, and lactic acid. ORF11 and ORF12 are genes involved in the biosynthesis of benzylmalonic acid and metabolism of picolinic acid, serine, and lactic acid. ORF8 is a gene involved in the cleavage of a thioester bond of a polyketide synthase (PKS) and metabolism of picolinic acid, serine, lactic acid, and benzylmalonic acid.

Example 3

Screening of Genomic DNA Library

A portion of the sequence of ORF5 located upstream of the UK-2 biosynthetic genes was used as a probe for screening of the genomic DNA library prepared in Example 1, and prepared by PCR as described below.

PCR was carried out using the genomic DNA described in Example 1 as a template and oligo DNAs of visA'-F: 5'-GGGGCAGCCTGCTCGGCGAG-3' (SEQ ID NO: 36) and visA'-R: 5'-GGTGAGCTCCCCGATCAGGG-3' (SEQ ID NO: 37) as primers. The PCR was performed using LA Taq DNA polymerase (manufactured by Takara Bio Inc.) as a DNA polymerase and PERKIN ELMER GeneAmp PCR System 9700. The amount of the reaction solution was adjusted to 50 µl by addition of: 0.5 µl (corresponding to 0.5 µg in amount) of the genomic DNA, 25 µl of a buffer for two-fold concentration reaction accompanying the enzyme, 2.5 µl of a DMSO solution, 5 µl of a 2.5-mM dNTP solution, 0.25 µl of each of the primers whose concentration was adjusted to 100 pmol/µl, 0.3 µl of the enzyme, and 16.2 µl of sterilized water. The reaction was carried out as follows: the pretreatment at 95° C. for 10 minutes; incubation in 30 cycles each consisting of 95° C. for 30 seconds, 55° C. for 30 seconds, and 72° C. for 2 minutes; further incubation at 72° C. for 5 minutes. After the reaction was complete, a portion of the reaction solution was electrophoresed on an agarose gel. As a result, it was confirmed that approximately 1.3 kbp of a DNA fragment was specifically amplified. Then, the remaining reaction solution was subjected to extraction with a mixture solution (phenol:chloroform:isoamyl alcohol=25:24:1, V/V) for nucleic acid purification, followed by ethanol precipitation. The precipitate was dissolved again in sterilized water, and electrophoresed on an agarose gel. Approximately 1.3 kbp of a band was cut out according to a conventional method, and a DNA fragment was collected.

Colony hybridization was carried out using the DNA fragment as a probe and ECL Direct DNA/RNA Labeling and Detection System (manufactured by Amersham Pharmacia Biotech Inc.), and approximately 5000 colonies were screened. Several positive clones were obtained. A plasmid pUK2-B44 was isolated from one of the clones.

Further, a portion of ORF13 located downstream of the UK-2 biosynthetic genes was used as a probe, and prepared by PCR as described below.

PCR was carried out using the genomic DNA described in Example 1 as a template and oligo DNAs of caiC-F: 5'-GCGCTCGTACGCCTCGCTGAT-3' (SEQ ID NO: 38) and caiC-R: 5'-CGGGCTCGGTGGTGAGCAGG-3' (SEQ ID NO: 39) as primers. The PCR was performed using LA Taq DNA polymerase (manufactured by Takara Bio Inc.) as a DNA polymerase and PERKIN ELMER GeneAmp PCR System 9700. The amount of the reaction solution was adjusted to 50 µl by addition of: 0.5 µl (corresponding to 0.5 µg in amount) of the genomic DNA, 25 µl of a buffer for two-fold concentration reaction accompanying the enzyme, 2.5 µl of a DMSO solution, 5 µl of a 2.5-mM dNTP solution, 0.25 µl of each of the primers whose concentration was adjusted to 100 pmol/µl, 0.3 µl of the enzyme, and 16.2 µl of sterilized water. The reaction was carried out as follows: the pretreatment at 95° C. for 10 minutes; incubation in 30 cycles each consisting of 95° C. for 30 seconds, 59° C. for 30 seconds, and 72° C. for 2 minutes and 20 seconds. After the reaction was complete, a portion of the reaction solution was electrophoresed on an agarose gel. As a result, it was confirmed that approximately 2.3 kbp of a DNA fragment was specifically amplified. Then, the remaining reaction solution was subjected to extraction with the above-described mixture solution for nucleic acid purification, followed by ethanol precipitation. The precipitate was dissolved again in sterilized water, and electrophoresed on an agarose gel. Approximately 2.3 kbp of a band was cut out according to a conventional method, and a DNA fragment was collected.

Colony hybridization was carried out using the DNA fragment as a probe and ECL Direct DNA/RNA Labeling and Detection System (manufactured by Amersham Pharmacia Biotech Inc.), and approximately 5000 colonies were screened. Several positive clones were obtained. A plasmid pUK2-E4 was isolated from one of the clones.

Example 4

Construction of Plasmid pUK2-3 Comprising Biosynthetic Gene Cluster

Using the thus-obtained plasmids pUK2-B44 and pUK2-E4 respectively comprising the upstream region 1 to 21531 and the downstream region 16211 to 34641 of the expected biosynthesis cluster, a plasmid comprising the entire biosynthesis cluster region was constructed. First, both of the plasmids were digested with restriction enzymes ClaI and PspXI, followed by electrophoresis on agarose gels, and approximately 28 kbp and approximately 19 kbp of bands were respectively cut out according to a conventional method, and DNA fragments were collected. The DNA fragments were ligated using DNA Ligation Kit<Mighty Mix> (manufactured by Takara Bio Inc.) to prepare pUK2-16.

Next, using the redirect technology described in [Gust, B., et al, "Proceedings of the National Academy of Sciences of the United States of America," (US), 2003, vol. 100, pp. 1541-1546], the plasmid pUK2-16 was used as a vector capable of conjugal transfer to actinobacteria. First, the plasmid pUK2-16 was introduced in an *E. coli* BW25113/pIJ790 strain by electroporation, and an *E. coli* BW25113/pIJ790/pUK2-16 strain was obtained. This strain was inoculated into 100 ml of an LB liquid medium (1% bacto tryptone, 0.5% yeast extract, 0.5% sodium chloride) containing chloramphenicol, kanamycin and ampicillin respectively at concentrations of 25 µg/ml, 50 µg/ml and 50 µg/ml, and cultured at 30° C. overnight. Then, 100 µl of the culture solution was inoculated into 10 ml of an SOB medium (2% bacto tryptone, 0.5% yeast extract, 0.05% sodium chloride, 0.0186% potassium chloride) prepared in a 65-ml test tube containing chloramphenicol, kanamycin, ampicillin and L-arabinose respectively at concentrations of 25 µg/ml, 50 µg/ml, 50 µg/ml and 10 mM. The resulting culture was shake-cultured at 30° C. for 4 hours. The bacterial cells were collected from all of the culture solution, washed twice with an ice-cooled 10% glycerin solution, and resuspended to 100 µl of the 10% glycerin solution as cells for electroporation. Meanwhile, 5.2 kb of an SspI fragment containing oriT, attP, IntφC31 and an apramycin resistance gene derived from a plasmid pMJCOS1 (John Innes Centre (Norwich)) was purified. The DNA fragment (approximately 100 ng) and 50 µl of the cells thus prepared were transferred to an already ice-cooled cuvette with a gap of 2 mm, and subjected to electroporation (using Electro Cell Manipulator 600: manufactured by BM Equipment Co., Ltd.). After the treatment, 1 ml of a cooled LB liquid medium was added to the resultant, which was allowed to stand at 37° C. for 1 hour for culturing. This was then applied to an LB agar medium containing ampicillin and apramycin, and cultured at 37° C. overnight. The grown strain was cultured in an LB liquid medium containing ampicillin and apramycin, and a plasmid pUK2-3 was isolated. This pUK2-3 is a plasmid which is capable of conjugal transfer to actinobacteria, and which has oriT, attP, IntφC31 and the apramycin resistance gene in the vector portion and the entire region expected to be the UK-2 biosynthesis cluster.

Example 5

Construction of Biosynthetic Gene-Deficient Vector

A gene disrupted strain deficient in approximately 7.5 kbp corresponding to portions of ORF12 and ORF13 from the genomic DNA of *Streptoverticillium* sp. 3-7 was prepared by the method described below.

PCR was carried out using the genomic DNA described in Example 1 as a template and oligo DNAs of caiC-F: 5'-GCGCTCGTACGCCTCGCTGAT-3' (SEQ ID NO: 38) and 41c29-R: 5'-GTCCGTGGCGCCGCCGGATT-3' (SEQ ID NO: 40) as primers. The PCR was performed using LA Taq DNA polymerase (manufactured by Takara Bio Inc.) as a DNA polymerase and PERKIN ELMER GeneAmp PCR System 9700. The amount of the reaction solution was adjusted to 50 µl by addition of: 0.5 µl (corresponding to 0.5 µg in amount) of the genomic DNA, 25 µl of a buffer for two-fold concentration reaction accompanying the enzyme, 2.5 µl of a DMSO solution, 5 µl of a 2.5-mM dNTP solution, 0.25 µl of each of the primers whose concentration was adjusted to 100 pmol/µl, 0.3 µl of the enzyme, and 16.2 µl of sterilized water. The reaction was carried out as follows: the pretreatment at 95° C. for 10 minutes; incubation in 30 cycles each consisting of 95° C. for 30 seconds, 60° C. for 5 seconds, and 72° C. for 7 minutes. After the reaction was complete, a portion of the reaction solution was electrophoresed on an agarose gel. As a result, it was confirmed that approximately 7.5 kbp of a DNA fragment was specifically amplified. The DNA fragment was inserted into a pCR2.1-TOPO plasmid vector using TOPO TA cloning kit (manufactured by Invitrogen Corporation) in accordance with the protocol attached thereto. Thereby, a plasmid TOPO-41c29 was obtained.

Subsequently, an apramycin resistance gene was inserted into the inserted fragment of the plasmid TOPO-41c29 to prepare a plasmid TOPO-Δ41c29-μm as follows.

A plasmid pIJ773 [Gust, B., et al., "Proceedings of the National Academy of Sciences of the United States of America," (US), 2003, vol. 100, pp. 1541-1546] was double-digested with HindIII and EcoRI, followed by electrophoresis on an agarose gel. Then, a DNA fragment was cut out according to a conventional method and collected. Thus, approximately 1.3 kb of a DNA fragment comprising the target apramycin resistance gene was obtained. PCR was carried out using this fragment as a template and two types of synthetic primers of 41c30-apraF:
5'-GTCACCGTCCCCGCCTACGGCGACG-GCGTCGTCCTGGTGATTCCGGGGATC CGTCGACC-3' (SEQ ID NO: 41) and 41c30-apraR: 5'-GGTCGCGGGC-GAAGGCGTAGCCGGGCAGGTCGGGCAG-GATGTAGGCTGGAG CTGCTTC-3' (SEQ ID NO: 42). The PCR was performed using LA Taq DNA polymerase (manufactured by Takara Bio Inc.) as a DNA polymerase and PERKIN ELMER GeneAmp PCR System 9700.

The amount of the reaction solution was adjusted to 50 μl by addition of: 0.5 μl (corresponding to 0.5 μg in amount) of the genomic DNA, 25 μl of a buffer for two-fold concentration reaction accompanying the enzyme, 2.5 μl of a DMSO solution, 5 μl of a 2.5-mM dNTP solution, 0.25 μl of each of the primers whose concentration was adjusted to 100 pmol/μl, 0.3 μl of the enzyme, and 16.2 μl of sterilized water. The reaction was carried out as follows: the pretreatment at 94° C. for 2 minutes; incubation in 10 cycles each consisting of 94° C. for 45 seconds, 50° C. for 45 seconds, and 72° C. for 1 minute and 30 seconds; then, incubation in 15 cycles each consisting of 94° C. for 45 seconds, 55° C. for 45 seconds, and 72° C. for 1 minute and 30 seconds; a further reaction at 72° C. for 5 minutes. After the reaction was complete, a portion of the reaction solution was electrophoresed on an agarose gel. As a result, it was confirmed that approximately 1.4 kbp of a DNA fragment was specifically amplified.

Next, TOPO-Δ41c29 was introduced in E. coli BW25113/pIJ790 [Gust, B., et al., "Proceedings of the National Academy of Sciences of the United States of America," (US), 2003, vol. 100, pp. 1541-1546] to obtain an E. coli BW25113/pIJ790/TOPO-Δ41c29 strain. This strain was inoculated into 100 ml of an LB liquid medium containing chloramphenicol, kanamycin and ampicillin respectively at concentrations of 25 μg/ml, 25 μg/ml and 50 μg/ml, and cultured at 30° C. overnight. Then, 10 ml of an SOB medium was fed into a 65-ml test tube supplemented with chloramphenicol, kanamycin, ampicillin, and L-arabinose respectively at concentrations of 25 μg/ml, 25 μg/ml, 50 μg/ml, and 10 mM. To this, 100 μl of a culture solution of the E. coli BW25113/pIJ790/TOPO-Δ41c29 strain cultured overnight was transferred, and shake-cultured at 30° C. for 4 hours. All of the culture solution was centrifuged at 3000 rpm at 4° C. for 5 minutes to collect the bacterial cells which were then suspended in 10 ml of an ice-cooled 10% glycerin solution. After this operation was repeated, the resulting bacterial cells were resuspended in 100 μl of a cooled 10% glycerin solution. Next, 50 μl of the bacterial cell-suspension was collected into an Eppendorf tube to which 5 μl of a solution of approximately 1.4 kb of a DNA fragment containing the above-described apramycin resistance gene derived from pIJ773 was added. The mixture was transferred to an already ice-cooled electroporation cuvette with a gap of 2 mm (BM6200: manufactured by BM Equipment Co., Ltd.). Electroporation was conducted using Electro Cell Manipulator 600 (manufactured by BM Equipment Co., Ltd.) under conditions of 12.5 kV, 25 μF, and 128Ω.

After the treatment, 1 ml of an already ice-cooled LB liquid medium was added to the bacterial cells, which were then allowed to stand at 37° C. for 1 hour for culturing. This was applied to an LB agar medium supplemented with ampicillin and apramycin each at a concentration of 50 μg/ml. The resultant was cultured at 37° C. all the night to obtain a strain having resistance to both of ampicillin and apramycin. This strain was cultured in an LB liquid medium supplemented with ampicillin and apramycin each at a concentration of 50 μg/ml. Thus, a plasmid TOPO-Δ41c29-μm was isolated.

Example 6

Creation of Biosynthetic Gene-Deficient Strains

The plasmid TOPO-Δ41c29 was introduced in an E. coli ET12567/pUZ8002 strain ["Practical Streptomyces Genetics," The John Innes Foundation, (UK), Norwich, 2000] according to a conventional method to obtain E. coli ET12567/pUZ8002/TOPO-Δ41c29.

Streptoverticillium was conjugated to E. coli ET12567/pUZ8002/TOPO-Δ41c29 as follows. First, the Streptoverticillium strain was inoculated into 10 ml of a liquid medium (S#1) [Ueki, M, et al, "The Journal of Antibiotics," (Japan), 1996, vol. 49, pp. 639-643] prepared in a 65-ml test tube, and cultured at 30° C. for 24 hours. The resultant was applied to an MS agar medium (2% soybean flour, 2% mannitol, 2% agar), and cultured at 30° C. for 2 days. After the culturing, mycelia were collected by scraping with 3 ml of 20% glycerol to prepare a host mycelium solution.

After the bacterial cells were collected by centrifugation at 3000 rpm for 5 minutes, the bacterial cells were suspended in 3 ml of a 20% glycerin solution. Meanwhile, E. coli ET12567/pUZ8002/TOPO-Δ41c29-μm was cultured at 37° C. for 18 hours in an LB liquid medium supplemented with ampicillin and apramycin each at a concentration of 50 μg/ml. Then, 1 ml of the culture solution was transferred to 100 ml of an LB liquid medium (containing ampicillin and apramycin each at a concentration of 50 μg/ml), and cultured at 37° C. for 4 hours. Subsequently, 50 ml of the culture solution was centrifuged at 3000 rpm for 5 minutes to collect the bacterial cells. The bacterial cells were suspended in 20 ml of an LB liquid medium. After this operation was repeated twice, the bacterial cells were suspended in 2 ml of an LB liquid medium.

Next, 100 μl of the Streptoverticillium cell-suspension and 100 μl of a bacterial cell-suspension of E. coli ET12567/pUZ8002/cosmid203-7 were combined together in a 1.5-ml tube, and centrifuged to collect bacterial cells. After suspended in 100 μl of a 20% glycerin solution, this was applied to an MS agar medium having a volume of 20 ml and containing 10 mM $MgCl_2$. After the culturing at 30° C. for 18 hours, 1 ml of sterilized water containing 400 μg of apramycin and 1500 μg of nalidixic acid was overlaid thereon. After cultured at 30° C. for 5 days, Streptoverticillium colonies grown on the agar medium were subjected to pure culture and cultured at 30° C. for 2 days in a ½ MS agar medium (agar: 2%, mannitol: 1%, soybean flour: 1%, 10 mM $MgCl_2$) supplemented with 250 μg/ml of apramycin and 250 μg/ml of kanamycin. A colony grew in any plate and was subcultured for several passages by: inoculation into an S#1 medium, followed by culturing at 30° C. for 24 hours, inoculation into an modified YEME medium (10 ml in a 65-ml test tube), followed by shake-culturing at 30° C. for 1 day, and further inoculation of 1 ml of the resulting culture into another fresh modified YEME medium (50 ml in a 250-ml Erlenmeyer flask). After this operation was repeated five times, the resulting culture was diluted in such a manner as to obtain an appropriate number of living bacterial cells. This culture solution was applied to a ½ MS agar medium containing 250

μg/ml of apramycin, and cultured at 30° C. for 4 days. A colony thus grown was replicated in a ½ MS agar medium supplemented with 250 μg/ml of apramycin and 250 μg/ml of kanamycin. Two kanamycin-susceptible strains (D1 strain, D2 strain) were selected which did not grow in a kanamycin-containing medium but grew in an apramycin-containing medium.

The genomic DNAs of the obtained two strains were prepared, and a PCR reaction was carried out using a combination of primers of 41c30F4: 5'-CGTGACCGAGGTG-GCGCG-3' (SEQ ID NO: 43) and 41c30RR2: 5'-GTCGTCGGATGCGCCGTGCG-3' (SEQ ID NO: 44). It was confirmed that the two strains were disrupted strains as designed because approximately 0.5 kbp of an amplified DNA fragment was not obtained.

Example 7

Culturing of Biosynthetic Gene-Deficient Strains, and Quantification of UK-2A in Culture Solution The disrupted strains, D1 strain and D2 strain, were each inoculated into 50 ml of an S#1 medium [Ueki, M, et al, "The Journal of Antibiotics," (Japan), 1996, vol. 49, pp. 639-643] prepared in a 250-ml Erlenmeyer flask, and shake-cultured at 30° C. for 24 hours. Then, 1 ml of the culture solution was inoculated into a production medium, and shake-cultured at 30° C. for 4 days. Then, 4 ml of acetone was added to 1 ml of the resulting culture solution to thereby extract UK-2A which was then filtered to obtain an extraction liquid. Of this, 5 μl was subjected to HPLC analysis. In the HPLC analysis, HPLC System LC-2010C (manufactured by Shimadzu Corporation) was used for the analysis. As the analysis conditions, the column was Inertsil ODS-3 4.6×250 mm, the mobile phase was acetonitrile:water:phosphoric acid=60:40:0.1, the flow rate was 1.1 ml/min, the column temperature was 40° C., and the UV wavelength was 340 nm. The obtained pattern was compared with that of the UK-2A reference standard. The peak derived from UK-2A was identified. Based on the area thereof, UK-2A was quantified.

At the same time, the same culturing and quantification of UK-2A in a culture solution were carried out also for *Streptoverticillium* sp. 3-7, which was the parental strain of the transformants. As a result, the UK-2A productivity by the D1 and D2 strains was 0 μg/ml.

Example 8

Creation of Biosynthetic Gene Cluster-Introduced Transformant

Constructed pUK2-3 was introduced in *Streptoverticillium* sp. 3-7 according to a method generally used for actinobacteria ["Practical *Streptomyces* Genetics," The John Innes Foundation, (UK), Norwich, 2000, pp. 311-338]. First, the plasmid pUK2-3 was introduced in an *E. coli* ET12567/pUZ8002 strain by electroporation according to a conventional method to obtain *E. coli* ET12567/pUZ8002/pUK2-3. This strain was cultured at 37° C. for 18 hours in an LB liquid medium supplemented with chloramphenicol, kanamycin and apramycin respectively at concentrations of 25 μg/ml, 50 μg/ml and 50 μg/ml. Then, 1 ml of the culture solution was transferred to 100 ml of an LB liquid medium (containing chloramphenicol, kanamycin and apramycin respectively at concentrations of 25 μg/ml, 25 μg/ml and 50 μg/ml), and cultured at 37° C. for 4 hours. Subsequently, 50 ml of the culture solution was centrifuged at 3000 rpm for 5 minutes to collect the bacterial cells. The bacterial cells were suspended in 50 ml of an LB liquid medium. After this operation was repeated twice, the bacterial cells were suspended in 100 μL of an LB liquid medium.

Meanwhile, *Streptoverticillium* sp. 3-7 was applied to an MS agar medium, and cultured at 30° C. for 2 days. After the culturing, mycelia were scraped with 1 ml of 20% glycerol to prepare a host mycelium solution.

Next, 500 μl of the host mycelium solution and 500 μl of the *Escherichia coli* solution comprising the plasmid pUK2-3 prepared as described above were mixed together, and the bacterial cells were collected. Then, the bacterial cells were applied to an MS agar medium which had been diluted by addition of 10 mM $MgCl_2$ in such a manner as to bring the final concentration to 10 mmol/L. After the culturing at 30° C. for 20 hours, 0.5 ml of sterilized water containing 6 mg of apramycin and 0.5 mg of nalidixic acid was overlaid thereon. After further cultured at 30° C. for 5 days, a transformant was obtained as an apramycin-resistant strain.

Example 9

Culturing of Gene-Introduced Transformant, and Quantification of UK-2A in Culture Solution The gene-introduced transformant was cultured by the method described in Example 7. As a result, as shown in Table 3, the UK-2A productivity of the gene-introduced transformant was improved 58 to 77 times in comparison with that of the parental strain.

TABLE 3

| Strains | Productivity in culture solution (μg/ml) UK-2A | Relative productivity |
| --- | --- | --- |
| Parental strain (3-7) | 2 | 1 |
| Transformant 1 (3-7-1) | 116 | 58 |
| Transformant 2 (3-7-2) | 153 | 77 |

Example 10

Culturing of Gene-Introduced Transformant, and Quantifications of UK-2A, UK-2B, and sum of UK-2C and UK-2D in Culture Solution The gene-introduced trans formant was cultured by the method described in Example 7. Specifically, 4 ml of acetone was added to 1 ml of the resulting culture solution to thereby extract UK-2A, UK-2B, UK-2C and UK-2D which were then filtered to obtain an extraction liquid. Of this, 5 μl was subjected to HPLC analysis. In the HPLC analysis, HPLC solution system (manufactured by Shimadzu Corporation) was used for the analysis. As the analysis conditions, the column was Inertsil ODS-3 4.6×150 mm; the mobile phase was a solution obtained by dissolving 7.8 g of sodium dihydrogen phosphate dihydrate in approximately 800 mL of water, adjusting the pH of the resultant to 4.0 using phosphoric acid, adding water thereto to prepare 1000 ml of a phosphoric acid aqueous solution, and adding 650 mL of acetonitrile for liquid chromatography to 350 mL of the phosphoric acid aqueous solution; the flow rate was 1.0 ml/min; the column temperature was 40° C.; and the UV wavelength was 230 nm. The obtained pattern was compared with those of the UK-2A, UK-2B, and UK-2C and UK-2D reference standards. The respective peaks derived from UK-2A, UK-2B, UK-2C and UK-2D were identified. Based on the areas thereof, the amount of UK-2A, the amount of UK-2B, and the sum of UK-2C and UK-2D were determined.

As a result, as shown in Table 4, the productivities of UK-2A, UK-2B, and the sum of UK-2C and UK-2D of the gene-introduced transformant were respectively improved 37 to 57 times, 10 to 11 times, and 12 to 13 times in comparison with those of the parental strain.

TABLE 4

| Strains | UK-2A Productivity in culture solution (μg/ml) | UK-2A Relative productivity | UK-2B Productivity in culture solution (μg/ml) | UK-2B Relative productivity | UK-2C and UK-2D (sum) Productivity in culture solution (μg/ml) | UK-2C and UK-2D (sum) Relative productivity |
|---|---|---|---|---|---|---|
| Strain (3-7) | 10 | 1 | 1 | 1 | 7 | 1 |
| Transformant (3-7-1) | 368 | 37 | 11 | 11 | 86 | 12 |
| Transformant (3-7-2) | 565 | 57 | 10 | 10 | 89 | 13 |

Example 11

Quantification of Number of Copies of UK-2 Biosynthetic Gene Cluster in Transformant Genomic DNAs of the two strains of the transformant confirmed in Example 9 to have the UK-2 productivity improved and *Streptoverticillium* sp. 3-7, which was the host cell, were prepared by the method described in Example 1. PCR reactions were carried out using the genomic DNAs as templates and StepOnePlus Real-Time PCR System (manufactured by Applied BioSystems Inc.) in accordance with the protocol attached thereto. Amplified fragments thus obtained were quantified. Table 5 shows the obtained result.

Note that, in the PCR reactions, the following primer set was designed, synthesized and used to amplify a region in the introduced UK-2 biosynthetic gene cluster.

UK-2 F2 (RT): 5'-GCACCTTCATGTCCGGGTTG-3' (SEQ ID NO: 45)

UK-2 R2 (RT): 5'-ATCGCCGCGTACACCATGAC-3' (SEQ ID NO: 46).

Further, the following primer set was designed, synthesized and used as an internal control to amplify a region other than the UK-2 biosynthetic gene cluster.

cont F1 (RT): 5'-CGAAGGTCCGGTTGATGGTG-3' (SEQ ID NO: 47)

Cont R1 (RT): 5'-ATCGCTGCGACACCCTGGAG-3' (SEQ ID NO: 48)

TABLE 5

| Strains | Number of copies |
|---|---|
| Parental strain (3-7) | 1.00 |
| Transformant (3-7-1) | 2.35 |
| Transformant (3-7-2) | 2.08 |

As shown in Table 5, it was revealed that the number of copies of the UK-2 biosynthetic gene cluster in the transformant was double that of the parental strain sp. 3-7.

As described hereinabove, the present invention makes it possible to provide a transformant having high UK-2 productivity by introduction of a UK-2 biosynthetic gene or a UK-2 biosynthetic gene cluster.

Therefore, by using the transformant of the present invention, mass production of UK-2 at low cost is made possible. Accordingly, the present invention is useful in producing rice blast control agents, agricultural and horticultural fungicides, and medical antifungal agents.

[Reference to Deposited Biological Material]
[Accession Number]
1.
(1) Indication for identification: *Streptoverticillium* sp. 3-7
(2) Accession number: FERM BP-11437
(3) Date of deposition: Nov. 9, 2011
(4) Depository institution: International Patent Organism Depositary, National Institute of Advanced Industrial Science and Technology
(5) The deposit of the patent microorganisms by International Patent Organism Depositary, National Institute of Advanced Industrial Science and Technology (former name: IPOD) was succeeded by National Institute of Technology and Evaluation (NITE) on April, 2012.

What is claimed is:

1. A recombinant vector comprising a nucleic acid, wherein the nucleic acid is an isolated nucleic acid that induces UK-2 biosynthesis and improves UK-2 productivity, and is at least one nucleic acid selected from the group consisting of the following (a) to (q):

(a) a nucleic acid encoding a protein comprising an amino acid sequence of SEQ ID NO: 3, a nucleic acid encoding an amino acid sequence having a homology of 95% or more with an amino acid sequence of SEQ ID NO: 3, or a nucleic acid hybridizing under stringent conditions to a nucleic acid comprising a base sequence of SEQ ID NO: 2;

(b) a nucleic acid encoding a protein comprising an amino acid sequence of SEQ ID NO: 5, a nucleic acid encoding an amino acid sequence having a homology of 95% or more with an amino acid sequence of SEQ ID NO: 5, or a nucleic acid hybridizing under stringent conditions to a nucleic acid comprising a base sequence of SEQ ID NO: 4;

(c) a nucleic acid encoding a protein comprising an amino acid sequence of SEQ ID NO: 7, a nucleic acid encoding an amino acid sequence having a homology of 95% or more with an amino acid sequence of SEQ ID NO: 7, or a nucleic acid hybridizing under stringent conditions to a nucleic acid comprising a base sequence of SEQ ID NO: 6;

(d) a nucleic acid encoding a protein comprising an amino acid sequence of SEQ ID NO: 9, a nucleic acid encoding an amino acid sequence having a homology of 95% or more with an amino acid sequence of SEQ ID NO: 9, or a nucleic acid hybridizing under stringent conditions to a nucleic acid comprising a base sequence of SEQ ID NO: 8;

(e) a nucleic acid encoding a protein comprising an amino acid sequence of SEQ ID NO: 11, a nucleic acid encoding an amino acid sequence having a homology of 95% or more with an amino acid sequence of SEQ ID NO: 11, or a nucleic acid hybridizing under stringent conditions to a nucleic acid comprising a base sequence of SEQ ID NO: 10;

(f) a nucleic acid encoding a protein comprising an amino acid sequence of SEQ ID NO: 13, a nucleic acid encoding an amino acid sequence having a homology of 95% or more with an amino acid sequence of SEQ ID NO: 13, or a nucleic acid hybridizing under stringent conditions to a nucleic acid comprising a base sequence of SEQ ID NO: 12;

(g) a nucleic acid encoding a protein comprising an amino acid sequence of SEQ ID NO: 15, a nucleic acid encoding an amino acid sequence having a homology of 95% or more with an amino acid sequence of SEQ ID NO: 15, or a nucleic acid hybridizing under stringent conditions to a nucleic acid comprising a base sequence of SEQ ID NO: 14;

(h) a nucleic acid encoding a protein comprising an amino acid sequence of SEQ ID NO: 17, a nucleic acid encoding an amino acid sequence having a homology of 95% or more with an amino acid sequence of SEQ ID NO: 17, or a nucleic acid hybridizing under stringent conditions to a nucleic acid comprising a base sequence of SEQ ID NO: 16;

(i) a nucleic acid encoding a protein comprising an amino acid sequence of SEQ ID NO: 19, a nucleic acid encoding an amino acid sequence having a homology of 95% or more with an amino acid sequence of SEQ ID NO: 19, or a nucleic acid hybridizing under stringent conditions to a nucleic acid comprising a base sequence of SEQ ID NO: 18;

(j) a nucleic acid encoding a protein comprising an amino acid sequence of SEQ ID NO: 21, a nucleic acid encoding an amino acid sequence having a homology of 95% or more with an amino acid sequence of SEQ ID NO: 21, or a nucleic acid hybridizing under stringent conditions to a nucleic acid comprising a base sequence of SEQ ID NO: 20;

(k) a nucleic acid encoding a protein comprising an amino acid sequence of SEQ ID NO: 23, a nucleic acid encoding an amino acid sequence having a homology of 95% or more with an amino acid sequence of SEQ ID NO: 23, or a nucleic acid hybridizing under stringent conditions to a nucleic acid comprising a base sequence of SEQ ID NO: 22;

(l) a nucleic acid encoding a protein comprising an amino acid sequence of SEQ ID NO: 25, a nucleic acid encoding an amino acid sequence having a homology of 95% or more with an amino acid sequence of SEQ ID NO: 25, or a nucleic acid hybridizing under stringent conditions to a nucleic acid comprising a base sequence of SEQ ID NO: 24;

(m) a nucleic acid encoding a protein comprising an amino acid sequence of SEQ ID NO: 27, a nucleic acid encoding an amino acid sequence having a homology of 95% or more with an amino acid sequence of SEQ ID NO: 27, or a nucleic acid hybridizing under stringent conditions to a nucleic acid comprising a base sequence of SEQ ID NO: 26;

(n) a nucleic acid encoding a protein comprising an amino acid sequence of SEQ ID NO: 29, a nucleic acid encoding an amino acid sequence having a homology of 95% or more with an amino acid sequence of SEQ ID NO: 29, or a nucleic acid hybridizing under stringent conditions to a nucleic acid comprising a base sequence of SEQ ID NO: 28;

(o) a nucleic acid encoding a protein comprising an amino acid sequence of SEQ ID NO: 31, a nucleic acid encoding an amino acid sequence having a homology of 95% or more with an amino acid sequence of SEQ ID NO: 31, or a nucleic acid hybridizing under stringent conditions to a nucleic acid comprising a base sequence of SEQ ID NO: 30;

(p) a nucleic acid encoding a protein comprising an amino acid sequence of SEQ ID NO: 33, a nucleic acid encoding an amino acid sequence having a homology of 95% or more with an amino acid sequence of SEQ ID NO: 33, or a nucleic acid hybridizing under stringent conditions to a nucleic acid comprising a base sequence of SEQ ID NO: 32; and (q) a nucleic acid encoding a protein comprising an amino acid sequence of SEQ ID NO: 35, a nucleic acid encoding an amino acid sequence having a homology of 95% or more with an amino acid sequence of SEQ ID NO: 35, or a nucleic acid hybridizing under stringent conditions to a nucleic acid comprising a base sequence of SEQ ID NO: 34.

2. A bacterium transformant comprising a nucleic acid, wherein UK-2 biosynthesis is induced and UK-2 production is increased in comparison to a parental strain bacterium, and the nucleic acid is an isolated nucleic acid that induces UK-2 biosynthesis and improves UK-2 productivity, and is at least one nucleic acid selected from the group consisting of the following (a) to (q):

(a) a nucleic acid encoding a protein comprising an amino acid sequence of SEQ ID NO: 3, a nucleic acid encoding an amino acid sequence having a homology of 95% or more with an amino acid sequence of SEQ ID NO: 3, or a nucleic acid hybridizing under stringent conditions to a nucleic acid comprising a base sequence of SEQ ID NO: 2;

(b) a nucleic acid encoding a protein comprising an amino acid sequence of SEQ ID NO: 5, a nucleic acid encoding an amino acid sequence having a homology of 95% or more with an amino acid sequence of SEQ ID NO: 5, or a nucleic acid hybridizing under stringent conditions to a nucleic acid comprising a base sequence of SEQ ID NO: 4;

(c) a nucleic acid encoding a protein comprising an amino acid sequence of SEQ ID NO: 7, a nucleic acid encoding an amino acid sequence having a homology of 95% or more with an amino acid sequence of SEQ ID NO: 7, or a nucleic acid hybridizing under stringent conditions to a nucleic acid comprising a base sequence of SEQ ID NO: 6;

(d) a nucleic acid encoding a protein comprising an amino acid sequence of SEQ ID NO: 9, a nucleic acid encoding an amino acid sequence having a homology of 95% or more with an amino acid sequence of SEQ ID NO: 9, or a nucleic acid hybridizing under stringent conditions to a nucleic acid comprising a base sequence of SEQ ID NO: 8;

(e) a nucleic acid encoding a protein comprising an amino acid sequence of SEQ ID NO: 11, a nucleic acid encoding an amino acid sequence having a homology of 95% or more with an amino acid sequence of SEQ ID NO: 11, or a nucleic acid hybridizing under stringent conditions to a nucleic acid comprising a base sequence of SEQ ID NO: 10;

(f) a nucleic acid encoding a protein comprising an amino acid sequence of SEQ ID NO: 13, a nucleic acid encoding an amino acid sequence having a homology of 95% or more with an amino acid sequence of SEQ ID NO: 13, or a nucleic acid hybridizing under stringent conditions to a nucleic acid comprising a base sequence of SEQ ID NO: 12;

(g) a nucleic acid encoding a protein comprising an amino acid sequence of SEQ ID NO: 15, a nucleic acid encoding an amino acid sequence having a homology of 95% or more with an amino acid sequence of SEQ ID NO: 15, or a nucleic acid hybridizing under stringent conditions to a nucleic acid comprising a base sequence of SEQ ID NO: 14;

(h) a nucleic acid encoding a protein comprising an amino acid sequence of SEQ ID NO: 17, a nucleic acid encoding an amino acid sequence having a homology of 95% or more with an amino acid sequence of SEQ ID NO: 17, or a nucleic acid hybridizing under stringent conditions to a nucleic acid comprising a base sequence of SEQ ID NO: 16;

(i) a nucleic acid encoding a protein comprising an amino acid sequence of SEQ ID NO: 19, a nucleic acid encoding an amino acid sequence having a homology of 95% or more with an amino acid sequence of SEQ ID NO: 19, or a nucleic acid hybridizing under stringent conditions to a nucleic acid comprising a base sequence of SEQ ID NO: 18;

(j) a nucleic acid encoding a protein comprising an amino acid sequence of SEQ ID NO: 21, a nucleic acid encoding an amino acid sequence having a homology of 95% or more with an amino acid sequence of SEQ ID NO: 21, or a nucleic acid hybridizing under stringent conditions to a nucleic acid comprising a base sequence of SEQ ID NO: 20;

(k) a nucleic acid encoding a protein comprising an amino acid sequence of SEQ ID NO: 23, a nucleic acid encoding an amino acid sequence having a homology of 95% or more with an amino acid sequence of SEQ ID NO: 23, or a nucleic acid hybridizing under stringent conditions to a nucleic acid comprising a base sequence of SEQ ID NO: 22;

(l) a nucleic acid encoding a protein comprising an amino acid sequence of SEQ ID NO: 25, a nucleic acid encoding an amino acid sequence having a homology of 95% or more with an amino acid sequence of SEQ ID NO: 25, or a nucleic acid hybridizing under stringent conditions to a nucleic acid comprising a base sequence of SEQ ID NO: 24;

(m) a nucleic acid encoding a protein comprising an amino acid sequence of SEQ ID NO: 27, a nucleic acid encoding an amino acid sequence having a homology of 95% or more with an amino acid sequence of SEQ ID NO: 27, or a nucleic acid hybridizing under stringent conditions to a nucleic acid comprising a base sequence of SEQ ID NO: 26;

(n) a nucleic acid encoding a protein comprising an amino acid sequence of SEQ ID NO: 29, a nucleic acid encoding an amino acid sequence having a homology of 95% or more with an amino acid sequence of SEQ ID NO: 29, or a nucleic acid hybridizing under stringent conditions to a nucleic acid comprising a base sequence of SEQ ID NO: 28;

(o) a nucleic acid encoding a protein comprising an amino acid sequence of SEQ ID NO: 31, a nucleic acid encoding an amino acid sequence having a homology of 95% or more with an amino acid sequence of SEQ ID NO: 31, or a nucleic acid hybridizing under stringent conditions to a nucleic acid comprising a base sequence of SEQ ID NO: 30;

(p) a nucleic acid encoding a protein comprising an amino acid sequence of SEQ ID NO: 33, a nucleic acid encoding an amino acid sequence having a homology of 95% or more with an amino acid sequence of SEQ ID NO: 33, or a nucleic acid hybridizing under stringent conditions to a nucleic acid comprising a base sequence of SEQ ID NO: 32; and (q) a nucleic acid encoding a protein comprising an amino acid sequence of SEQ ID NO: 35, a nucleic acid encoding an amino acid sequence having a homology of 95% or more with an amino acid sequence of SEQ ID NO: 35, or a nucleic acid hybridizing under stringent conditions to a nucleic acid comprising a base sequence of SEQ ID NO: 34.

3. A bacterium comprising the recombinant vector according to claim 1, wherein UK-2 production is increased in comparison to a parental strain of the bacterium.

4. A bacterium transformant wherein one or two or more copies of a nucleic acid are present per cell, and
the nucleic acid is an isolated nucleic acid that induces UK-2 biosynthesis and improves UK-2 productivity, and is at least one nucleic acid selected from the group consisting of the following (a) to (q):

(a) a nucleic acid encoding a protein comprising an amino acid sequence of SEQ ID NO: 3, a nucleic acid encoding an amino acid sequence having a homology of 95% or more with an amino acid sequence of SEQ ID NO: 3, or a nucleic acid hybridizing under stringent conditions to a nucleic acid comprising a base sequence of SEQ ID NO: 2;
(b) a nucleic acid encoding a protein comprising an amino acid sequence of SEQ ID NO: 5, a nucleic acid encoding an amino acid sequence having a homology of 95% or more with an amino acid sequence of SEQ ID NO: 5, or a nucleic acid hybridizing under stringent conditions to a nucleic acid comprising a base sequence of SEQ ID NO: 4;
(c) a nucleic acid encoding a protein comprising an amino acid sequence of SEQ ID NO: 7, a nucleic acid encoding an amino acid sequence having a homology of 95% or more with an amino acid sequence of SEQ ID NO: 7, or a nucleic acid hybridizing under stringent conditions to a nucleic acid comprising a base sequence of SEQ ID NO: 6;
(d) a nucleic acid encoding a protein comprising an amino acid sequence of SEQ ID NO: 9, a nucleic acid encoding an amino acid sequence having a homology of 95% or more with an amino acid sequence of SEQ ID NO: 9, or a nucleic acid hybridizing under stringent conditions to a nucleic acid comprising a base sequence of SEQ ID NO: 8;
(e) a nucleic acid encoding a protein comprising an amino acid sequence of SEQ ID NO: 11, a nucleic acid encoding an amino acid sequence having a homology of 95% or more with an amino acid sequence of SEQ ID NO: 11, or a nucleic acid hybridizing under stringent conditions to a nucleic acid comprising a base sequence of SEQ ID NO: 10;
(f) a nucleic acid encoding a protein comprising an amino acid sequence of SEQ ID NO: 13, a nucleic acid encoding an amino acid sequence having a homology of 95% or more with an amino acid sequence of SEQ ID NO: 13, or a nucleic acid hybridizing under stringent conditions to a nucleic acid comprising a base sequence of SEQ ID NO: 12;
(g) a nucleic acid encoding a protein comprising an amino acid sequence of SEQ ID NO: 15, a nucleic acid encoding an amino acid sequence having a homology of 95% or more with an amino acid sequence of SEQ ID NO: 15, or a nucleic acid hybridizing under stringent conditions to a nucleic acid comprising a base sequence of SEQ ID NO: 14;
(h) a nucleic acid encoding a protein comprising an amino acid sequence of SEQ ID NO: 17, a nucleic acid encoding an amino acid sequence having a homology of 95% or more with an amino acid sequence of SEQ ID NO: 17, or a nucleic acid hybridizing under stringent conditions to a nucleic acid comprising a base sequence of SEQ ID NO: 16;
(i) a nucleic acid encoding a protein comprising an amino acid sequence of SEQ ID NO: 19, a nucleic acid encoding an amino acid sequence having a homology of 95% or more with an amino acid sequence of SEQ ID NO: 19, or a nucleic acid hybridizing under stringent conditions to a nucleic acid comprising a base sequence of SEQ ID NO: 18;
(j) a nucleic acid encoding a protein comprising an amino acid sequence of SEQ ID NO: 21, a nucleic acid encoding an amino acid sequence having a homology of 95% or more with an amino acid sequence of SEQ ID NO: 21, or a nucleic acid hybridizing under stringent conditions to a nucleic acid comprising a base sequence of SEQ ID NO: 20;
(k) a nucleic acid encoding a protein comprising an amino acid sequence of SEQ ID NO: 23, a nucleic acid encoding an amino acid sequence having a homology of 95% or more with an amino acid sequence of SEQ ID NO: 23, or a nucleic acid hybridizing under stringent conditions to a nucleic acid comprising a base sequence of SEQ ID NO: 22;
(l) a nucleic acid encoding a protein comprising an amino acid sequence of SEQ ID NO: 25, a nucleic acid encoding an amino acid sequence having a homology of 95% or more with an amino acid sequence of SEQ ID NO: 25, or a nucleic acid hybridizing under stringent conditions to a nucleic acid comprising a base sequence of SEQ ID NO: 24;
(m) a nucleic acid encoding a protein comprising an amino acid sequence of SEQ ID NO: 27, a nucleic acid encoding an amino acid sequence having a homology of 95% or more with an amino acid sequence of SEQ ID NO: 27, or a nucleic acid hybridizing under stringent conditions to a nucleic acid comprising a base sequence of SEQ ID NO: 26;
(n) a nucleic acid encoding a protein comprising an amino acid sequence of SEQ ID NO: 29, a nucleic acid encoding an amino acid sequence having a homology of 95% or more with an amino acid sequence of SEQ ID NO: 29, or a nucleic acid hybridizing under stringent conditions to a nucleic acid comprising a base sequence of SEQ ID NO: 28;
(o) a nucleic acid encoding a protein comprising an amino acid sequence of SEQ ID NO: 31, a nucleic acid encoding an amino acid sequence having a homology of 95% or more with an amino acid sequence of SEQ ID NO: 31, or a nucleic acid hybridizing under stringent conditions to a nucleic acid comprising a base sequence of SEQ ID NO: 30;
(p) a nucleic acid encoding a protein comprising an amino acid sequence of SEQ ID NO: 33, a nucleic acid encoding an amino acid sequence having a homology of 95% or more with an amino acid sequence of SEQ ID NO: 33, or a nucleic acid hybridizing under stringent conditions to a nucleic acid comprising a base sequence of SEQ ID NO: 32; and
(q) a nucleic acid encoding a protein comprising an amino acid sequence of SEQ ID NO: 35, a nucleic acid encoding an amino acid sequence having a homology of 95% or more with an amino acid sequence of SEQ ID NO: 35, or a nucleic acid hybridizing under stringent conditions to a nucleic acid comprising a base sequence of SEQ ID NO: 34.

5. The bacterium transformant according to claim 2, which is any one of *Streptoverticillium, Streptomyces, Escherichia coli, Bacillus subtilis*, yeasts, filamentous fungi and *Corynebacterium glutamicum*.

6. A method for producing UK-2, comprising the step of: culturing the bacterium according to claim 2, and collecting UK-2 from a culture of the bacterium.

7. A bacterium transformant selectable by a method for determining UK-2 productivity, comprising detecting, in a test bacterium, the presence of a nucleic acid comprising a base sequence of a UK-2 biosynthetic gene or a base sequence complementary to the sequence, and the UK-2 biosynthetic gene induces UK-2 biosynthesis and improves UK-2 productivity, and is at least one nucleic acid selected from the group consisting of the following (a) to (q):
(a) a nucleic acid encoding a protein comprising an amino acid sequence of SEQ ID NO: 3, a nucleic acid encoding an amino acid sequence having a homology of 95% or more with an amino acid sequence of SEQ ID NO: 3, or a nucleic acid hybridizing under stringent conditions to a nucleic acid comprising a base sequence of SEQ ID NO: 2;

(b) a nucleic acid encoding a protein comprising an amino acid sequence of SEQ ID NO: 5, a nucleic acid encoding an amino acid sequence having a homology of 95% or more with an amino acid sequence of SEQ ID NO: 5, or a nucleic acid hybridizing under stringent conditions to a nucleic acid comprising a base sequence of SEQ ID NO: 4;

(c) a nucleic acid encoding a protein comprising an amino acid sequence of SEQ ID NO: 7, a nucleic acid encoding an amino acid sequence having a homology of 95% or more with an amino acid sequence of SEQ ID NO: 7, or a nucleic acid hybridizing under stringent conditions to a nucleic acid comprising a base sequence of SEQ ID NO: 6;

(d) a nucleic acid encoding a protein comprising an amino acid sequence of SEQ ID NO: 9, a nucleic acid encoding an amino acid sequence having a homology of 95% or more with an amino acid sequence of SEQ ID NO: 9, or a nucleic acid hybridizing under stringent conditions to a nucleic acid comprising a base sequence of SEQ ID NO: 8;

(e) a nucleic acid encoding a protein comprising an amino acid sequence of SEQ ID NO: 11, a nucleic acid encoding an amino acid sequence having a homology of 95% or more with an amino acid sequence of SEQ ID NO: 11, or a nucleic acid hybridizing under stringent conditions to a nucleic acid comprising a base sequence of SEQ ID NO: 10;

(f) a nucleic acid encoding a protein comprising an amino acid sequence of SEQ ID NO: 13, a nucleic acid encoding an amino acid sequence having a homology of 95% or more with an amino acid sequence of SEQ ID NO: 13, or a nucleic acid hybridizing under stringent conditions to a nucleic acid comprising a base sequence of SEQ ID NO: 12;

(g) a nucleic acid encoding a protein comprising an amino acid sequence of SEQ ID NO: 15, a nucleic acid encoding an amino acid sequence having a homology of 95% or more with an amino acid sequence of SEQ ID NO: 15, or a nucleic acid hybridizing under stringent conditions to a nucleic acid comprising a base sequence of SEQ ID NO: 14;

(h) a nucleic acid encoding a protein comprising an amino acid sequence of SEQ ID NO: 17, a nucleic acid encoding an amino acid sequence having a homology of 95% or more with an amino acid sequence of SEQ ID NO: 17, or a nucleic acid hybridizing under stringent conditions to a nucleic acid comprising a base sequence of SEQ ID NO: 16;

(i) a nucleic acid encoding a protein comprising an amino acid sequence of SEQ ID NO: 19, a nucleic acid encoding an amino acid sequence having a homology of 95% or more with an amino acid sequence of SEQ ID NO: 19, or a nucleic acid hybridizing under stringent conditions to a nucleic acid comprising a base sequence of SEQ ID NO: 18;

(j) a nucleic acid encoding a protein comprising an amino acid sequence of SEQ ID NO: 21, a nucleic acid encoding an amino acid sequence having a homology of 95% or more with an amino acid sequence of SEQ ID NO: 21, or a nucleic acid hybridizing under stringent conditions to a nucleic acid comprising a base sequence of SEQ ID NO: 20;

(k) a nucleic acid encoding a protein comprising an amino acid sequence of SEQ ID NO: 23, a nucleic acid encoding an amino acid sequence having a homology of 95% or more with an amino acid sequence of SEQ ID NO: 23, or a nucleic acid hybridizing under stringent conditions to a nucleic acid comprising a base sequence of SEQ ID NO: 22;

(l) a nucleic acid encoding a protein comprising an amino acid sequence of SEQ ID NO: 25, a nucleic acid encoding an amino acid sequence having a homology of 95% or more with an amino acid sequence of SEQ ID NO: 25, or a nucleic acid hybridizing under stringent conditions to a nucleic acid comprising a base sequence of SEQ ID NO: 24;

(m) a nucleic acid encoding a protein comprising an amino acid sequence of SEQ ID NO: 27, a nucleic acid encoding an amino acid sequence having a homology of 95% or more with an amino acid sequence of SEQ ID NO: 27, or a nucleic acid hybridizing under stringent conditions to a nucleic acid comprising a base sequence of SEQ ID NO: 26;

(n) a nucleic acid encoding a protein comprising an amino acid sequence of SEQ ID NO: 29, a nucleic acid encoding an amino acid sequence having a homology of 95% or more with an amino acid sequence of SEQ ID NO: 29, or a nucleic acid hybridizing under stringent conditions to a nucleic acid comprising a base sequence of SEQ ID NO: 28;

(o) a nucleic acid encoding a protein comprising an amino acid sequence of SEQ ID NO: 31, a nucleic acid encoding an amino acid sequence having a homology of 95% or more with an amino acid sequence of SEQ ID NO: 31, or a nucleic acid hybridizing under stringent conditions to a nucleic acid comprising a base sequence of SEQ ID NO: 30;

(p) a nucleic acid encoding a protein comprising an amino acid sequence of SEQ ID NO: 33, a nucleic acid encoding an amino acid sequence having a homology of 95% or more with an amino acid sequence of SEQ ID NO: 33, or a nucleic acid hybridizing under stringent conditions to a nucleic acid comprising a base sequence of SEQ ID NO: 32; and (q) a nucleic acid encoding a protein comprising an amino acid sequence of SEQ ID NO: 35, a nucleic acid encoding an amino acid sequence having a homology of 95% or more with an amino acid sequence of SEQ ID NO: 35, or a nucleic acid hybridizing under stringent conditions to a nucleic acid comprising a base sequence of SEQ ID NO: 34.

* * * * *